United States Patent
Varasi et al.

(10) Patent No.: US 9,944,589 B2
(45) Date of Patent: Apr. 17, 2018

(54) CYCLOPROPLYAMINE DERIVATIVES USEFUL AS INHIBITORS OF HISTONE DEMETHYLASES KDM1A

(71) Applicant: Istituto Europeo de Oncologia S.r.L., Milan (IT)

(72) Inventors: Mario Varasi, Milan (IT); Paola Vianello, Milan (IT); Florian Thaler, Milan (IT); Paolo Trifiro', Milan (IT); Ciro Mercurio, Milan (IT); Giuseppe Meroni, Milan (IT)

(73) Assignee: Istituto Europeo di Oncologia S.r.l., Milan (IT)

(*) Notice: Subject to any disclaimer, the term of this patent is extended or adjusted under 35 U.S.C. 154(b) by 245 days.

(21) Appl. No.: 14/650,292

(22) PCT Filed: Dec. 3, 2013

(86) PCT No.: PCT/EP2013/075409
§ 371 (c)(1),
(2) Date: Jun. 5, 2015

(87) PCT Pub. No.: WO2014/086790
PCT Pub. Date: Jun. 12, 2014

(65) Prior Publication Data
US 2015/0315126 A1    Nov. 5, 2015

(30) Foreign Application Priority Data

Dec. 5, 2012  (EP) .................... 12195597

(51) Int. Cl.

| | |
|---|---|
| C07C 211/40 | (2006.01) |
| A61K 31/4025 | (2006.01) |
| A61K 31/404 | (2006.01) |
| A61K 31/4164 | (2006.01) |
| A61K 31/496 | (2006.01) |
| C07D 215/12 | (2006.01) |
| C07D 295/195 | (2006.01) |
| C07D 207/50 | (2006.01) |
| C07D 213/61 | (2006.01) |
| C07D 311/70 | (2006.01) |
| C07D 211/58 | (2006.01) |
| C07D 263/04 | (2006.01) |
| C07D 233/02 | (2006.01) |
| C07D 271/113 | (2006.01) |
| C07C 209/00 | (2006.01) |
| C07C 231/12 | (2006.01) |
| C07C 269/06 | (2006.01) |
| C07C 303/36 | (2006.01) |
| C07D 319/16 | (2006.01) |

(Continued)

(52) U.S. Cl.
CPC .......... *C07C 211/40* (2013.01); *A61K 31/404* (2013.01); *A61K 31/4025* (2013.01); *A61K 31/4164* (2013.01); *A61K 31/496* (2013.01); *C07C 209/00* (2013.01); *C07C 211/49* (2013.01); *C07C 215/42* (2013.01); *C07C 217/58* (2013.01); *C07C 217/74* (2013.01); *C07C 231/12* (2013.01); *C07C 233/44* (2013.01); *C07C 233/80* (2013.01); *C07C 237/06* (2013.01); *C07C 247/16* (2013.01); *C07C 269/06* (2013.01); *C07C 271/28* (2013.01); *C07C 303/36* (2013.01); *C07C 311/21* (2013.01); *C07D 207/50* (2013.01); *C07D 211/58* (2013.01); *C07D 213/61* (2013.01); *C07D 213/64* (2013.01); *C07D 215/12* (2013.01); *C07D 233/02* (2013.01); *C07D 233/32* (2013.01); *C07D 239/42* (2013.01); *C07D 249/06* (2013.01); *C07D 263/04* (2013.01); *C07D 263/22* (2013.01); *C07D 271/10* (2013.01); *C07D 271/113* (2013.01); *C07D 295/155* (2013.01); *C07D 295/195* (2013.01); *C07D 307/54* (2013.01); *C07D 311/70* (2013.01); *C07D 319/16* (2013.01); *C07C 2601/02* (2017.05)

(58) Field of Classification Search
None
See application file for complete search history.

(56) References Cited

FOREIGN PATENT DOCUMENTS

| | | |
|---|---|---|
| GB | 950388 | 2/1964 |
| WO | WO 96/40126 | 12/1996 |

(Continued)

OTHER PUBLICATIONS

Shintani, R. et al., "Guiding the Nitrogen Nucleophile to the middle:Palladium-catalyzed decarboxylative cyclopropanation of 2-alkylidenetrimethylene carbonates with isocyanates", *Chem. Comm.*, 2011, vol. 47. No. 11, pp. 3057-3059.

Zirkle, C. L. et al., "2-substituted cyclorpopylamines. II. Effect of Structure Upon Monoamine Oxidase-Inhibitory Activity as Measured in Vivo by Potentiation of Tryptamine Convulsions", Journal of Medicinal and Pharmaceutical Chemistry, American Chemical Society, 1962, vol. 5, pp. 1265-1284.

(Continued)

*Primary Examiner* — Kortney L. Klinkel
*Assistant Examiner* — Tori Strong
(74) *Attorney, Agent, or Firm* — Cooley LLP; Heidi A. Erlacher; Thomas J. Paxton

(57) ABSTRACT

The present invention relates to cyclopropyl derivatives of general formula (I), wherein A, $R^1$, and $R^2$ are as defined in the specification. The present application also relates to pharmaceutical compositions containing such compounds and to their use in therapy.

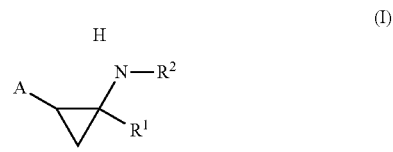

25 Claims, No Drawings

(51) Int. Cl.

| | | |
|---|---|---|
| C07D 233/32 | (2006.01) | |
| C07D 239/42 | (2006.01) | |
| C07D 249/06 | (2006.01) | |
| C07D 263/22 | (2006.01) | |
| C07D 271/10 | (2006.01) | |
| C07D 295/155 | (2006.01) | |
| C07D 213/64 | (2006.01) | |
| C07D 307/54 | (2006.01) | |
| C07C 271/28 | (2006.01) | |
| C07C 211/49 | (2006.01) | |
| C07C 215/42 | (2006.01) | |
| C07C 217/58 | (2006.01) | |
| C07C 217/74 | (2006.01) | |
| C07C 233/44 | (2006.01) | |
| C07C 233/80 | (2006.01) | |
| C07C 237/06 | (2006.01) | |
| C07C 247/16 | (2006.01) | |
| C07C 311/21 | (2006.01) | |

(56) References Cited

FOREIGN PATENT DOCUMENTS

| WO | WO 2007/134799 | 11/2007 |
|---|---|---|
| WO | WO 2008/018823 | 2/2008 |
| WO | WO 2010/143582 A1 | 12/2010 |
| WO | WO 2011/131576 A1 | 10/2011 |
| WO | WO 2012/013728 | 2/2012 |
| WO | WO 2012/135113 A2 | 10/2012 |

OTHER PUBLICATIONS

Heshmatollah, Alinezhad et al., "Reductive Amination of Aldehydes and Ketones in a Heterogeneous System in THF and under Solvent-Free Conditions Using Sodium Borohydride-Silica Phosphoric Acid", Chemical Monthly, 2007, vol. 139, No. 1, pp. 21-25.
"Amine I. Herstellung and physikalische Eigenschaften" In: Morrison, Robert T. Boyd, Robert N: "Lehrbuch der Organischen Chemie", 1986, VCH Verlagsgesellschaft, vol. 3, p. 1012.
Moreau, Benoit et al., "Catalytic asymmetric synthesis of nitrocyclopropane carboxylates", Tetrahedron, vol. 68, No. 17, Apr. 2012, pp. 3487-3496.
International Search Report dated Feb. 20, 2014 from corresponding PCT Application No. PCT/EP2013/075409.
Bertus, P. et al. "New and easy route to primary cyclopropylamines from nitriles", *Chem. Commun.*, 2001, pp. 1792-1793.
Huisgen, R. et al. "The Question of a Primary 1.1-Addition for the Cycloadditions of Nitrilium and Diazonium Betaines", *Chem. Ber.*, 1972, vol. 105, pp. 1324-1339.
Kang, G.I. et al. "Quantitative Structure-Activity Relationships in MAO-Inhibitory 2-Phenylcyclopropylamines: Insights into the Topograpy of MAO-A and MAO-B" *Arch. Phar. Res.*, 1990, vol. 13, No. 1, pp. 82-96.
Lohse, B. et al. "Inhibitors of histone demethylases" *Bioorganic & Medicinal Chemistry*, 2011, vol. 19, pp. 3625-3636.
Patel, A.R. "1,2-Diarylcyclopropane Derivatives", *Acta Chem. Scand.*, 1966, vol. 20, No. 5, pp. 1424-1426.
CAS RN 1017463-54-5, STN Entry Date Apr. 27, 2008.
CAS RN 1017433-83-8, STN Entry Date Apr. 25, 2008.

CYCLOPROPLYAMINE DERIVATIVES USEFUL AS INHIBITORS OF HISTONE DEMETHYLASES KDM1A

CROSS-REFERENCE TO RELATED APPLICATIONS

This application is a U.S. National Phase entry of PCT/EP2013/075409, filed Dec. 3, 2013, under 35 U.S.C. § 371, and claims priority to European Patent Application No. 12195597.5, filed Dec. 5, 2012, each of which is incorporated herein by reference in their entireties.

FIELD OF THE INVENTION

The present invention relates to cyclopropyl derivatives, pharmaceutical compositions containing such compounds and to their use in therapy.

BACKGROUND OF THE INVENTION

Alterations in the structural and functional states of chromatin, mainly determined by post-translational modification of histone components, are involved in the pathogenesis of a variety of diseases. These reversible modifications confer to the dynamicity of chromatin remodeling and are tightly controlled by the opposing activities of enzyme families. The enzymatic processes governing these post-translational modifications on the nucleosomes have become potential targets for the so-called epigenetic therapies (Portela, A. et al. Nat. Biotechnol. 2010, 28, 1057-1068).

The discovery of an increasing number of histone lysine demethylases has highlighted the dynamic nature of the regulation of histone methylation, a key chromatin modification that is involved in eukaryotic genome and gene regulation. Histone lysine demethylases represent attractive targets for epigenetic drugs, since their expression and/or activities are often misregulated in cancer (Varier, R. A. et al. Biochim. Biophys. Acta. 2011, 1815, 75-89). A lysine can be mono-, di-, and tri-methylated and each modification, even on the same amino acid, can exert different biological effects.

Histone lysine demethylases can be grouped into two major families with different enzymatic mechanisms (Anand, R. et al. J. Biol. Chem. 2007, 282, 35425-35429; Metzger, E. et al. Nat. Struct. Mol. Biol. 2007, 14, 252-254). On one side, we find the large protein family of Jumonji C (JmjC) domain-containing proteins, where the demethylation reaction is carried out by JmjC domain proteins and where a conserved JmjC domain, the presence of Fe(II) and α-ketoglutarate is required to generate formaldehyde and succinate and to allow the removal of mono-, di-, and trimethylated lysines. The demethylation reaction of the other class, which includes two proteins, is a flavin dependent oxidative process and is limited to mono- and di-methylated substrates. Mammals contain two flavin dependent amino oxidase histone lysine demethylases: KDM1A (also known as LSD1) and KDM1B (also known as LSD2). KDM1A is a constituent in several chromatin-remodeling complexes and is often associated with the co-repressor protein CoREST. It recruits in this form other histone modifying enzymes such as histone deacetylases 1/2 (HDAC1/2) forming a multienzyme unit typically involved in gene repression regulation (Ballas, N. et al. Neuron 2001, 31, 353-365). KDM1A specifically removes the methyl groups from both mono- and di-methyl Lys4 of histone H3, which is a well-characterized gene activation mark.

KDM1A represents an interesting target for epigenetic drugs as supported by data related to its over-expression in solid and hematological tumors (Schulte, J. H. et al. Cancer Res. 2009, 69, 2065-2071; Lim, S. et al. Carcinogenesis 2010, 31, 512-520; Hayami, S. et al. Int. J. Cancer 2011, 128, 574-586; Schildhaus, H. U. et al. Hum. Pathol. 2011, 42, 1667-1675; Bennani-Baiti, I. M. et al. Hum. Pathol. 2012, 43, 1300-1307), to the correlation of its over-expression and tumor recurrence in prostate cancer (Kahl, P. et al. Cancer Res. 2006, 66, 11341-11347), to its role in various differentiation processes as adipogenesis (Musri, M. M. et al. J. Biol. Chem. 2010, 285, 30034-30041), muscle skeletal differentiation (Choi, J. et al. Biochem. Biophys. Res. Commun. 2010, 401, 327-332), and hematopoiesis (Hu, X. et al. Proc. Natl. Acad. Sci. USA 2009, 106, 10141-10146; Li, Y. et al. Oncogene. 2012, 31, 5007-18), to its regulation of cellular energy expenditure (Hino S. Et al. Nat Commun. 2012, doi: 10.1038/ncomms1755), to its involvement in the control of checkpoints of viral gene expression in productive and latent infections (Roizman, B. J. Virol. 2011, 85, 7474-7482) and more specifically in the control of herpes virus infection (Gu, H. J. Virol. 2009, 83, 4376-4385) and HIV transcription (Sakane, N. et al. PLoS Pathog. 2011, 7(8): e1002184). The role of KDM1A in the regulation of neural stem cell proliferation (Sun, G. et al. Mol. Cell Biol. 2010, 30, 1997-2005) as well as in the control of neuritis morphogenesis (Zibetti, C. et al. J. Neurosci. 2010, 30, 2521-2532) suggest its possible involvement for neurodegenerative diseases.

Furthermore, there are evidences of the relevance of KDM1A in the control of other important cellular processes, such as DNA methylation (Wang, J. et al. Nat. Genet. 2009, 41(1):125-129), cell proliferation (Scoumanne, A. et al. J. Biol. Chem. 2007, 282, 15471-15475; Cho, H. S. et al. Cancer Res. 2011, 71, 655-660), epithelial mesenchimal transition (Lin, T. et al. Oncogene. 2010, 29, 4896-4904), and chromosome segregation (Lv, S. et al. Eur. J. Cell Biol. 2010, 89, 557-563). Moreover, several inhibitors of KDM1A have been identified in the last years and it was found that KDM1A inhibitors were able to reactivate silenced tumor suppressor genes (Huang, Y. et al. Proc. Natl. Acad. Sci. USA. 2007, 104, 8023-8028; Huang, Y. et al. Clin. Cancer Res. 2009, 15, 7217-7228), to target selectively cancer cells with pluripotent stem cells properties (Wang, J. et al. Cancer Res. 2011, 71, 7238-7249), as well as to reactivate the all-trans-retinoic acid differentiation pathway in acute myeloid leukemia (Schenk, T. et al. Nat Med. 2012, 18, 605-611).

The more recently discovered demethylase KDM1B (LSD2) displays—similarly to KDM1A—specificity for mono- and di-methylated Lys4 of histone H3. KDM1B, differently from KDM1A, does not bind CoREST and it has not been found up to now in any of KDM1A-containing protein complex (Karytinos, A. et al. J. Biol. Chem. 2009, 284, 17775-17782). On the contrary, KDM1B forms active complexes with euchromatic histone methyltransferases G9a and NSD3 as well as with cellular factors involved in transcription elongation. In agreement, KDM1B has been reported to have a role as regulator of transcription elongation rather than that of a transcriptional repressor as proposed for KDM1A (Fang, R. et al. Mol. Cell 2010, 39, 222-233).

KDM1A and KDM1B are both flavo amino oxidases dependent proteins sharing a FAD coenzyme-binding motif, a SWIRM domain and an amine oxidase domain, all of which are integral to the enzymatic activity of KDM1 family members. Moreover, both KDM1A and KDM1B show a structural similarity with the monoamine oxidases MAO-A and MAO-B.

Indeed, tranylcypromine, a MAO inhibitor used as antidepressive agent, was found to be also able to inhibit LSD1. The compound acts as an irreversible inhibitor forming a covalent adduct with the FAD cofactor. (Lee, M. G. et al. Chem. Biol. 2006, 13, 563; Schmidt, D. M. Z. et al. Biochemistry 2007, 46, 4408).

The synthesis of tranylcypromine analogs and their LSD1 inhibitory activity has been described by Gooden, D. M. et al. in Bioorg. Med. Chem. Lett. 2008, 18, 3047-3051 and by Benelkebir, H. et al. in Bioorg. Med. Chem. 2011, 19, 3709-3716. Further arylcyclopropylamine and heteroarylcyclopropylamine derivatives as LSD1, MAO-A and/or MAO-B enzyme inhibitors are disclosed in US2010/324147, WO2012/013727 and in WO2012/045883.

Oryzon Genomics S. A. disclosed in WO2010/043721, WO2010/084160, WO2011/035941, WO2011/042217, and in WO2012/013728, cyclopropylaminoalkylamides, N-heterocyclyl-, aryl-, or heteroarylalkylcyclopropylamines with LSD1, MAO-A and/or MAO-B inhibitory activity, however no example of 2-aryl or heteroarylcyclopropylamine derivative substituted in position 1 of the cyclopropyl have been disclosed.

Further cyclopropylamines with LSD1 inhibitory activity and with the following general formula have been disclosed in WO2013/057320 and WO2013/057322:

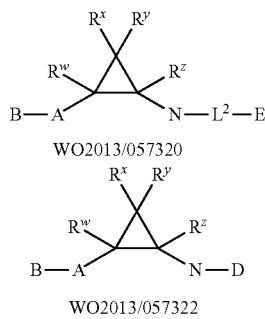

WO2013/057320

WO2013/057322 wherein $R^W$, $R^X$, $R^Y$, and $R^Z$ are independently selected from hydrogen, fluoro and $C_{1-4}$ alkyl, preferably from hydrogen, fluoro and methyl. A more preferred embodiment of the inventions are compounds, wherein $R^Z$ is hydrogen. No specific compound with $R^Z$ other than hydrogen has been disclosed in the two PCT patent applications.

GB950388 discloses phenylcyclopropylamine derivatives as monoamine oxidase inhibitors of following formula:

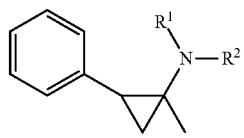

with $R^1$ and $R^2$ hydrogen or methyl having anorectic and antidepressant activity. WO1996/40126 describes 1H-4(5)-substituted imidazole derivatives having H3 histamine receptor agonist activity being useful in the treatment of diseases such as allergy, inflammation, cardio or cerebrovascular disease, gastrointestinal disorders and CNS disorders involving psychiatric disorders.

Substituted 1-methyl-2-phenyl- or 1-ethyl-2-phenylcyclopropylamine derivatives are described in WO2007/134799 as intermediates for the synthesis of macrobiocide derivatives. Additional cyclopropylamines substituted in position 1 are described by Patel, A. R. Acta Chem. Scand., 1966, 1424-1426, by Huisgen, R. et al. Chem. Berichte, 1972, 1324-1339, by Bertus, P. et al. Chem. Commun. (Camb.), 2001, 18, 1792-1793, by Shintani, R. et al. Chem. Commun. (Camb.), 2011, 47, 3057-3059, and Osipova, A. PhD "Synthesis of Diverse Polyfunctional Amides as Precursors to Potentially Interesting Peptidomimetics" Thesis Göttingen 2006.

The present invention relates to substituted cyclopropylamine derivatives having highly potent inhibitory activities of the KDM1A enzyme and/or of the KDM1B enzyme and low inhibitory activity of monoamine oxidases (MAOs), useful in the prevention or therapy of diseases and conditions associated with the activity of the histone demethylases. MAOs are well known targets for the treatment of diseases of the central nervous system, such as depression or Parkinson's disease. However, inhibition of the MAOs are associated with side effects, among them tyramine-induced hypertensive crisis or the serotonin syndrome, which occurs in situation of concomitant use of MAO inhibitors and other serotoninergic drugs. (Wimbiscus, M. et al. Cleve. Clin. J. Med., 2010, 859-882; Iqbal, M. M. Ann. Clin. Psychiatry, 2012, 24, 310-318).

DESCRIPTION OF THE INVENTION

According to the present invention there are provided compounds, endowed with a potent KDM1A (LSD1) inhibitory activity, of general formula (I)

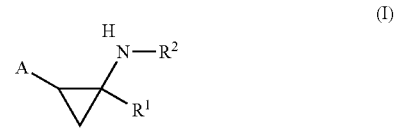

wherein:

A is aryl or heteroaryl, wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, OH, $C_1$-$C_6$ alkylamino, and R-L-;

R is aryl, wherein the aryl may be optionally substituted by one, two or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, $C_1$-$C_6$ alkylamino optionally substituted by OH, heterocyclylamino optionally substituted by $C_1$-$C_6$ alkyl, OH, phenyl, heterocyclyl optionally substituted by $C_1$-$C_6$ alkyl, heterocyclyl substituted by oxo, heteroaryl, and benzyloxycarbonylamino; or heteroaryl;

L is a single bond; $C_1$-$C_6$ alkylene; $C_2$-$C_6$ alkenylene; —$(CH_2)_m$X—$(CH_2)_n$—; —$(CH_2)_o(SO_2)$NH—; —$(CH_2)_p(CO)NR^3$—; —$(CH_2)_qNR^4(CO)$—; heterocyclyl substituted by oxo; or heteroaryl;

$R^1$ is $C_1$-$C_6$ alkyl, optionally substituted by aryl or heteroaryl; aryl; heteroaryl; or —$(CH_2)_r$—Y—$R^5$; and wherein the aryl or heteroaryl group may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, nitro, acetamido, and phenyl;

$R^2$ is hydrogen; $C_1$-$C_6$ alkyl, optionally substituted by aryl, heteroaryl, or by heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$;

m, n, o, p, q are, independently, zero or an integer from 1 to 6;

r is an integer from 1 to 6;

X, Y are, independently, $NR^8$; O; or S;

$R^3$, $R^4$ are, independently, hydrogen; or $C_1$-$C_6$ alkyl;

$R^5$ is hydrogen, aryl or heteroaryl, wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and phenyl;

$R^6$, $R^7$ are, independently, hydrogen; $C_1$-$C_6$ alkyl; or $R^6$ and $R^7$ together with the nitrogen to which they are bound form a $C_4$-$C_{10}$-heterocyclic ring, optionally containing one or more further heteroatoms in the ring independently selected from $NR^9$, O or S and being optionally substituted by $NH_2$;

$R^8$ is hydrogen; $C_1$-$C_6$ alkyl, optionally substituted by aryl or heterocyclyl; or $C_{3-6}$ cycloalkyl;

$R^9$ is hydrogen or $C_1$-$C_6$ alkyl;

or stereoisomers or pharmaceutically acceptable salts thereof, for use in the treatment of diseases and conditions which are mediated by an excessive or inappropriate KDM1A (LSD1) activity.

Particularly preferred compounds of general formula (I) for the treatment of diseases and conditions, which are mediated by excessive or inappropriate KDM1A (LSD1) activity are selected from the following list:

(1S,2R)-1-ethyl-2-phenyl-cyclopropanamine;
(1R,2S)-1-ethyl-2-phenyl-cyclopropanamine;
trans-1-methyl-2-phenyl-cyclopropanamine;
(1R,2S)-1-methyl-2-phenyl-cyclopropanamine;
(1S,2R)-1-methyl-2-phenyl-cyclopropanamine;
trans-1-propyl-2-phenyl-cyclopropanamine;
trans-1-isopropyl-2-phenyl-cyclopropanamine;
trans-1-benzyl-2-phenyl-cyclopropanamine;
(1S,2S)-1-benzyl-2-phenyl-cyclopropanamine;
(1R,2R)-1-benzyl-2-phenyl-cyclopropanamine;
trans-1-phenethyl-2-phenyl-cyclopropanamine;
trans-2-(4-bromophenyl)-1-ethyl-cyclopropanamine;
trans-1-benzyl-2-(4-bromophenyl)cyclopropanamine;
trans-1-ethyl-2-(6-quinolyl)cyclopropanamine;
trans-1-(2-naphthylmethyl)-2-phenyl-cyclopropanamine;
trans-1-ethyl-2-(4-fluorophenyl)cyclopropanamine;
trans-1-ethyl-2-(4-chlorophenyl)cyclopropanamine;
trans-1-ethyl-2-[3-(trifluoromethyl)phenyl]cyclopropanamine;
trans-1-ethyl-2-[4-(trifluoromethyl)phenyl]cyclopropanamine;
trans-1-ethyl-2-(3-fluorophenyl)cyclopropanamine;
trans-1-ethyl-2-(3-chlorophenyl)-cyclopropanamine;
trans-1-ethyl-2-(3-bromophenyl)-cyclopropanamine;
trans-1-ethyl-2-[3-methoxyphenyl]cyclopropanamine;
1-ethyl-(trans)-2-[4-(trifluoromethoxy)phenyl]cyclopropanamine;
trans-1-ethyl-2-(2-fluorophenyl)-cyclopropanamine;
trans-1-ethyl-2-(2-chlorophenyl)-cyclopropanamine;
trans-1-ethyl-2-(2-bromophenyl)-cyclopropanamine;
trans-1-(1-naphthylmethyl)-2-phenyl-cyclopropanamine;
trans-2-(4-bromophenyl)-1-(2-naphthylmethyl)cyclopropanamine;
trans-N-[4-[2-amino-2-ethyl-cyclopropyl]phenyl]naphthalene-2-carboxamide;
N-[2-[(trans)-2-amino-2-ethyl-cyclopropyl]phenyl]benzamide;
benzyl N-[3-[[2-[(trans)-2-amino-2-ethyl-cyclopropyl]phenyl]carbamoyl]phenyl]carbamate;
benzyl N-[3-[[3-[(trans)-2-amino-2-ethyl-cyclopropyl]phenyl]carbamoyl]phenyl]carbamate;
N-[4-[(trans)-2-amino-2-ethyl-cyclopropyl]phenyl]-3-chloro-benzamide
N-[4-[(trans)-2-amino-2-ethyl-cyclopropyl]phenyl]-3-phenyl-benzamide;
N-[4-[(trans)-2-amino-2-ethyl-cyclopropyl]phenyl]-4-phenyl-benzamide
benzyl N-[3-[[4-[(trans)-2-amino-2-ethyl-cyclopropyl]phenyl]carbamoyl]phenyl]carbamate;
benzyl N-[4-[[4-[(trans)-2-amino-2-ethyl-cyclopropyl]phenyl]carbamoyl]phenyl]carbamate;
N-[4-[(trans)-2-amino-2-ethyl-cyclopropyl]phenyl]-2-phenyl-acetamide;
N-[4-[(trans)-2-amino-2-ethyl-cyclopropyl]phenyl]-3-phenyl-propanamide;
2-(4-benzyloxyphenyl)-trans-1-ethyl-cyclopropanamine;
N-[4-[(2-amino-trans-2-ethyl-cyclopropyl]phenyl]benzenesulfonamide;
trans-1-benzyl-2-(4-benzyloxyphenyl)cyclopropanamine;
N-[4-[trans-2-amino-2-(2-naphthylmethyl)cyclopropyl]phenyl]benzamide;
Benzyl-N-[3-[[4-[(trans)-2-amino-2-(2-naphthylmethyl)cyclopropyl]phenyl]carbamoyl]phenyl]carbamate;
N-[4-[(trans)-2-amino-2-(2-naphthylmethyl)cyclopropyl]phenyl]-2-phenyl-acetamide;
N-[4-[trans-2-amino-2-ethyl-cyclopropyl]phenyl]benzamide;
trans-4-(2-amino-2-ethyl-cyclopropyl)aniline;
trans-2-(3-azidophenyl)-1-ethyl-cyclopropanamine;
1-amino-(trans)-2-phenyl-cyclopropyl]methanol;
1-amino-(cis)-2-phenyl-cyclopropyl]methanol;
(1R,2S)-1-ethyl-N-[(2-methoxyphenyl)methyl]-2-phenyl-cyclopropanamine;
(1R,2S)-1-ethyl-N-[(2-methoxy-1-naphthyl)methyl]-2-phenyl-cyclopropanamine;
2-[[(1S,2R)-1-methyl-2-phenyl-cyclopropyl]amino]-1-(4-methylpiperazin-1-yl)ethanone;
2-[[(1S,2S)-1-methyl-2-phenyl-cyclopropyl]amino]-1-(4-methylpiperazin-1-yl)ethanone;
1-[(3S)-3-aminopyrrolidin-1-yl]-2-[[(1S,2R)-1-methyl-2-phenyl-cyclopropyl]amino]ethanone;
trans-2-[[(1-ethyl-2-phenyl-cyclopropyl]amino]-1-(4-methylpiperazin-1-yl)ethanone;
cis-2-[[(1-ethyl-2-phenyl-cyclopropyl]amino]-1-(4-methylpiperazin-1-yl)ethanone;
trans-1-ethyl-N-methyl-2-phenyl-cyclopropanamine;
cis-1-ethyl-N-methyl-2-phenyl-cyclopropanamine;
trans-1-ethyl-N-ethyl-2-phenyl-cyclopropanamine;
cis-1-ethyl-N-ethyl-2-phenyl-cyclopropanamine;
trans-2-[[1-ethyl-2-phenyl-cyclopropyl]amino]acetamide;
trans-N-benzyl-1-ethyl-2-phenyl-cyclopropanamine;
trans-N-[(3,4-dimethoxyphenyl)methyl]-1-ethyl-2-phenyl-cyclopropanamine;
trans-N-[(4,7-dimethoxy-1-naphthyl)methyl]-1-ethyl-2-phenyl-cyclopropanamine;
trans-N-[(2-chloro-3-pyridyl)methyl]-1-ethyl-2-phenyl-cyclopropanamine;

trans-N-[(2,2-dimethylchroman-6-yl)methyl]-1-ethyl-2-phenyl-cyclopropanamine;
cis-1,2-diphenylcyclopropanamine;
trans-1,2-diphenylcyclopropanamine;
trans-1-ethyl-2-phenyl-cyclopropanamine;
trans-2-(4-bromo-3-fluoro-phenyl)-1-ethyl-cyclopropanamine;
trans 2-(3-bromophenyl)-1-phenethyl-cyclopropanamine;
(1R,2S)-1,2-diphenylcyclopropanamine;
(1S,2R)-1,2-diphenylcyclopropanamine;
trans-2-(4-fluorophenyl)-1-(2-naphthylmethyl)cyclopropanamine;
trans-2-(4-chlorophenyl)-1-(2-naphthylmethyl)cyclopropanamine;
trans-2-(3-chlorophenyl)-1-(2-naphthylmethyl)cyclopropanamine;
trans-2-(3-bromophenyl)-1-(2-naphthylmethyl)cyclopropanamine;
trans-2-(4-chlorophenyl)-1-phenethyl-cyclopropanamine;
trans-2-(4-fluorophenyl)-1-phenethyl-cyclopropanamine;
trans-1-benzyl-2-(4-fluorophenyl)cyclopropanamine;
trans-1-benzyl-2-(4-chlorophenyl)cyclopropanamine;
trans 2-(4-bromophenyl)-1-phenethyl-cyclopropanamine;
cis-1-ethyl-2-phenyl-cyclopropanamine;
N-[4-(trans-2-amino-2-ethyl-cyclopropyl)phenyl]-3-[(1-methyl-4-piperidyl)amino]-4-phenyl-benzamide;
2-(4-benzyloxyphenyl)-1-(2-naphthylmethyl)cyclopropanamine;
N-[4-trans-[2-amino-2-ethyl-cyclopropyl]phenyl]-2-(1-naphthyl)acetamide;
N-[4-trans-[2-amino-2-ethyl-cyclopropyl]phenyl]-2-(4-nitrophenyl)acetamide;
benzyl N-[4-[[4-[trans-2-amino-2-(2-naphthylmethyl)cyclopropyl]phenyl]carbamoyl]phenyl]carbamate;
N-[4-(trans-2-amino-2-ethyl-cyclopropyl)phenyl]naphthalene-1-carboxamide;
N-[4-[trans-2-amino-2-(2-naphthylmethyl)cyclopropyl]phenyl]naphthalene-2-carboxamide;
N-[4-[trans-2-amino-2-(2-naphthylmethyl)cyclopropyl]phenyl]-4-phenyl-benzamide;
N-[4-trans-2-amino-2-ethyl-cyclopropyl]phenyl]-2-(2-naphthyl)acetamide;
N-[4-[trans-2-amino-2-phenyl-cyclopropyl]phenyl]benzamide;
N-[4-[trans-2-amino-2-(2-naphthylmethyl)cyclopropyl]phenyl]-2-(1-naphthyl)acetamide;
N-[3-[trans-2-amino-2-ethyl-cyclopropyl]phenyl]-2-(1-naphthyl)acetamide;
N-[4-[trans-2-amino-2-ethyl-cyclopropyl]phenyl]-4-(3-furyl)benzamide;
N-[4-[trans-2-amino-2-(2-naphthylmethyl)cyclopropyl]phenyl]-3-chloro-benzamide;
N-[3-[trans-2-amino-2-ethyl-cyclopropyl]phenyl]-3-chloro-benzamide;
N-[4-[trans-2-amino-2-(2-naphthylmethyl)cyclopropyl]phenyl]-3-phenyl-propanamide;
N-[4-[trans-2-amino-2-(2-naphthylmethyl)cyclopropyl]phenyl]-3-phenyl-benzamide;
N-[4-[trans-2-amino-2-ethyl-cyclopropyl]phenyl]-4-(2-oxooxazolidin-3-yl)benzamide;
benzyl N-[3-[(4-[trans-2-amino-2-phenyl-cyclopropyl]phenyl)carbamoyl]phenyl]carbamate;
N-[4-[trans-2-amino-2-phenyl-cyclopropyl]phenyl]naphthalene-2-carboxamide;
N-[4-[trans-2-amino-2-ethyl-cyclopropyl]-2-fluoro-phenyl]benzamide;
N-[4-[trans-2-amino-2-ethyl-cyclopropyl]-2-fluoro-phenyl]-4-phenyl-benzamide;
N-[4-[trans-2-amino-2-ethyl-cyclopropyl]phenyl]-4-morpholino-benzamide;
N-[4-[trans-2-amino-2-phenyl-cyclopropyl]phenyl]-4-phenyl-benzamide;
N-[4-[trans-2-amino-2-phenyl-cyclopropyl]phenyl]naphthalene-1-carboxamide;
N-[3-[trans-2-amino-2-ethyl-cyclopropyl]phenyl]-4-phenyl-benzamide;
N-[3-[trans-2-amino-2-ethyl-cyclopropyl]phenyl]naphthalene-2-carboxamide;
N-[3-[trans-2-amino-2-ethyl-cyclopropyl]phenyl]benzamide;
N-[4-[trans-2-amino-2-ethyl-cyclopropyl]-2-fluoro-phenyl]-2-(1-naphthyl)acetamide;
benzyl N-[4-[[4-[trans-2-amino-2-ethyl-cyclopropyl]-2-fluoro-phenyl]carbamoyl]phenyl]carbamate;
N-[4-[trans-2-amino-2-ethyl-cyclopropyl]-2-fluoro-phenyl]-4-(4-methylpiperazin-1-yl)benzamide;
N-[4-[trans-2-amino-2-ethyl-cyclopropyl]phenyl]-4-(4-methylpiperazin-1-yl)benzamide;
N-[4-[trans-2-amino-2-ethyl-cyclopropyl]phenyl]-3-(2-oxooxazolidin-3-yl)benzamide;
benzyl N-[5-[[4-[trans-2-amino-2-ethyl-cyclopropyl]phenyl]carbamoyl]-2-morpholino-phenyl]carbamate;
N-[4-[trans-2-amino-2-ethyl-cyclopropyl]phenyl]-4-(1-methyl-4-piperidyl)benzamide;
N-[4-(trans-2-amino-2-ethyl-cyclopropyl)phenyl]pyridine-4-carboxamide;
N-[4-[trans-2-amino-2-ethyl-cyclopropyl]phenyl]-4-(4-pyridyl)benzamide;
N-[4-(trans-2-amino-2-phenyl-cyclopropyl)phenyl]-3-chloro-benzamide;
N-[4-(trans-2-amino-2-phenyl-cyclopropyl)phenyl]-2-(1-naphthyl)acetamide;
N-[4-(trans-2-amino-2-phenyl-cyclopropyl)phenyl]-2-phenyl-acetamide;
N-[4-(trans-2-amino-2-phenyl-cyclopropyl)phenyl]-3-phenyl-benzamide;
N-[4-(trans-2-amino-2-phenyl-cyclopropyl)phenyl]-2-(2-naphthyl)acetamide;
N-[4-(trans-2-amino-2-phenyl-cyclopropyl)phenyl]pyridine-4-carboxamide;
N-[4-(trans-2-amino-2-phenyl-cyclopropyl)phenyl)-4-(1-methyl-4-piperidyl)benzamide;
N-[4-(trans-2-amino-2-phenyl-cyclopropyl)phenyl]-4-(4-methylpiperazin-1-yl)benzamide;
N-[4-(trans-2-amino-2-phenyl-cyclopropyl)phenyl]-3-(2-oxooxazolidin-3-yl)benzamide;
N-[4-(trans-2-amino-2-phenethyl-cyclopropyl)phenyl]pyridine-4-carboxamide;
N-[4-(trans-2-amino-2-phenethyl-cyclopropyl)phenyl]-4-phenyl-benzamide;
N-[4-trans-2-amino-2-phenethyl-cyclopropyl)phenyl]benzamide;
N-[4-(trans-2-amino-2-phenethyl-cyclopropyl)phenyl]-4-(1-methyl-4-piperidyl)benzamide;
N-[4-(trans-2-amino-2-phenethyl-cyclopropyl)phenyl]-4-(4-methyl piperazin-1-yl)benzamide;
benzyl N-[5-[[4-[trans-2-amino-2-ethyl-cyclopropyl]phenyl]carbamoyl]-2-(4-methylpiperazin-1-yl)phenyl]carbamate;
N-[4-(trans-2-amino-2-phenethyl-cyclopropyl)phenyl]-3-(2-oxooxazolidin-3-yl)benzamide;
4-[trans-2-amino-2-(2-naphthylmethyl)cyclopropyl]aniline;

N-[4-(trans-2-amino-2-ethyl-cyclopropyl]phenyl)-4-(2-hydroxyethylamino)benzamide;
benzyl N-[3-[1-[4-[2-amino-2-ethyl-cyclopropyl]phenyl]triazol-4-yl]phenyl]carbamate;
trans-1-ethyl-2-[3-(4-phenyltriazol-1-yl)phenyl]cyclopropanamine;
benzyl N-[3-[1-[4-[2-amino-2-(2-naphthylmethyl)cyclopropyl]phenyl]triazol-4-yl]phenyl]carbamate;
trans-1-(2-naphthylmethyl)-2-[4-(4-phenyltriazol-1-yl)phenyl]cyclopropanamine;
trans 1-ethyl-2-[2-(4-phenyltriazol-1-yl)phenyl]cyclopropanamine;
trans-1-benzyl-2-[4-(4-phenyltriazol-1-yl)phenyl]cyclopropanamine;
N-[4-[(1S,2R)-2-amino-2-ethyl-cyclopropyl]phenyl]-4-phenyl-benzamide;
N-[4-[(1R,2S)-2-amino-2-ethyl-cyclopropyl]phenyl]-4-phenyl-benzamide;
trans 1-benzyl-2-(3-methoxyphenyl)cyclopropanamine;
1-[3-[(trans-2-amino-2-ethyl-cyclopropyl]phenyl]-3-phenyl-imidazolidin-2-one;
trans-1-ethyl-2-[4-(4-phenyltriazol-1-yl)phenyl]cyclopropanamine;
trans 1-[(benzylamino)methyl]-2-phenyl-cyclopropanamine;
trans 1-[(cyclopropylamino)methyl]-2-phenyl-cyclopropanamine;
trans 1-[(4-methylpiperazin-1-yl)methyl]-2-phenyl-cyclopropanamine;
5-{[(trans-1-methyl-2-phenyl-cyclopropyl)amino]methyl}pyrimidin-2-amine;
trans-N-[(2-methoxy-3-pyridyl)methyl]-1-methyl-2-phenyl-cyclopropanamine;
trans-N-(2,3-dihydro-1,4-benzodioxin-6-ylmethyl)-1-methyl-2-phenyl-cyclopropanamine;
cis-N,1-dimethyl-2-phenyl-cyclopropanamine;
2-[[trans-1,2-diphenylcyclopropyl]amino]-1-(4-methylpiperazin-1-yl)ethanone;
1-(4-methylpiperazin-1-yl)-2-[[trans-1-(2-naphthylmethyl)-2-phenyl-cyclopropyl]amino]ethanone;
2-[[(1R,2S)-1-methyl-2-phenyl-cyclopropyl]amino]-1-(4-methylpiperazin-1-yl)ethanone;
2-[[(1R,2R)-1-methyl-2-phenyl-cyclopropyl]amino]-1-(4-methylpiperazin-1-yl)ethanone;
2-[[trans-1-methyl-2-phenyl-cyclopropyl]amino]-1-(4-methyl piperazin-1-yl)ethanone;
2-[[cis-1-methyl-2-phenyl-cyclopropyl]amino]-1-(4-methylpiperazin-1-yl)ethanone;
trans-N,1-dimethyl-2-phenyl-cyclopropanamine;
2-[[trans-1-ethyl-2-phenyl-cyclopropyl]amino]-1-(1-piperidyl)ethanone; trans-1-ethyl-2-phenyl-N-[2-(1-piperidyl)ethyl]cyclopropanamine;
5-[[[trans-1-methyl-2-phenyl-cyclopropyl]amino]methyl]-1,3,4-oxadiazol-2-amine;
trans-1-(4-nitrophenyl)-2-phenyl-cyclopropanamine;
trans-2-(4-chlorophenyl)-1-phenyl-cyclopropanamine;
trans-2-(4-bromophenyl)-1-phenyl-cyclopropanamine;
N-[4-(trans-1-amino-2-phenyl-cyclopropyl]phenyl]acetamide;
or stereoisomers or pharmaceutically acceptable salts thereof.

In another embodiment, the invention provides compounds of general formula (I) as defined above provided that when A is an unsubstituted phenyl or imidazolyl, $R^1$ is methyl, then $R^2$ cannot be hydrogen or methyl; or stereoisomers or pharmaceutically acceptable salts thereof, for the use as a medicament.

Particularly preferred compounds of general formula (I) for the use as a medicament include:
(1S,2R)-1-ethyl-2-phenyl-cyclopropanamine;
(1R,2S)-1-ethyl-2-phenyl-cyclopropanamine;
trans-1-propyl-2-phenyl-cyclopropanamine;
trans-1-isopropyl-2-phenyl-cyclopropanamine;
trans-1-benzyl-2-phenyl-cyclopropanamine;
(1S,2S)-1-benzyl-2-phenyl-cyclopropanamine;
(1R,2R)-1-benzyl-2-phenyl-cyclopropanamine;
trans-1-phenethyl-2-phenyl-cyclopropanamine;
trans-2-(4-bromophenyl)-1-ethyl-cyclopropanamine;
trans-1-benzyl-2-(4-bromophenyl)cyclopropanamine;
trans-1-ethyl-2-(6-quinolyl)cyclopropanamine;
trans-1-(2-naphthylmethyl)-2-phenyl-cyclopropanamine;
trans-1-ethyl-2-(4-fluorophenyl)cyclopropanamine;
trans-1-ethyl-2-(4-chlorophenyl)cyclopropanamine;
trans-1-ethyl-2-[3-(trifluoromethyl)phenyl]cyclopropanamine;
trans-1-ethyl-2-[4-(trifluoromethyl)phenyl]cyclopropanamine;
trans-1-ethyl-2-(3-fluorophenyl)cyclopropanamine;
trans-1-ethyl-2-(3-chlorophenyl)-cyclopropanamine;
trans-1-ethyl-2-(3-bromophenyl)-cyclopropanamine;
trans-1-ethyl-2-[3-methoxyphenyl]cyclopropanamine;
1-ethyl-(trans)-2-[4-(trifluoro methoxy)phenyl]cyclopropanamine;
trans-1-ethyl-2-(2-fluorophenyl)cyclopropanamine;
trans-1-ethyl-2-(2-chlorophenyl)-cyclopropanamine;
trans-1-ethyl-2-(2-bromophenyl)-cyclopropanamine;
trans-1-(1-naphthylmethyl)-2-phenyl-cyclopropanamine;
trans-2-(4-bromophenyl)-1-(2-naphthylmethyl)cyclopropanamine;
trans-N-[4-[2-amino-2-ethyl-cyclopropyl]phenyl]naphthalene-2-carboxamide;
N-[2-[(trans)-2-amino-2-ethyl-cyclopropyl]phenyl]benzamide;
benzyl N-[3-[[2-[(trans)-2-amino-2-ethyl-cyclopropyl]phenyl]carbamoyl]phenyl]carbamate;
benzyl N-[3-[[3-[(trans)-2-amino-2-ethyl-cyclopropyl]phenyl]carbamoyl]phenyl]carbamate;
N-[4-[(trans)-2-amino-2-ethyl-cyclopropyl]phenyl]-3-chloro-benzamide
N-[4-[(trans)-2-amino-2-ethyl-cyclopropyl]phenyl]-3-phenyl-benzamide;
N-[4-[(trans)-2-amino-2-ethyl-cyclopropyl]phenyl]-4-phenyl-benzamide
benzyl N-[3-[[4-[(trans)-2-amino-2-ethyl-cyclopropyl]phenyl]carbamoyl]phenyl]carbamate;
benzyl N-[4-[[4-[(trans)-2-amino-2-ethyl-cyclopropyl]phenyl]carbamoyl]phenyl]carbamate;
N-[4-[(trans)-2-amino-2-ethyl-cyclopropyl]phenyl]-2-phenyl-acetamide;
N-[4-[(trans)-2-amino-2-ethyl-cyclopropyl]phenyl]-3-phenyl-propanamide;
2-(4-benzyloxyphenyl)-trans-1-ethyl-cyclopropanamine;
N-[4-[(2-amino-trans-2-ethyl-cyclopropyl]phenyl]benzenesulfonamide;
trans-1-benzyl-2-(4-benzyloxyphenyl)cyclopropanamine;
N-[4-[trans-2-amino-2-(2-naphthylmethyl)cyclopropyl]phenyl]benzamide;
Benzyl-N-[3-[[4-[(trans)-2-amino-2-(2-naphthylmethyl)cyclopropyl]phenyl]carbamoyl]phenyl]carbamate;
N-[4-[(trans)-2-amino-2-(2-naphthylmethyl)cyclopropyl]phenyl]-2-phenyl-acetamide;
N-[4-[trans-2-amino-2-ethyl-cyclopropyl]phenyl]benzamide;
trans-4-(2-amino-2-ethyl-cyclopropyl)aniline;

trans-2-(3-azidophenyl)-1-ethyl-cyclopropanamine;
1-amino-(trans)-2-phenyl-cyclopropyl]methanol;
1-amino-(cis)-2-phenyl-cyclopropyl]methanol;
(1R,2S)-1-ethyl-N-[(2-methoxyphenyl)methyl]-2-phenyl-cyclopropanamine;
(1R,2S)-1-ethyl-N-[(2-methoxy-1-naphthyl)methyl]-2-phenyl-cyclopropanamine;
2-[[(1S,2R)-1-methyl-2-phenyl-cyclopropyl]amino]-1-(4-methylpiperazin-1-yl)ethanone;
2-[[(1S,2S)-1-methyl-2-phenyl-cyclopropyl]amino]-1-(4-methylpiperazin-1-yl)ethanone;
1-[(3S)-3-aminopyrrolidin-1-yl]-2-[[(1S,2R)-1-methyl-2-phenyl -cyclopropyl]amino]ethanone;
trans-2-[[(1-ethyl-2-phenyl-cyclopropyl]amino]-1-(4-methylpiperazin-1-yl)ethanone;
cis-2-[[(1-ethyl-2-phenyl-cyclopropyl]amino]-1-(4-methyl-piperazin-1-yl)ethanone;
trans-1-ethyl-N-methyl-2-phenyl-cyclopropanamine;
cis-1-ethyl-N-methyl-2-phenyl-cyclopropanamine;
trans-1-ethyl-N-ethyl-2-phenyl-cyclopropanamine;
cis-1-ethyl-N-ethyl-2-phenyl-cyclopropanamine;
trans-2-[[1-ethyl-2-phenyl-cyclopropyl]amino]acetamide;
trans-N-benzyl-1-ethyl-2-phenyl-cyclopropanamine;
trans-N-[(3,4-dimethoxyphenyl)methyl]-1-ethyl-2-phenyl-cyclopropanamine;
trans-N-[(4,7-dimethoxy-1-naphthyl)methyl]-1-ethyl-2-phenyl-cyclopropanamine;
trans-N-[(2-chloro-3-pyridyl)methyl]-1-ethyl-2-phenyl-cyclopropanamine;
trans-N-[(2,2-dimethylchroman-6-yl)methyl]-1-ethyl-2-phenyl-cyclopropanamine;
cis-1,2-diphenylcyclopropanamine;
trans-1,2-diphenylcyclopropanamine;
trans-1-ethyl-2-phenyl-cyclopropanamine;
trans-2-(4-bromo-3-fluoro-phenyl)-1-ethyl-cyclopropanamine;
trans 2-(3-bromophenyl)-1-phenethyl-cyclopropanamine;
(1R,2S)-1,2-diphenylcyclopropanamine;
(1S,2R)-1,2-diphenylcyclopropanamine;
trans-2-(4-fluorophenyl)-1-(2-naphthylmethyl)cyclopropanamine;
trans-2-(4-chlorophenyl)-1-(2-naphthylmethyl)cyclopropanamine;
trans-2-(3-chlorophenyl)-1-(2-naphthylmethyl)cyclopropanamine;
trans-2-(3-bromophenyl)-1-(2-naphthylmethyl)cyclopropanamine;
trans-2-(4-chlorophenyl)-1-phenethyl-cyclopropanamine;
trans-2-(4-fluorophenyl)-1-phenethyl-cyclopropanamine;
trans-1-benzyl-2-(4-fluorophenyl)cyclopropanamine;
trans-1-benzyl-2-(4-chlorophenyl)cyclopropanamine;
trans 2-(4-bromophenyl)-1-phenethyl-cyclopropanamine;
cis-1-ethyl-2-phenyl-cyclopropanamine;
N-[4-(trans-2-amino-2-ethyl-cyclopropyl)phenyl]-3-[(1-methyl-4-piperidyl)amino]-4-phenyl-benzamide;
2-(4-benzyloxyphenyl)-1-(2-naphthylmethyl)cyclopropanamine;
N-[4-trans-[2-amino-2-ethyl-cyclopropyl]phenyl]-2-(1-naphthyl)acetamide;
N-[4-trans-[2-amino-2-ethyl-cyclopropyl]phenyl]-2-(4-nitrophenyl)acetamide;
benzyl N-[4-[[4-[trans-2-amino-2-(2-naphthylmethyl)cyclopropyl]phenyl]carbamoyl]phenyl]carbamate;
N-[4-(trans-2-amino-2-ethyl-cyclopropyl)phenyl]naphthalene-1-carboxamide;
N-[4-[trans-2-amino-2-(2-naphthylmethyl)cyclopropyl]phenyl]naphthalene-2-carboxamide;
N-[4-[trans-2-amino-2-(2-naphthylmethyl)cyclopropyl]phenyl]-4-phenyl-benzamide;
N-[4-trans-2-amino-2-ethyl-cyclopropyl]phenyl]-2-(2-naphthyl)acetamide;
N-[4-[trans-2-amino-2-phenyl-cyclopropyl]phenyl]benzamide;
N-[4-[trans-2-amino-2-(2-naphthylmethyl)cyclopropyl]phenyl]-2-(1-naphthyl)acetamide;
N-[3-[trans-2-amino-2-ethyl-cyclopropyl]phenyl]-2-(1-naphthyl)acetamide;
N-[4-[trans-2-amino-2-ethyl-cyclopropyl]phenyl]-4-(3-furyl)benzamide;
N-[4-[trans-2-amino-2-(2-naphthylmethyl)cyclopropyl]phenyl]-3-chloro-benzamide;
N-[3-[trans-2-amino-2-ethyl-cyclopropyl]phenyl]-3-chloro-benzamide;
N-[4-[trans-2-amino-2-(2-naphthylmethyl)cyclopropyl]phenyl]-3-phenyl-propanamide;
N-[4-[trans-2-amino-2-(2-naphthylmethyl)cyclopropyl]phenyl]-3-phenyl-benzamide;
N-[4-[trans-2-amino-2-ethyl-cyclopropyl]phenyl]-4-(2-oxooxazolidin-3-yl)benzamide;
benzyl N-[3-[(4-[trans-2-amino-2-phenyl-cyclopropyl]phenyl)carbamoyl]phenyl]carbamate;
N-[4-[trans-2-amino-2-phenyl-cyclopropyl]phenyl]naphthalene-2-carboxamide;
N-[4-[trans-2-amino-2-ethyl-cyclopropyl]-2-fluoro-phenyl]benzamide;
N-[4-[trans-2-amino-2-ethyl-cyclopropyl]-2-fluoro-phenyl]-4-phenyl-benzamide;
N-[4-[trans-2-amino-2-phenyl-cyclopropyl]phenyl]-4-morpholino-benzamide;
N-[4-[trans-2-amino-2-phenyl-cyclopropyl]phenyl]-4-phenyl-benzamide;
N-[4-[trans-2-amino-2-phenyl-cyclopropyl]phenyl]naphthalene-1-carboxamide;
N-[3-[trans-2-amino-2-ethyl-cyclopropyl]phenyl]-4-phenyl-benzamide;
N-[3-[trans-2-amino-2-ethyl-cyclopropyl]phenyl]naphthalene-2-carboxamide;
N-[3-[trans-2-amino-2-ethyl-cyclopropyl]phenyl]benzamide;
N-[4-[trans-2-amino-2-ethyl-cyclopropyl]-2-fluoro-phenyl]-2-(1-naphthyl)acetamide;
benzyl N-[4-[[4-[trans-2-amino-2-ethyl-cyclopropyl]-2-fluoro-phenyl]carbamoyl]phenyl]carbamate;
N-[4-[trans-2-amino-2-ethyl-cyclopropyl]-2-fluoro-phenyl]-4-(4-methylpiperazin-1-yl)benzamide;
N-[4-[trans-2-amino-2-ethyl-cyclopropyl]phenyl]-4-(4-methylpiperazin-1-yl)benzamide;
N-[4-[trans-2-amino-2-ethyl-cyclopropyl]phenyl]-3-(2-oxooxazolidin-3-yl)benzamide;
benzyl N-[5-[[4-[trans-2-amino-2-ethyl-cyclopropyl]phenyl]carbamoyl]-2-morpholino-phenyl]carbamate;
N-[4-[trans-2-amino-2-ethyl-cyclopropyl]phenyl]-4-(1-methyl-4-piperidyl)benzamide;
N-[4-(trans-2-amino-2-ethyl-cyclopropyl)phenyl]pyridine-4-carboxamide;
N-[4-(trans-2-amino-2-ethyl-cyclopropyl)phenyl]-4-(4-pyridyl)benzamide;
N-[4-(trans-2-amino-2-phenyl-cyclopropyl)phenyl]-3-chloro-benzamide;
N-[4-(trans-2-amino-2-phenyl-cyclopropyl)phenyl]-2-(1-naphthyl)acetamide;
N-[4-(trans-2-amino-2-phenyl-cyclopropyl)phenyl]-2-phenyl-acetamide;

N-[4-(trans-2-amino-2-phenyl-cyclopropyl)phenyl]-3-phenyl-benzamide;
N-[4-(trans-2-amino-2-phenyl-cyclopropyl)phenyl]-2-(2-naphthyl)acetamide;
N-[4-(trans-2-amino-2-phenyl-cyclopropyl)phenyl]pyridine-4-carboxamide;
N-[4-(trans-2-amino-2-phenyl-cyclopropyl]phenyl)-4-(1-methyl-4-piperidyl)benzamide;
N-[4-(trans-2-amino-2-phenyl-cyclopropyl)phenyl]-4-(4-methylpiperazin-1-yl)benzamide;
N-[4-(trans-2-amino-2-phenyl-cyclopropyl)phenyl]-3-(2-oxooxazolidin-3-yl)benzamide;
N-[4-(trans-2-amino-2-phenethyl-cyclopropyl)phenyl]pyridine-4-carboxamide;
N-[4-(trans-2-amino-2-phenethyl-cyclopropyl)phenyl]-4-phenyl-benzamide;
N-[4-trans-2-amino-2-phenethyl-cyclopropyl)phenyl]benzamide;
N-[4-(trans-2-amino-2-phenethyl-cyclopropyl)phenyl]-4-(1-methyl-4-piperidyl)benzamide;
N-[4-(trans-2-amino-2-phenethyl-cyclopropyl)phenyl]-4-(4-methylpiperazin-1-yl)benzamide;
benzyl N-[5-[[4-[trans-2-amino-2-ethyl-cyclopropyl]phenyl]carbamoyl]-2-(4-methylpiperazin-1-yl)phenyl]carbamate;
N-[4-(trans-2-amino-2-phenethyl-cyclopropyl)phenyl]-3-(2-oxooxazolidin-3-yl)benzamide;
4-[trans-2-amino-2-(2-naphthylmethyl)cyclopropyl]aniline;
N-[4-(trans-2-amino-2-ethyl-cyclopropyl)phenyl)-4-(2-hydroxyethylamino)benzamide;
benzyl N-[3-[1-[4-[2-amino-2-ethyl-cyclopropyl]phenyl]triazol-4-yl]phenyl]carbamate;
trans-1-ethyl-2-[3-(4-phenyltriazol-1-yl)phenyl]cyclopropanamine;
benzyl N-[3-[1-[4-[2-amino-2-(2-naphthylmethyl)cyclopropyl]phenyl]triazol-4-yl]phenyl]carbamate;
trans-1-(2-naphthylmethyl)-2-[4-(4-phenyltriazol-1-yl)phenyl]cyclopropanamine hydrochloride;
trans 1-ethyl-2-[2-(4-phenyltriazol-1-yl)phenyl]cyclopropanamine;
trans-1-benzyl-2-[4-(4-phenyltriazol-1-yl)phenyl]cyclopropanamine;
N-[4-[(1S,2R)-2-amino-2-ethyl-cyclopropyl]phenyl]-4-phenyl-benzamide;
N-[4-[(1R,2S)-2-amino-2-ethyl-cyclopropyl]phenyl]-4-phenyl-benzamide;
trans 1-benzyl-2-(3-methoxyphenyl)cyclopropanamine;
1-[3-[(trans-2-amino-2-ethyl-cyclopropyl)phenyl]-3-phenyl-imidazolidin-2-one;
trans-1-ethyl-2-[4-(4-phenyltriazol-1-yl)phenyl]cyclopropanamine;
trans 1-[(benzylamino)methyl]-2-phenyl-cyclopropanamine;
trans 1-[(cyclopropylamino)methyl]-2-phenyl-cyclopropanamine;
trans 1-[(4-methylpiperazin-1-yl)methyl]-2-phenyl-cyclopropanamine;
5-[[[trans-1-methyl-2-phenyl-cyclopropyl]amino]methyl]pyrimidin-2-amine;
trans-N-[(2-methoxy-3-pyridyl)methyl]-1-methyl-2-phenyl-cyclopropanamine;
trans-N-(2,3-dihydro-1,4-benzodioxin-6-ylmethyl)-1-methyl-2-phenyl-cyclopropanamine;
2-[[trans-1,2-diphenylcyclopropyl]amino]-1-(4-methylpiperazin-1-yl)ethanone;
1-(4-methylpiperazin-1-yl)-2-[[trans-1-(2-naphthylmethyl)-2-phenyl-cyclopropyl]amino]ethanone;
2-[[(1R,2S)-1-methyl-2-phenyl-cyclopropyl]amino]-1-(4-methylpiperazin-1-yl)ethanone;
2-[[(1R,2R)-1-methyl-2-phenyl-cyclopropyl]amino]-1-(4-methylpiperazin-1-yl)ethanone;
2-[[trans-1-methyl-2-phenyl-cyclopropyl]amino]-1-(4-methylpiperazin-1-yl)ethanone;
2-[[cis-1-methyl-2-phenyl-cyclopropyl]amino]-1-(4-methylpiperazin-1-yl)ethanone;
2-[[trans-1-ethyl-2-phenyl-cyclopropyl]amino]-1-(1-piperidyl)ethanone; trans-1-ethyl-2-phenyl-N-[2-(1-piperidyl)ethyl]cyclopropanamine;
5-[[[trans-1-methyl-2-phenyl-cyclopropyl]amino]methyl]-1,3,4-oxadiazol-2-amine;
trans-1-(4-nitrophenyl)-2-phenyl-cyclopropanamine;
trans-2-(4-chlorophenyl)-1-phenyl-cyclopropanamine;
trans-2-(4-bromophenyl)-1-phenyl-cyclopropanamine;
N-[4-(trans-1-amino-2-phenyl-cyclopropyl)phenyl]acetamide;
or stereoisomers or pharmaceutically acceptable salts thereof.

In a further embodiment, the invention provides compounds of general formula (I) as defined above, provided that when A is an unsubstituted phenyl or imidazolyl, $R^1$ is methyl, then $R^2$ cannot be hydrogen or methyl;

that when A is an unsubstituted phenyl, $R^1$ is n-propyl, phenyl, 2-fluoro- or 4-fluoro-phenyl, 3-chloro-, 4-chloro- or 2,4-dichlorophenyl, 2-methoxy-, 4-methoxy- or 3,4-dimethoxy-phenyl, 1-naphthyl, benzyl or 4-chlorobenzyl, then $R^2$ cannot be hydrogen;

that when A is 4-chloro- or 2,4 dichlorophenyl, 4-fluoro- or 2,4-difluorophenyl, 2-chloro-4-fluorophenyl, 2-fluoro-4-chlorophenyl, 4-trifluoromethylphenyl, 4-trifluoromethoxyphenyl or 4-(4-chlorophenyl)phenyl, $R^1$ is methyl or ethyl;

then $R^2$ cannot be hydrogen; and with the exclusion of the following compounds:
2-[2-chloro-4-(4-chlorophenyl)phenyl]-1-methyl-cyclopropanamine;
2-(4-chlorophenyl)-1-phenyl-cyclopropanamine;
2-(4-methoxyphenyl)-1-phenyl-cyclopropanamine;
[1-(benzylamino)-2-phenyl-cyclopropyl]methanol;
or stereoisomers or pharmaceutically acceptable salts thereof.

In a preferred embodiment, the invention provides compounds of general formula (I) as defined above, provided that when A is phenyl substituted by 4-methoxy, 4-trifluoromethyl, 4-trifluoromethoxy, 4-(4-chlorophenyl) or by one or two halogens selected from fluoro or chloro; and $R^1$ is methyl; ethyl; n-propyl; phenyl, optionally substituted by one or two fluoro, chloro or methoxy; 1-naphthyl; or benzyl, then $R^2$ cannot be hydrogen; and with the exclusion of the following compounds:
2-[2-chloro-4-(4-chlorophenyl)phenyl]-1-methyl-cyclopropanamine;
[1-(benzylamino)-2-phenyl-cyclopropyl]methanol;
or stereoisomers or pharmaceutically acceptable salts thereof.

In a preferred embodiment A is phenyl substituted by R-L-, L is —$(CH_2)_p$(CO)$NR^3$— and $R^2$ is hydrogen.

In a further preferred embodiment $R^1$ is ethyl substituted by phenyl.

In another preferred embodiment $R^2$ is $C_1$-$C_6$ alkyl, optionally substituted by aryl, heteroaryl, or by heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy and $NH_2$; or —$CH_2(CO)NR^6R^7$.

Particularly preferred compounds of general formula (I) include:
(1S,2R)-1-ethyl-2-phenyl-cyclopropanamine;
(1R,2S)-1-ethyl-2-phenyl-cyclopropanamine;
trans-1-isopropyl-2-phenyl-cyclopropanamine;
trans-1-phenethyl-2-phenyl-cyclopropanamine;
trans-2-(4-bromophenyl)-1-ethyl-cyclopropanamine;
trans-1-benzyl-2-(4-bromophenyl)cyclopropanamine;
trans-1-ethyl-2-(6-quinolyl)cyclopropanamine;
1-(2-naphthylmethyl)-2-phenyl-cyclopropanamine;
trans-1-ethyl-2-[3-(trifluoromethyl)phenyl]cyclopropanamine;
trans-1-ethyl-2-(3-fluorophenyl)cyclopropanamine;
trans-1-ethyl-2-(3-chlorophenyl)-cyclopropanamine;
trans-1-ethyl-2-(3-bromophenyl)-cyclopropanamine;
trans-1-ethyl-2-[3-methoxyphenyl]cyclopropanamine;
trans-1-ethyl-2-(2-fluorophenyl)cyclopropanamine;
trans-1-ethyl-2-(2-chlorophenyl)-cyclopropanamine;
trans-1-ethyl-2-(2-bromophenyl)-cyclopropanamine;
trans-1-(1-naphthylmethyl)-2-phenyl-cyclopropanamine;
trans-2-(4-bromophenyl)-1-(2-naphthylmethyl)cyclopropanamine;
trans-N-[4-[2-amino-2-ethyl-cyclopropyl]phenyl]naphthalene-2-carboxamide;
N-[2-[(trans)-2-amino-2-ethyl-cyclopropyl]phenyl]benzamide;
benzyl N-[3-[[2-[(trans)-2-amino-2-ethyl-cyclopropyl]phenyl]carbamoyl]phenyl]carbamate;
benzyl N-[3-[[3-[(trans)-2-amino-2-ethyl-cyclopropyl]phenyl]carbamoyl]phenyl]carbamate;
N-[4-[(trans)-2-amino-2-ethyl-cyclopropyl]phenyl]-3-chloro-benzamide
N-[4-[(trans)-2-amino-2-ethyl-cyclopropyl]phenyl]-3-phenyl-benzamide;
N-[4-[(trans)-2-amino-2-ethyl-cyclopropyl]phenyl]-4-phenyl-benzamide
benzyl N-[3-[[4-[(trans)-2-amino-2-ethyl-cyclopropyl]phenyl]carbamoyl]phenyl]carbamate;
benzyl N-[4-[[4-[(trans)-2-amino-2-ethyl-cyclopropyl]phenyl]carbamoyl]phenyl]carbamate;
N-[4-[(trans)-2-amino-2-ethyl-cyclopropyl]phenyl]-2-phenyl-acetamide;
N-[4-[(trans)-2-amino-2-ethyl-cyclopropyl]phenyl]-3-phenyl-propanamide;
2-(4-benzyloxyphenyl)-trans-1-ethyl-cyclopropanamine;
N-[4-[(2-amino-trans-2-ethyl-cyclopropyl]phenyl]benzenesulfonamide;
trans-1-benzyl-2-(4-benzyloxyphenyl)cyclopropanamine;
N-[4-[trans-2-amino-2-(2-naphthylmethyl)cyclopropyl]phenyl]benzamide;
Benzyl-N-3-[[4-[(trans)-2-amino-2-(2-naphthylmethyl)cyclopropyl]phenyl]carbamoyl]phenyl]carbamate;
N-[4-[(trans)-2-amino-2-(2-naphthylmethyl)cyclopropyl]phenyl]-2-phenyl-acetamide;
N-[4-[trans-2-amino-2-ethyl-cyclopropyl]phenyl]benzamide;
trans-4-(2-amino-2-ethyl-cyclopropyl)aniline;
trans-2-(3-azidophenyl)-1-ethyl-cyclopropanamine;
1-amino-(trans)-2-phenyl-cyclopropyl]methanol;
1-amino-(cis)-2-phenyl-cyclopropyl]methanol;
(1R,2S)-1-ethyl-N-[(2-methoxyphenyl)methyl]-2-phenyl-cyclopropanamine;
(1R,2S)-1-ethyl-N-[(2-methoxy-1-naphthyl)methyl]-2-phenyl-cyclopropanamine;
2-[[(1S,2R)-1-methyl-2-phenyl-cyclopropyl]amino]-1-(4-methylpiperazin-1-yl)ethanone;
2-[[(1S,2S)-1-methyl-2-phenyl-cyclopropyl]amino]-1-(4-methylpiperazin-1-yl)ethanone;
1-[(3S)-3-aminopyrrolidin-1-yl]-2-[[(1S,2R)-1-methyl-2-phenyl-cyclopropyl]amino]ethanone;
trans-2-[[(1-ethyl-2-phenyl-cyclopropyl]amino]-1-(4-methylpiperazin-1-yl)ethanone;
cis-2-[[(1-ethyl-2-phenyl-cyclopropyl]amino]-1-(4-methylpiperazin-1-yl)ethanone;
trans-1-ethyl-N-methyl-2-phenyl-cyclopropanamine;
cis-1-ethyl-N-methyl-2-phenyl-cyclopropanamine;
trans-1-ethyl-N-ethyl-2-phenyl-cyclopropanamine;
cis-1-ethyl-N-ethyl-2-phenyl-cyclopropanamine;
trans-2-[[1-ethyl-2-phenyl-cyclopropyl]amino]acetamide;
trans-N-benzyl-1-ethyl-2-phenyl-cyclopropanamine;
trans-N-[(3,4-dimethoxyphenyl)methyl]-1-ethyl-2-phenyl-cyclopropanamine;
trans-N-[(4,7-dimethoxy-1-naphthyl)methyl]-1-ethyl-2-phenyl-cyclopropanamine;
trans-N-[(2-chloro-3-pyridyl)methyl]-1-ethyl-2-phenyl-cyclopropanamine;
trans-N-[(2,2-dimethylchroman-6-yl)methyl]-1-ethyl-2-phenyl-cyclopropanamine;
trans-1-ethyl-2-phenyl-cyclopropanamine;
trans-2-(4-bromo-3-fluoro-phenyl)-1-ethyl-cyclopropanamine;
trans 2-(3-bromophenyl)-1-phenethyl-cyclopropanamine;
trans-2-(4-fluorophenyl)-1-(2-naphthylmethyl)cyclopropanamine;
trans-2-(4-chlorophenyl)-1-(2-naphthylmethyl)cyclopropanamine;
trans-2-(3-chlorophenyl)-1-(2-naphthylmethyl)cyclopropanamine;
trans-2-(3-bromophenyl)-1-(2-naphthylmethyl)cyclopropanamine;
trans-2-(4-chlorophenyl)-1-phenethyl-cyclopropanamine;
trans-2-(4-fluorophenyl)-1-phenethyl-cyclopropanamine;
trans-1-benzyl-2-(4-fluorophenyl)cyclopropanamine;
trans-1-benzyl-2-(4-chlorophenyl)cyclopropanamine;
trans 2-(4-bromophenyl)-1-phenethyl-cyclopropanamine;
cis-1-ethyl-2-phenyl-cyclopropanamine;
N-[4-(trans-2-amino-2-ethyl-cyclopropyl)phenyl]-3-[(1-methyl-4-piperidyl)amino]-4-phenyl-benzamide;
2-(4-benzyloxyphenyl)-1-(2-naphthylmethyl)cyclopropanamine;
N-[4-trans-[2-amino-2-ethyl-cyclopropyl]phenyl]-2-(1-naphthyl)acetamide;
N-[4-trans-[2-amino-2-ethyl-cyclopropyl]phenyl]-2-(4-nitrophenyl)acetamide;
benzyl N-[4-[[4-[trans-2-amino-2-(2-naphthylmethyl)cyclopropyl]phenyl]carbamoyl]phenyl]carbamate;
N-[4-(trans-2-amino-2-ethyl-cyclopropyl)phenyl]naphthalene-1-carboxamide;
N-[4-[trans-2-amino-2-(2-naphthylmethyl)cyclopropyl]phenyl]naphthalene-2-carboxamide;
N-[4-[trans-2-amino-2-(2-naphthylmethyl)cyclopropyl]phenyl]-4-phenyl-benzamide;
N-[4-trans-2-amino-2-ethyl-cyclopropyl]phenyl]-2-(2-naphthyl)acetamide;
N-[4-[trans-2-amino-2-phenyl-cyclopropyl]phenyl]benzamide;
N-[4-[trans-2-amino-2-(2-naphthylmethyl)cyclopropyl]phenyl]-2-(1-naphthyl)acetamide;
N-[3-[trans-2-amino-2-ethyl-cyclopropyl]phenyl]-2-(1-naphthyl)acetamide;

N-[4-[trans-2-amino-2-ethyl-cyclopropyl]phenyl]-4-(3-furyl)benzamide;
N-[4-[trans-2-amino-2-(2-naphthylmethyl)cyclopropyl]phenyl]-3-chloro-benzamide;
N-[3-[trans-2-amino-2-ethyl-cyclopropyl]phenyl]-3-chloro-benzamide;
N-[4-[trans-2-amino-2-(2-naphthylmethyl)cyclopropyl]phenyl]-3-phenyl-propanamide;
N-[4-[trans-2-amino-2-(2-naphthylmethyl)cyclopropyl]phenyl]-3-phenyl-benzamide;
N-[4-[trans-2-amino-2-ethyl-cyclopropyl]phenyl]-4-(2-oxooxazolidin-3-yl)benzamide;
benzyl N-[3-[(4-[trans-2-amino-2-phenyl-cyclopropyl]phenyl)carbamoyl]phenyl]carbamate;
N-[4-[trans-2-amino-2-phenyl-cyclopropyl]phenyl]naphthalene-2-carboxamide;
N-[4-[trans-2-amino-2-ethyl-cyclopropyl]-2-fluoro-phenyl]benzamide;
N-[4-[trans-2-amino-2-ethyl-cyclopropyl]-2-fluoro-phenyl]-4-phenyl-benzamide;
N-[4-[trans-2-amino-2-ethyl-cyclopropyl]phenyl]-4-morpholino-benzamide;
N-[4-[trans-2-amino-2-phenyl-cyclopropyl]phenyl]-4-phenyl-benzamide;
N-[4-[trans-2-amino-2-phenyl-cyclopropyl]phenyl]naphthalene-1-carboxamide;
N-[3-[trans-2-amino-2-ethyl-cyclopropyl]phenyl]-4-phenyl-benzamide;
N-[3-[trans-2-amino-2-ethyl-cyclopropyl]phenyl]naphthalene-2-carboxamide;
N-[3-[trans-2-amino-2-ethyl-cyclopropyl]phenyl]benzamide;
N-[4-[trans-2-amino-2-ethyl-cyclopropyl]-2-fluoro-phenyl]-2-(1-naphthyl)acetamide;
benzyl N-[4-[[4-[trans-2-amino-2-ethyl-cyclopropyl]-2-fluoro-phenyl]carbamoyl]phenyl]carbamate;
N-[4-[trans-2-amino-2-ethyl-cyclopropyl]-2-fluoro-phenyl]-4-(4-methylpiperazin-1-yl)benzamide;
N-[4-[trans-2-amino-2-ethyl-cyclopropyl]phenyl]-4-(4-methylpiperazin-1-yl)benzamide;
N-[4-[trans-2-amino-2-ethyl-cyclopropyl]phenyl]-3-(2-oxooxazolidin-3-yl)benzamide;
benzyl N-[5-[[4-[trans-2-amino-2-ethyl-cyclopropyl]phenyl]carbamoyl]-2-morpholino-phenyl]carbamate;
N-[4-[trans-2-amino-2-ethyl-cyclopropyl]phenyl]-4-(1-methyl-4-piperidyl)benzamide;
N-[4-(trans-2-amino-2-ethyl-cyclopropyl)phenyl]pyridine-4-carboxamide;
N-[4-(trans-2-amino-2-ethyl-cyclopropyl]phenyl)-4-(4-pyridyl)benzamide;
N-[4-(trans-2-amino-2-phenyl-cyclopropyl]phenyl]-3-chloro-benzamide;
N-[4-(trans-2-amino-2-phenyl-cyclopropyl)phenyl]-2-(1-naphthyl)acetamide;
N-[4-(trans-2-amino-2-phenyl-cyclopropyl)phenyl]-2-phenyl-acetamide;
N-[4-(trans-2-amino-2-phenyl-cyclopropyl)phenyl]-3-phenyl-benzamide;
N-[4-(trans-2-amino-2-phenyl-cyclopropyl)phenyl]-2-(2-naphthyl)acetamide;
N-[4-(trans-2-amino-2-phenyl-cyclopropyl)phenyl]pyridine-4-carboxamide;
N-[4-(trans-2-amino-2-phenyl-cyclopropyl]phenyl)-4-(1-methyl-4-piperidyl)benzamide;
N-[4-(trans-2-amino-2-phenyl-cyclopropyl)phenyl]-4-(4-methylpiperazin-1-yl)benzamide;
N-[4-(trans-2-amino-2-phenyl-cyclopropyl)phenyl]-3-(2-oxooxazolidin-3-yl)benzamide;
N-[4-(trans-2-amino-2-phenethyl-cyclopropyl)phenyl]pyridine-4-carboxamide;
N-[4-(trans-2-amino-2-phenethyl-cyclopropyl)phenyl]-4-phenyl-benzamide;
N-[4-trans-2-amino-2-phenethyl-cyclopropyl)phenyl]benzamide;
N-[4-(trans-2-amino-2-phenethyl-cyclopropyl)phenyl]-4-(1-methyl-4-piperidyl)benzamide;
N-[4-(trans-2-amino-2-phenethyl-cyclopropyl)phenyl]-4-(4-methyl piperazin-1-yl)benzamide;
benzyl N-[5-[[4-[trans-2-amino-2-ethyl-cyclopropyl]phenyl]carbamoyl]-2-(4-methylpiperazin-1-yl)phenyl]carbamate;
N-[4-(trans-2-amino-2-phenethyl-cyclopropyl)phenyl]-3-(2-oxooxazolidin-3-yl)benzamide;
4-[trans-2-amino-2-(2-naphthylmethyl)cyclopropyl]aniline;
N-[4-(trans-2-amino-2-ethyl-cyclopropyl]phenyl)-4-(2-hydroxyethylamino)benzamide;
benzyl N-[3-[1-[4-[2-amino-2-ethyl-cyclopropyl]phenyl]triazol-4-yl]phenyl]carbamate;
trans-1-ethyl-2-[3-(4-phenyltriazol-1-yl)phenyl]cyclopropanamine;
benzyl N-[3-[1-[4-[2-amino-2-(2-naphthylmethyl)cyclopropyl]phenyl]triazol-4-yl]phenyl]carbamate;
trans-1-(2-naphthylmethyl)-2-[4-(4-phenyltriazol-1-yl)phenyl]cyclopropanamine;
trans 1-ethyl-2-[2-(4-phenyltriazol-1-yl)phenyl]cyclopropanamine;
trans-1-benzyl-2-[4-(4-phenyltriazol-1-yl)phenyl]cyclopropanamine;
N-[4-[(1S,2R)-2-amino-2-ethyl-cyclopropyl]phenyl]-4-phenyl-benzamide;
N-[4-[(1R,2S)-2-amino-2-ethyl-cyclopropyl]phenyl]-4-phenyl-benzamide;
trans 1-benzyl-2-(3-methoxyphenyl)cyclopropanamine;
1-[3-[(trans-2-amino-2-ethyl-cyclopropyl]phenyl]-3-phenyl-imidazolidin-2-one;
trans-1-ethyl-2-[4-(4-phenyltriazol-1-yl)phenyl]cyclopropanamine;
trans 1-[(benzylamino)methyl]-2-phenyl-cyclopropanamine;
trans 1-[(cyclopropylamino)methyl]-2-phenyl-cyclopropanamine;
trans 1-[(4-methylpiperazin-1-yl)methyl]-2-phenyl-cyclopropanamine;
5-[[[trans-1-methyl-2-phenyl-cyclopropyl]amino]methyl]pyrimidin-2-amine;
trans-N-[(2-methoxy-3-pyridyl)methyl]-1-methyl-2-phenyl-cyclopropanamine;
trans-N-(2,3-dihydro-1,4-benzodioxin-6-ylmethyl)-1-methyl-2-phenyl-cyclopropanamine;
2-[[trans-1,2-diphenylcyclopropyl]amino]-1-(4-methylpiperazin-1-yl)ethanone;
1-(4-methylpiperazin-1-yl)-2-[[trans-1-(2-naphthylmethyl)-2-phenyl -cyclopropyl]amino]ethanone;
2-[[(1R,2S)-1-methyl-2-phenyl-cyclopropyl]amino]-1-(4-methylpiperazin-1-yl)ethanone;
2-[[(1R,2R)-1-methyl-2-phenyl-cyclopropyl]amino]-1-(4-methylpiperazin-1-yl)ethanone;
2-[[trans-1-methyl-2-phenyl-cyclopropyl]amino]-1-(4-methylpiperazin-1-yl)ethanone;
2-[[cis-1-methyl-2-phenyl-cyclopropyl]amino]-1-(4-methylpiperazin-1-yl)ethanone;
2-[[trans-1-ethyl-2-phenyl-cyclopropyl]amino]-1-(1-piperidyl)ethanone;

trans-1-ethyl-2-phenyl-N-[2-(1-piperidyl)ethyl]cyclopropanamine;
5-[[[trans-1-methyl-2-phenyl-cyclopropyl]amino]methyl]-1,3,4-oxadiazol-2-amine;
trans-1-(4-nitrophenyl)-2-phenyl-cyclopropanamine;
trans-2-(4-bromophenyl)-1-phenyl-cyclopropanamine;
N-[4-(trans-1-amino-2-phenyl-cyclopropyl)phenyl]acetamide;
or stereoisomers or pharmaceutically acceptable salts thereof.

In the instant invention, "aryl" represents a mono or bicyclic aromatic ring system of, respectively, 6, 9 or 10 atoms, examples of such an aryl are phenyl, indenyl, indanyl and naphthyl and tetrahydronaphthalenyl.

"Heteroaryl" represents a mono or bicyclic heteroaromatic ring system of, respectively, 5 to 10 members, which contains one, two, three or four heteroatoms selected from nitrogen, oxygen or sulphur and one to nine carbon atoms. Examples of said heteroaryls include, but are not limited to: pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl. "Heterocyclyl" represents a mono or bicyclic saturated or partially saturated non-aromatic ring system of, respectively, 4 to 12 members, which contains one, two, or three heteroatoms selected from nitrogen, oxygen, and sulphur and three to eleven carbon atoms. Examples of such heterocycles include, but are not limited to: pyrrolidinyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azepinyl, and diazapinyl. "Heterocyclyl substituted by oxo" represents a mono or bicyclic saturated or partially saturated non-aromatic ring system of, respectively, 4 to 12 members, which contains one, two, or three heteroatoms selected from nitrogen, oxygen, and sulphur, and which is substituted by an oxo group. Examples include, but are not limited to 2-oxooxazolidin-3-yl.

"Heterocyclylamino" represents a mono or bicyclic saturated or partially saturated non-aromatic ring system of, respectively, 4 to 12 members, which contains one, two, or three heteroatoms selected from nitrogen, oxygen, and sulphur, substituted with to NH—. Examples include, but are not limited to 4-piperidylamino.

The "$C_4$-$C_{10}$-heterocyclic ring" represents a mono or bicyclic saturated or partially saturated non-aromatic ring system of, respectively, 4 to 10 members, which contains one nitrogen and optionally one or more heteroatoms selected from nitrogen, oxygen, and sulphur. Examples of such heterocycles include, but are not limited to: pyrrolidinyl, piperidinyl, piperazinyl, morpholinyl, thiomorpholinyl, tetrahydroquinolinyl, tetrahydroisoquinolinyl, azepinyl, and diazapinyl.

The term "halogen" refers to fluoro, chloro, bromo, or iodo.

The term "$C_1$-$C_6$ alkyl" refers to a straight or branched hydrocarbon chain radical, consisting solely of carbon and hydrogen atoms, having from one to six carbon atoms. The term "$C_2$-$C_6$ alkyl" refers to a straight or branched hydrocarbon chain radical, consisting solely of carbon and hydrogen atoms, having from two to six carbon atoms. Suitable examples of $C_1$-$C_6$ alkyl or $C_2$-$C_6$ alkyl include ethyl, n-propyl, ispropyl, butyl, tert-butyl, pentyl, and hexyl. A further suitable example for $C_1$-$C_6$ alkyl is methyl.

The term "$C_{3-6}$ cycloalkyl" refers to a saturated monocyclic hydrocarbon ring system having three to six carbon atoms. Suitable examples of $C_{3-6}$-cycloalkyl groups include cyclopropyl, cyclobutyl, cyclopentyl, and cyclohexyl.

The term "$C_1$-$C_6$ alkoxy" refers to a straight or branched O—$C_1$-$C_6$ alkyl, where alkyl is as defined herein. The "$C_1$-$C_6$ alkoxy" group is preferably a linear or branched $C_1$-$C_4$ alkoxy group, more preferably a $C_1$-$C_2$ alkoxy group.

The term "$C_1$-$C_6$ haloalkyl" refers to a straight or branched hydrocarbon chain radical, which is substituted by one or more halogen atoms and having from one to six carbon atoms. The "$C_1$-$C_6$ haloalkyl" group is preferably a linear or branched $C_1$-$C_4$ haloalkyl group, more preferably a $C_1$-$C_2$ haloalkyl group, being in particular $CF_3$.

The term "$C_1$-$C_6$ haloalkoxy" refers to a straight or branched O—$C_1$-$C_6$ haloalkyl, where haloalkyl is as defined herein. The "$C_1$-$C_6$ haloalkoxy" group is preferably a linear or branched $C_1$-$C_4$ haloalkoxy group, more preferably a $C_1$-$C_2$ haloalkoxy group, being in particular $OCF_3$, $OCHF_2$ or $OCH_2F$.

The term "$C_1$-$C_6$ alkylamino" refers to a straight or branched —NH—$C_1$-$C_6$ alkyl, where $C_1$-$C_6$ alkyl is as defined herein.

The term "$C_1$-$C_6$ alkylene" refers to a $C_1$-$C_6$ alkyl group, as defined above, wherein one of the alkyl group's hydrogen atoms has been replaced with a bond and having one to six carbon atoms.

The term "$C_2$-$C_6$ alkenylene" refers to a $C_2$-$C_6$ alkenyl group, wherein one of the alkenyl group's hydrogen atoms has been replaced with a bond and having two to six carbon atoms. The term "$C_2$-$C_6$ alkenyl" refers to a straight or branched hydrocarbon chain radical, consisting solely of carbon and hydrogen atoms, having from two to six carbon atoms and containing at least one carbon-carbon double bond.

Pharmaceutically acceptable salts comprise conventional non-toxic salts obtained by salification of a compound of formula (I) with inorganic acids (e.g. hydrochloric, hydrobromide, sulphuric, or phosphoric acids), or with organic acids (e.g. acetic, propionic, succinic, benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this invention and these form a further aspect of the invention. The invention includes within its scope all possible stoichiometric and non-stoichiometric forms of the salts of the compounds of formula (I).

In addition, the compounds of formula (I) may exist in unsolvated as well as in solvated forms with pharmaceutically acceptable solvents such as water, EtOH and the like.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted.

Likewise, it is understood that compounds of the invention may exist in tautomeric forms other than that shown in the formula and these are also included within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as 3H or $^{14}$C is incorporated, are useful in drug and/or substrate tissue distribution studies. Tritiated $^3$H, and carbon-14 $^{14}$C, isotopes are particularly preferred for their ease of preparation and detectability. Further, substitution with isotopes such as deuterium $^2$H, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the examples hereafter using appropriate isotopic variations of suitable reagents.

The invention also provides pharmaceutical compositions comprising one or more compounds of this invention and one or more pharmaceutically acceptable excipient and/or diluent. The pharmaceutical compositions containing the active ingredient may be in the form of tablets, capsules, oral preparations, powders, granules, pills, injectable or infusible liquid, solutions, suspensions, emulsions, suppositories, ointments, creams, lotions, gels, pastes, transdermal delivery devices.

Compounds of general formula (I), wherein R$^2$ is hydrogen, may be prepared according to Scheme A:

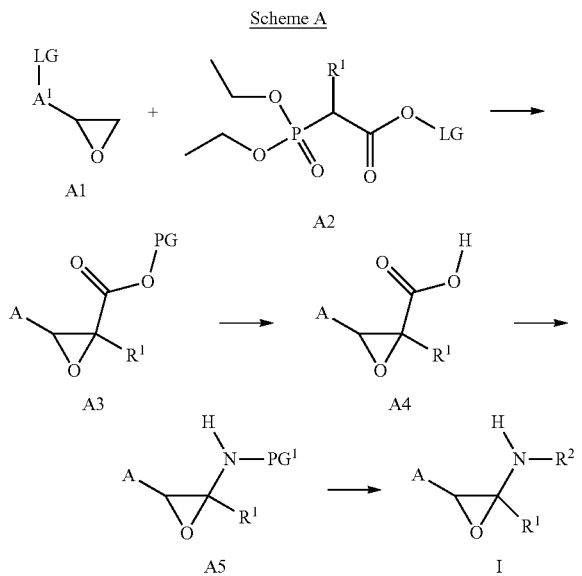

wherein A and R$^1$ are as defined above for formula (I), R$^2$ is hydrogen, and PG and PG$^1$ are protecting groups chosen among those known in the art, for example methyl, ethyl etc.

for PG and carboxybenzyl, tert-butyloxycarbonyl (BOC), 9-fluorenylmethyloxycarbonyl, etc. for PG$^1$.

Compounds of formula A1 are known compounds or may be prepared by known methods (as for example described in J. Med. Chem. 1991, 34, 2638-2643 or Chem. Rev. 1997, 97, 2341-2372). Compounds of formula A2 are known compounds or may be prepared by known methods, e.g. by reaction of ethyl 2-diethoxyphosphorylacetate with R$^1$—W in presence of a suitable base, such as NaH, in a suitable solvent, such as 1,2-dimethoxyethane, at temperatures ranging from about 0 to 60° C., wherein R$^1$ is defined as above and W is a halogen atom, e.g. chloride or bromide.

A compound of formula A3 may conventionally be prepared by reaction of a compound of formula A1 with the phosphonate of formula A2 in the presence of a suitable base (for example butyl lithium) in a suitable solvent (for example DME) at a temperature ranging from approximately room temperature to the boiling point of the solvent, preferably under microwave irradiation.

Particularly compounds of general formula (I), wherein R$^2$ is hydrogen, and A is aryl or heteroaryl substituted by R-L, and wherein R is as defined above for formula (I) and L is —(CH$_2$)$_p$(CO)NH—; —(CH$_2$)$_m$X—; —(CH$_2$)$_o$(SO$_2$)NH— or —(CH$_2$)$_p$(CO)NR$^3$—; and wherein m, o, p, R, R$^3$, and X are as defined above for formula (I), may be prepared according to Scheme A1:

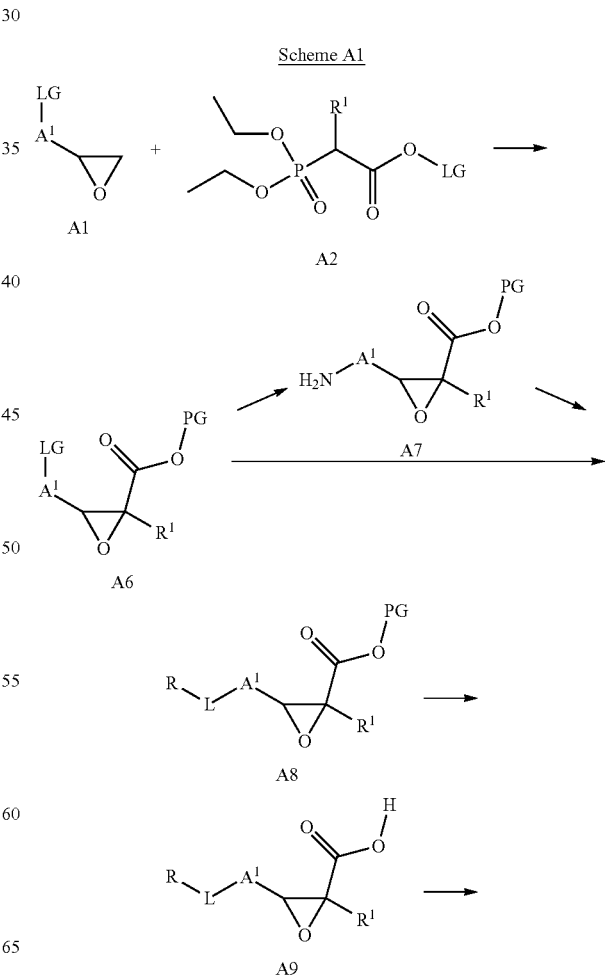

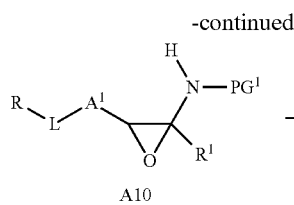

wherein $R^1$ is as defined for formula (I), PG and $PG^1$ are as defined above, $A^1$ is aryl or heteroaryl, and LG is a leaving group for example Br, I, or Cl.

A compound of formula A6, in the specific case corresponds to a compound of formula A3, wherein A is aryl or heteroaryl substituted by LG. A compound of formula A7, may be prepared according to the Ullmann type reaction by reacting a compound of formula A6 with CuI, $NaN_3$ and 2-aminoethanol in a suitable solvent, for example in dimethylacetamide, at temperature ranging from room temperature to the boiling point of the solvent.

A compound of formula A8, wherein L is $—(CH_2)_p(CO)NH—$, may be prepared by reaction of a compound of formula A7 with $R—(CH_2)_p(CO)—W$, wherein R and W are defined as above, in the presence of a suitable base, such as triethylamine, in an appropriate solvent, for example in tetrahydrofuran, at temperature ranging from 0° C. to the boiling point of the solvent.

Alternatively, a compound of formula A8, wherein L is $—(CH_2)_mX—$, $—(CH_2)_o(SO_2)NH—$, or, $—(CH_2)_p(CO)NR^3$ may be prepared by reaction of A6 with $R—(CH_2)_p(CO)NHR^3$, $R—(CH_2)_o(SO_2)NH_2$, or $R—(CH_2)_mXH$, and CuI, in the presence of a suitable base, such as NN-dimethylethane-1,2-diamine or N,N'-dimethylcyclohexane-1,2-diamine, 8-hydroxychinolin in an appropriate solvent, for example in dioxan, at temperature ranging from 0° C. to the boiling point of the solvent.

A compound of formula A3 may be deprotected to obtain a compound of formula A4 and a compound of formula A8 may be deprotected to obtain a compound of formula A9 according to known methods, e.g. by treatment of an ethyl ester with LiOH, NaOH or KOH in a suitable solvent, for example in an ethanol/water, methanol/water, or in a dioxane/ethanol/water mixture. The hydrolysis of the ethyl ester may be carried out at a temperature ranging from 0° C. to the boiling point of the solvent.

The carboxylic acid of formula A4 or of formula A9 may be converted to obtain the protected amine of formula A5 or of formula A10, respectively, by reaction with a suitable azide, such as diphenyl phosphorazidate, in the presence of a suitable base (e.g. triethylamine) and in a suitable solvent such as tert-butanol at a temperature ranging from room temperature to the boiling point of the solvent.

A compound of formula A5 or of formula A10 may be deprotected to obtain a compound of formula (I) according to known methods, e.g. by treatment of a BOC derivative with HCl or TFA (trifluoroacetic acid) in a suitable solvent such as dioxane, $Et_2O$, or dichloromethane, at a temperature ranging from 0° C. to room temperature.

Alternatively, compounds of general formula (I), wherein $R^1$ is $CH_2OH$ and $R^2$ is hydrogen, may be prepared according to Scheme B:

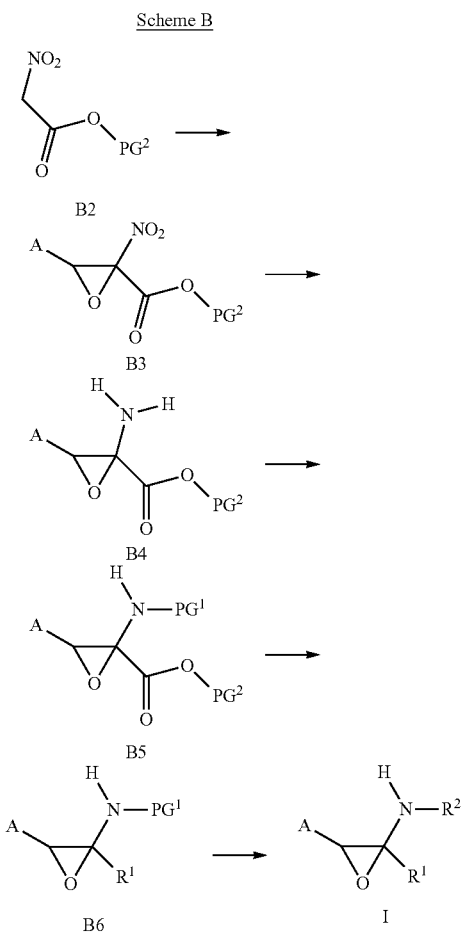

Scheme B wherein A is as defined above for formula (I), and $PG^1$ is as defined above, and $PG^2$ is a protecting group chosen among those known in the art, for example ethyl etc.

Compounds of formula B1 and of formula B2 are known compounds or may be prepared by known methods.

A compound of formula B3 may be prepared via reaction of a compound of formula B1 with a compound of formula B2 in the presence of a catalyst (for example rhodium acetate) and (diacetoxyiodo)benzene at temperatures around room temperature.

An amine of formula B4 may be prepared via reduction of a compound of formula B3, with a suitable reducing agent eg. with zinc dust and hydrogen chloride in a suitable solvent (for example i-PrOH) at room temperature. The amino group of a compound of formula B4, may be protected to obtain a compound of formula B5 according to known methods, eg. with tert-butoxycarbonyl-tert-butyl carbonate in the presence of a suitable base (e.g. N,N-diisopropylethylamine) and in a suitable solvent (for example $CH_2Cl_2$).

A compound of formula B6 may be prepared via reduction of the ester of formula B5 with a suitable reducing agent (e.g. $LAIH_4$) in suitable solvent (for example THF) at a temperature ranging from 0° C. to room temperature.

Deprotection of a compound of formula B6 to obtain a compound of formula (I) may be achieved by known methods, for example in the case of the BOC protecting group with HCl or TFA (trifluoroacetic acid) in a suitable solvent such as dioxane, $Et_2O$, or dichloromethane, at a temperature ranging from 0° C. to room temperature. Compounds of general formula (I), wherein $R^2$ is $C_1$-$C_6$ alkyl, optionally substituted by aryl, heteroaryl, or by heterocyclyl and wherein the aryl or heteraryl may be optionally substituted by one or more substituents independently selected from halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$, with $R^6$ and $R^7$ as defined for formula (I), may be prepared according to Scheme C:

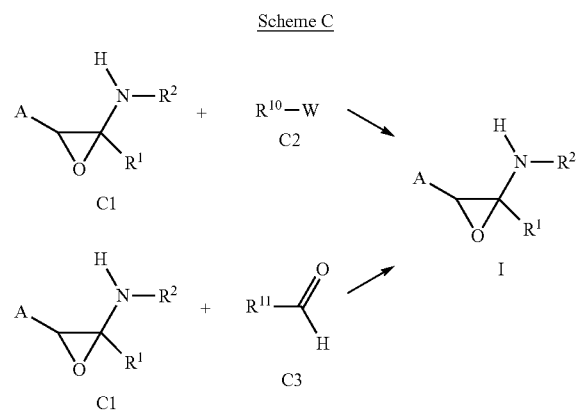

wherein A and $R^1$ are as defined above for fomula (I), via reaction of a compound of formula C1 with a compound of formula $R^{10}$—W (C2), wherein $R^{10}$ is $C_1$-$C_6$ alkyl, optionally substituted by aryl, heteroaryl, or by heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$, with $R^6$, $R^7$, and W is as defined above, in a suitable solvent (e.g. DMF) in the presence of a suitable base (e.g. NaH). The reaction may be carried out at a temperature between 0° C. to the boiling point of the solvent. In the case it is necessary to protect the cyclopropylamino group, said chemical group may be protected and deprotected according to known methods (e.g. a protecting group is a tert-butyloxycarbonyl group).

Alternatively, compounds of general formula (I), wherein $R^2$ is $C_1$-$C_6$ alkyl, optionally substituted by aryl, heteroaryl, or by heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy and $NH_2$, may be prepared according to Scheme C via reaction of a compound of formula C1 with a compound of formula $R^{11}$—CHO (C3), wherein $R^{11}$ is hydrogen; $C_1$-$C_5$ alkyl, optionally substituted by aryl, heteroaryl, or by heterocyclyl; and wherein the aryl or heteraryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy and $NH_2$, preferably under nitrogen atmosphere, in a suitable organic solvent (e.g. $CH_2Cl_2$, MeOH, EtOH or tetrahydrofuran) at a temperature between about 0° C. and 70° C. in the presence of a reducing agent such as sodium borohydride, sodium triacetoxyborohydride or sodium cyanoborohydride. Compounds of formula C1 may be for example prepared according to Scheme A, A1, or B.

In the case it is necessary to protect a chemical group of a compound of the present invention and/or an intermediate thereof, before carrying out one of the aforedescribed reactions, said chemical group may be protected and deprotected according to known methods. A thorough discussion for suitable protecting groups and the means for protection/deprotection steps can be found for example in Greene and Wuts (Greene, T. W.; Wuts, P. G. M. "Protective Groups in Organic Synthesis", John Wiley & Sons Inc., 1991) or in Kocienski (Kocienski, P. J. "Protecting Groups", George Thieme Verlag, 1994).

Salification of the compounds of formula (I), and preparation of compounds of formula (I), free of their salts, may be carried out by known conventional methods.

The invention also comprises a method for preventing and/or treating diseases linked to the disregulation of histone demethylase KDM1A (LSD1) activity characterized by administering to a patient a pharmacologically useful quantity of one or more compounds of formula (I), as previously defined. The invention includes the same compounds for use in the prevention or treatment of the aforesaid diseases. Further provided by the invention is the use of the same compounds for the manufacture of a medicament for the prevention or treatment of the aforesaid diseases.

In view of the above described mechanisms of action, the compounds of the present invention are useful in the prevention or treatment of tumor type diseases, including but not limited to: acute and chronic myeloid leukaemia, acute and chronic lymphoblastic leukaemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas; osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (for example advanced prostate cancer), thyroid carcinomas (for example tyroid follicular cancer), colon cancers (for example colon adenocarcinoma, colon adenoma), gastric tumors and gastrointestinal adenocarcinomas, hepatic carcinomas, pancreatic carcinomas (for example exocrine pancreatic carcinoma), renal tumors, teratocarcinomas and embryonic carcinomas.

The compounds of the invention are also useful in the prevention or treatment of infections, including, but not limited to, infections caused by protozoa, fungi, phytotoxic agents, viruses and parasites, for example HIV or herpes virus infections.

The compounds of the invention are also useful in the prevention or treatment of other diseases dependent by energy expenditure such as obesity.

The compounds of formula (I) can also be used in combination with additional agents, in particular anti-tumor and differentiating agents, either by separate administrations, or by including the two active principles in the same pharmaceutical formulation. Non-exhaustive examples of suitable additional agents include:

a) histone deacetylase inhibitors (for example, but not limited to SAHA, PXD101, JNJ-26481585, SB939, ITF-2357, LBH589, PCI-24781, valproic acid, butyric acid, MS-275, MGCD0103 and FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (for example platin derivatives like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (for example anthracyclines like aclarubicin, amrubicin, daunomycin, doxorubicin, epirubicin, idarabicin, valrubicin, zorubicine; mitoxantrone; or antibiotics from streptomyces like actinomycin, bleomycin, mitomycin, or plicamycin); antimitotic agents (for example vinca alkaloids like vincristine, vinblastine, vindesine or vinorelbine; taxoids like docetaxel, paclitaxel or tesetaxel; epothilones like ixabepilone) and topoisomerase inhibitors (for example epipodophyllotoxins like etoposide and teniposide; amsacrine, camptothecin, irinotecan, rubitecan, and topotecan);

d) cytostatic agents such as antioestrogens (for example tamoxifen, toremifene, raloxifene, droloxifene and idoxifene), oestrogen receptor down regulators (for example fulvestrant), antiandrogens (for example bicalutamide, flutamide, nilutamide, liarozole or cyproterone acetate), LHRH antagonists or LHRH agonists (for example goserelin, leuprorelin or buserelin), progestogens (for example megestrol acetate), aromatase inhibitors (for example as anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example the anti-erbb2 antibody trastuzumab, the anti-erbbl antibody cetuximab and panitumumab, the anti IGF1R antibody figitumumab), farnesyl transferase inhibitors, MEK inhibitors, tyrosine kinase inhibitors and serine/threonine kinase inhibitors, for example enzastaurin, dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, for example the anti-vascular endothelial cell growth factor antibody bevacizumab, lenalidomide or thalidomide;

h) cell cycle inhibitors including for example CDK inhibitors (for example but not limited to flavopiridol, roscovitine) and other inhibitors of cell cycle checkpoints; inhibitors of aurora kinase and other kinases involved in mitosis and cytokinesis regulation;

i) proteasome inhibitors (for example lactacystin, bortezomib, epoxomicin);

j) HSP90 inhibitors (for example but not limited to AT-13387, KOS-953, KOS-1022, CNF-1010, CNF-2024, SNX 5422, STA-9090, NVP-HSP990, NVP-AUY922, PU-H17 and XL-888)

k) Selective COX-2 inhibitors (for example celecoxib), or non selective NSAIDs (for example diclofenac, flurbiprofen, ibuprofen, ketoprofen, or naproxen).

In another aspect, a compound of general formula (I) can be used in combination with radiation therapy. In yet another aspect, a compound of general formula (I) may be administered in combination with standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The compounds of formula (I) can be pharmaceutically formulated according to known methods. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable, or infusible liquid solutions, suspensions, or suppositories.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present invention may be employed alone as a sole therapy or in combination with other therapeutic agents for the treatment of the above-mentioned conditions. The combination can be administered as separate compositions (simultaneous, sequential) of the individual components of the treatment or as a single dosage form containing both agents. When the compounds of this invention are in combination with others active ingredients, the active ingredients may be separately formulated into single-ingredient preparations of one of the above-described forms and then provided as combined preparations, which are given at the same time or different times, or may be formulated together into a two- or more-ingredient preparation.

Compounds of general formula (I) may be administered to a patient in a total daily dose of, for example, from 0.001 to 1000 mg/kg body weight daily. Dosage unit compositions may contain such amounts of submultiples thereof to make up the daily dose. The determination of optimum dosages for a particular patient is well known to one skilled in the art.

As is common practice, the compositions are normally accompanied by written or printed instructions for use in the treatment in question.

The following examples and biological data are presented in order to further illustrate the invention.

1. Chemical Synthesis

Unless otherwise indicated, commercially available reagents and solvents (HPLC grade) were used without further purification. Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | μL (microlitres) |
| mL (millilitres) | mmol (millimoles) |
| nm (nanometers) | μM (micromolar) |
| M (molarity) | $R_t$ (retention time in minutes) |
| RT (room temperature) | MW (microwave) |
| BOC or boc (tert-butyloxycarbonyl) | $CH_2Cl_2$ (dichloromethane) |
| $CH_3CN$ (acetonitrile) | DCE (1,2-dichloroethane) |
| DIPEA (N,N-diisopropylethylamine) | DME (1,2-dimethoxyethane) |
| DMF (dimethylformamide) | DMSO-$d_6$ (deuterated dimethyl sulfoxide) |
| EDC (1-3(dimethylaminopropyl)-3-ethylcarbodiimide hydrochloride) | $Et_2O$ (diethyl ether) |
| EtOAc (ethyl acetate) | EtOH (ethanol) |
| HCl (hydrochloric acid) | HOBt (1-hydroxybenzotriazole) |
| $LiAlH_4$ (lithium aluminium hydride) | LiOH (lithium hydroxide) |
| MeOH (methanol) | MeOH-d4 (deuterated methanol) |
| $NaBH(OAc)_3$ (sodium triacetoxyborohydride) | $Na_2CO_3$ (sodium carbonate) |
| $Na_2SO_4$ (sodium sulphate) | $NH_3$ (ammonia) |
| PDC (pyridinium dichromate) | i-PrOH (isopropyl alcohol) |
| TEA (triethylamine) | tert-BuOH (tert-butanol) |
| THF (tetrahydrofuran) | TFA (trifluoroacetic acid) |

Except where indicated otherwise, all temperatures are expressed in ° C. (degrees centigrade) or K (Kelvin).

The $^1$H-NMR spectra were acquired with a Varian 500 MHz instrument. The chemical shifts are expressed in parts per million (ppm, δ units). The coupling constants are expressed in Hertz (Hz) and the splitting patterns are described as s (singlet), bs (broad singlet), d (doublet), t (triplet), q (quartet), quint (quintet), m (multiplet).

The LC-MS analyses were carried out on a Waters Acquity UPLC or Waters Acquity UPLC H-Class linked to with a SQD Single quadrupole (Waters) using an Acquity UPLC BEH C18 (50×2.1 mm, 1.7 μm) or Acquity UPLC HSS T3 (50×2.1 mm, 1.8 μm) column. Phase A was composed by either Milli-Q water/$CH_3CN$ 95/5+0.07% formic acid or Milli-Q water+0.07% formic acid; Phase B by $CH_3CN$+0.05% formic acid; flow rate: 0.6 mL/min; UV detection (DIODE array) from 210 to 400 nm; ESI+ detection in the 100-2000 m/z range. The yields were calculated assuming that products were 100% pure if not stated otherwise.

Intermediate 1: Ethyl 2-diethoxyphosphoryl-3-(2-naphthyl)propanoate

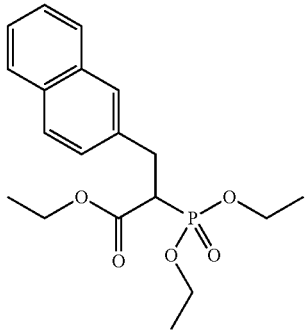 [SMILES: CCOC(=O)C(Cc1ccc2ccccc2c1)P(=O)(OCC)OCC]

13 g (58 mmol) of triethyl phosphonoacetate (Sigma Aldrich, Cat No. T61301) was slowly added dropwise over 40 min to an ice-cooled suspension of 2.6 g (64 mmol) sodium hydride in 100 mL of dry DME. After stirring for 2 h at 25° C., 14 g (64 mmol) of 2-chloromethylnaphthalene (Sigma Aldrich, Cat No. 726419) was added and the mixture was stirred for 2 h at 60° C. The reaction mixture was then poured into 200 mL of ice-water and extracted with EtOAc, and the combined organic phases were washed with water and brine and dried over $Na_2SO_4$. Then, the solvent was evaporated and the product was purified by column chromatography (eluent: hexane/EtOAc 1:1) to give 10.5 g (50%) of ethyl 2-diethoxyphosphoryl-3-(2-naphthyl)propanoate as a colorless oil. $^1$H NMR (CDCl$_3$) δ (ppm): 7.85-7.73 (m, 3 H), 7.69-7.64 (m, 1 H), 7.51-7.41 (m, 2 H), 7.37-7.30 (m, 1 H), 4.29-4.17 (m, 4 H), 4.16-4.01 (m, 2 H), 3.50-3.31 (m, 3 H), 1.42-1.33 (m, 6 H), 1.12 (t, J=7.3 Hz, 3 H). MS (ESI): m/z: 365 [M+H]$^+$

Intermediate 2: Ethyl 2-diethoxyphosphoryl-4-phenyl-butanoate

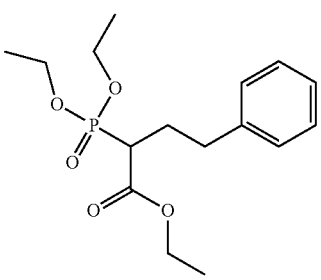 [SMILES: CCOC(=O)C(CCc1ccccc1)P(=O)(OCC)OCC]

2.00 g triethyl phosphonoacetate (8.92 mmol) was slowly added dropwise to a cooled suspension of 0.43 g sodium hydride (11 mmol) in 10 mL dry DME. After stirring for 1 h at 25° C., 1.25 g 2-bromoethylbenzene (6.75 mmol) was added and the mixture was stirred for 1.5 h at 60° C. The reaction mixture was then poured into 20 mL of ice-water and extracted with EtOAc. The organic solution was washed with water and brine, dried over $Na_2SO_4$, filtered, and evaporated to an oil, which was purified by flash column chromatography (hexane/EtOAc, 1:1) to give 1.096 g ethyl 2-diethoxyphosphoryl-4-phenyl-butanoate (37%) as a colorless oil. $^1$H NMR (CDCl$_3$) δ (ppm): 7.32-7.25 (m, 2 H), 7.23-7.15 (m, 3 H), 4.28-4.17 (m, 2 H), 4.17-4.05 (m, 4 H), 3.02-2.90 (m, 1 H), 2.79-2.67 (m, 1 H), 2.65-2.51 (m, 1 H), 2.41-2.26 (m, 1 H), 2.21-2.06 (m, 1 H), 1.37-1.23 (m, 9 H). MS (ESI): m/z: 351 [M-FI-1]$^+$ Triethyl 2-phosphonopropionate (Sigma Aldrich, Cat No. 174653), triethyl 2-phosphonobutanoate (Sigma Aldrich, Cat No. 417467), and triethyl 2-phosphonopentanoate (Alfa Aesar, Cat. No. 30413) are commercially available. The preparation of ethyl 2-(diethoxyphosphoryl)-3-methylbutanoate is described in J. Org. Chem. 1970, 37, 4396-4399, ethyl 2-(diethoxyphosphoryl)-3-phenylpropanoate in Eur. J. Org. Chem. 2011, 31, 6314-6319, and triethyl phosphonophenylacetate in J. Org. Chem. 1993, 58, 7009-7015.

Intermediate 3: Benzyl N-(5-carbamoyl-2-morpholino-phenyl)carbamate

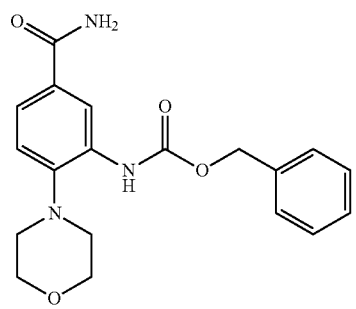 [SMILES: NC(=O)c1ccc(N2CCOCC2)c(NC(=O)OCc2ccccc2)c1]

0.26 g (2.40 mmol) $Na_2CO_3$ and 0.21 mL (1.44 mmol) benzyl chloroformate were added to a solution of 0.213 g (0.96 mmol) 3-amino-4-morpholino-benzamide (Fluorochem, Cat No. 57762) in 3 mL THF/water (1:1). The mixture was stirred at RT for 2.5 h and was then concentrated. Water was added and the solid was filtered off, washed with water and dried to give 0.303 g benzyl N-(5-carbamoyl-2-morpholino-phenyl)carbamate (89%) as a pale pink solid. $^1$H NMR (DMSO-d$_6$) δ (ppm): 8.55 (s, 1 H), 8.11 (bs, 1 H), 7.85 (bs, 1 H), 7.61 (dd, J=2.4, 8.3 Hz, 1 H), 7.45-7.28 (m, 5 H), 7.23 (bs, 1 H), 7.14 (d, J=8.3 Hz, 1 H), 5.17 (s, 2 H), 3.77-3.67 (m, 4 H), 2.89-2.76 (m, 4 H). MS (ESI): m/z: 356 [M+H]$^+$

Intermediate 4: Benzyl N-(5-carbamoyl-2-morpholino-phenyl)carbamate

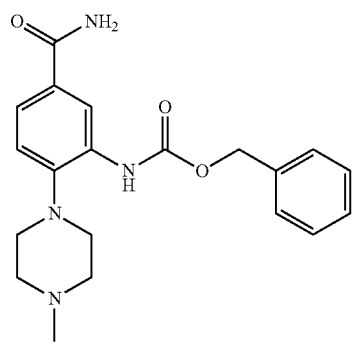 [SMILES: CN1CCN(c2ccc(C(N)=O)cc2NC(=O)OCc2ccccc2)CC1]

tert-butyl 3-nitro-4-(4-methylpiperazin-1-yl)-benzoate

A suspension di 0.3 g tert-butyl 4-chloro-3-nitro-benzoate (1.16 mmol, U.S. Pat. No. 5,304,644), 0.321 g K$_2$CO$_3$ (2.32 mmol) and 0.64 mL N-methylpiperazine (5.8 mmol) was stirred overnight at 90° C. The reaction mixture was quenched with 50 mL of H$_2$O and extracted with EtOAc. The combined organic phases were washed with brine, dried over Na$_2$SO$_4$, concentrated and purified by column chromatography (eluent: CH$_3$Cl/MeOH 40:1, v:v) to obtain 0.25 g of tert-butyl 3-nitro-4-(4-methylpiperazin-1-yl)benzoate (68%). MS (ESI): m/z: 322 [M+H]$^+$ tert-butyl 3-amino-4-(4-methylpiperazin-1-yl)benzoate 0.25 g of tert-butyl 3-nitro-4-(4-methylpiperazin-1-yl)benzoate (0.78 mmol) in 20 mL dry MeOH was hydrogenated in a Parr shaker for 5 h (Pd/C (1/20 mmol) pressure 3.44 bar) Then, the solution is filtered and the obtained residue was purified by silica column chromatography (eluent CHCl$_3$/MeOH 20:1, v:v). MS (ESI): m/z: 292[M+H]$^+$ tert-butyl 3-(benzyloxycarbonylamino)-4-(4-methylpiperazin-1-yl)benzoate 0.155 mL (1.11 mmol) TEA was added to a mixture of 0.162 g (0.55 mmol) tert-butyl 3-amino-4-(4-methylpiperazin-1-yl)benzoate in 2.5 mL dry THF cooled to 0° C. Then, 0.48 ml (3.32 mmol) benzyl chloroformate and 0.465 mL TEA (3.33 mmol) were added in four portions and. the mixture was allowed to reach RT. The solvent was then removed, the crude mixture partitioned between water and EtOAc, the organic phase was dried over Na$_2$SO$_4$, filtered, concentrated and purified by flash chromatography (eluent CH$_2$Cl$_2$/MeOH, 97:3) providing 0.096 g of tert-butyl 3-(benzyloxycarbonylamino)-4-(4-methylpiperazin-1-yl) benzoate (40%) as a colourless oil. $^1$H NMR (DMSO-d$_6$) δ (ppm): 8.44-8.33 (m, 1 H), 8.13 (bs, 1 H), 7.64-7.57 (m, 1 H), 7.44-7.28 (m, 5 H), 7.19-7.12 (m, 1 H), 5.17 (s, 2 H), 2.91-2.82 (m, 4 H), 2.48-2.41 (m, 4 H), 2.21 (s, 3 H), 1.51 (s, 9 H). MS (ESI): m/z: 426 [M+H]$^+$

3-(benzyloxycarbonylamino)-4-(4-methylpiperazin-1-yl)benzoic acid 0.078 mL (1.058 mmol) TFA was added to a solution of 0.90 mg (0.211 mmol) tert-butyl 3-(benzyloxycarbonylamino)-4-(4-methylpiperazin-1-yl)benzoate in 2 mL dry CH$_2$Cl$_2$ and the resulting mixture was stirred at RT. After 4.5 h further 0.078 ml TFA was added and stirring was continued until complete conversion (40 h). The solvent was removed and the white solid was triturated in Et$_2$O, filtered and washed to afford 77 mg 3-(benzyloxycarbonylamino)-4-(4-methylpiperazin-1-yl)benzoic acid (98%). $^1$H NMR (DMSO-d$_6$) δ (ppm): 12.88 (bs, 1 H), 9.56 (bs, 1 H), 8.68 (s, 1 H), 8.35 (s, 1 H), 7.72-7.59 (m, 1 H), 7.51-7.29 (m, 4 H), 7.27-7.06 (m, 1 H), 5.20 (s, 2 H), 3.80-3.37 (m, 2 H), 3.34-3.16 (m, 4 H), 3.04-2.91 (m, 2 H), 2.85 (s, 3 H). MS (ESI): m/z: 370 [M+H]$^+$ benzyl N-[5-carbamoyl-2-(4-methylpiperazin-1-yl)phenyl]carbamate

A mixture of 0.078 g (0.21 mmol) 3-(benzyloxycarbonylamino)-4-(4-methylpiperazin-1-yl)benzoic acid in 1 mL dry CH$_2$Cl$_2$ was treated with 0.019 mL (0.26 mmol) thionyl chloride and 2 drops of dry DMF. Then mixture was stirred under reflux for 1.5 h, then the mixture was cooled to RT and poured in 1 mL NH$_3$ (28-30% in water). After 1 h the resulting mixture was partitioned between CH$_2$Cl$_2$ and a 10% solution of Na$_2$CO$_3$, The aqueous phase was extracted with CH$_2$Cl$_2$ and the organic layers were dried over Na$_2$SO$_4$ and concentrated to give 0.057 g benzyl N-[5-carbamoyl-2-(4-methylpiperazin-1-yl)phenyl]carbamate (74%) as a beige solid. $^1$H NMR (DMSO-d$_6$) δ (ppm): 8.36 (s, 1 H), 8.11 (s, 1 H), 7.85 (bs, 1 H), 7.59 (dd, J=2.0, 8.3 Hz, 1 H), 7.45-7.30 (m, 5 H), 7.22 (bs, 1 H), 7.13 (d, J=8.3 Hz, 1 H), 5.17 (s, 2 H), 2.87-2.81 (m, 4 H), 2.45 (bs, 4 H), 2.21 (s, 3 H). MS (ESI): m/z: 369 [M+H]$^+$ Intermediate 5: 3-(2-Oxooxazolidin-3-yl)benzamide

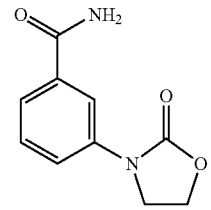 [SMILES: NC(=O)c1cccc(N2CCOC2=O)c1]

A suspension of 0.56 g (2.7 mmol) 3-(2-oxooxazolidin-3-yl)benzoic acid (WO2003/045913) in 15 mL dry CH$_2$Cl$_2$ was treated with 0.246 mL (3.38 mmol) thionyl chloride and 2 drops of dry DMF. After stirring at reflux for 2 h, the mixture was cooled to RT and poured in 4 mL NH$_3$ (28-30% in water). After 1 h the resulting mixture was filtered off to afford a white solid that was washed with water. The aqueous phases were extracted with CH$_2$Cl$_2$, and the combined organic layers were dried over Na$_2$SO$_4$ and filtered to give 0.549 g of 3-(2-oxooxazolidin-3-yl)benzamide (98%) as a white solid. $^1$H NMR (DMSO-d$_6$) δ (ppm): 8.01 (bs, 1 H), 7.94-7.88 (m, 1 H), 7.84-7.78 (m, 1 H), 7.61 (d, J=7.8 Hz, 1 H), 7.52-7.34 (m, 2 H), 4.49-4.39 (m, 2 H), 4.14-3.98 (m, 2 H). MS (ESI): m/z: 207 [M+H]$^+$ Intermediate 6: 4-(2-Oxooxazolidin-3-yl)benzamide

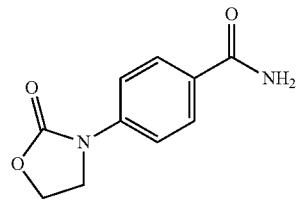 [SMILES: NC(=O)c1ccc(N2CCOC2=O)cc1]

Intermediate 6 was prepared according to the procedure for Intermediate 5 starting from 4-(2-oxooxazolidin-3-yl) benzoic acid (Enamine, Cat No. EN300-39599). $^1$H NMR (DMSO-d$_6$) δ (ppm): 88.01-7.79 (m, 3 H), 7.67-7.53 (m, 2 H), 7.28 (bs, 1 H), 4.44 (t, J=7.6 Hz, 2 H), 4.08 (t, J=7.6 Hz, 2 H). MS (ESI): m/z: 207 [M+H]$^+$ Benzamide (Sigma Aldrich, Cat No. 135828), 3-chlorobenzamide (Sigma Aldrich, Cat No. CDS003328), 2-phenylacetamide (Apollo, Cat No. OR0700, 3-phenylpropionamide (TCI, Cat No. P1845), naphthalene-1-carboxamide (ABCR, Cat No. AB150028-0005.00-GRM), naphthalene- 2-carboxamide (ABCR, Cat No. AB178532-0010.00-G), 2-(1-naphthyl)acetamide (Alfa-Aesar, Cat No. B23986-22), 2-(2-naphthyl)acetamide (Enamine, EN300-68829), 4-phenylbenzamide (ABCR, Cat No. AB110526-0005.00-GRM), benzenesulfonamide (Sigma Aldrich, Cat No. 108146), pyridine-4-carboxamide (Sigma Aldrich, Cat No. 117451) are commercially available.

4-(4-pyridyl)benzamide and 4-(3-furyl)benzamide are described in J. Comb. Chem. 2009, 11, 576-586, 3-phenylbenzamide is described in Tetrahedron Lett. 1997, 38, 1197-1200, 4-nitrobenzamide in WO1995/05363, the preparation of 4-(1-methylpiperidin-4-yl)benzamide in WO2009055077, the synthesis of 4-(4-methylpiperazin-1-yl)benzamide is described in US2008146542, the preparation of 4-morpholinobenzamide in Eur. J. Med. Chem. 2010, 45, 3709-3718, the preparation of benzyl N-(4-carbamoylphenyl)carbamate and benzyl N-(3-carbamoylphenyl)carbamate in Biorg. Med. Chem. Lett. 2007, 17, 4670-4677,

EXAMPLE A-1

(1S,2R)-1-Ethyl-2-phenyl-cyclopropanamine hydrochloride

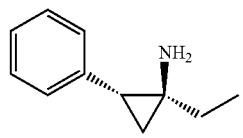

Ethyl
(1S,2R)-1-ethyl-2-phenyl-cyclopropanecarboxylate 2.5 mL (2.5 mol/L) buthyl lithium was added to a solution of 1.5 g (5.4 mmol) ethyl 2-diethoxyphosphorylbutanoate (Sigma Aldrich) in 5 mL dry DME under $N_2$ atmosphere at RT. After 5 min, 0.50 g (4.2 mmol) styrene epoxide (Sigma Aldrich) was added dropwise. The mixture was stirred for 20 min at RT and then heated at 130° C. under MW irradiation for 1 h. Aqueous $NH_4Cl$ was added, and the product was extracted with $CH_2Cl_2$. The combined organic layers were dried over $MgSO_4$ and concentrated. The dry residue was purified by column chromatography (eluent: EtOAc/hexane, 0:100 to 10:100) to give ethyl (1S,2R)-1-ethyl-2-phenyl-cyclopropanecarboxylate (570 mg, 63%) as a colorless oil. $^1$H NMR (CDCl$_3$) δ (ppm): 7.35-7.16 (m, 5 H), 4.32-4.05 (m, 2 H), 2.89-2.75 (m, 1 H), 1.73-1.58 (m, 2 H), 1.30 (t, J=7.1 Hz, 3 H), 1.20-1.14 (m, 1 H), 1.06-0.79 (m, 4 H).

(1S,2R)-1-Ethyl-2-phenyl-cyclopropanecarboxylic acid 20 mL of EtOH/water (1:1) was added to 570 mg (2.61 mmol) ethyl (1S,2R)-1-ethyl-2-phenyl-cyclopropanecarboxylate in 4 mL THF. The solution was cooled down to 0° C., then 0.25 g (10 mmol) of LiOH was added and the mixture was stirred under reflux for 4 h. The solution was then concentrated, quenched with 2 M HCl, and the formed precipitate was filtered off, washed with water and dried giving 0.33 g (66.44%) of the (1S,2R)-1-ethyl-2-phenyl-cyclopropanecarboxylic acid. $^1$H NMR (DMSO-d$_6$) δ (ppm): 12.25 (s, 1 H), 7.34-7.26 (m, 2 H), 7.25-7.17 (m, 3 H), 2.74-2.65 (m, 1 H), 1.50-1.35 (m, 2 H), 1.34-1.25 (m, 1 H), 0.98-0.85 (m, 1 H), 0.76 (t, J=1.0 Hz, 3 H). MS (ESI): m/z: 189 [M−H]$^-$.

tert-Butyl-N-[(1S,2R)-1-ethyl-2-phenyl-cyclopropyl] carbamate 0.43 g (1.6 mmol) diphenyl phosphorazidate (Sigma Aldrich) and 0.19 g (1.8 mmol) TEA were added to a solution of 0.27 g (1.4 mmol) (1S,2R)-1-ethyl-2-phenyl-cyclopropanecarboxylic acid in 15 mL dry tert-BuOH, and the resulting solution was stirred at 90° C. for 16 h. Then, the mixture was concentrated and the residue was partitioned between 10% aqueous $Na_2CO_3$ and $Et_2O$. The combined organic layers were dried ($Na_2SO_4$), filtered, concentrated, and then purified by column chromatography (eluent: EtOAc/cyclohexane, 1:100 to 20:100) to give 0.16 g (43%) of the tert-butyl-N-[(1S,2R)-1-ethyl-2-phenyl-cyclopropyl] carbamate. $^1$H NMR (CDCl$_3$) δ (ppm): 7.40-7.16 (m, 5 H), 5.02 (s, 1 H), 2.57-2.31 (m, 1 H), 1.64-1.38 (m, 10 H), 1.19-1.09 (m, 1 H), 1.05-0.98 (m, 1 H), 0.98-0.77 (m, 4 H). MS (ESI): m/z: 162 [M−100]$^+$ (1S,2R)-1-Ethyl-2-phenyl-cyclopropanamine hydrochloride A solution of 40 mg (0.1530 mmol) of the tert-butyl-N-[(1S,2R)-1-ethyl-2-phenyl-cyclopropyl]carbamate in $Et_2O$ was cooled down to 0° C. Then, 4 M HCl in dioxane was added and the solution was stirred at RT for 20 h. Then, the solvent was evaporated, and the residue triturated twice with $Et_2O$ giving 21 mg (69%) (1S,2R)-1-ethyl-2-phenyl-cyclopropanamine hydrochloride as a white solid. $^1$H NMR (DMSO-d$_6$) δ (ppm): 8.35 (s, 3 H), 7.36-7.29 (m, 2 H), 7.27-7.18 (m, 3 H), 2.58-2.50 (m, 1 H), 1.43-1.28 (m, 3 H), 1.26-1.13 (m, 1 H), 0.79 (t, J=7.6 Hz, 3 H). MS (ESI): m/z: 162 [M+H]$^+$.

According to the procedure described for example A-1 the following compounds (Table 1) were synthesized starting from the appropriate styrene oxide and phosphonoacetate. Alternatively to the above described hydrolysis of the BOC protecting group with HCl in dioxane, 4% TFA in $CH_2Cl_2$ at RT overnight was used to prepare the desired amines as trifluoroacetate salts.

TABLE 1

| Ex. | Name | Structure | LC-MS | NMR |
|---|---|---|---|---|
| A-2 | (1R,2S)-1-ethyl-2-phenyl-cyclopropanamine hydrochloride | 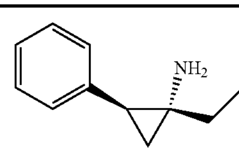 | 162 ([M + H]$^+$) | $^1$H NMR (DMSO-d$_6$) δ (ppm): 8.28 (s, 3 H), 7.36-7.29 (m, 2 H), 7.28-7.21 (m, 3 H), 2.59-2.44 (m, 1 H), 1.39-1.27 (m, 3 H), 1.27-1.16 (m, 1 H), 0.79 (t, J = 7.6 Hz, 3 H) |

TABLE 1-continued

| Ex. | Name | Structure | LC-MS | NMR |
|---|---|---|---|---|
| A-3 | trans-1-methyl-2-phenyl-cyclopropanamine 2,2,2-trifluoroacetic acid | 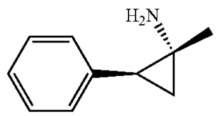 | 149 ([M + H]+) | |
| A-4 | (1R,2S)-1-methyl-2-phenyl-cyclopropanamine 2,2,2-trifluoroacetic acid | 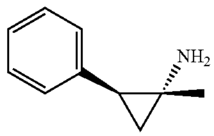 | 149 ([M + H]+) | $^1$H NMR (CDCl$_3$) δ (ppm): 8.27 (bs, 2 H), 7.26-7.14 (m, 3 H), 7.13-7.07 (m, 2 H), 2.68-2.53 (m, 1 H), 1.53-1.43 (m, 1 H), 1.14 (s, 3H), 1.11-1.04 (m, 1 H) |
| A-5 | (1S,2R)-1-methyl-2-phenyl-cyclopropanamine 2,2,2-trifluoroacetic acid | 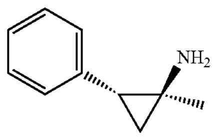 | 149 ([M + H]+) | $^1$H NMR (CDCl$_3$) δ (ppm): 8.30 (s, 2 H), 7.26-7.14 (m, 3 H), 7.13-7.07 (m, 2 H), 2.65-2.54 (m, 1 H), 1.54-1.40 (m, 1 H), 1.14 (s, 3 H), 1.11-1.03 (m, 1 H) |
| A-6 | trans-2-phenyl-1-propyl-cyclopropanamine hydrochloride | 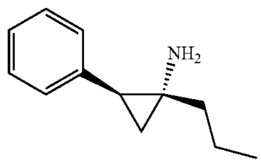 | 176 ([M + H]+) | $^1$H NMR (DMSO-d$_6$) δ (ppm): 8.46 (s, 3 H), 7.41-7.28 (m, 2 H), 7.28-7.14 (m, 3 H), 2.58-2.51 (m, 1 H), 1.43-1.18 (m, 5 H), 1.12-0.99 (m, 1 H), 0.67 (t, J = 1.0 Hz, 3 H) |
| A-7 | trans-1-isopropyl-2-phenyl-cyclopropanamine hydrochloride | 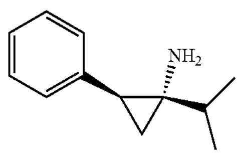 | 176 ([M + H]+) | $^1$H NMR (DMSO-d6) δ (ppm): 8.20 (s, 3 H), 7.57-7.05 (m, 5 H), 2.58-2.51 (m, 1 H), 1.46-1.24 (m, 2 H), 1.11-1.04 (m, 1 H), 1.00 (d, J = 1.0 Hz, 3 H), 0.68 (d, J = 6.8 Hz, 3 H) |
| A-8 | trans-1-benzyl-2-phenyl-cyclopropanamine hydrochloride | 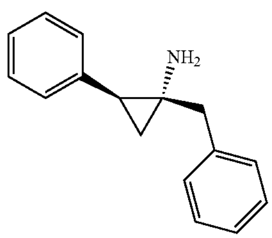 [SMILES: N[C@]1(Cc2ccccc2)C[C@H]1c1ccccc1] | 224 ([M + H]+) | $^1$H NMR (,DMSO-d$_6$) δ (ppm): 8.30 (s, 3 H), 7.45-7.20 (m, 8 H), 7.14-6.99 (m, 2 H), 2.82 (d, 1 H), 2.69-2.57 (m, 1 H), 2.33 (d, 1H), 1.79-1.58 (m, 1 H), 1.49-1.32 (m, 1 H) |
| A-9 | (1S,2S)-1-benzyl-2-phenyl-cyclopropanamine hydrochloride | 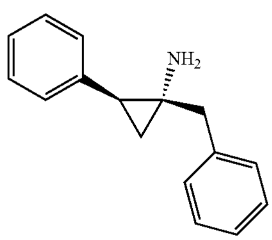 [SMILES: N[C@]1(Cc2ccccc2)C[C@H]1c1ccccc1] | 224 ([M + H]+) | $^1$H NMR (DMSO-d$_6$) δ (ppm): 8.30 (s, 3 H), 7.45-7.20 (m, 8 H), 7.14-6.99 (m, 2 H), 2.82 (d, 1H), 2.69-2.57 (m, 1 H), 2.33 (d, 1H), 1.79-1.58 (m, 1 H), 1.49-1.32 (m, 1 H) |
| A-10 | (1R,2R)-1-benzyl-2-phenyl-cyclopropanamine hydrochloride | 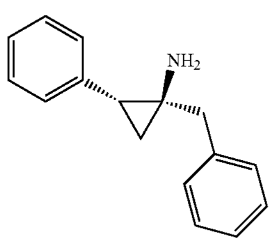 [SMILES: N[C@@]1(Cc2ccccc2)C[C@@H]1c1ccccc1] | 224 ([M + H]+) | $^1$H NMR (DMSO-d$_6$) δ (ppm): 8.32 (s, 3 H), 7.42-7.20 (m, 8 H), 7.14-7.05 (m, 2 H), 2.82 (d, 1H), 2.70-2.60 (m, 1 H), 2.33 (d, 1H), 1.74-1.65 (m, 1 H), 1.47-1.34 (m, 1 H) |

TABLE 1-continued

| Ex. | Name | Structure | LC-MS | NMR |
|---|---|---|---|---|
| A-11 | trans-1-phenethyl-2-phenyl-cyclopropanamine hydrochloride | 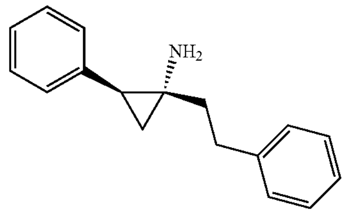 [SMILES: N[C@]1(CCc2ccccc2)C[C@H]1c1ccccc1] | 238 ([M + H]⁺) | ¹H NMR (DMSO-d₆) δ (ppm): 8.33 (s, 3 H), 7.40-7.32 (m, 2 H), 7.31-7.23 (m, 3 H), 7.22-7.14 (m, 2 H), 7.13-7.06 (m, 1 H), 6.87-6.76 (m, 2 H), 2.66-2.53 (m, 2 H), 2.48-2.40 (m, 1 H), 1.58-1.45 (m, 2 H), 1.44-1.53 (m, 2 H) |
| A-12 | trans-2-(4-bromophenyl)-1-ethyl-cyclopropanamine hydrochloride | 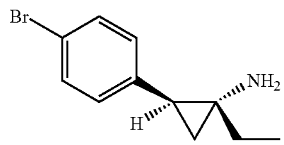 | 240 ([M + H]⁺) | ¹H NMR (DMSO-d₆) δ (ppm): 8.48 (bs, 3 H), 7.56-7.47 (m, 2 H), 7.21 (d, J = 8.3 Hz, 2 H), 2.57-2.50 (m, 1 H), 1.43-1.27 (m, 3 H), 1.26-1.13 (m, 1 H), 0.79 (t, J = 7.6 Hz, 3 H). |
| A-13 | trans-1-benzyl-2-(4-bromophenyl)cyclopropanamine hydrochloride | 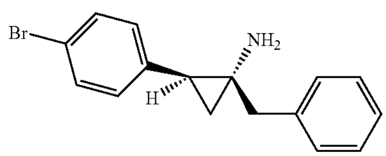 [SMILES: N[C@]1(Cc2ccccc2)C[C@H]1c1ccc(Br)cc1] | 302 ([M + H]⁺) | ¹H NMR (DMSO-d₆) δ (ppm): 8.36 (bs, 3 H), 7.56 (d, J = 8.3 Hz, 2 H), 7.36-7.20 (m, 5 H), 7.13 (d, J = 6.8 Hz, 2 H), 2.82 (d, J = 15.2 Hz, 1 H), 2.63 (t, J = 8.6 Hz, 1 H), 2.29 (d, J = 15.2 Hz, 1 H), 1.70 (t, J = 6.8 Hz, 1 H), 1.43 (dd, J = 7.1, 9.5 Hz, 1 H). |
| A-14 | trans-1-ethyl-2-(6-quinolyl)cyclopropanamine dihydrochloride | 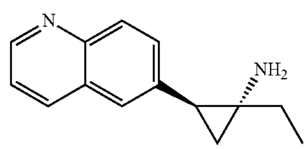 [SMILES: CC[C@@]1(N)C[C@H]1c1ccc2ncccc2c1] | 213 ([M + H]⁺) | ¹H NMR (DMSO-d₆) δ (ppm): 9.12 (d, J = 4.9 Hz, 1 H), 8.89-8.58 (m, 4 H), 8.36-8.14 (m, 1 H), 8.08-7.94 (m, 2 H), 7.92-7.80 (m, 1 H), 2.92-2.72 (m, 1 H), 1.61-1.48 (m, 2 H), 1.44-1.32 (m, 1 H), 1.31-1.21 (m, 1 H), 0.78 (t, J = 7.6 Hz, 3 H). |
| A-15 | trans-1-(2-naphthylmethyl)-2-phenyl-cyclopropanamine hydrochloride | 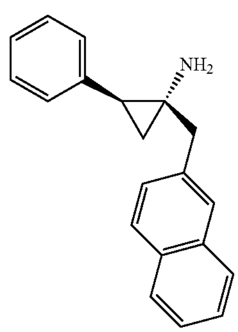 [SMILES: N[C@]1(Cc2ccc3ccccc3c2)C[C@H]1c1ccccc1] | 274 ([M + H]⁺) | ¹H NMR (DMSO-d₆) δ (ppm): 8.28 (s, 3 H), 7.93-7.69 (m, 3 H), 7.62-7.12 (m, 9 H), AB System: VA = 2.96, VB = 2.53, J$_{AB}$ = 15.2 Hz, 2.75-2.59 (m, 1 H), 1.87-1.72 (m, 1 H), 1.51-1.37 (m, 1 H). |
| A-16 | trans-1-ethyl-2-(4-fluorophenyl)cyclopropanamine hydrochloride | 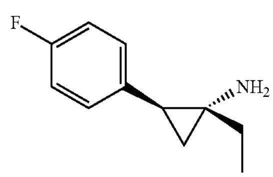 | 180 ([M + H]⁺) | ¹H NMR (DMSO-d₆) δ (ppm): 8.63 (bs, 3 H), 7.32-7.28 (m, 2 H), 7.17-7.13 (m, 2 H), 2.60-2.50 (m, 1 H), 1.42-1.16 (m, 4 H), 0.83 (t, J = 7.6 Hz, 3 H). |
| A-17 | trans-1-ethyl-2-(4-chlorophenyl)cyclopropanamine; hydrochloride | 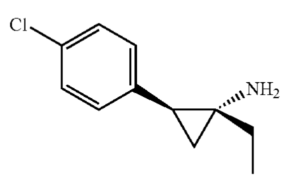 | 196 ([M + H]⁺) | ¹H NMR (DMSO-d₆) δ (ppm): 8.65 (bs, 3 H), 7.40-7.38 (m, 2 H), 7.30-7.29 (m, 2 H), 2.61-2.51 (m, 1 H), 1.44-1.18 (m, 4 H), 0.83 (t, J = 7.6 Hz, 3 H). |

| Ex. | Name | Structure | LC-MS | NMR |
|---|---|---|---|---|
| A-18 | trans-1-ethyl-2-[3-(trifluoromethyl)phenyl]cyclo-propanamine hydrochloride | 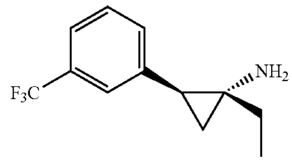 [SMILES: CC[C@@]1(N)C[C@H]1c1cccc(C(F)(F)F)c1] | 230 ([M + H]$^+$) | $^1$H NMR (DMSO-d$_6$) δ (ppm): 8.66 (bs, 3 H), 7.64-7.58 (m, 4 H), 2.73-2.69 (m, 1 H), 1.48-1.07 (m, 4 H), 0.82 (t, J = 7.6 Hz, 3 H). |
| A-19 | trans-1-ethyl-2-[4-(trifluoromethyl)phenyl]cyclo-propanamine hydrochloride | 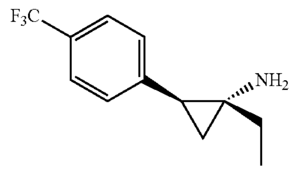 [SMILES: CC[C@@]1(N)C[C@H]1c1ccc(C(F)(F)F)cc1] | 230 ([M + H]$^+$) | $^1$H NMR (DMSO-d$_6$) δ (ppm): 8.73 (bs, 3 H), 7.70-7.67 (m, 2 H), 7.51-7.49 (m, 2 H), 2.73-2.68 (m, 1 H), 1.52-1.17 (m, 4 H), 0.80 (t, J = 7.6 Hz, 3 H). |
| A-20 | trans-1-ethyl-2-(3-fluorophenyl)cyclopropanamine hydrochloride | 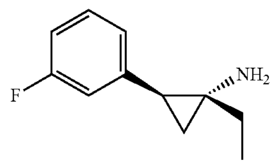 | 180 ([M + H]$^+$) | $^1$H NMR (DMSO-d$_6$) δ (ppm): 8.71 (bs, 3 H), 7.40-7.33 (m, 1 H), 7.13-7.04 (m, 3 H), 2.66-2.60 (m, 1 H), 1.45-1.18 (m, 4 H), 0.81 (t, J = 7.6 Hz, 3 H). |
| A-21 | trans-1-ethyl-2-(3-chlorophenyl)-cyclopropanamine hydrochloride | 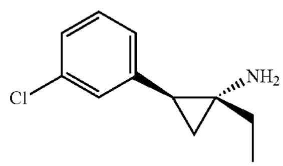 | 196 ([M + H]$^+$) | $^1$H NMR (DMSO-d$_6$) δ (ppm): 8.65 (bs, 3 H), 7.38-7.23 (m, 4 H), 2.64-2.57 (m, 1 H), 1.44-1.13 (m, 4 H), 0.81 (t, J = 7.6 Hz, 3 H). |
| A-22 | trans-1-ethyl-2-(3-bromophenyl)-cyclopropanamine hydrochloride | 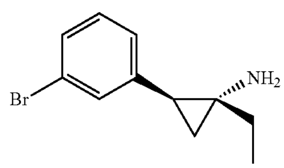 | 240 ([M + H]$^+$) | |
| A-23 | trans-1-ethyl-2-[3-methoxyphenyl]cyclopro-panamine hydrochloride | 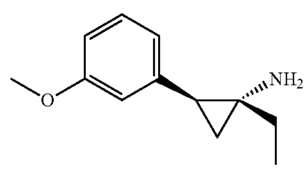 | 228 ([M + H]$^+$) | $^1$H NMR (DMSO-d$_6$) δ (ppm): 8.55 (bs, 3 H), 7.27-7.21 (m, 1 H), 6.83-6.80 (m, 3 H), 3.74 (s, 3 H), 2.58-2.50 (m, 1 H), 1.45-1.15 (m, 4 H), 0.82 (t, J = 7.6 Hz, 3 H). |
| A-24 | 1-ethyl-(trans)-2-[4-(trifluoromethoxy)phenyl]cyclopropanamine hydrochloride | 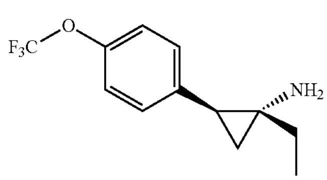 | 282 ([M + H]$^+$) | $^1$H NMR (DMSO-d$_6$) δ (ppm): 8.52 (bs, 3 H), 7.41-7.31 (m, 4 H), 2.63-2.49 (m, 1 H), 1.44-1.13 (m, 4 H), 0.84 (t, J = 7.6 Hz, 3 H). |
| A-25 | trans-1-ethyl-2-(2-fluorophenyl)cyclopropanamine hydrochloride | 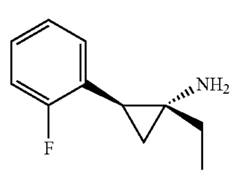 | 180 ([M + H]$^+$) | $^1$H NMR (DMSO-d$_6$) δ (ppm): 8.70 (bs, 3 H), 7.36-7.13 (m, 4 H), 2.67-2.61 (m, 1 H), 1.46-1.18 (m, 4 H), 0.81 (t, J = 7.6 Hz, 3 H). |
| A-26 | trans-1-ethyl-2-(2-chlorophenyl)-cyclopropanamine hydrochloride | 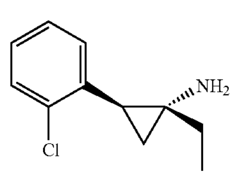 | 196 ([M + H]$^+$) | $^1$H NMR (DMSO-d$_6$) δ (ppm): 8.69 (bs, 3 H), 7.52-7.46 (m, 1 H), 7.33-7.20 (m, 3 H), 2.73-2.67 (m, 1 H), 1.50-1.37 (m, 3 H), 1.09-0.96 (m, 1 H), 0.83 (t, J = 7.6 Hz, 3 H). |

TABLE 1-continued

| Ex. | Name | Structure | LC-MS | NMR |
|---|---|---|---|---|
| A-27 | trans-1-ethyl-2-(2-bromophenyl)-cyclopropanamine hydrochloride | 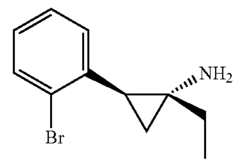 | 240 ([M + H]$^+$) | $^1$H NMR (DMSO-d$_6$) δ (ppm): 8.56 (bs, 3 H), 7.70-7.61 (m, 1 H), 7.40-7.17 (m, 3 H), 2.69-2.57 (m, 1 H), 1.53-0.89 (m, 4 H), 0.89-0.77 (m, 3 H). |
| A-28 | trans-1-(1-naphthylmethyl)-2-phenyl-cyclopropanamine hydrochloride | 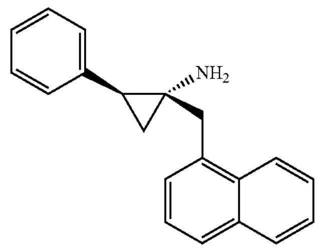 [SMILES: N[C@]1(Cc2cccc3ccccc23)C[C@H]1c1ccccc1] | 274 ([M + H]$^+$) | $^1$H NMR (DMSO-d$_6$) δ (ppm): 8.37 (s, 3 H), 8.02-7.13 (m, 12 H), 3.38 (d, J = 15.7 Hz, 1 H), 2.82-2.68 (m, 2 H), 1.71-1.60 (m, 1 H), 1.55-1.45 (m, 1 H). |
| A-29 | trans-2-(4-bromophenyl)-1-(2-naphthylmethyl)cyclopropanamine hydrochloride | 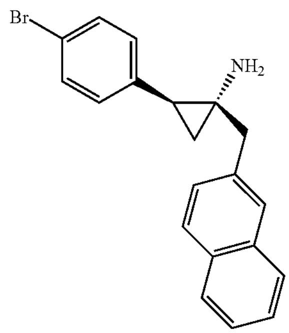 [SMILES: N[C@]1(Cc2ccc3ccccc3c2)C[C@H]1c1ccc(Br)cc1] | 352 ([M + H]$^+$) | $^1$H NMR (DMSO-d$_6$) δ (ppm): 8.40 (s, 3 H), 8.00-7.07 (m, 11 H), AB System: VA = 2.99, VB = 2.5, JAB = 14.9 Hz, 2.74-2.60 (m, 1 H), 1.87-1.76 (m, 1 H), 1.54-1.41 (m, 1 H). |

EXAMPLE A-30 trans-N-[4-[2-amino-2-ethyl-cyclopropyl]phenyl]naphthalene-2-carboxamide hydrochloride

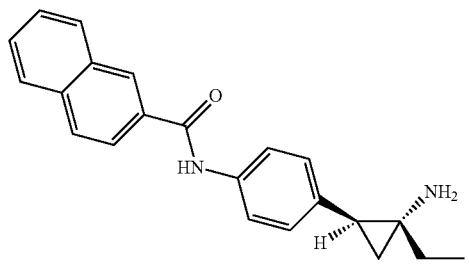 [SMILES: CC[C@@]1(N)C[C@H]1c1ccc(NC(=O)c2ccc3ccccc3c2)cc1]

Ethyl trans-1-ethyl-2-(4-bromophenyl)-cyclopropanecarboxylate 2.4 mL (2.5 mol/L) buthyl lithium was added to a solution of 1.5 g (5.4 mmol) ethyl 2-diethoxyphosphorylbutanoate (Sigma Aldrich) in 5 mL dry DME under N$_2$ atmosphere at RT. After 5 min, 1.0 g (5.0 mmol) 2-(4-bromophenyl) oxirane (Sigma Aldrich) was added dropwise. The mixture was stirred for 20 min at RT and then heated at 135° C. under MW irradiation for 1 h. Aqueous NH$_4$Cl was added, and the product was extracted with CH$_2$Cl$_2$. The combined organic layers were dried over MgSO$_4$ and concentrated. The dry residue was purified by column chromatography (eluent: EtOAc/hexane, 0:100 to 10:100) to give ethyl trans-1-ethyl-2-(4-bromophenyl)-cyclopropanecarboxylate (910 mg, 61%) as a colorless oil. $^1$H NMR (CDCl$_3$) δ (ppm): 7.44-7.40 (m, 2H) 7.10-7.06 (m, 2H), 4.29-4.11 (m, 2 H), 2.80-2.69 (m, 1 H), 1.70-1.63 (m, 1 H), 1.62-1.51 (m, 1 H), 1.30 (t, J=7.1 Hz, 3 H), 1.14-1.10 (m, 1H) 0.98-0.82 (m, 4 H).

trans-1-Ethyl-2-(4-bromophenyl)-cyclopropanecarboxylic acid 20 mL of EtOH/water (1:1) was added to 910 mg (3.06 mmol) ethyl trans-1-ethyl-2-(4-bromophenyl)-cyclopropanecarboxylate. The solution was cooled down to 0° C., then 0.29 g (12.2 mmol) of LiOH was added and the mixture was stirred under reflux for 6 h. The solution was then concentrated, quenched with 2 M HCl, and the formed precipitate was filtered off, washed with water and dried giving 0.77 g (93%) of the trans-1-Ethyl-2-(4-bromophenyl)-cyclopropanecarboxylic acid. $^1$H NMR (DMSO-d$_6$) δ (ppm): 7.48-7.41 (m, 2 H), 7.12-7.08 (m, 2H) 2.93-2.79 (m, 1 H), 1.78-1.74 (m, 1H), 1.69-1.54 (m, 1 H), 1.26-1.16 (m, 1 H), 0.96-0.79 (m, 4 H). MS (ESI): m/z: 268 [M−H]$^−$.

tert-Butyl-N-[trans-1-ethyl-2-(4-bromophenyl)-cyclopropyl]carbamate 0.87 g (3.1 mmol) diphenyl phosphorazidate and 0.38 g (3.7 mmol) TEA were added to a solution of 0.77 g (2.8 mmol) trans-1-ethyl-2-(4-bromophenyl)-cyclopropanecarboxylic acid in 20 mL dry tert-BuOH, and the resulting solution was stirred at 90° C. for 20 h. Then, the mixture was concentrated and the residue was partitioned between 10% aqueous Na₂CO₃ and Et₂O. The combined organic layers were dried (Na₂SO₄), filtered, concentrated, and then purified by column chromatography (eluent: EtOAc/cyclohexane, 1:100 to 20:100) to give 0.47 g (48%) of the tert-butyl-N-[trans-1-ethyl-2-(4-bromophenyl)-cyclopropyl]carbamate. $^1$H NMR (CDCl₃) δ (ppm): 7.45-7.20 (m, 4 H), 5.01 (br. s., 1 H), 2.40 (t, J=8.1 Hz, 1 H), 1.70-1.22 (m, 10 H), 1.14-1.08 (m, 1H) 0.98-0.93 (m, 1H) 0.92-0.72 (m, 4 H). MS (ESI): m/z: 240 [M−100]⁺ trans-tert-Butyl N-[1-ethyl-2-[4-(naphthalene-2-carbonylamino)-phenyl]-cyclopropyl]-carbamate CuI (2 mg, 0.01 mmol), tert-butyl-N-[trans-1-ethyl-2-(4-bromophenyl)-cyclopropyl]carbamate (80 mg, 0.23 mmol), naphthalene-2-carboxamide (44 mg, 0.26 mmol) and K₂CO₃ (65 mg, 0.47 mmol) were placed in a vial and charged with nitrogen. Dioxane (1 mL) and N,N'-dimethylethane-1,2-diamine (2 mg, 0.02 mmol) were added with a syringe, and the vial was heated at 110° C. for 20 h. The resulting suspension was cooled down to RT, then filtered through a silica gel pad and eluted with 15 ml of a CH₂Cl₂/EtOAc (1:1, v:v) mixture. The filtrate was concentrated and the residue was purified by chromatography (CH₂Cl₂ to CH₂Cl₂/EtOAc 95/5) giving 80 mg (79%) of the title compound as a white solid. $^1$H NMR (CDCl₃) δ (ppm): 8.39 (s, 1 H), 8.04-7.29 (m, 11 H), 5.03 (bs, 1 H), 2.45 (t, J=7.8 Hz, 1 H), 1.61-1.43 (m, 10 H), 1.19-1.09 (m, 1 H), 1.05-0.97 (m, 1 H), 0.97-0.77 (m, 4 H). MS (ESI): m/z: 431 [M+H]⁺.

trans-N-[4-[2-Amino-2-ethyl-cyclopropyl]phenyl] naphthalene-2-carboxamide hydrochloride 0.31 ml of a 2 M hydrochloric acid solution in Et₂O (0.6 mmol) was added to a solution of tert-butyl N-[1-ethyl-2-[4-(naphthalene-2-carbonylamino)-phenyl]-cyclopropyl]-carbamate (27 mg, 0.06 mmol) in 1 mL Et₂O at 0° C. The mixture was allowed to stir at RT for 20 h, then the formed solid was filtered, washed with Et₂O and dried to give 17 mg (74%) of trans-N-[4-[2-amino-2-ethyl-cyclopropyl]phenyl] naphthalene-2-carboxamide-hydrochloride as yellow solid. $^1$H NMR (DMSO-d₆) δ (ppm): 10.44 (s, 1 H), 8.57 (s, 1 H), 8.40 (bs, 3 H), 8.14-7.25 (m, 10 H), 2.58-2.51 (m, 1 H), 1.45-1.20 (m, 4 H), 0.83 (t, J=7.3 Hz, 3 H). MS (ESI): m/z: 331 [M+H]⁺.

The following compounds (table 2) were synthesized starting from the appropriate amine or amide and the appropriate bromophenyl intermediate according to the Ullmann type reaction procedure described for example A-30. The benzyloxy compounds A-41 and A-43 were synthesized analogously from the appropriate bromophenyl intermediate and benzyl alcohol according to the Ullmann type reaction procedure with the following modified conditions: the Cu ligand employed was 8-hydroxy-quinoline instead of DMEDA and the base was K₃PO₄ instead of K₂CO₃. Benzyl alcohol was both reactant and solvent of the reaction.

TABLE 2

| Ex. | Name | Structure | LC-MS | NMR |
|---|---|---|---|---|
| A-31 | N-[2-[(trans)-2-amino-2-ethyl-cyclopropyl]phenyl]benzamide hydrochloride | 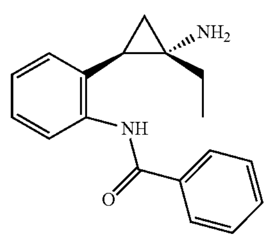 [SMILES: CC[C@]1(N)C[C@@H]1c1ccccc1NC(=O)c1ccccc1] | 281 ([M + H]⁺) | $^1$H NMR (DMSO-d₆) δ (ppm): 10.07 (s, 1 H), 8.40-7.06 (m, 12 H), 2.72-2.61 (m, 1 H), 1.64-1.51 (m, 1 H), 1.37-1.15 (m, 2 H), 1.12-0.97 (m, 1 H), 0.93-0.78 (m, 3 H) |
| A-32 | benzyl N-[3-[[2-[(trans)-2-amino-2-ethyl-cyclopropyl]phenyl]carbamoyl]phenyl]carbamate hydrochloride | 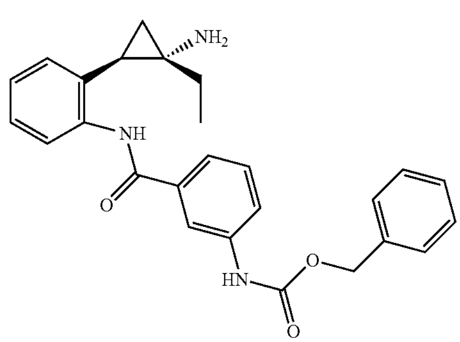 [SMILES: CC[C@]1(N)C[C@@H]1c1ccccc1NC(=O)c1cccc(NC(=O)OCc2ccccc2)c1] | 430 ([M + H]⁺) | $^1$H NMR (DMSO-d₆) δ (ppm): 9.99 (bs, 2 H), 8.23 (bs, 3 H), 8.13-7.01 (m, 13 H), 5.17 (s, 2 H), 2.69-2.58 (m, 1 H), 1.65-1.49 (m, 1 H), 1.36-1.16 (m, 2 H), 1.10-0.95 (m, 1 H), 0.91-0.75 (m, 3 H) |

TABLE 2-continued

| Ex. | Name | Structure | LC-MS | NMR |
|---|---|---|---|---|
| A-33 | benzyl N-[3-[[3-[(trans)-2-amino-2-ethyl-cyclopropyl]phenyl]carbamoyl]phenyl]carbamate hydrochloride | 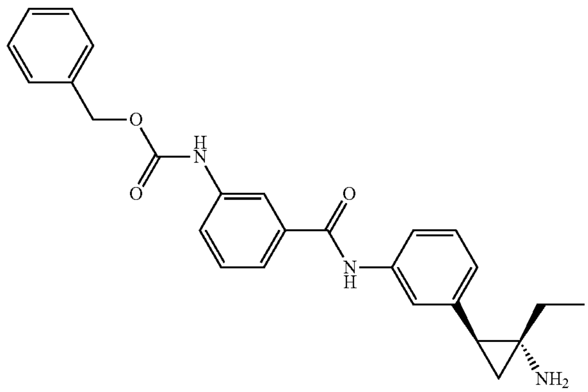 [SMILES: CC[C@@]1(N)C[C@H]1c1cccc(NC(=O)c2cccc(NC(=O)OCc3ccccc3)c2)c1] | 430 ([M + H]$^+$) | $^1$H NMR (DMSO-d$_6$) δ (ppm): 10.24 (s, 1 H), 10.00 (s, 1 H), 8.42 (s, 3 H), 8.15-6.76 (m, 13 H), 5.17 (s, 2 H), 2.61-2.51 (m, 1 H), 1.46-1.16 (m, 4 H), 0.83 (t, J = 7.3 Hz, 3 H) |
| A-34 | N-[4-[(trans-2-amino-2-ethyl-cyclopropyl]phenyl]-3-chloro-benzamide hydrochloride | 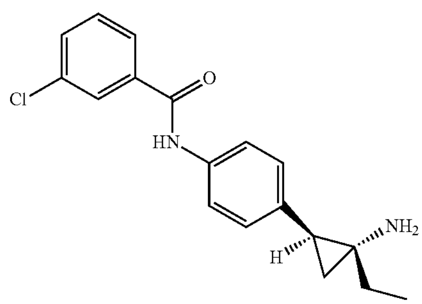 [SMILES: CC[C@@]1(N)C[C@H]1c1ccc(NC(=O)c2cccc(Cl)c2)cc1] | 315 ([M + H]$^+$) | $^1$H NMR (DMSO-d$_6$) δ (ppm): 10.37 (s, 1 H), 8.34 (bs, 3 H), 8.03-7.96 (m, 1 H), 7.92-7.88 (m, 1H), 7.75-7.71 (m, 2H), 7.70-7.64 (m, 1 H), 7.62-7.53 (m, 1 H), 7.26-7.22 (m, 2H), 2.54-2.50 (m, 1 H), 1.45-1.19 (m, 4 H), 0.81 (t, J = 7.3 Hz, 3 H) |
| A-35 | N-[4-[(trans-2-amino-2-ethyl-cyclopropyl]phenyl]-3-phenyl-benzamide 2,2,2-trifluoroacetic acid | 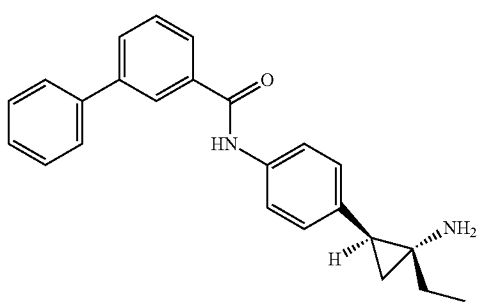 [SMILES: CC[C@@]1(N)C[C@H]1c1ccc(NC(=O)c2cccc(-c3ccccc3)c2)cc1] | 357 ([M + H]$^+$) | $^1$H NMR (CD$_3$OD) δ (ppm): 10.31-10.21 (m, 1 H), 8.19 (s, 1 H), 7.95-7.90 (m, 1 H), 7.88-7.84 (m, 1 H), 7.78-7.68 (m, 4 H), 7.63-7.59 (m, 1 H), 7.53-7.46 (m, 2 H), 7.43-7.36 (m, 1 H), 7.31-7.27 (m, 2H), 2.59-2.52 (m, 1 H), 1.59-1.48 (m, 1 H), 1.43-1.39 (m, 3 H), 0.95 (t, J = 7.6 Hz, 3 H) |
| A-36 | N-[4-[(trans)-2-amino-2-ethyl-cyclopropyl]phenyl]-4-phenyl-benzamide hydrochloride | 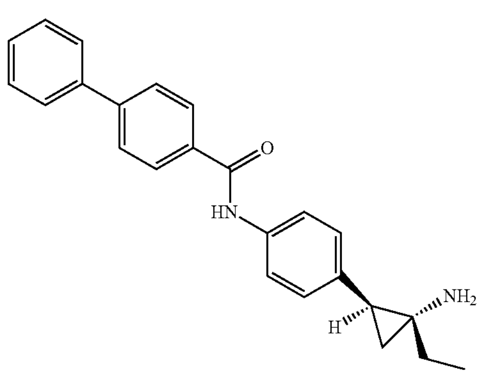 [SMILES: CC[C@@]1(N)C[C@H]1c1ccc(NC(=O)c2ccc(-c3ccccc3)cc2)cc1] | 357 ([M + H]$^+$) | $^1$H NMR (DMSO-d$_6$) δ (ppm): 10.31 (s, 1 H), 8.41 (bs, 3 H), 8.10-8.01 (m, 2 H), 7.86-7.80 (m, 2 H), 7.79-7.73 (m, 4 H), 7.55-7.47 (m, 2 H), 7.46-7.39 (m, 1 H), 7.28-7.19 (m, 2 H), 2.56-2.51 (m, 1 H), 1.44-1.18 (m, 4 H), 0.82 (t, J = 7.3 Hz, 3 H) |

TABLE 2-continued

| Ex. | Name | Structure | LC-MS | NMR |
|---|---|---|---|---|
| A-37 | benzyl N-[3-[[4-[(trans)-2-amino-2-ethyl-cyclopropyl]phenyl]carbamoyl]phenyl]carbamate hydrochloride | 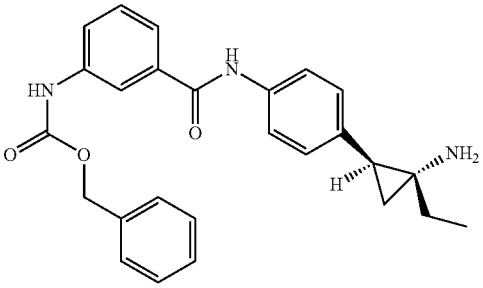 [SMILES: CC[C@@]1(N)C[C@H]1c1ccc(NC(=O)c2cccc(NC(=O)OCc3ccccc3)c2)cc1] | 430 ([M + H]$^+$) | $^1$H NMR (DMSO-d$_6$) δ (ppm): 10.26 (s, 1 H), 10.00 (bs, 1 H), 8.32 (bs, 3 H), 8.01 (bs, 1 H), 7.73-7.69 (m, 2H)7.63 (bs, 1 H), 7.57-7.53 (m, 1H)7.48-7.28 (m, 6 H), 7.24-7.20 (m, 2H) 5.17 (s, 2 H), 2.51-2.48 (m, 1H), 1.31 (d, J = 8.3 Hz, 4 H), 0.81 (t, J = 7.3 Hz, 3 H) |
| A-38 | benzyl N-[4-[[4-[(trans)-2-amino-2-ethyl-cyclopropyl]phenyl]carbamoyl]phenyl]carbamate hydrochloride | 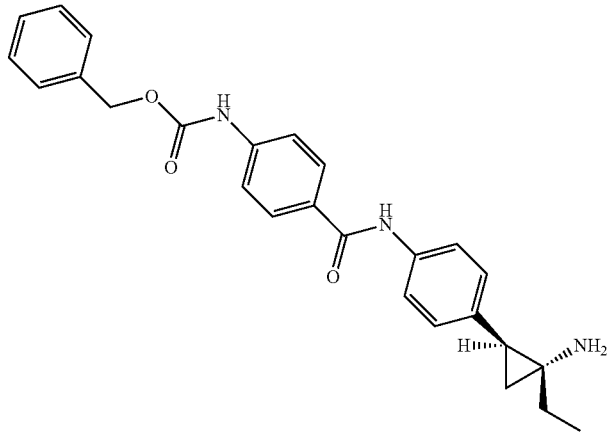 [SMILES: CC[C@@]1(N)C[C@H]1c1ccc(NC(=O)c2ccc(NC(=O)OCc3ccccc3)cc2)cc1] | 430 ([M + H]$^+$) | $^1$H NMR (DMSO-d$_6$) δ (ppm): 10.11 (m, 2 H), 8.29 (bs, 3 H), 7.92-7.88 (m, 2H), 7.73-7.69 (m, 2H), 7.61-7.57 (m, 2H), 7.49-7.30 (m, 5 H), 7.23-7.19 (m, 2H), 5.18 (s, 2 H), 2.47 (m, 1 H), 1.45-1.17 (m, 4 H), 0.81 (t, J = 7.3 Hz, 3 H) |
| A-39 | N-[4-[(trans-2-amino-2-ethyl-cyclopropyl]phenyl]-2-phenyl-acetamide hydrochloride | 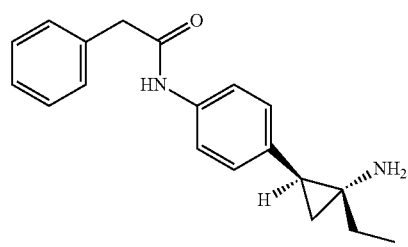 [SMILES: CC[C@@]1(N)C[C@H]1c1ccc(NC(=O)Cc2ccccc2)cc1] | 295 ([M + H]$^+$) | $^1$H NMR (DMSO-d$_6$) δ (ppm): 10.25 (s, 1 H), 8.41 (bs, 3 H), 7.57-7.53 (m, 2H), 7.35-7.29 (m, 4 H), 7.26-7.21 (m, 1 H), 7.20-7.11 (m, 2 H), 3.62 (s, 2 H), 2.49-2.45 (m, 1 H), 1.35-1.19 (m, 4 H), 0.78 (t, J = 7.6 Hz, 3 H) |
| A-40 | N-[4-[(trans)-2-amino-2-ethyl-cyclopropyl]phenyl]-3-phenyl-propanamide hydrochloride | 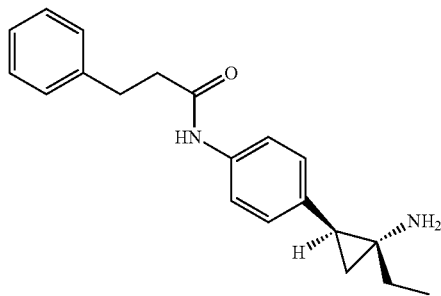 [SMILES: CC[C@@]1(N)C[C@H]1c1ccc(NC(=O)CCc2ccccc2)cc1] | 309 ([M + H]$^+$) | $^1$H NMR (DMSO-d$_6$) δ (ppm): 9.97 (s, 1 H), 8.59-8.34 (m, 3 H), 7.55-7.51 (m, 2H), 7.34-7.10 (m, 7 H), 2.89 (t, J = 7.6 Hz, 2 H), 2.61 (t, J = 7.6 Hz, 2 H), 2.49-2.45 (m, 1 H), 1.43-1.11 (m, 4 H), 0.79 (t, J = 7.3 Hz, 3 H) |
| A-41 | 2-(4-benzyloxyphenyl)-trans-1-ethyl-cyclopropanamine hydrochloride | 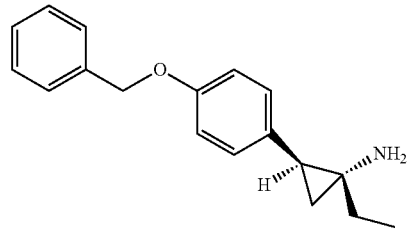 [SMILES: CC[C@@]1(N)C[C@H]1c1ccc(OCc2ccccc2)cc1] | 268 ([M + H]$^+$) | $^1$H NMR (DMSO-d$_6$) δ (ppm): 8.39 (bs, 3 H), 7.48-7.36 (m, 4 H), 7.35-7.31 (m, 1 H), 7.18-7.14 (m, 2H), 6.98-6.94 (m, 2H), 5.07 (s, 2 H), 2.49-2.45 (m, 1 H), 1.42-1.08 (m, 4 H), 0.80 (t, J = 7.3 Hz, 3 H) |

TABLE 2-continued

| Ex. | Name | Structure | LC-MS | NMR |
|---|---|---|---|---|
| A-42 | N-[4-[(2-amino-trans-2-ethyl-cyclopropyl]phenyl] benzene sulfonamide hydrochloride | 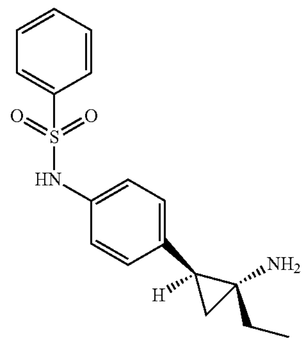 [SMILES: CC[C@@]1(N)C[C@H]1c1ccc(NS(=O)(=O)c2ccccc2)cc1] | 317 ([M + H]$^+$) | $^1$H NMR (DMSO-d$_6$) δ (ppm): 10.25 (s, 1 H), 8.37 (bs, 3 H), 7.73-7.69 (m, 2 H), 7.63-7.56 (m, 1 H), 7.55-7.47 (m, 2 H), 7.13-7.06 (m, 2 H), 7.04-7.00 (m, 2H), 2.47-2.37 (m, 1 H), 1.35-1.12 (m, 4 H), 0.72 (t, J = 7.3 Hz, 3 H) |
| A-43 | trans-1-benzyl-2-(4-benzyloxyphenyl) cyclopropanamine hydrochloride | 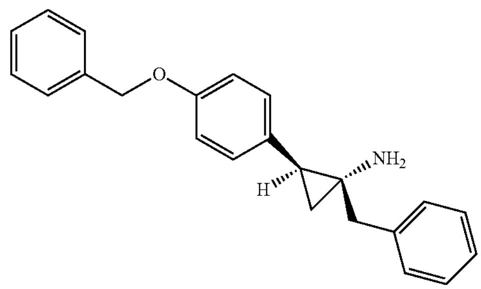 [SMILES: N[C@]1(Cc2ccccc2)C[C@H]1c1ccc(OCc2ccccc2)cc1] | 330 ([M + H]$^+$) | $^1$H NMR (DMSO-d$_6$) δ (ppm): 8.36-8.05 (m, 3 H), 7.53-7.20 (m, 10 H), 7.13-7.09 (m, 2H), 7.04-7.00 (m, 2H), 5.10 (s, 2 H), 2.85-2.75 (m, 1 H), 2.59-2.53 (m, 1 H), 2.33-2.29 (m, 1H), 1.64-1.60 (m, 1 H), 1.39-1.32 (m, 1 H) |
| A-44 | N-[4-[tyrans-2-amino-2-(2-naphthylmethyl) cyclopropyl]phenyl] benzamide hydrochloride | 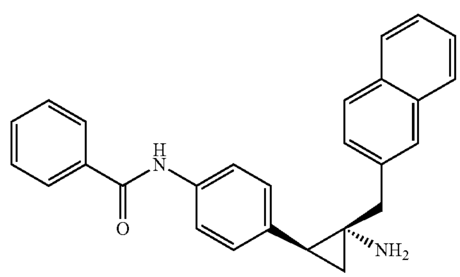 [SMILES: N[C@]1(Cc2ccc3ccccc3c2)C[C@H]1c1ccc(NC(=O)c2ccccc2)cc1] | 393 ([M + H]$^+$) | $^1$H NMR (DMSO-d$_6$) δ (ppm): 10.31 (s, 1 H), 8.34 (s, 3 H), 8.05-7.22 (m, 16 H), AB System: VA = 2.99, VB = 2.55, JAB = 15.2 Hz, 2.71-2.61 (m, J = 7.6, 9.5 Hz, 1 H), 1.83-1.71 (m, J = 6.8, 6.8 Hz, 1 H), 1.49-1.37 (m, 1 H) |
| A-45 | benzyl N-[3-[[4-[(trans)-2-amino-2-(2-naphthylmethyl) cyclopropyl]phenyl] carbamoyl]phenyl] carbamate hydrochloride | 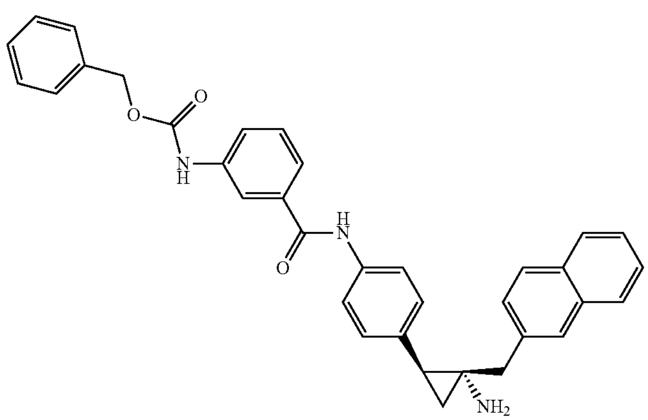 [SMILES: N[C@]1(Cc2ccc3ccccc3c2)C[C@H]1c1ccc(NC(=O)c2cccc(NC(=O)OCc3ccccc3)c2)cc1] | 542 ([M + H]$^+$) | $^1$H NMR (DMSO-d$_6$) δ (ppm): 10.30 (s, 1 H), 10.00 (s, 1 H), 8.30 (s, 3 H), 8.07-6.93 (m, 20 H), 5.17 (s, 2 H), AB System: VA = 2.98, VB = 2.55, JAB = 15.2 Hz, 2.69-2.60 (m, 1 H), 1.82-1.71 (m, 1 H), 1.48-1.39 (m, 1 H) |

TABLE 2-continued

| Ex. | Name | Structure | LC-MS | NMR |
|---|---|---|---|---|
| A-46 | N-[4-[(trans-2-amino-2-(2-naphthylmethyl)cyclopropyl]phenyl]-2-phenyl-acetamide hydrochloride | 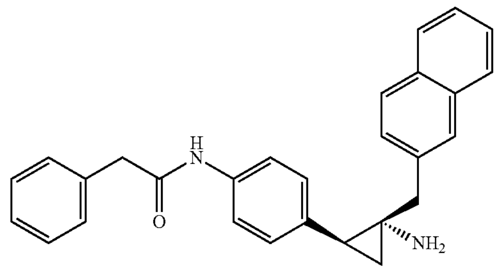 [SMILES: N[C@]1(Cc2ccc3ccccc3c2)C[C@H]1c1ccc(NC(=O)Cc2ccccc2)cc1] | 407 ([M + H]⁺) | ¹H NMR (DMSO-d₆) δ (ppm): 10.27 (s, 1 H), 8.31 (s, 3 H), 7.96-7.14 (m, 16 H), 3.64 (s, 2 H), 3.02-2.85 (m, 1 H), 2.67-2.56 (m, 1 H), 2.54-2.50 (m, 1 H), 1.74 (s, 1 H), 1.49-1.23 (m, 1 H) |

Example A-47

N-[4-[trans-2-amino-2-ethyl-cyclopropyl]phenyl] benzamide hydrochloride

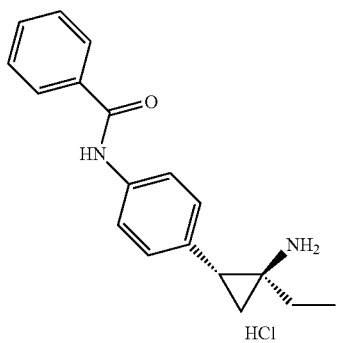 [SMILES: CC[C@]1(N)C[C@@H]1c1ccc(NC(=O)c2ccccc2)cc1 ; Cl]

tert-Butyl-N-[trans-2-(4-aminophenyl)-1-ethyl-cyclopropyl]carbamate

A mixture of CuI (55 mg, 0.29 mmol), tert-butyl-N-[trans-1-ethyl-2-(4-bromophenyl)-cyclopropyl]carbamate (50 mg, 0.15 mmol, Example 30, 3ʳᵈ step), 2-aminoethanol (0.005 mL, 0.2 mmol) and NaN₃ (10 mg, 0.147 mmol) in dry DMA (0.500 mL) was stirred at 95° C. overnight under N₂ atmosphere. After 20 h of heating the reaction mixture was diluted with EtOAc (15 mL) and then filtered through a Celite pad. The filtrate was concentrated under reduced pressure and the resulting residue was purified by chromatography (eluent: n-hexane/EtOAc 95:05) to give 16 mg (40%) of tert-butyl N -[trans-2-(4-aminophenyl)-1-ethyl-cyclopropyl]carbamate as a brown oil. ¹H NMR (CDCl₃) δ (ppm): 7.22-6.94 (m, 2 H), 6.74-6.55 (m, 2 H), 5.00 (s, 1 H), 2.99 (bs, 2 H), 2.44-2.22 (m, 1 H), 1.77-1.31 (m, 10 H), 1.15-1.01 (m, 1 H), 0.98-0.76 (m, 5 H). MS (ESI): m/z: 277 [M+H]⁺.

tert-Butyl N-[trans-(2-(4-benzamidophenyl)-1-ethyl-cyclopropyl]carbamate

A solution of tert-butyl N-[trans-2-(4-aminophenyl)-1-ethyl-cyclopropyl]carbamate (25 mg, 0.090 mmol) in dry THF (1.500 mL) under nitrogen was cooled down to 0° C. TEA (0.015 mL, 0.11 mmol) was then added and after 5 minutes benzoyl chloride (0.012 mL, 0.099 mmol) was added in one portion. After 30 min the reaction mixture was concentrated and the resulting residue was purified by chromatography (eluent: n-hexane/EtOAc 80:20) to give 26 mg (76%) of tert-butyl N-[trans-(2-(4-benzamidophenyl)-1-ethyl-cyclopropyl]carbamate as a white solid. ¹H NMR (CDCl₃) δ (ppm): 7.93-7.86 (m, 2 H), 7.84 (s, 1 H), 7.67-7.53 (m, 3 H), 7.53-7.43 (m, 2 H), 7.40-7.30 (m, 2 H), 5.01 (s, 1 H), 2.49-2.34 (m, 1 H), 1.67-1.41 (m, 10 H), 1.18-1.06 (m, 1 H), 1.03-0.96 (m, 1 H), 0.96-0.81 (m, 4 H). MS (ESI): m/z: 381 [M+H]⁺.

trans-N-[4-[2-Amino-2-ethyl-cyclopropyl]phenyl] benzamide hydrochloride trans-tert-Butyl N-[(2-(4-benzamidophenyl)-1-ethyl-cyclopropyl]carbamate (8 mg, 0.02 mmol) was dissolved in Et₂O (1.0 mL). The solution was cooled down to 0° C. and then 0.053 mL of a 1.25 M HCl solution in Et₂O (0.10 mmol) was added. The mixture was stirred 4 h at RT and then the solvent was evaporated and the residue was crystallized with methanol and Et₂O obtaining 4 mg (60%) of trans-N-[4-[2-amino-2-ethyl -cyclopropyl]phenyl]benzamide hydrochloride as a yellow solid. ¹H NMR (DMSO-d₆) δ (ppm): 10.26 (s, 1 H), 8.33 (s, 3 H), 8.02-7.85 (m, 2 H), 7.79-7.68 (m, 2 H), 7.65-7.44 (m, 3 H), 7.34-7.08 (m, 2 H), 2.56-2.46 (m, 1 H), 1.49-1.11 (m, 4 H), 0.81 (t, J=7.3 Hz, 3 H). MS (ESI): m/z: 281 [M+H]⁺.

EXAMPLE A-48 trans-4-(2-Amino-2-ethyl-cyclopropyl)aniline dihydrochloride

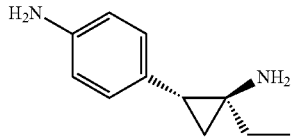

tert-butyl-N-[trans-2-(4-aminophenyl)-1-ethyl-cyclopropyl]carbamate (10 mg, 0.028 mmol), obtained as described for Example 47, was dissolved in Et₂O (0.5 mL). The solution was cooled to 0° C. and 1.39 mL of a 1.25 M HCl solution in methanol (0.174 mmol) was added. The reaction was stirred 48 h at RT. The solvents were evaporated and the residue triturated with Et₂O obtaining 6 mg (83%) of trans-4-(2-amino-2-ethyl -cyclopropyl)aniline dihydrochloride as a yellow solid. ¹H NMR (DMSO-d₆) δ (ppm):

10.13-8.78 (m, 3 H), 8.50 (s, 3 H), 7.43-6.92 (m, 4 H), 2.62-2.45 (m, 1 H), 1.54-1.04 (m, 4 H), 0.79 (t, J=1.0 Hz, 3 H). MS (ESI): m/z: 177 [M+H]+.

EXAMPLE A-49 trans-2-(3-Azidophenyl)-1-ethyl-cyclopropanamine hydrochloride

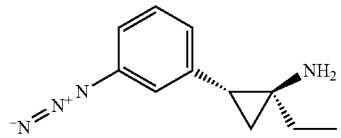

trans-tert-Butyl N-[2-(3-azidophenyl)-1-ethyl-cyclopropyl]carbamate 120 mg (0.3526 mmol) of tert-butyl N-[(1S,2R)-2-(3-bromophenyl)-1-ethyl -cyclopropyl]carbamate, 0.010 g (0.053 mmol) of CuI, 10 mg (0.053 mmol) of sodium (2R)-2-[(1S)-1,2-dihydroxyethyl]-4-hydroxy-5-oxo-2H-furan-3-olate, 12 µl (0.078 mmol) of (1R,2R)—N,N'-dimethylcyclohexane-1,2-diamine and 25 mg (0.39 mmol) sodium azide in 2 ml ethanol were placed in a vial and charged with nitrogen. The vial was heated at 80° C. for 1 h. The resulting suspension was cooled down to RT and concentrated. The solid was triturated with Et$_2$O and then purified by column chromatography (eluent: EtOAc/hexane, 5:100 to 30:100) to give 80 mg (75%) of the trans-tert-butyl N-[2-(3-azidophenyl)-1-ethyl-cyclopropyl]carbamate. $^1$H NMR (CDCl$_3$) δ (ppm): 0.76-0.92 (m, 4 H) 0.93-1.05 (m, 1 H) 1.08-1.21 (m, 1 H) 1.39-1.67 (m, 10 H) 2.34-2.52 (m, 1 H) 4.90-5.08 (m, 1 H) 6.82-7.33 (m, 4 H).

trans-2-(3-Azidophenyl)-1-ethyl-cyclopropanamine hydrochloride trans-tert-butyl N-[2-(3-azidophenyl)-1-ethyl-cyclopropyl]carbamate was hydrolyzed following the procedures described for Example 48 giving trans-2-(3-azidophenyl)-1-ethyl-cyclopropanamine hydrochloride as white solid. $^1$H NMR (DMSO-d$_6$) δ (ppm): 8.48-8.15 (m, 3 H), 7.37 (t, J=7.83 Hz, 1 H), 7.13-6.91 (m, 3 H), 2.58-2.42 (m, 1 H), 1.49-1.29 (m, 3 H), 1.27-1.11 (m, 3 H), 0.81 (t, J=7.34 Hz, 3 H). MS (ESI): m/z: 203 [M+H]+.

EXAMPLE B-1

1-amino-(trans)-2-phenyl-cyclopropyl]methanol

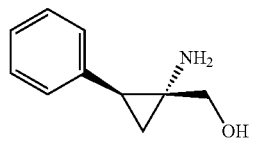 [SMILES: N[C@]1(CO)C[C@H]1c1ccccc1]

Ethyl 1-nitro-2-phenyl-cyclopropanecarboxylate

Styrene (4.32 mL, 37.6 mmol) was added to a flask containing rhodium acetate (20 mg, 0.04 mmol) and ethyl nitroacetate (1.0 g, 7.5 mmol). Iodobenzene diacetate (2.7 g, 8.3 mmol) was then added in one portion and the mixture allowed to stir for 2 h open to air. The solvent, excess of styrene and iodobenzene were removed under reduced pressure resulting a brownish oil, which was used in the next step without any further purification.

Ethyl 1-amino-2-phenylcyclopropancarboxylate 75.131 mL of 1 M HCl (75.131 mmol) was added to a solution of crude ethyl 1-nitro-2-phenyl-cyclopropanecarboxylate in 100 mL i-PrOH. 9.829 g (150.26 mmol) Zinc dust was then added in small portions over 15 min and the solution was allowed to stir for 3 h at RT. The suspension was quenched with saturated NaHCO$_3$, stirred for 15 min, then filtered through a celite pad and rinsed with EtOAc. The aqueous phase was extracted with CH$_2$Cl$_2$ and the combined organic phases were dried over Na$_2$SO$_4$, filtered and evaporated under reduced pressure. The crude mixture composed by the cis/trans isomer was utilized in the next step without further purification.

Ethyl-1-(tert-butoxycarbonylamino)-2-phenyl-cyclopropanecarboxylate

Crude ethyl 1-amino-2-phenyl-cyclopropanecarboxylate and 0.971 g (7.51 mmol) DIPEA were added to a solution of 1.640 g (7.513 mmol) tert-butoxycarbonyl-tert-butyl carbonate in 20 mL CH$_2$Cl$_2$. The mixture was stirred for 20 h at RT. Water was added and the product was extracted with CH$_2$Cl$_2$. The combined organic phases were dried over Na$_2$SO$_4$ and evaporated. The crude mixture was purified by column chromatography (hexane/EtOAc 9:1). 400 mg of trans isomer as colorless oil and 180 mg of cis isomer as yellow solid were obtained. 25% yield from ethyl nitroacetate. Cis analogue: $^1$H NMR (CDCl$_3$) δ (ppm): 7.40-7.11 (m, 5 H), 4.59 (bs, 1 H), 4.32-4.10 (m, 2 H), 2.94 (t, J=8.8 Hz, 1 H), 2.12 (bs, 1 H), 1.75 (d, J=6.8 Hz, 1 H), 1.47-1.08 (m, 12 H). MS (ESI): m/z: 206 [M−100+H]+. Trans analogue: $^1$H NMR (DMSO-d$_6$) δ (ppm): =7.79 (s, 1 H), 7.36-7.09 (m, 5 H), 3.81-3.55 (m, 2 H), 2.72 (t, J=8.8 Hz, 1 H), 2.08-1.92 (m, 1 H), 1.47-1.20 (m, 10 H), 0.90-0.65 (m, 3 H). MS (ESI): m/z: 206 [M−100+H]+.

tert-Butyl-N-[1-(hydroxymethyl)-(trans)-2-phenyl-cyclopropyl]carbamate 0.100 g (0.327 mmol) of ethyl-1-(tert-butoxycarbonylamino)-2-phenyl-cyclopropanecarboxylate was dissolved in 1 mL THF and added dropwise to a suspension of 0.017 g (0.46 mmol) LiAlH$_4$ in 2 mL THF at 0° C. The reaction mixture was allowed to reach RT and stirred for 6 h. The suspension was cooled down to 0° C. and quenched with saturated sodium bisulfate. The suspension was diluted with EtOAc and filtered through a celite pad. The solution was dried, concentrated, and the crude mixture was purified by column chromatography (hexane/EtOAc from 8:2 to 1:1) to give 38 mg (44%) of tert-butyl-N-[1-(hydroxymethyl)-(trans)-2-phenyl-cyclopropyl]carbamate as a colorless oil. $^1$H NMR (CDCl$_3$) δ (ppm): 7.44-7.15 (m, 5 H), 5.28 (bs, 1 H), 3.54-3.28 (m, 2 H), 2.53 (dd, J=7.6, 9.0 Hz, 1 H), 1.62-1.42 (m, 9 H), 1.35 (t, J=6.4 Hz, 1 H), 1.31-1.23 (m, 1 H). MS (ESI): m/z: 286 [M+Na]+.

[1-Amino-(trans)-2-phenyl-cyclopropyl]methanol 0.5 mL 4 M HCl in dioxane was added to a solution of 0.03 g (0.1 mmol) tert-butyl N-[1-(hydroxymethyl)-2-phenyl-cyclopropyl]carbamate in 0.5 mL dioxane. The reaction mixture was stirred at RT for 4 h, then the solvent was evaporated under vacuum and the product was triturated with Et$_2$O. Crystallization from MeOH/Et$_2$O gave 16 mg (70%, hydrochloride) of the trans-1-amino-2-phenyl-cyclopropyl]methanol as white solid. $^1$H NMR (DMSO-d$_6$) δ (ppm): 8.41 (bs, 3 H), 7.39-7.16 (m, 5 H), 5.16 (bs, 1 H), 3.29 (dd, J=4.6, 12.0 Hz, 1 H), 3.21-3.07 (m, 1 H), 2.57 (t, J=8.6 Hz, 1 H), 1.37 (d, J=7.3 Hz, 2 H). MS (ESI): m/z: 164 [M+H]$^+$.

EXAMPLE B-2

[1-Amino-(cis)-2-phenyl-cyclopropyl]methanol

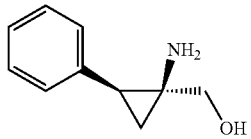 [SMILES: N[C@@]1(CO)C[C@H]1c1ccccc1]

The compound was prepared analogously starting from the ethyl 1-(tert -butoxycarbonylamino)-(cis)-2-phenyl-cyclopropanecarboxylate. $^1$H NMR (DMSO-d$_6$) δ (ppm): 8.01 (bs, 3 H), 7.43-7.22 (m, 5 H), 5.44 (t, J=5.1 Hz, 1 H), 3.74 (dd, J=5.9, 11.7 Hz, 1 H), 3.48 (dd, J=3.9, 11.7 Hz, 1 H), 2.40 (dd, J=7.3, 9.3 Hz, 1 H), 1.36 (t, J=6.8 Hz, 1 H), 1.28 (dd, J=6.4, 9.8 Hz, 1 H). MS (ESI): m/z: 164 [M+H]$^+$.

EXAMPLE C-1

(1R,2S)-1-ethyl-N-[(2-methoxyphenyl)methyl]-2-phenyl-cyclopropanamine

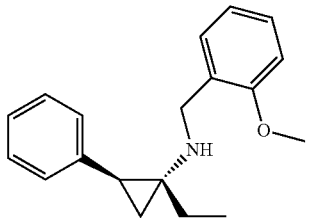 [SMILES: CC[C@@]1(NCc2ccccc2OC)C[C@H]1c1ccccc1]

A mixture of 0.030 g (0.15 mmol) (1R,2S)-1-ethyl-2-phenyl-cyclopropanamine hydrochloride and 0.025 g (0.18 mmol) 2-methoxybenzaldehyde (Sigma Aldrich) in 1.2 mL CH$_2$Cl$_2$ and 0.05 mL water was vigorously stirred at RT for 10 min. Then, 0.048 g (0.23 mmol) NaBH(OAc)$_3$ was slowly added and the reaction was allowed to continue for further 2 h. The reaction mixture was washed with 1 ml of an aqueous saturated NaHCO$_3$ solution and extracted with CH$_2$Cl$_2$. The organic layer was dried over Na$_2$SO$_4$, filtered off and evaporated. The crude mixture was purified by column chromatography (eluent: CH$_2$Cl$_2$) to give 25 mg (58%) of (1R,2S)-1-ethyl-N-[(2-methoxyphenyl)methyl]-2-phenyl-cyclopropanamine as colorless oil. $^1$H NMR (CDCl$_3$) δ (ppm): 7.69-7.65 (m, 1H), 7.40-7.30 (m, 1 H), 7.27-7.14 (m, 3 H), 7.04-6.88 (m, 4 H), 4.29-4.11 (m, 2 H), 3.94 (s, 3 H), 3.01-2.97 (m, 1H), 1.91-1.87 (m, 1H), 1.63-1.53 (m, 1 H), 1.17-0.98 (m, 5 H). MS (ESI): m/z: 282 [M+H]$^+$.

EXAMPLE C-2

(1R,2S)-1-ethyl-N-[(2-methoxy-1-naphthyl)methyl]-2-phenyl-cyclopropanamine

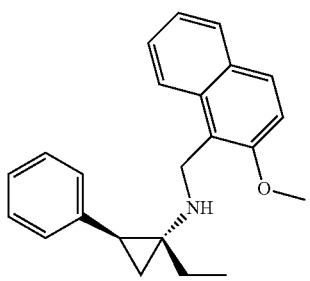 [SMILES: CC[C@@]1(NCc2c(OC)ccc3ccccc23)C[C@H]1c1ccccc1]

The following compound was prepared analogously to Example C-1 starting from the (1R,2S)-1-ethyl-2-phenyl-cyclopropanamine hydrochloride and 2-methoxynaphthalene-1-carbaldehyde (Sigma Aldrich). $^1$H NMR (CDCl$_3$) δ (ppm): 8.13-8.09 (m, 1H), 7.86-7.76 (m, 2 H), 7.56-7.51 (m, 1H), 7.38-7.34 (m, 1H), 7.32-7.15 (m, 6 H), 4.44-4.28 (m, 2 H), 4.00 (s, 3 H), 2.45 (bs, 1 H), 1.72-1.54 (m, 1 H), 1.25-1.07 (m, 2 H), 1.05-0.92 (m, 4 H). MS (ESI): m/z: 332 [M+H]$^+$.

EXAMPLE C-3

2-[[(1S,2R)-1-methyl-2-phenyl-cyclopropyl]amino]-1-(4-methylpiperazin-1-yl)ethanone dihydrochloride

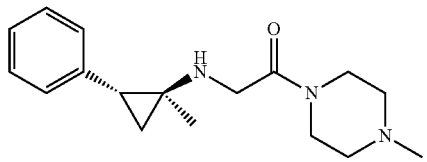 [SMILES: CN1CCN(C(=O)CN[C@@]2(C)C[C@@H]2c2ccccc2)CC1]

tert-Butyl-N-[(1S,2R)-1-methyl-2-phenyl-cyclopropyl]carbamate 0.77 g (2.8 mmol) Diphenyl phosphorazidate and 0.34 g (3.3 mmol) TEA were added to a solution of 0.45 g (2.6 mmol) of (1S,2R)-1-methyl-2-phenyl-cyclopropanecarboxylic acid in 25 mL dry tert-BuOH. The resulting solution was stirred at 90° C. for 20 h. The solvent was then removed and the residue partitioned between 10% aqueous Na$_2$CO$_3$ and Et$_2$O. The combined organic layers were dried over Na$_2$SO$_4$, concentrated, and purified by column chromatography (eluent: EtOAc/cyclohexane, 1:100 to 20:100) to give 370 mg (59%) of tert-butyl-N-[(1S,2R)-1-methyl-2-phenyl-cyclopropyl]carbamate. $^1$H NMR (CDCl$_3$) δ (ppm): 7.51-7.01 (m, 5 H), 5.02 (s, 1 H), 2.49-2.28 (m, 1 H), 1.74-1.36 (m, 9 H), 1.21-1.15 (m, 1 H), 1.11-0.98 (m, 4 H).

tert-Butyl-N-[(1S,2R)-1-methyl-2-phenyl-cyclopropyl]-N-[2-(4-methylpiperazin-1-yl)-2-oxo-ethyl]carbamate 0.05 g (0.20 mmol) of tert-butyl-N-[(1S,2R)-1-methyl-2-phenyl-cyclopropyl]carbamate in 2 mL anhydrous DMF was added to a suspension of 0.012 g (0.51 mmol) NaH in 3 mL anhydrous DMF at 0° C. After 30 min 0.047 g (0.22 mmol) 2-chloro-1-(4-methylpiperazin-1-yl)ethanone hydrochloride (ChemBridge Corp.) was added and the mixture was stirred at 0° C. for 1 h. Then, the solution was concentrated under vacuum and the residue purified by column chromatography (eluent: $CH_2Cl_2$ and $MeOH/NH_3$ (99:0.1) 95:5) to give 25 mg (32%) of the tert-butyl-N-[(1S,2R)-1-methyl-2-phenyl-cyclopropyl]-N-[2-(4-methylpiperazin-1-yl)-2-oxo-ethyl] carbamate as colorless oil. $^1$H NMR (DMSO-$d_6$) δ (ppm): 7.40-7.07 (m, 5 H), 4.09-4.01 (m, 2 H), 3.60-3.36 (m, 4 H), 2.47-2.38 (m, 1 H), 2.37-2.26 (m, 4 H), 2.20 (s, 3 H), 1.50-1.34 (m, 9 H), 1.31-1.18 (m, 1 H), 1.09-0.83 (m, 4 H). MS (ESI): m/z: 388 $[M+H]^+$.

2-[[(1S,2R)-1-methyl-2-phenyl-cyclopropyl]amino]-1-(4-methylpiperazin-1-yl)ethanone dihydrochloride 0.022 g (0.057 mmol) tert-butyl-N-[(1S,2R)-1-methyl-2-phenyl-cyclopropyl]-N-[2-(4-methylpiperazin-1-yl)-2-oxo-ethyl]carbamate was suspended in 0.200 mL of dry $CH_2Cl_2$ at 0° C. and treated with 1 mL of 4 M HCl in dioxane for 3 h. The solvent was evaporated obtaining an oil, which was triturated with dry $Et_2O$ and $CH_2Cl_2$ to give 10 mg (49%) of 2-[[(1S,2R)-1-methyl-2-phenyl-cyclopropyl]amino]-1-(4-methylpiperazin-1-yl)ethanone dihydrochloride as a white solid. $^1$H NMR ($D_2O$) δ (ppm): 7.31-7.24 (m, 2 H), 7.23-7.13 (m, 3 H), 4.49-4.37 (m, 1 H), 4.33-4.13 (m, 2 H), 3.98-3.86 (m, 1 H), 3.56-3.39 (m, 3 H), 3.14-2.93 (m, 3 H), 2.82 (s, 3 H), 2.69-2.56 (m, 1 H), 1.52-1.38 (m, 1 H), 1.32-1.22 (m, 1 H), 1.01 (s, 3 H). MS (ESI): m/z: 288 $[M+H]^+$.

EXAMPLE C-4

2-[[(1S,2S)-1-methyl-2-phenyl-cyclopropyl]amino]-1-(4-methylpiperazin-1-yl)ethanone

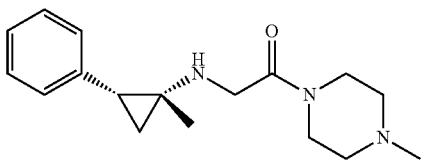 [SMILES: CN1CCN(C(=O)CN[C@]2(C)C[C@@H]2c2ccccc2)CC1]

About a 10% of cis derivative C-4 was formed during the last step of the synthesis of example C-3. A purification by preparative HPLC afforded 2-[[(1S,2S)-1-methyl-2-phenyl-cyclopropyl]amino]-1-(4-methylpiperazin-1-yl)ethanone as its trifluoro acetic salt. $^1$H NMR ($D_2O$) δ (ppm): 7.57-7.17 (m, 5 H), 3.31 (bs, 8 H), 2.77 (s, 3 H), 2.52-2.41 (m, 1 H), 1.62-1.53 (m, 1 H), 1.49 (s, 3 H), 1.27-1.06 (m, 1 H). MS (ESI): m/z: 288 $[M+H]^+$.

The following compounds (table 3) were synthesized starting from the appropriate BOC-protected amine and the appropriate chloro or bromo-alkyl derivative according to the procedure described for example C-3. The cis compound C-7 was prepared according to the procedure described for example C-4. The cis compounds C-9 and C-11 were obtained starting from their corresponding cis-BOC-protected intermediates (tert-butyl N-[cis-1-ethyl-2-phenyl-cyclopropyl]-N-methyl-carbamate for C-9 and tert-butyl N-ethyl -N-[cis-1-ethyl-2-phenyl-cyclopropyl]carbamate for C-11) which were formed by treatment of the trans-BOC intermediate with DMF and NaH according to the conditions described for the second step of the synthesis of example C-3 (about 10 to 20% relative to the trans analogues) and were separated from their corresponding trans analogues by column chromatography (eluent: EtOAc/hexane, 0:100 to 2:98).

TABLE 3

| Ex. | Name | Structure | LC-MS | NMR |
|---|---|---|---|---|
| C-5 | 1-[(3S)-3-aminopyrrolidin-1-yl]-2-[[(1S,2R)-1-methyl-2-phenyl-cyclopropyl]amino]ethanone hydrochloride | 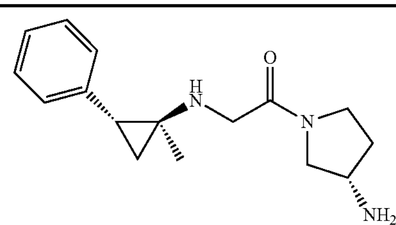 | 274 ([M + H]$^+$) | $^1$H NMR ($D_2O$) δ (ppm): 7.33-7.25 (m, 2 H), 7.25-7.14 (m, 3 H), 4.15-4.04 (m, 2 H), 4.03-3.90 (m, 1 H), 3.85-3.68 (m, 1 H), 3.64-3.47 (m, 3 H), 2.70-2.55 (m, 1 H), 2.45-2.21 (m, 1 H), 2.19-1.95 (m, 1 H), 1.52-1.39 (m, 1 H), 1.32-1.23 (m, 1 H), 1.02 (s, 3 H). |
| C-6 | trans-2-[[(1-ethyl-2-phenyl-cyclopropyl]amino]-1-(1-methylpiperazin-1-yl)ethanone trifluoroacetate | 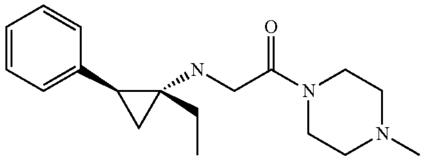 [SMILES: CC[C@@]1(NCC(=O)N2CCN(C)CC2)C[C@H]1c1ccccc1] | 302 ([M + H]$^+$) | $^1$H NMR ($CD_3OD$) δ (ppm): 7.35-7.30 (m, 5 H), 4.41-4.28 (m, 2 H), 4.17-3.35 (m, 8 H), 2.98 (s, 3 H), 2.80-2.70 (m, 1 H), 1.61-1.38 (m, 4 H), 0.89 (s, 3 H). |
| C-7 | cis-2-[[(1-ethyl-2-phenyl-cyclopropyl]amino]-1-(4-methylpiperazin-1-yl)ethanone; trifluoroacetate | 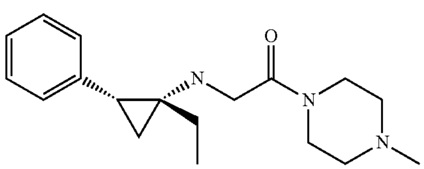 [SMILES: CC[C@@]1(NCC(=O)N2CCN(C)CC2)C[C@@H]1c1ccccc1] | 302 ([M + H]$^+$) | $^1$H NMR ($CD_3OD$) δ (ppm): 7.49-7.31 (m, 5 H), 4.15-4.04 (m, 2 H), 3.91-3.39 (m, 8 H), 2.98-2.87 (m, 3 H), 2.65-2.58 (m, 1 H), 2.14-2.07 (m, 1 H), 1.87-1.81 (m, 1 H), 1.67-1.60 (m, 1 H), 1.38-1.32 (m, 1 H), 1.19-1.10 (m, 3 H). MS |

TABLE 3-continued

| Ex. | Name | Structure | LC-MS | NMR |
|---|---|---|---|---|
| | | | | (ESI): m/z: 302 [M + H]⁺. |
| C-8 | trans-1-ethyl-N-methyl-2-phenyl-cyclopropanamine hydrochloride | 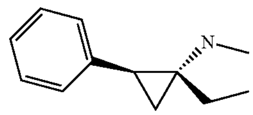 | 176 ([M + H]⁺) | $^1$H NMR (DMSO-d$_6$) δ (ppm): 9.03 (bs, 2 H), 7.41-7.16 (m, 5 H), 2.72-2.59 (m, 4 H), 1.50-1.41 (m, 2 H), 1.40-1.33 (m, 1 H), 1.16-1.05 (m, 1 H), 0.80 (t, J = 7.6 Hz, 3 H) |
| C-9 | cis-1-ethyl-N-methyl-2-phenyl-cyclopropanamine hydrochloride | 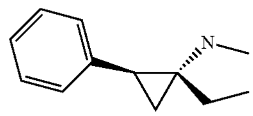 | 176 ([M + H]⁺) | $^1$H NMR (DMSO-d$_6$) δ (ppm): 8.69 (bs, 1 H), 7.82 (bs, 1 H), 7.47-7.24 (m, 5 H), 2.49-2.39 (m, 4 H), 2.12-1.99 (m, 1 H), 1.61-1.50 (m, 1 H), 1.45-1.38 (m, 1 H), 1.30-1.21 (m, 1 H), 1.06 (t, J = 7.6 Hz, 3 H) |
| C-10 | trans-1-ethyl-N-ethyl-2-phenyl-cyclopropanamine hydrochloride | 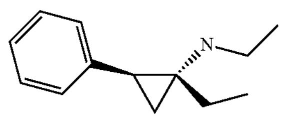 | 190 ([M + H]⁺) | $^1$H NMR (DMSO-d$_6$) δ (ppm): 9.12 (bs, 2 H), 7.39-7.19 (m, 5 H), 3.11 (bs., 2 H), 2.80-2.65 (m, 1 H), 1.55-1.47 (m, 1 H), 1.46-1.33 (m, 2 H), 1.29 (t, J = 7.3 Hz, 3 H), 1.19-1.07 (m, 1 H), 0.80 (t, J = 7.3 Hz, 3 H) |
| C-11 | cis-1-ethyl-N-ethyl-2-phenyl-cyclopropanamine hydrochloride | 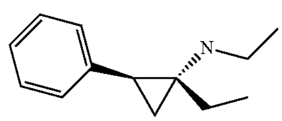 | 190 ([M + H]⁺) | $^1$H NMR (DMSO-d$_6$) δ (ppm): 8.32 (bs, 1 H), 8.09 (bs, 1 H), 7.48-7.24 (m, 5 H), 3.06-2.91 (m, 1 H), 2.86-2.70 (m, 1 H), 2.46-2.35 (m, 1 H), 2.12-1.99 (m, 1 H), 1.66-1.56 (m, 1 H), 1.54-1.47 (m, 1 H), 1.35-1.27 (m, 1 H), 1.05 (t, J = 7.3 Hz, 3 H), 1.00 (t, J = 7.1 Hz, 3 H) |
| C-12 | trans-2-[[1-ethyl-2-phenyl-cyclopropyl]amino] acetamide hydrochloride | 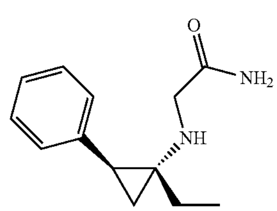 [SMILES: CC[C@@]1(NCC(N)=O)C[C@H]1c1ccccc1] | 219 ([M + H]⁺) | $^1$H NMR (DMSO-d$_6$) δ (ppm): 9.15 (bs, 2 H), 7.91 (bs, 1 H), 7.70 (bs, 1 H), 7.36-7.21 (m, 5 H), 3.96-3.72 (m, 2 H), 2.74-2.61 (m, 1 H), 1.53-1.45 (m, 1 H), 1.44-1.30 (m, 2 H), 1.16-1.03 (m, 1 H), 0.78 (t, J = 7.6 Hz, 3 H) |

According to the procedure described for example C-1 the following compounds (table 4) were synthesized starting from the appropriate amine and aldehyde:

TABLE 4

| C-13 | trans-N-benzyl-1-ethyl-2-phenyl-cyclopropanamine hydrochloride | | 252 ([M + H]⁺) | $^1$H NMR (DMSO-d$_6$) δ (ppm): 9.39-9.30 (m, 2 H), 7.70-7.60 (m, 2 H), 7.52-7.40 (m, 3 H), 7.33-7.27 (m, 2 H), 7.26-7.20 (m, 1 H), 7.16-7.11 (m, 2 H), 4.32 (bs, 2 H), 2.76-2.66 (m, 1 H), 1.64-1.47 (m, 2 H), 1.42-1.32 (m, 1 H), 1.25-1.13 (m, 1 H), 0.87 (t, J = 7.3 Hz, 3 H) |

TABLE 4-continued

| | | | | |
|---|---|---|---|---|
| C-14 | trans-N-[(3,4-dimethoxyphenyl)methyl]-1-ethyl-2-phenyl-cyclopropanamine hydrochloride | | 312 ([M + H]$^+$) | $^1$H NMR (DMSO-d$_6$) δ (ppm): 9.31 (bs, 2 H), 7.36 (d, J = 1.5 Hz, 1 H), 7.33-7.27 (m, 2 H), 7.26-7.21 (m, 1 H), 7.16-7.09 (m, 3 H), 7.02 (d, J = 8.3 Hz, 1 H), 4.24 (bs, 2 H), 3.79 (s, 3 H), 3.78 (s, 3 H), 2.75-2.66 (m, 1 H), 1.64-1.46 (m, 2 H), 1.39-1.32 (m, 1 H), 1.22-1.09 (m, 1 H), 0.87 (t, J = 7.3 Hz, 3 H) |
| C-15 | trans-N-[(4,7-dimethoxy-1-naphthyl)methyl]-1-ethyl-2-phenyl-cyclopropanamine hydrochloride | | 362 ([M + H]$^+$) | $^1$H NMR (DMSO-d$_6$) δ (ppm): 9.22-9.02 (m, 2 H), 8.18 (d, J = 9.3 Hz, 1 H), 7.74 (d, J = 7.8 Hz, 1 H), 7.41-7.31 (m, 5 H), 7.30-7.19 (m, 2 H), 6.94 (d, J = 8.3 Hz, 1 H), 4.73 (bs, 2 H), 3.99 (s, 3 H), 3.96 (s, 3 H), 2.85-2.74 (m, 1 H), 1.79-1.67 (m, 1 H), 1.61-1.53 (m, 1 H), 1.48-1.35 (m, 2 H), 0.93 (t, J = 7.3 Hz, 3 H) |
| C-16 | trans-N-[(2-chloro-3-pyridyl)methyl]-1-ethyl-2-phenyl-cyclopropanamine hydrochloride | | 287 ([M + H]$^+$) | $^1$H NMR (DMSO-d$_6$) δ (ppm): 9.62-9.43 (m, 2 H), 8.51 (d, J = 2.9 Hz, 1 H), 8.29 (d, J = 6.8 Hz, 1 H), 7.66-7.54 (m, 1 H), 7.42-7.22 (m, 5 H), 4.47 (bs, 2 H), 2.88-2.78 (m, 1 H), 1.69-1.54 (m, 2 H), 1.53-1.41 (m, 1 H), 1.36-1.21 (m, 1 H), 0.91 (t, J = 7.3 Hz, 3 H) |
| C-17 | trans-N-[(2,2-dimethylchroman-6-yl)methyl]-1-ethyl-2-phenyl-cyclopropanamine hydrochloride | | 336 ([M + H]$^+$) | $^1$H NMR (DMSO-d$_6$) δ (ppm): 9.15 (bs, 2 H), 7.35 (s, 1 H), 7.32-7.27 (m, 3 H), 7.26-7.21 (m, 1 H), 7.15-7.09 (m, 2 H), 6.78 (d, J = 8.3 Hz, 1 H), 4.19 (bs, 2 H), 2.75 (t, J = 6.6 Hz, 2 H), 2.69-2.62 (m, 1 H), 1.79 (t, J = 6.6 Hz, 2 H), 1.63-1.52 (m, 1 H), 1.50-1.43 (m, 1 H), 1.38-1.33 (m, 1 H), 1.29 (s, 3 H), 1.28 (s, 3 H), 1.20-1.11 (m, 1 H), 0.87 (t, J = 7.3 Hz, 3 H) |

EXAMPLE D-1

Cis-1,2-diphenylcyclopropanamine hydrochloride

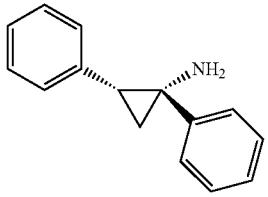 [SMILES: N[C@]1(c2ccccc2)C[C@@H]1c1ccccc1]

Cis-1,2-diphenylcyclopropanamine hydrochloride was prepared as described in Acta Chem. Scand., 1966, 1424-1426. $^1$H NMR (DMSO-d$_6$) δ (ppm): =8.57 (s, 3 H), 7.60-7.32 (m, 10 H), 2.68-2.61 (m, 1 H), 1.96-1.90 (m, 1 H), 1.87-1.80 (m, 1 H). MS (ESI): m/z: 210 [M+H]$^+$.

EXAMPLE D-2

Trans-1,2-diphenylcyclopropanamine hydrochloride

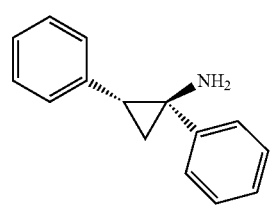 [SMILES: N[C@@]1(c2ccccc2)C[C@@H]1c1ccccc1]

Trans-1,2-diphenylcyclopanamine hydrochloride was prepared as described in Acta Chem. Scand., 1966, 1424-1426. $^1$H NMR (DMSO-d$_6$) δ (ppm): =8.94 (s, 3 H), 7.41-6.88 (m, 10 H), 2.93-2.82 (m, 1 H), 2.13-2.06 (m, 1 H), 1.87-1.75 (m, 1 H). MS (ESI): m/z: 210 [M+H]$^+$.

According to the procedure described for example A-1 the following compounds (Table 5) were synthesized starting from the appropriate styrene oxide and phosphonoacetate. Compounds A-62, A-70, A-81, A-84, A-88, A-89, A-96, A-97, A-98, A-99, A-100, A-106, A-107, A-117, and A-118 were purified by preparative HPLC. The cis compound A-63 was obtained using as starting material its corresponding cis-BOC-protected intermediate tert-butyl N-[cis-1-ethyl-2-phenyl-cyclopropyl]carbamate, which was formed by treatment of the trans-BOC intermediate with DMF and NaH according to the conditions described for the second step of the synthesis of example C-3 (about 50% relative to the trans analogue) and was separated from the trans analogue by column chromatography (eluent: EtOAc/hexane, 2:98 to 20:80).

TABLE 5

| ID | Name | Structure | MS | NMR |
|---|---|---|---|---|
| A-50 | trans-2-(4-bromo-3-fluoro-phenyl)-1-ethyl-cyclopropanamine hydrochloride | 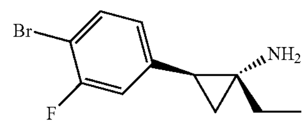 | 259 ([M + H]$^+$) | $^1$H NMR (DMSO-d$_6$) δ (ppm): 8.44 (bs, 3 H), 7.72-7.59 (m, 1 H), 7.32-7.23 (m, 1 H), 7.13-7.04 (m, 1 H), 2.58-2.51 (m, 1 H), 1.46-1.29 (m, 3 H), 1.27-1.13 (m, 1 H), 0.79 (t, J = 7.3 Hz, 3 H). |
| A-51 | trans 2-(3-bromophenyl)-1-phenethyl-cyclopropanamine hydrochloride | 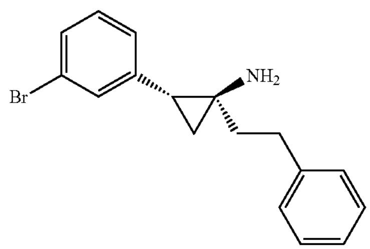 [SMILES: N[C@@]1(CCc2ccccc2)C[C@@H]1c1cccc(Br)c1] | 316 ([M + H]$^+$) | |
| A-52 | (1R,2S)-1,2-diphenylcyclopropanamine hydrochloride | 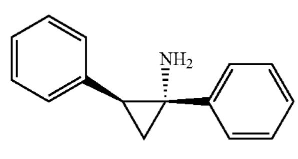 [SMILES: N[C@]1(c2ccccc2)C[C@H]1c1ccccc1] | 210 ([M + H]$^+$) | $^1$H NMR (DMSO-d$_6$) δ (ppm): 8.95 (s, 3 H), 7.37-7.31 (m, 2 H), 7.26-7.18 (m, 3 H), 7.12-7.00 (m, 3 H), 6.97-6.93 (m, 2 H), 2.87 (dd, J = 7.6, 10.0 Hz, 1 H), 2.13-2.06 (m, 1 H), 1.85-1.79 (m, 1 H). |
| A-53 | (1S,2R)-1,2-diphenylcyclopropanamine hydrochloride | 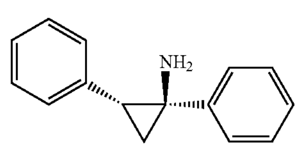 [SMILES: N[C@@]1(c2ccccc2)C[C@@H]1c1ccccc1] | 210 ([M + H]$^+$) | $^1$H NMR (DMSO-d$_6$) δ (ppm): 8.95 (s, 3 H), 7.37-7.31 (m, 2 H), 7.26-7.18 (m, 3 H), 7.12-7.00 (m, 3 H), 6.97-6.93 (m, 2 H), 2.87 (dd, J = 7.6, 10.0 Hz, 1 H), 2.13-2.06 (m, 1 H), 1.85-1.79 (m, 1 H). |
| A-54 | trans-2-(4-fluorophenyl)-1-(2-naphthylmethyl)cyclopropanamine hydrochloride | 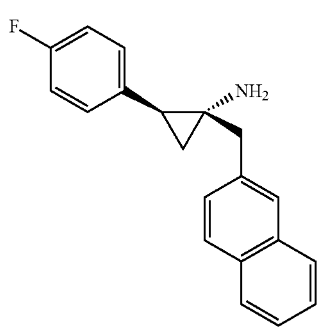 [SMILES: N[C@]1(Cc2ccc3ccccc3c2)C[C@H]1c1ccc(F)cc1] | 292 ([M + H]$^+$) | $^1$H NMR (DMSO-d$_6$) δ (ppm): 8.65 (s, 3 H), 7.90-7.21 (m, 11 H), 3.07 (d, J = 15.7 Hz, 1 H), 2.78-2.74 (m, 1 H), 2.47-2.46 (m, 1 H), 1.76-1.73 (m, 1 H), 1.54-1.50 (m, 1 H). |

| | | | | |
|---|---|---|---|---|
| A-55 | trans-2-(4-chlorophenyl)-1-(2-naphthylmethyl)cyclopropanamine hydrochloride | | 308 ([M + H]⁺) | ¹H NMR (DMSO-d₆) δ (ppm): 8.70 (s, 3 H), 7.90-7.30 (m, 11 H), 3.07 (d, J = 15.7 Hz, 1 H), 2.80-2.76 (m, 1 H), 2.49-2.48 (m, 1 H), 1.79-1.75 (m, 1 H), 1.57-1.53 (m, 1 H). |
| A-56 | trans-2-(3-chlorophenyl)-1-(2-naphthylmethyl)cyclopropanamine hydrochloride | | 308 ([M + H]⁺) | ¹H NMR (DMSO-d₆) δ (ppm): 8.57 (s, 3 H), 7.91-7.30 (m, 11 H), 3.04 (d, J = 15.7 Hz, 1 H), 2.77-2.73 (m, 1 H), 2.55-2.54 (m, 1 H), 1.88-1.85 (m, 1 H), 1.54-1.50 (m, 1 H). |
| A-57 | trans-2-(3-bromophenyl)-1-(2-naphthylmethyl)cyclopropanamine hydrochloride | | 352 ([M + H]⁺) | ¹H NMR (DMSO-d₆) δ (ppm): 8.57 (s, 3 H), 7.91-7.30 (m, 11 H), 2.91 (d, J = 15.7 Hz, 1 H), 2.59-2.53 (m, 2 H), 1.79-1.72 (m, 1 H), 1.46-1.40 (m, 1 H). |
| A-58 | trans-2-(4-chlorophenyl)-1-phenethyl-cyclopropanamine hydrochloride | | 272 ([M + H]⁺) | ¹H NMR (DMSO-d₆) δ (ppm): 8.87 (s, 3 H), 7.42-7.39 (m, 2 H), 7.34-7.10 (m, 5 H), 6.91-6.89 (m, 2 H), 2.67-2.56 (m, 3 H), 1.63-1.37 (m, 4 H). |
| A-59 | trans-2-(4-fluorophenyl)-1-phenethyl-cyclopropanamine hydrochloride | | 256 ([M + H]⁺) | ¹H NMR (DMSO-d₆) δ (ppm): 8.80 (s, 3 H), 7.39-7.32 (m, 2 H), 7.22-7.08 (m, 5 H), 6.92-6.88 (m, 2 H), 2.66-2.53 (m, 2 H), 2.48-2.40 (m, 1 H), 1.60-1.33 (m, 4 H) |
| A-60 | trans-1-benzyl-2-(4-fluorophenyl)cyclopropanamine | | 242 ([M + H]⁺) | ¹H NMR (DMSO-d₆) δ (ppm): 8.62 (s, 3 H), 7.39-7.13 (m, 9 H), 2.91 (d, 1H), 2.75-2.70 (m, 1 H), 2.28 (d, 1H), 1.65-1.62 (m, 1 H), 1.49-1.45 (m, 1 H). |

TABLE 5-continued

| Ex. | Name | Structure | LC-MS | NMR |
|---|---|---|---|---|
| A-61 | trans-1-benzyl-2-(4-chlorophenyl)cyclo-propanamine hydrochloride | 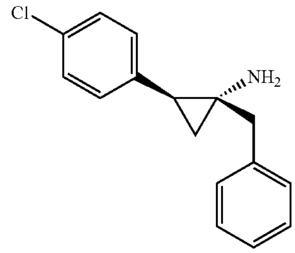 [SMILES: N[C@]1(Cc2ccccc2)C[C@H]1c1ccc(Cl)cc1] | | ¹H NMR (DMSO-$d_6$) δ (ppm): 8.67 (s, 3 H), 7.44-7.14 (m, 9 H), 2.91 (d, 1H), 2.77-2.73 (m, 1 H), 2.28 (d, 1H), 1.67-1.63 (m, 1 H), 1.52-1.49 (m, 1 H). |
| A-62 | trans 2-(4-bromophenyl)-1-phenethyl-cyclopropanamine 2,2,2-trifluoroacetic acid | 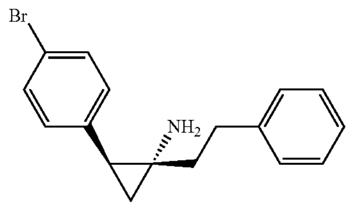 [SMILES: N[C@]1(CCc2ccccc2)C[C@H]1c1ccc(Br)cc1] | 316 ([M + H]$^+$) | ¹H NMR (DMSO-$d_6$) δ (ppm): 8.29 (bs, 3 H), 7.57-7.48 (m, 2 H), 7.29-7.06 (m, 5 H), 6.92-6.83 (m, 2 H), 2.65-2.41 (m, 3 H), 1.61-1.31 (m, 4 H). |
| A-63 | cis-1-ethyl-2-phenyl-cyclopropanamine hydrochloride | 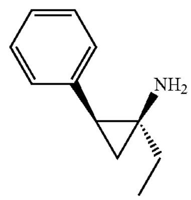 | 162 ([M + H]$^+$) | ¹H NMR (DMSO-$d_6$) δ (ppm): 7.95 (bs, 3 H), 7.43-7.26 (m, 5 H), 2.35-2.25 (m, 1 H), 2.03-1.91 (m, 1 H), 1.57-1.46 (m, 1 H), 1.42-1.9 (m, 2 H), 1.09-1.00 (m, 3 H). |
| A-64 | (1R,2S)-1-methyl-2-phenyl-cyclopropanamine hydrochloride | 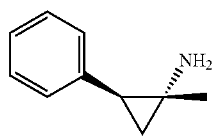 | 148 ([M + H]$^+$) | ¹H NMR (DMSO-$d_6$) δ (ppm): 8.45 (s, 3 H), 7.36-7.30 (m, 2 H), 7.27-7.21 (m, 3 H), 2.50-2.46 (m, 1 H), 1.41-1.35 (m, 1 H), 1.26-1.21 (m, 1 H), 1.02 (s, 3 H). |
| A-65 | trans-1-methyl-2-phenyl-cyclopropanamine hydrochloride | 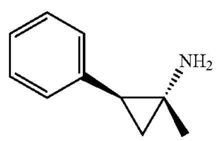 | 148 ([M + H]$^+$) | ¹H NMR (DMSO-$d_6$) δ (ppm): 8.42 (bs, 3 H), 7.40-7.13 (m, 5 H), 2.48-2.45 (m, 1 H), 1.41-1.34 (m, 1 H), 1.28-1.20 (m, 1 H), 1.02 (s, 3 H). |

The following compounds (table 6) were synthesized starting from the appropriate amine or amide and the appropriate bromophenyl intermediate according to the Ullmann type reaction procedure described for example A-30. The benzyloxy compound A-67 was synthesized analogously from the appropriate bromophenyl intermediate and benzyl alcohol according to the Ullmann type reaction procedure with the following modified conditions: the Cu ligand employed was 8-hydroxy-quinoline instead of DMEDA and the base was $K_3PO_4$ instead of $K_2CO_3$. Benzyl alcohol was both reactant and solvent of the reaction.

TABLE 6

| Ex. | Name | Structure | LC-MS | NMR |
|---|---|---|---|---|
| A-66 | N-[4-(trans-2-amino-2-ethyl-cyclopropyl)phenyl]-3-[(1-methyl-4-piperidyl)amino]-4-phenyl-benzamide dihydrochloride | 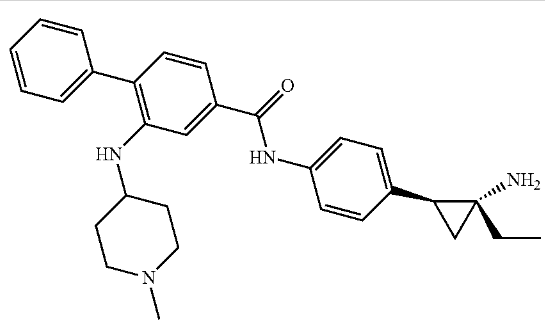 | 542 ([M + H]$^+$) | |

TABLE 6-continued

| Ex. | Name | Structure | LC-MS | NMR |
|---|---|---|---|---|
| A-67 | 2-(4-benzyloxyphenyl)-1-(2-naphthylmethyl)cyclopropanamine hydrochloride | 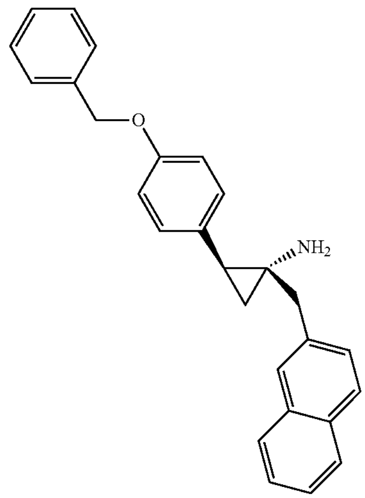 [SMILES: N[C@]1(Cc2ccc3ccccc3c2)C[C@H]1c1ccc(OCc2ccccc2)cc1] | 380 ([M + H]$^+$) | $^1$H NMR (DMSO-d$_6$) δ (ppm): 8.26 (s, 3 H), 7.92-6.99 (m, 16 H), 5.12 (s, 2 H), 3.01-2.92 (m, 1 H), 2.62-2.56 (m, 1 H), 2.53-2.49 (m, 1 H), 1.75-1.68 (m, 1 H), 1.44-1.37 (m, 1 H). |
| A-68 | N-[4-trans-[2-amino-2-ethyl-cyclopropyl]phenyl]-2-(1-naphthyl)acetamide hydrochloride | 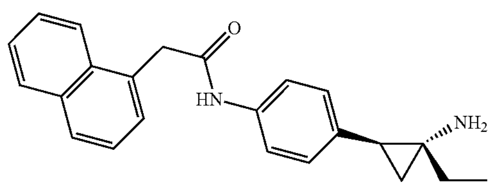 [SMILES: CC[C@@]1(N)C[C@H]1c1ccc(NC(=O)Cc2cccc3ccccc23)cc1] | 345 ([M + H]$^+$) | $^1$H NMR (DMSO-d$_6$) δ (ppm): 10.35 (s, 1 H), 8.27 (bs, 3 H), 8.17-7.11 (m, 11 H), 4.13 (s, 2 H), 2.47-2.41 (m, 1 H), 1.39-1.13 (m, 4 H), 0.78 (t, J = 7.6 Hz, 3 H). |
| A-69 | N-[4-trans-[2-amino-2-ethyl-cyclopropyl]phenyl]-2-(4-nitrophenyl)acetamide hydrochloride | 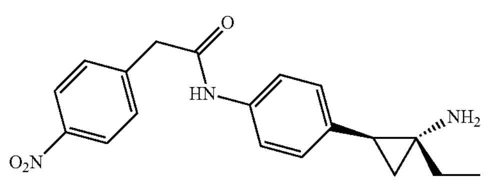 [SMILES: CC[C@@]1(N)C[C@H]1c1ccc(NC(=O)Cc2ccc([N+](=O)[O-])cc2)cc1] | 340 ([M + H]$^+$) | $^1$H NMR (DMSO-d$_6$) δ (ppm): 10.37 (s, 1 H), 8.53-8.27 (m, 3 H), 8.23-8.14 (m, 2 H), 7.65-7.47 (m, 4 H), 7.21-7.10 (m, 2 H), 3.83 (s, 2 H), 2.47-2.38 (m, 1 H), 1.40-1.16 (m, 4 H), 0.87-0.71 (m, 3 H). |
| A-70 | benzyl N-[4-[[4-[trans-2-amino-2-(2-naphthylmethyl)cyclopropyl]phenyl]carbamoyl]phenyl]carbamate 2,2,2-trifluoroacetic acid | 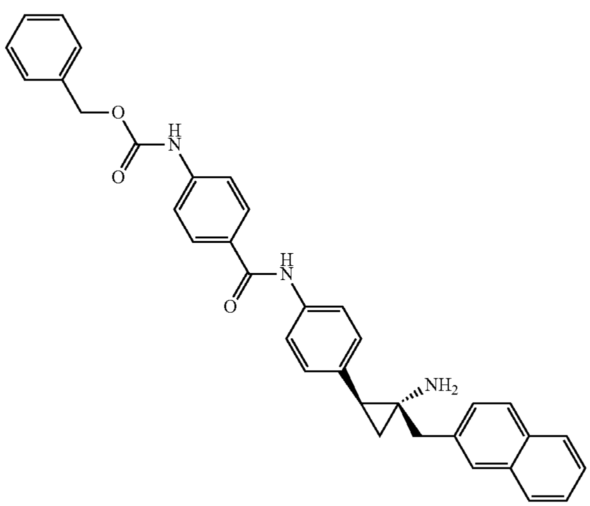 [SMILES: N[C@]1(Cc2ccc3ccccc3c2)C[C@H]1c1ccc(NC(=O)c2ccc(NC(=O)OCc3ccccc3)cc2)cc1] | 542 ([M + H]$^+$) | $^1$H NMR (DMSO-d$_6$) δ (ppm): 10.13 (d, J = 15.7 Hz, 2 H), 8.20 (s, 3 H), 7.97-7.13 (m, 20 H), 5.18 (s, 2 H), 2.96 (d, J = 15.2 Hz, 1 H), 2.68-2.52 (m, 2 H), 1.86-1.75 (m, 1 H), 1.48-1.36 (m, 1 H). |

TABLE 6-continued

| Ex. | Name | Structure | LC-MS | NMR |
| --- | --- | --- | --- | --- |
| A-71 | N-[4-(trans-2-amino-2-ethyl-cyclopropyl)phenyl] naphthalene-1-carboxamide hydrochloride | 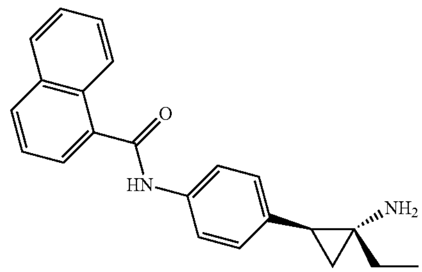 [SMILES: CC[C@@]1(N)C[C@H]1c1ccc(NC(=O)c2cccc3ccccc23)cc1] | 331 ([M + H]⁺) | ¹H NMR (DMSO-d₆) δ (ppm): 10.58 (s, 1 H), 8.46 (bs, 3 H), 8.21-7.95 (m, 3 H), 7.82-7.68 (m, 3 H), 7.64-7.51 (m, 3 H), 7.29-7.19 (m, 2 H), 2.58-2.50 (m, 1 H), 1.46-1.19 (m, 4 H), 0.83 (t, J = 7.3 Hz, 3 H). |
| A-72 | N-[4-[trans-2-amino-2-(2-naphthylmethyl) cyclopropyl]phenyl] naphthalene-2-carboxamide hydrochloride | 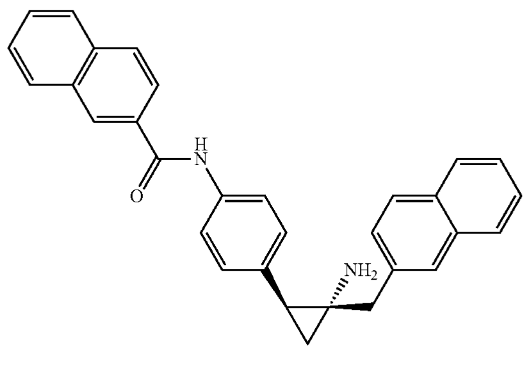 [SMILES: N[C@]1(Cc2ccc3ccccc3c2)C[C@H]1c1ccc(NC(=O)c2ccc3ccccc3c2)cc1] | 443 ([M + H]⁺) | ¹H NMR (DMSO-d₆) δ (ppm): 10.51 (s, 1 H), 8.67-6.89 (m, 21 H), 3.07-2.95 (m, 1 H), 2.73-2.62 (m, 1 H), 2.63-2.53 (m, 1 H), 1.84-1.36 (m, 2 H). |
| A-73 | N-[4-[trans-2-amino-2-(2-naphthylmethyl) cyclopropyl] phenyl]-4-phenyl-benzamide hydrochloride | 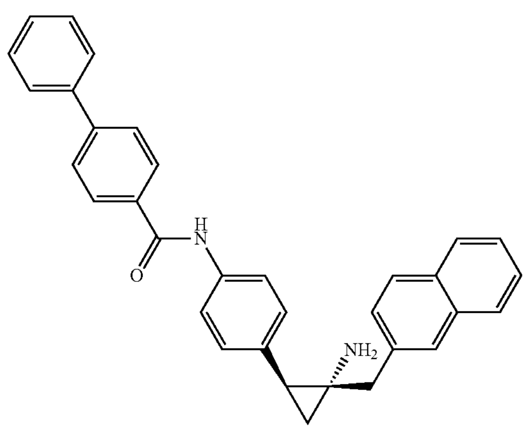 [SMILES: N[C@]1(Cc2ccc3ccccc3c2)C[C@H]1c1ccc(NC(=O)c2ccc(-c3ccccc3)cc2)cc1] | 469 ([M + H]⁺) | ¹H NMR (DMSO-d₆) δ (ppm): 10.37 (s, 1 H), 8.31 (bs, 3 H), 8.12-7.23 (m, 20 H), 3.04-2.93 (m, 1 H), 2.71-2.60 (m, 1 H), 2.60-2.53 (m, 1 H), 1.84-1.41 (m, 2 H). |
| A-74 | N-[4-trans-2-amino-2-ethyl-cyclopropyl] phenyl]-2-(2-naphthyl) acetamide hydrochloride | 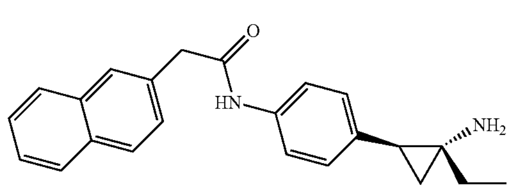 [SMILES: CC[C@@]1(N)C[C@H]1c1ccc(NC(=O)Cc2ccc3ccccc3c2)cc1] | 345 ([M + H]⁺) | ¹H NMR (DMSO-d₆) δ (ppm): 10.32 (s, 1 H), 8.51-8.26 (m, 3 H), 7.95-7.77 (m, 4 H), 7.62-7.42 (m, 5 H), 7.23-7.10 (m, 2 H), 3.81 (s, 2 H), 2.48-2.39 (m, 1 H), 1.38-1.12 (m, 4 H), 0.78 (t, J = 7.6 Hz, 3 H). |

TABLE 6-continued

| Ex. | Name | Structure | LC-MS | NMR |
|---|---|---|---|---|
| A-75 | N-[4-[trans-2-amino-2-phenyl-cyclopropyl]phenyl]benzamide hydrochloride | 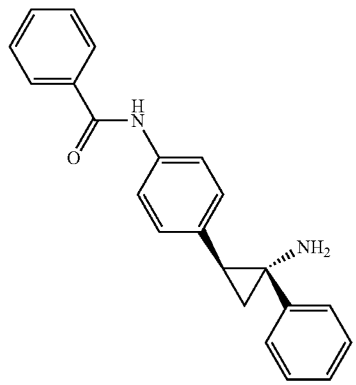 [SMILES: N[C@]1(c2ccccc2)C[C@H]1c1ccc(NC(=O)c2ccccc2)cc1] | 329 ([M + H]+) | $^1$H NMR (DMSO-$d_6$) δ (ppm): 10.10 (s, 1 H), 8.95-8.77 (m, 3 H), 7.97-6.55 (m, 14 H), 2.91-2.72 (m, 1 H), 2.22-2.02 (m, 1 H), 1.86-1.70 (m, 1 H). |
| A-76 | N-[4-[trans-2-amino-2-(2-naphthylmethyl)cyclopropyl]phenyl]-2-(1-naphthyl)acetamide hydrochloride | 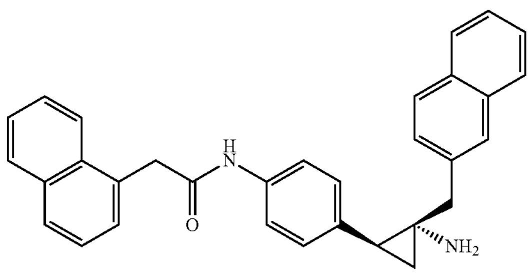 [SMILES: N[C@]1(Cc2ccc3ccccc3c2)C[C@H]1c1ccc(NC(=O)Cc2cccc3ccccc23)cc1] | 455 ([M + H]+) | $^1$H NMR (DMSO-$d_6$) δ (ppm): 10.44 (s, 1 H), 8.43-8.23 (m, 3 H), 8.17-7.18 (m, 18 H), 4.16 (s, 2 H), 3.00-2.90 (m, 1 H), 2.67-2.44 (m, 2 H), 1.75 (s, 1 H), 1.41 (d, J = 9.8 Hz, 1 H). |
| A-77 | N-[3-[trans-2-amino-2-ethyl-cyclopropyl]phenyl]-2-(1-naphthyl)acetamide hydrochloride | 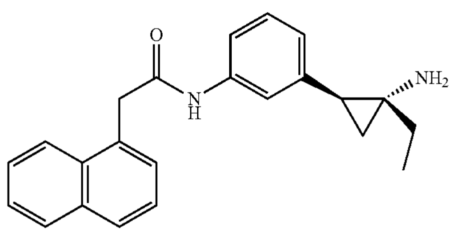 [SMILES: CC[C@@]1(N)C[C@H]1c1cccc(NC(=O)Cc2cccc3ccccc23)c1] | 345 ([M + H]+) | $^1$H NMR (DMSO-$d_6$) δ (ppm): 10.40 (s, 1 H), 8.37 (bs, 3 H), 8.20-6.84 (m, 11 H), 4.15 (s, 2 H), 2.54-2.44 (m, 1 H), 1.39-1.29 (m, 2 H) 1.25-1.14 (m, 2 H), 0.80 (t, J = 7.34 Hz, 3 H). |
| A-78 | N-[4-[trans-2-amino-2-ethyl-cyclopropyl]phenyl]-4-(3-furyl)benzamide hydrochloride | 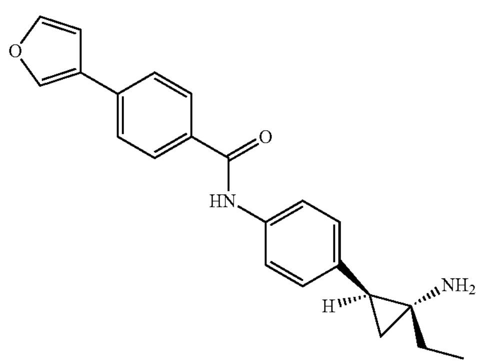 [SMILES: CC[C@@]1(N)C[C@H]1c1ccc(NC(=O)c2ccc(-c3ccoc3)cc2)cc1] | 347 ([M + H]+) | $^1$H NMR (DMSO-$d_6$) δ (ppm): 10.24 (s, 1 H), 8.47-8.27 (m, 4 H), 8.02-7.93 (m, 2 H), 7.85-7.66 (m, 5 H), 7.28-7.16 (m, 2 H), 7.11-7.01 (m, 1 H), 2.58-2.52 (m, 1 H), 1.43-1.17 (m, 4 H), 0.81 (t, J = 7.3 Hz, 3 H). |
| A-79 | N-[4-[trans-2-amino-2-(2-naphthylmethyl)cyclopropyl]phenyl]-3-chloro-benzamide hydrochloride | 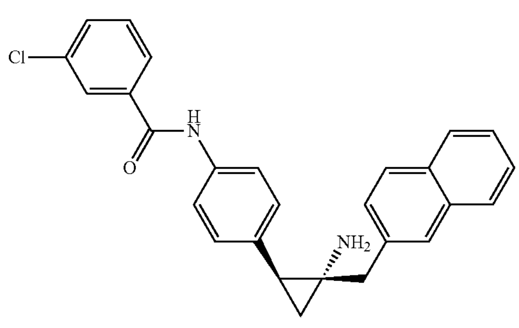 [SMILES: N[C@]1(Cc2ccc3ccccc3c2)C[C@H]1c1ccc(NC(=O)c2cccc(Cl)c2)cc1] | 427 ([M + H]+) | $^1$H NMR (DMSO-$d_6$) δ (ppm): 10.42 (s, 1 H), 8.31 (bs, 3 H), 8.05-7.22 (m, 15 H), 3.03-2.93 (m, 1 H), 2.72-2.52 (m, 2 H), 1.84-1.74 (m, 1 H), 1.52-1.39 (m, 1 H). |

TABLE 6-continued

| Ex. | Name | Structure | LC-MS | NMR |
|---|---|---|---|---|
| A-80 | N-[3-[trans-2-amino-2-ethyl-cyclopropyl]phenyl]-3-chloro-benzamide hydrochloride | 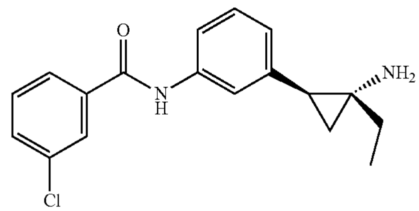 [SMILES: CC[C@@]1(N)C[C@H]1c1cccc(NC(=O)c2cccc(Cl)c2)c1] | 315 ([M + H]+) | 1H NMR (DMSO-d6) δ (ppm): 10.36 (s, 1 H), 8.38 (bs, 3 H), 8.06-6.90 (m, 8 H), 2.603-2.53 (m, 1 H), 1.47-1.17 (m, 4 H), 0.84 (t, J = 7.58 Hz, 3 H). |
| A-81 | N-[4-[trans-2-amino-2-(2-naphthylmethyl)cyclopropyl]phenyl]-3-phenyl-propanamide 2,2,2-trifluoroacetic acid | 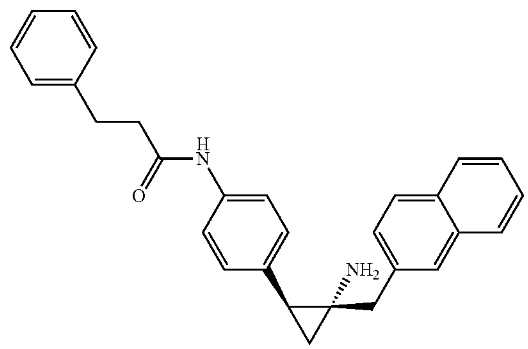 [SMILES: N[C@]1(Cc2ccc3ccccc3c2)C[C@H]1c1ccc(NC(=O)CCc2ccccc2)cc1] | 421 ([M + H]+) | 1H NMR (DMSO-d6) δ (ppm): 9.97 (s, 1 H), 8.19 (bs, 3 H), 7.92-7.12 (m, 16 H), 2.98-2.86 (m, 3 H), 2.67-2.51 (m, 4 H), 1.81-1.69 (m, 1 H), 1.44-1.32 (m, 1 H). |
| A-82 | N-[4-[trans-2-amino-2-(2-naphthylmethyl)cyclopropyl]phenyl]-3-phenyl-benzamide hydrochloride | 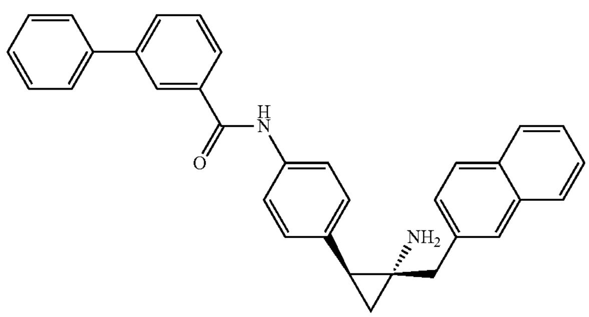 [SMILES: N[C@]1(Cc2ccc3ccccc3c2)C[C@H]1c1ccc(NC(=O)c2cccc(-c3ccccc3)c2)cc1] | 467 ([M + H]+) | 1H NMR (DMSO-d6) δ (ppm): 10.41 (s, 1 H), 8.45-8.12 (m, 3 H), 8.01-7.00 (m, 20 H), 3.05-2.93 (m, 1 H), 2.72-2.63 (m, 1 H), 2.60-2.51 (m, 1 H), 1.83-1.73 (m, 1 H), 1.51-1.35 (m, 1 H). |
| A-83 | N-[4-[trans-2-amino-2-ethyl-cyclopropyl]phenyl]-4-(2-oxooxazolidin-3-yl)benzamide hydrochloride | 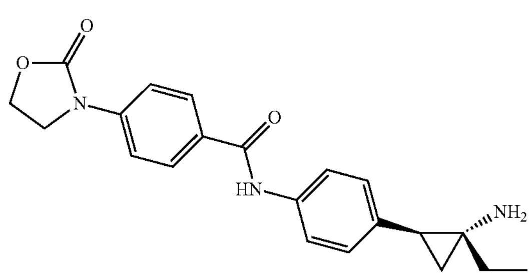 [SMILES: CC[C@@]1(N)C[C@H]1c1ccc(NC(=O)c2ccc(N3CCOC3=O)cc2)cc1] | 366 ([M + H]+) | 1H NMR (DMSO-d6) δ (ppm): 10.19 (s, 1 H), 8.33 (bs, 3 H), 8.05-7.93 (m, 2 H), 7.77-7.65 (m, 4 H), 7.27-7.15 (m, 2 H), 4.52-4.41 (m, 2 H), 4.17-4.04 (m, 2 H), 1.42-1.16 (m, 4 H), 0.81 (t, J = 7.6 Hz, 3 H). |

TABLE 6-continued

| Ex. | Name | Structure | LC-MS | NMR |
|---|---|---|---|---|
| A-84 | benzyl N-[3-[(4-[trans-2-amino-2-phenyl-cyclopropyl]phenyl)carbamoyl]phenyl]carbamate 2,2,2-trifluoroacetic acid | 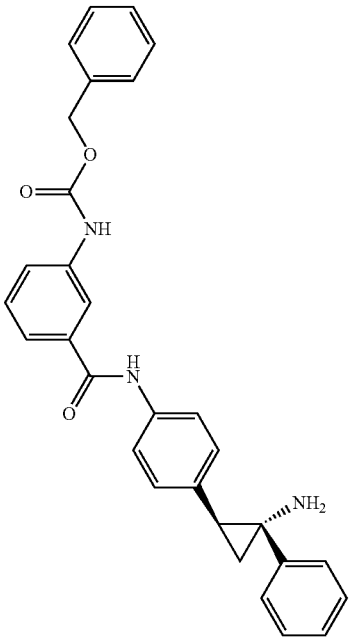 [SMILES: N[C@]1(c2ccccc2)C[C@H]1c1ccc(NC(=O)c2cccc(NC(=O)OCc3ccccc3)c2)cc1] | 478 ([M + H]+) | 1H NMR (DMSO-d6) δ (ppm): 10.16-9.87 (m, 2 H), 8.66 (bs, 3 H), 8.01-7.84 (m, 1 H), 7.68-6.77 (m, 17 H), 5.15 (s, 2 H), 2.86-2.70 (m, 1 H), 2.17-2.05 (m, 1 H), 1.79-1.65 (m, 1 H). |
| A-85 | N-[4-[trans-2-amino-2-phenyl-cyclopropyl]phenyl]naphthalene-2-carboxamide hydrochloride | 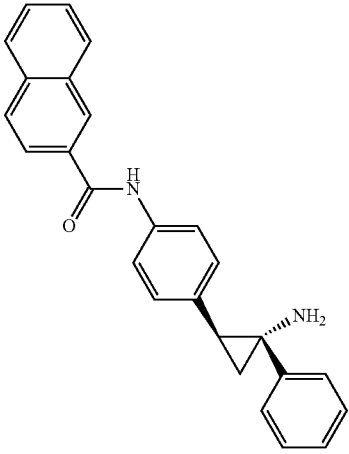 [SMILES: N[C@]1(c2ccccc2)C[C@H]1c1ccc(NC(=O)c2ccc3ccccc3c2)cc1] | 379 ([M + H]+) | 1H NMR (DMSO-d6) δ (ppm): 10.29 (s, 1 H), 8.87 (s, 3 H), 8.58-8.43 (m, 1 H), 8.15-6.78 (m, 15 H), 2.94-2.77 (m, 1 H), 2.17-2.03 (m, 1 H), 1.90-1.72 (m, 1 H) |
| A-86 | N-[4-[trans-2-amino-2-ethyl-cyclopropyl]-2-fluoro-phenyl]benzamide hydrochloride | 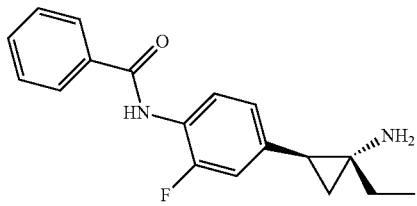 [SMILES: CC[C@@]1(N)C[C@H]1c1ccc(NC(=O)c2ccccc2)c(F)c1] | 299 ([M + H]+) | 1H NMR (DMSO-d6) δ (ppm): 10.09 (s, 1 H), 8.42 (bs, 3 H), 8.02-7.89 (m, 2 H), 7.66-7.46 (m, 4 H), 7.24-7.08 (m, 2 H), 2.60-2.50 (m, 1 H), 1.46-1.17 (m, 4 H), 0.83 (t, J = 7.3 Hz, 3 H). |
| A-87 | N-[4-[trans-2-amino-2-ethyl-cyclopropyl]-2-fluoro-phenyl]-4-phenyl-benzamide hydrochloride | 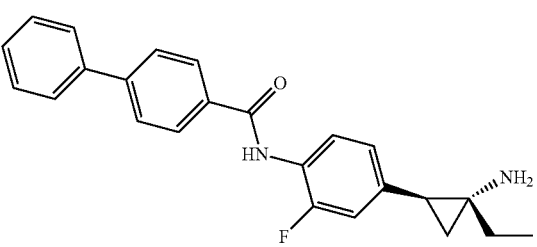 [SMILES: CC[C@@]1(N)C[C@H]1c1ccc(NC(=O)c2ccc(-c3ccccc3)cc2)c(F)c1] | 375 ([M + H]+) | 1H NMR (DMSO-d6) δ (ppm): 10.14 (s, 1 H), 8.41 (s, 3 H), 8.09-8.02 (m, 2 H), 7.87-7.80 (m, 2 H), 7.79-7.72 (m, 2 H), 7.61-7.54 (m, 1 H), 7.54-7.39 (m, 3 H), 7.24-7.18 (m, 1 H), 7.17-7.10 (m, 1 H), 2.60-2.52 (m, 1 H), 1.48-1.22 (m, 4 H), 0.84 (t, J = 7.3 Hz, 3 H). |

TABLE 6-continued

| Ex. | Name | Structure | LC-MS | NMR |
|---|---|---|---|---|
| A-88 | N-[4-[trans-2-amino-2-ethyl-cyclopropyl]phenyl]-4-morpholino-benzamide 2,2,2-trifluoroacetic acid | 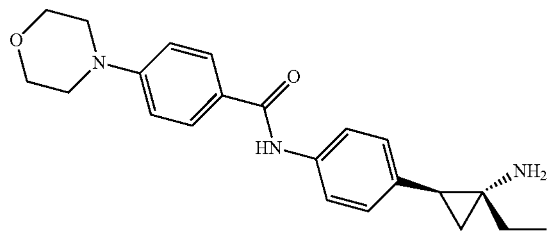 [SMILES: CC[C@@]1(N)C[C@H]1c1ccc(NC(=O)c2ccc(N3CCOCC3)cc2)cc1] | 366 ([M + H]$^+$) | $^1$H NMR (DMSO-d$_6$) δ (ppm): 9.95 (s, 1 H), 8.22 (bs, 3 H), 7.93-7.81 (m, 2 H), 7.76-7.65 (m, 2 H), 7.24-7.14 (m, 2 H), 7.07-6.97 (m, 2 H), 3.83-3.65 (m, 4 H), 3.29-3.16 (m, 4 H), 2.47-2.39 (m, 1 H), 1.44-1.16 (m, 4 H), 0.80 (t, J = 7.3 Hz, 3 H). |
| A-89 | N-[4-[trans-2-amino-2-phenyl-cyclopropyl]phenyl]-4-phenyl-benzamide 2,2,2-trifluoroacetic acid | 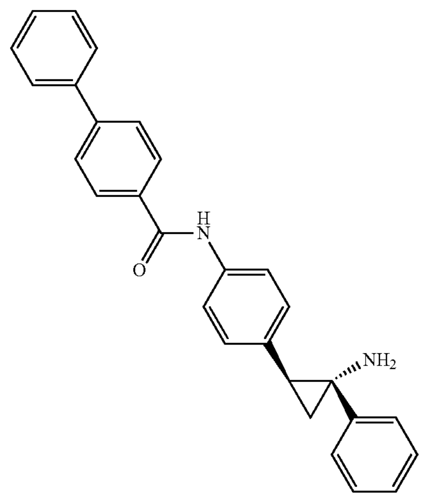 [SMILES: N[C@]1(c2ccccc2)C[C@H]1c1ccc(NC(=O)c2ccc(-c3ccccc3)cc2)cc1] | 405 ([M + H]$^+$) | $^1$H NMR (DMSO-d$_6$) δ (ppm): 10.14 (s, 1 H), 8.69 (s, 3 H), 8.07-6.73 (m, 18 H), 2.91-2.72 (m, 1 H), 2.19-2.04 (m, 1 H), 1.79-1.61 (m, 1 H). |
| A-90 | N-[4-[trans-2-amino-2-phenyl-cyclopropyl]phenyl]naphthalene-1-carboxamide hydrochloride | 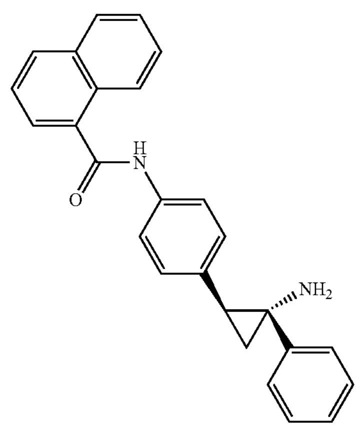 [SMILES: N[C@]1(c2ccccc2)C[C@H]1c1ccc(NC(=O)c2cccc3ccccc23)cc1] | 379 ([M + H]$^+$) | $^1$H NMR (DMSO-d$_6$) δ (ppm): 10.43 (s, 1 H), 8.88 (s, 3 H), 8.20-6.88 (m, 16 H), 2.95-2.75 (m, 1 H), 2.19-2.01 (m, 1 H), 1.87-1.74 (m, 1 H). |
| A-91 | N-[3-[trans-2-amino-2-ethyl-cyclopropyl]phenyl]-4-phenyl-benzamide hydrochloride | 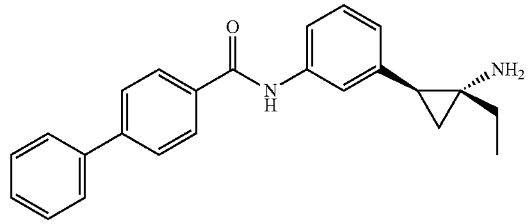 [SMILES: CC[C@@]1(N)C[C@H]1c1cccc(NC(=O)c2ccc(-c3ccccc3)cc2)c1] | 357 ([M + H]$^+$) | $^1$H NMR (DMSO-d$_6$) δ (ppm): 10.30 (s, 1 H), 8.41 (s, 3 H), 8.11-6.94 (m, 13 H), 2.61-2.53 (m, 1 H), 1.48-1.33 (m, 2 H), 1.33-1.19 (m, 2 H), 0.84 (t, J = 7.34 Hz, 3 H). |
| A-92 | N-[3-[trans-2-amino-2-ethyl-cyclopropyl]phenyl]naphthalene-2-carboxamide hydrochloride | 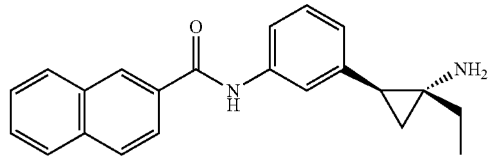 [SMILES: CC[C@@]1(N)C[C@H]1c1cccc(NC(=O)c2ccc3ccccc3c2)c1] | 331 ([M + H]$^+$) | $^1$H NMR (DMSO-d$_6$) δ (ppm): 10.43 (s, 1 H), 8.63-6.93 (m, 14 H), 2.62-2.54 (m, 1 H), 1.48-1.34 (m, 2 H), 1.34-1.18 (m, 2 H), 0.84 (t, J = 7.34 Hz, 3 H). |

TABLE 6-continued

| Ex. | Name | Structure | LC-MS | NMR |
|---|---|---|---|---|
| A-93 | N-[3-[trans-2-amino-2-ethyl-cyclopropyl]phenyl]benzamide hydrochloride | 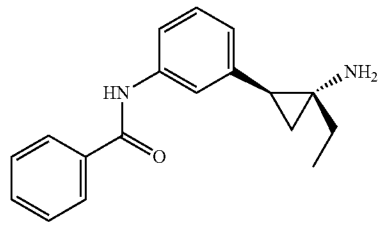 [SMILES: CC[C@@]1(N)C[C@H]1c1cccc(NC(=O)c2ccccc2)c1] | 281 ([M + H]+) | $^1$H NMR (DMSO-d$_6$) δ (ppm): 10.24 (bs, 1 H), 8.52 (bs, 3 H), 8.01-6.89 (m, 9 H), 2.65-2.53 (m, 1 H), 1.46-1.31 (m, 2 H), 1.30-1.14 (m, 2 H), 0.81 (t, J = 7.09 Hz, 3 H). |
| A-94 | N-[4-[trans-2-amino-2-ethyl-cyclopropyl]-2-fluoro-phenyl]-2-(1-naphthyl)acetamide hydrochloride | 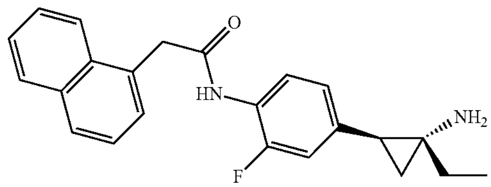 | 366 ([M + H]+) | $^1$H NMR (DMSO-d$_6$) δ (ppm): 10.11 (s, 1 H), 8.46 (bs, 3 H), 8.19-8.08 (m, 1 H), 8.02-7.89 (m, 1 H), 7.89-7.74 (m, 2 H), 7.62-7.41 (m, 4 H), 7.22-7.10 (m, 1 H), 7.08-6.97 (m, 1 H), 4.22 (s, 2 H), 2.59-2.52 (m, 1 H), 1.48-1.13 (m, 4 H), 0.80 (t, J = 7.3 Hz, 3 H). |
| A-95 | benzyl N-[4-[[4-[trans-2-amino-2-ethyl-cyclopropyl]-2-fluoro-phenyl]carbamoyl]phenyl]carbamate hydrochloride | 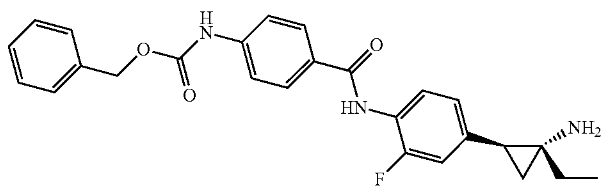 [SMILES: CC[C@@]1(N)C[C@H]1c1ccc(NC(=O)c2ccc(NC(=O)OCc3ccccc3)cc2)c(F)c1] | 448 ([M + H]+) | $^1$H NMR (DMSO-d$_6$) δ (ppm): 10.13 (s, 1 H), 9.93 (s, 1 H), 8.40 (bs, 3 H), 7.98-7.85 (m, 2 H), 7.67-7.28 (m, 8 H), 7.24-7.02 (m, 2 H), 5.17 (s, 2 H), 2.63-2.52 (m, 1 H), 1.49-1.16 (m, 4 H), 0.82 (t, J = 7.3 Hz, 3 H). |
| A-96 | N-[4-[trans-2-amino-2-ethyl-cyclopropyl]-2-fluoro-phenyl]-4-(4-methylpiperazin-1-yl)benzamide 2,2,2-trifluoroacetic acid | 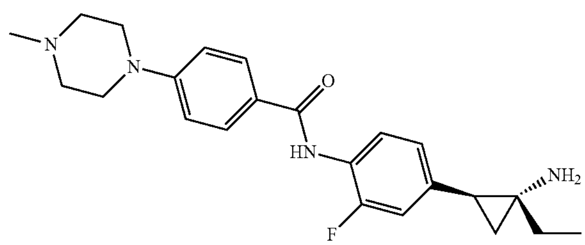 [SMILES: CC[C@@]1(N)C[C@H]1c1ccc(NC(=O)c2ccc(N3CCN(C)CC3)cc2)c(F)c1] | 397 ([M + H]+) | $^1$H NMR (DMSO-d$_6$) δ (ppm): 9.87-9.71 (m, 2 H), 8.25 (s, 3 H), 7.97-7.83 (m, 2 H), 7.58-7.48 (m, 1 H), 7.23-7.14 (m, 1 H), 7.12-7.03 (m, 3 H), 4.09-4.02 (m, 2 H), 3.57-3.49 (m, 2 H), 3.25-2.99 (m, 4 H), 2.87 (bs, 3 H), 2.55-2.51 (m, 1 H), 1.47-1.18 (m, 4 H), 0.82 (t, J = 7.3 Hz, 3 H). |
| A-97 | N-[4-[trans-2-amino-2-ethyl-cyclopropyl]phenyl]-4-(4-methylpiperazin-1-yl)benzamide 2,2,2-trifluoroacetic acid | 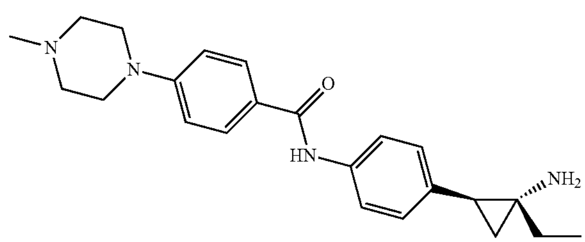 [SMILES: CC[C@@]1(N)C[C@H]1c1ccc(NC(=O)c2ccc(N3CCN(C)CC3)cc2)cc1] | 379 ([M + H]+) | $^1$H NMR (DMSO-d$_6$) δ (ppm): 9.99 (s, 1 H), 9.84-9.67 (m, 1 H), 8.23 (s, 3 H), 7.95-7.86 (m, 2 H), 7.77-7.66 (m, 2 H), 7.26-7.02 (m, 4 H), 4.10-4.00 (m, 2 H), 3.58-3.47 (m, 2 H), 3.23-3.00 (m, 4 H), 2.87 (bs, 3 H), 2.47-2.40 (m, 1 H), 1.44-1.18 (m, 4 H), 0.81 (t, J = 7.3 Hz, 3 H). |
| A-98 | N-[4-[trans-2-amino-2-ethyl-cyclopropyl]phenyl]-3-(2-oxooxazolidin-3-yl)benzamide 2,2,2-trifluoroacetic acid | 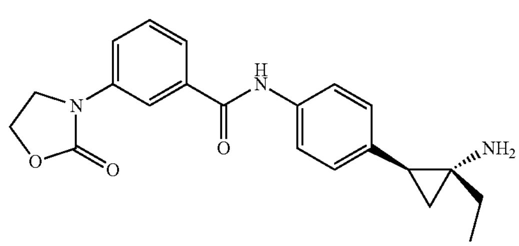 [SMILES: CC[C@@]1(N)C[C@H]1c1ccc(NC(=O)c2cccc(N3CCOC3=O)c2)cc1] | 366 ([M + H]+) | $^1$H NMR (DMSO-d$_6$) δ (ppm): 10.29 (s, 1 H), 8.21 (bs, 3 H), 8.06-8.00 (m, 1 H), 7.80 (dd, J = 1.6, 8.3 Hz, 1 H), 7.75-7.65 (m, 3 H), 7.58-7.51 (m, 1 H), 7.28-7.17 (m, 2 H), 4.52-4.41 (m, 2 H), 4.17-4.05 (m, 2 H), 2.48-2.42 (m, 1 H), 1.42-1.19 (m, 4 H), 0.81 (t, J = 7.3 Hz, 3 H). |

TABLE 6-continued

| Ex. | Name | Structure | LC-MS | NMR |
|---|---|---|---|---|
| A-99 | benzyl N-[5-[[4-[trans-2-amino-2-ethyl-cyclopropyl]phenyl]carbamoyl]-2-morpholino-phenyl]carbamate 2,2,2-trifluoroacetic acid | 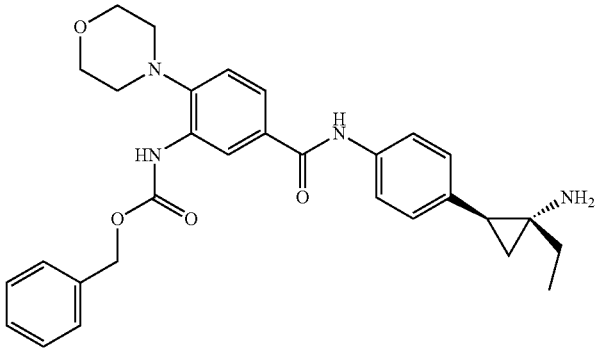 [SMILES: CC[C@@]1(N)C[C@H]1c1ccc(NC(=O)c2ccc(N3CCOCC3)c(NC(=O)OCc3ccccc3)c2)cc1] | 515 ([M + H]$^+$) | $^1$H NMR (DMSO-d$_6$) δ (ppm): 10.15 (s, 1 H), 8.64 (s, 1 H), 8.26-8.09 (m, 4 H), 7.79-7.64 (m, 3 H), 7.46-7.30 (m, 5 H), 7.26-7.18 (m, 3 H), 5.19 (s, 2 H), 3.79-3.61 (m, 4 H), 2.91-2.82 (m, 4 H), 2.48-2.42 (m, 1 H), 1.42-1.17 (m, 4 H), 0.81 (t, J = 7.3 Hz, 3 H). |
| A-100 | N-[4-[trans-2-amino-2-ethyl-cyclopropyl]phenyl]-4-(1-methyl-4-piperidyl)benzamide 2,2,2-trifluoroacetic acid | 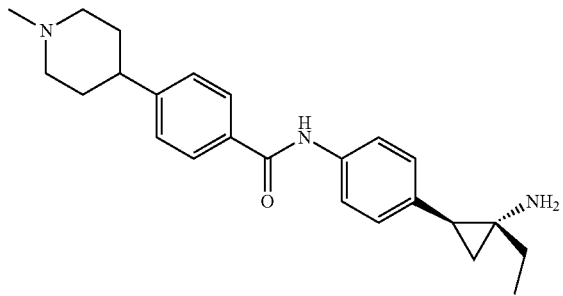 [SMILES: CC[C@@]1(N)C[C@H]1c1ccc(NC(=O)c2ccc(C3CCN(C)CC3)cc2)cc1] | 378 ([M + H]$^+$) | $^1$H NMR (DMSO-d$_6$) δ (ppm): 10.21 (s, 1 H), 9.74 (bs, 1 H), 8.31 (bs, 3 H), 7.95-7.88 (m, 2 H), 7.76-7.70 (m, 2 H), 7.43-7.36 (m, 2 H), 7.25-7.18 (m, 2 H), 3.56-3.46 (m, 2 H), 3.13-3.02 (m, 2 H), 2.96-2.85 (m, 1 H), 2.81 (d, J = 4.4 Hz, 3 H), 2.48-2.44 (m, 1 H), 2.09-1.99 (m, 2 H), 1.96-1.80 (m, 2 H), 1.40-1.18 (m, 4 H), 0.81 (t, J = 7.3 Hz, 3 H). |
| A-101 | N-[4-(trans-2-amino-2-ethyl-cyclopropyl)phenyl]pyridine-4-carboxamide dihydrochloride | 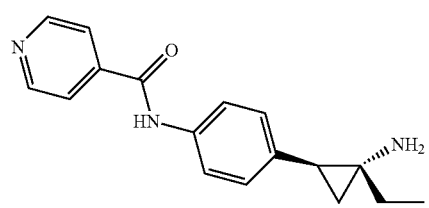 [SMILES: CC[C@@]1(N)C[C@H]1c1ccc(NC(=O)c2ccncc2)cc1] | 282 ([M + H]$^+$) | $^1$H NMR (DMSO-d$_6$) δ (ppm): 10.81 (s, 1 H), 9.40-8.79 (m, 2 H), 8.59 (bs, 3 H), 8.34-8.05 (m, 2 H), 7.84-7.68 (m, 2 H), 7.32-7.19 (m, 2 H), 2.57 (dd, J = 7.3, 9.3 Hz, 1 H), 1.47-1.17 (m, 4 H), 0.81 (t, J = 7.6 Hz, 3 H). |
| A-102 | N-[4-(trans-2-amino-2-ethyl-cyclopropyl]phenyl]-4-(4-pyridyl)benzamide dihydrochloride | 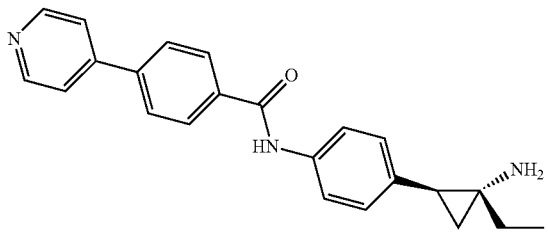 [SMILES: CC[C@@]1(N)C[C@H]1c1ccc(NC(=O)c2ccc(-c3ccncc3)cc2)cc1] | 358 ([M + H]$^+$) | $^1$H NMR (DMSO-d$_6$) δ (ppm): 10.46 (s, 1 H), 9.22-8.81 (m, 2 H), 8.52 (bs, 3 H), 8.34 (bs, 2 H), 8.21-8.06 (m, 4 H), 7.83-7.71 (m, 2 H), 7.30-7.18 (m, 2 H), 2.59-2.52 (m, 1 H), 1.48-1.16 (m, 4 H), 0.82 (t, J = 7.3 Hz, 3 H). |
| A-103 | N-[4-(trans-2-amino-2-phenyl-cyclopropyl]phenyl]-3-chloro-benzamide hydrochloride | 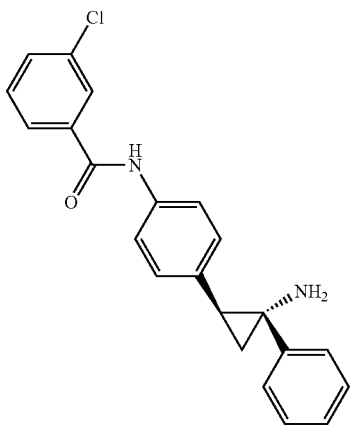 [SMILES: N[C@]1(c2ccccc2)C[C@H]1c1ccc(NC(=O)c2cccc(Cl)c2)cc1] | 363 ([M + H]$^+$) | $^1$H NMR (DMSO-d$_6$) δ (ppm): 10.21 (s, 1 H), 8.89 (s, 3 H), 7.95-6.89 (m, 13 H), 2.87-2.79 (m, 1 H), 2.13-2.07 (m, 1 H), 1.83-1.75 (m, 1 H). |

TABLE 6-continued

| Ex. | Name | Structure | LC-MS | NMR |
|---|---|---|---|---|
| A-104 | N-[4-(trans-2-amino-2-phenyl-cyclopropyl)phenyl]-2-(1-naphthyl)acetamide hydrochloride | 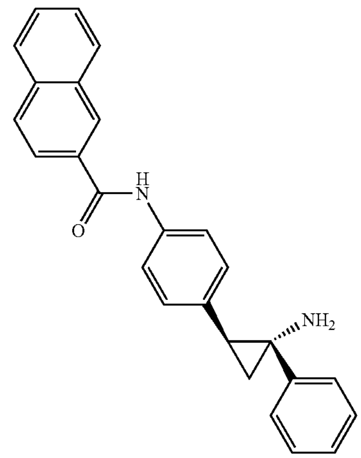 [SMILES: N[C@]1(c2ccccc2)C[C@H]1c1ccc(NC(=O)c2ccc3ccccc3c2)cc1] | 393 ([M + H]$^+$) | $^1$H NMR (DMSO-d$_6$) δ (ppm): 10.22 (s, 1 H), 8.86 (s, 3 H), 8.11-6.81 (m, 16 H), 4.07 (s, 2 H), 2.83-2.76 (m, 1 H), 2.10-2.00 (m, 1 H), 1.80-1.71 (m, 1 H). |
| A-105 | N-[4-(trans-2-amino-2-phenyl-cyclopropyl)phenyl]-2-phenyl-acetamide hydrochloride | 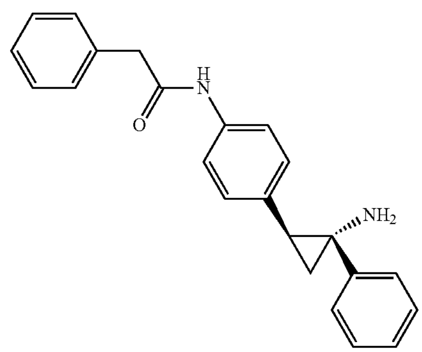 [SMILES: N[C@]1(c2ccccc2)C[C@H]1c1ccc(NC(=O)Cc2ccccc2)cc1] | 343 ([M + H]$^+$) | $^1$H NMR (DMSO-d$_6$) δ (ppm): 10.05 (s, 1 H), 8.82 (s, 3 H), 7.44-6.79 (m, 14 H), 3.56 (s, 2 H), 2.86-2.71 (m, 1 H), 2.12-1.98 (m, 1 H), 1.81-1.67 (m, 1 H). |
| A-106 | N-[4-(trans-2-amino-2-phenyl-cyclopropyl)phenyl]-3-phenyl-benzamide 2,2,2-trifluoroacetic acid | 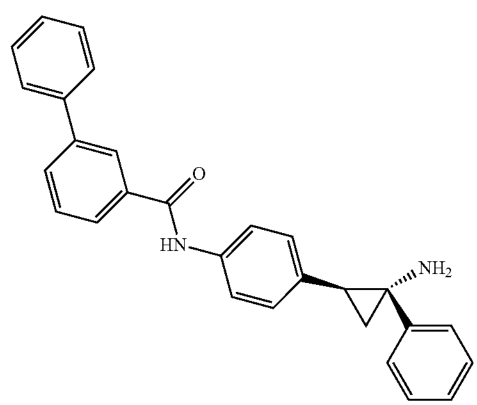 [SMILES: N[C@]1(c2ccccc2)C[C@H]1c1ccc(NC(=O)c2cccc(-c3ccccc3)c2)cc1] | 405 ([M + H]$^+$) | $^1$H NMR (DMSO-d$_6$) δ (ppm): 10.19 (s, 1 H), 8.71 (s, 3 H), 8.21-6.78 (m, 18 H), 2.88-2.69 (m, 1 H), 2.21-2.05 (m, 1 H), 1.82-1.64 (m, 1 H). |
| A-107 | N-[4-(trans-2-amino-2-phenyl-cyclopropyl)phenyl]-2-(2-naphthyl)acetamide 2,2,2-trifluoroacetic acid | 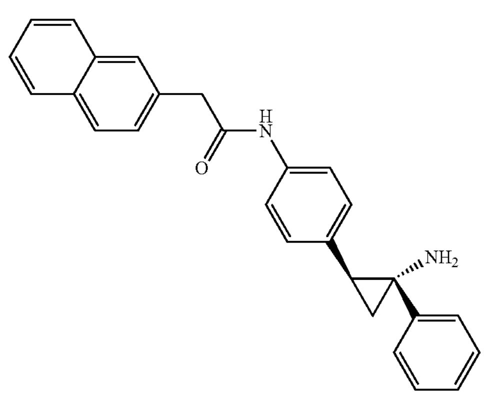 [SMILES: N[C@]1(c2ccccc2)C[C@H]1c1ccc(NC(=O)Cc2ccc3ccccc3c2)cc1] | 393 ([M + H]$^+$) | $^1$H NMR (DMSO-d$_6$) δ (ppm): 10.09 (s, 1 H), 8.68 (s, 3 H), 8.05-6.72 (m, 16 H), 3.73 (s, 2 H), 2.81-2.66 (m, 1 H), 2.10-2.00 (m, 1 H), 1.79-1.63 (m, 1 H). |

TABLE 6-continued

| Ex. | Name | Structure | LC-MS | NMR |
|---|---|---|---|---|
| A-108 | N-[4-(trans-2-amino-2-phenyl-ccyclopropyl)phenyl]pyridine-4-carboxamide dihydrochloride | 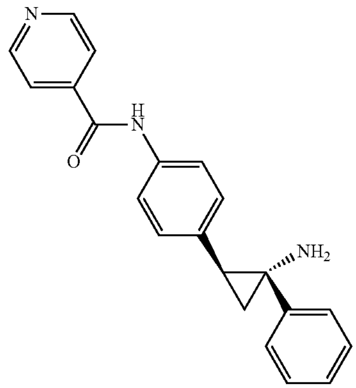 [SMILES: N[C@]1(c2ccccc2)C[C@H]1c1ccc(NC(=O)c2ccncc2)cc1] | 330 ([M + H]+) | 1H NMR (DMSO-d6) δ (ppm): 10.58 (s, 1 H), 9.04 (s, 3 H), 8.92-8.78 (m, 2 H), 8.10-7.95 (m, 2 H), 7.60-6.88 (m, 9 H), 2.96-2.81 (m, 1 H), 2.18-2.03 (m, 1 H), 1.87-1.79 (m, 1 H). |
| A-109 | N-[4-(trans-2-amino-2-phenyl-cyclopropyl]phenyl]-4-(1-methyl-4-piperidyl)benzamide dihydrochloride | 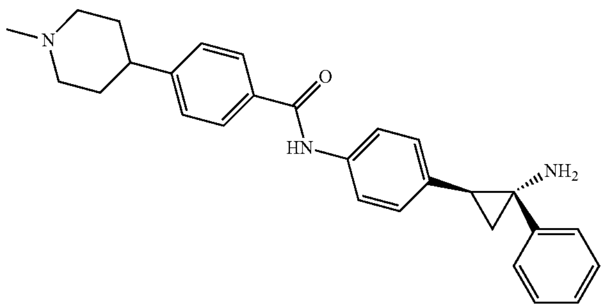 [SMILES: CN1CCC(c2ccc(C(=O)Nc3ccc([C@@H]4C[C@]4(N)c4ccccc4)cc3)cc2)CC1] | 426 ([M + H]+) | 1H NMR (DMSO-d6) δ (ppm): 10.58-10.28 (m, 1 H), 10.07 (s, 1 H), 8.98 (s, 3 H), 7.94-7.80 (m, 2 H), 7.56-7.14 (m, 9 H), 6.99-6.87 (m, 2 H), 3.57-3.42 (m, 2 H), 3.11-2.98 (m, 2 H), 2.91-2.82 (m, 2 H), 2.76 (d, J = 4.4 Hz, 3 H), 2.12-2.05 (m, 1 H), 2.01-1.94 (m, 4 H), 1.85-1.77 (m, 1 H). |
| A-110 | N-[4-(trans-2-amino-2-phenyl-cyclopropyl)phenyl]-4-(4-methylpiperazin-1-yl)benzamide hydrochloride | 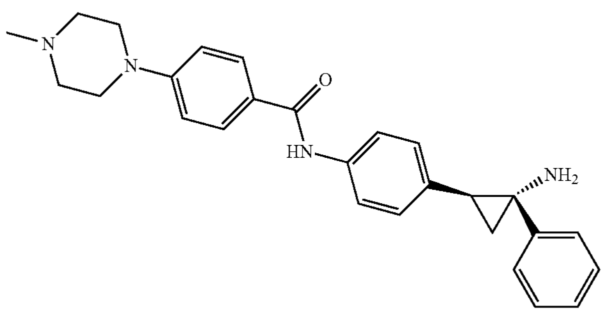 [SMILES: CN1CCN(c2ccc(C(=O)Nc3ccc([C@@H]4C[C@]4(N)c4ccccc4)cc3)cc2)CC1] | 427 ([M + H]+) | 1H NMR (DMSO-d6) δ (ppm): 10.71 (s, 1 H), 9.86 (s, 1 H), 8.97 (s, 3 H), 7.93-6.78 (m, 13 H), 4.04-3.93 (m, 2 H), 3.51-3.45 (m, 2 H), 3.22-3.03 (m, 4 H), 2.89-2.77 (m, 4 H), 2.11-2.03 (m, 1 H), 1.84-1.75 (m, 1 H). |
| A-111 | N-[4-(trans-2-amino-2-phenyl-cyclopropyl)phenyl]-3-(2-oxoxazolidin-3-yl)benzamide hydrochloride | 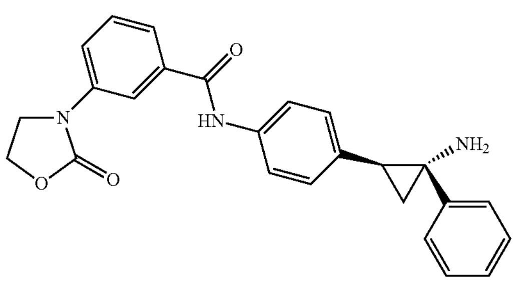 [SMILES: N[C@]1(c2ccccc2)C[C@H]1c1ccc(NC(=O)c2cccc(N3CCOC3=O)c2)cc1] | 414 ([M + H]+) | 1H NMR (DMSO-d6) δ (ppm): 10.16 (s, 1 H), 8.88 (s, 3 H), 8.08-6.62 (m, 13 H), 4.52-4.37 (m, 2 H), 4.19-4.04 (m, 2 H), 2.89-2.77 (m, 1 H), 2.17-2.04 (m, 1 H), 1.86-1.71 (m, 1 H). |
| A-112 | N-[4-(trans-2-amino-2-phenethyl-cyclopropyl)phenyl]pyridine-4-carboxamide hydrochloride | 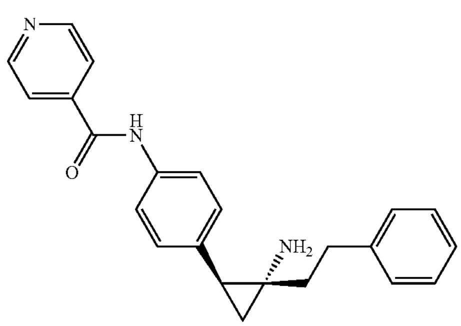 [SMILES: N[C@]1(CCc2ccccc2)C[C@H]1c1ccc(NC(=O)c2ccncc2)cc1] | 358 ([M + H]+) | 1H NMR (DMSO-d6) δ (ppm): 10.67 (s, 1 H), 8.92-8.80 (m, 2 H), 8.66 (bs, 3 H), 8.06-7.95 (m, 2 H), 7.81-7.66 (m, 2 H), 7.35-7.23 (m, 2 H), 7.23-6.74 (m, 5 H), 2.68-2.50 (m, 3 H), 1.67-1.33 (m, 4 H). |

TABLE 6-continued

| Ex. | Name | LC-MS | NMR |
|---|---|---|---|
| A-113 | N-[4-(trans-2-amino-2-phenethyl-cyclopropyl)phenyl]-4-phenyl-benzamide hydrochloride | 433 ([M + H]$^+$) | $^1$H NMR (DMSO-d$_6$) δ (ppm): 10.31 (s, 1 H), 8.55 (bs, 3 H), 8.05 (d, J = 8.8 Hz, 2 H), 7.86-7.81 (m, 2 H), 7.79-6.89 (m, 14 H), 2.67-2.52 (m, 3 H), 1.68-1.32 (m, 4 H). |
| A-114 | N-[4-trans-2-amino-2-phenethyl-cyclopropyl)phenyl] benzamide hydrochloride | 357 ([M + H]$^+$) | $^1$H NMR (DMSO-d$_6$) δ (ppm): 10.26 (s, 1 H), 8.56 (bs, 3 H), 7.95-7.90 (m, 2 H), 7.79-7.71 (m, 2 H), 7.63-6.85 (m, 10 H), 2.67-2.51 (m, 3 H), 1.66-1.33 (m, 4 H). |
| A-115 | N-[4-(trans-2-amino-2-phenethyl-cyclopropyl)phenyl]-4-(1-methyl-4-piperidyl)benzamide dihydrochloride | 452 ([M + H]$^+$) | $^1$H NMR (DMSO-d$_6$) δ (ppm): 10.22 (bs, 2 H), 8.60 (bs, 3 H), 7.99-7.85 (m, 2 H), 7.79-7.63 (m, 2 H), 7.45-6.83 (m, 9 H), 3.54-3.42 (m, 2 H), 3.12-2.98 (m, 2 H), 2.95-2.83 (m, 1 H), 2.78 (bs, 3 H), 2.67-2.52 (m, 3 H), 2.00 (bs, 4 H), 1.66-1.32 (m, 4 H). |

TABLE 6-continued

| Ex. | Name | Structure | LC-MS | NMR |
|---|---|---|---|---|
| A-116 | N-[4-(trans-2-amino-2-phenethyl-cyclopropyl)phenyl]-4-(4-methylpiperazin-1-yl)benzamide dihydrochloride | 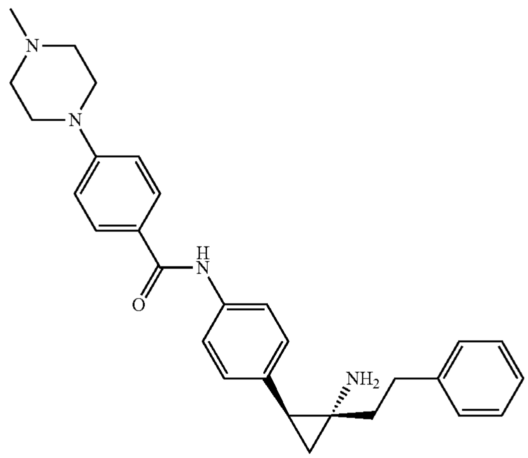 [SMILES: CN1CCN(c2ccc(C(=O)Nc3ccc([C@@H]4C[C@]4(N)CCc4ccccc4)cc3)cc2)CC1] | 455 ([M + H]$^+$) | $^1$H NMR (DMSO-d$_6$) δ (ppm): 10.63 (bs, 1 H), 10.02 (s, 1 H), 8.62 (bs, 3 H), 7.97-7.84 (m, 2 H), 7.79-7.67 (m, 2 H), 7.30-6.81 (m, 9 H), 4.01 (bs, 2 H), 3.49 (bs, 2 H), 3.14 (bs, 4 H), 2.81 (s, 3 H), 2.66-2.52 (m, 3 H), 1.67-1.28 (m, 4 H). |
| A-117 | benzyl N-[5-[[4-[trans-2-amino-2-ethyl-cyclopropyl]phenyl]carbamoyl]-2-(4-methylpiperazin-1-yl)phenyl]carbamate 2,2,2-trifluoroacetic acid | 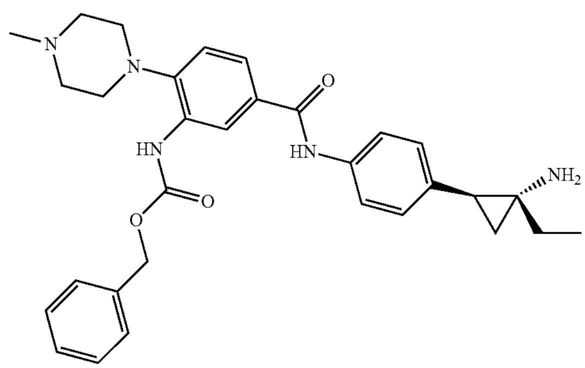 [SMILES: CC[C@@]1(N)C[C@H]1c1ccc(NC(=O)c2ccc(N3CCN(C)CC3)c(NC(=O)OCc3ccccc3)c2)cc1] | 528 ([M + H]$^+$) | $^1$H NMR (DMSO-d$_6$) δ (ppm): 10.18 (s, 1 H), 9.77 (bs, 1 H), 8.72 (s, 1 H), 8.36-8.28 (m, 1 H), 8.24 (bs, 3 H), 7.76-7.65 (m, 3 H), 7.46-7.32 (m, 5 H), 7.28-7.24 (m, 1 H), 7.24-7.20 (m, 2 H), 5.21 (s, 2 H), 3.57-3.46 (m, 2 H), 3.31-3.17 (m, 4 H), 3.06-2.94 (m, 2 H), 2.86 (bs, 3 H), 2.48-2.43 (m, 1 H), 1.42-1.19 (m, 4 H), 0.81 (t, J = 7.3 Hz, 3 H). |
| A-118 | N-[4-(trans-2-amino-2-phenethyl-cyclopropyl)phenyl]-3-(2-oxooxazolidin-3-yl)benzamide 2,2,2-trifluoroacetic acid | 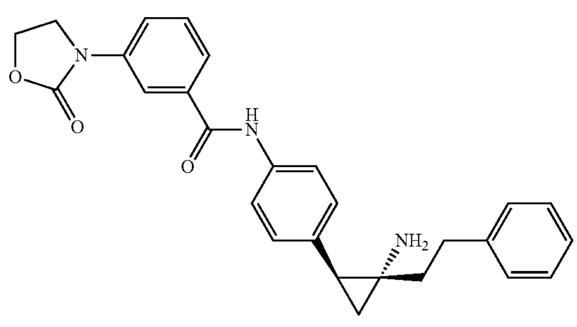 [SMILES: N[C@]1(CCc2ccccc2)C[C@H]1c1ccc(NC(=O)c2cccc(N3CCOC3=O)c2)cc1] | 442 ([M + H]$^+$) | $^1$H NMR (DMSO-d$_6$) δ (ppm): 10.30 (s, 1 H), 8.36 (s, 3 H), 8.08-7.94 (m, 1 H), 7.86-7.48 (m, 5 H), 7.34-6.80 (m, 7 H) 4.54-4.38 (m, 2 H), 4.19-4.01 (m, 2 H), 2.66-2.49 (m, 3 H), 1.66-1.29 (m, 4 H). |

EXAMPLE A-119

4-[trans-2-amino-2-(2-naphthylmethyl)cyclopropyl]aniline 2,2,2-trifluoroacetic acid

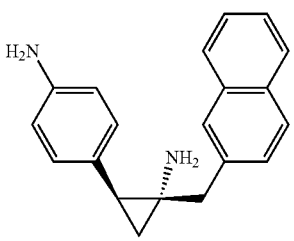 [SMILES: Nc1ccc([C@@H]2C[C@]2(N)Cc2ccc3ccccc3c2)cc1]

The compound was prepared as described for Example 48 starting from ethyl 2-diethoxyphosphoryl-3-(2-naphthyl)propanoate (Intermediate 1) and purified by preparative HPLC. $^1$H NMR (DMSO-$d_6$) δ (ppm): 8.36-6.62 (m, 17 H), 2.92 (d, J=15.2 Hz, 1 H), 2.56-2.51 (m, 2 H), 1.72-1.60 (m, 1 H), MS (ESI): m/z: 289 [M+H]$^+$.

EXAMPLE A-120

N-[4-(trans-2-amino-2-ethyl-cyclopropyl]phenyl)-4-(2-hydroxyethylamino)benzamide hydrochloride

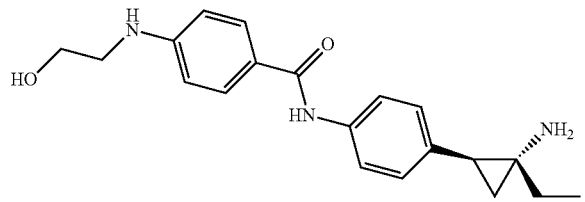 [SMILES: CC[C@@]1(N)C[C@H]1c1ccc(NC(=O)c2ccc(NCCO)cc2)cc1]

The compound was prepared starting from 4-(2-oxooxazolidin-3-yl)benzamide and tert-butyl N-[trans-2-(4-bromophenyl)-1-ethyl-cyclopropyl]carbamate according to the Ullmann type reaction procedure described for example 30. The tert-butyl N-[trans-1-ethyl-2-[4-[[4-(2-oxooxazolidin-3-yl)benzoyl]amino]phenyl]cyclopropyl]carbamate intermediate in H$_2$O/EtOH (1:1) was treated with LiOH at 70° C. for 3 h. After evaporation of the solvents were evaporated, the mixture was washed with H$_2$O and filtered to give the tert-butyl N-[trans-1-ethyl-2-[4-[[4-(2-hydroxyethylamino)benzoyl]amino]phenyl]cyclopropyl]carbamate intermediate, which was hydrolysed with HCl following to procedure for Example 30, last step to give N-[4-(trans-2-amino-2-ethyl-cyclopropyl]phenyl)-4-(2-hydroxyethylamino)benzamide hydrochloride. $^1$H NMR (DMSO-$d_6$) δ (ppm): 9.78 (s, 1 H), 8.36 (bs, 3 H), 7.83-7.59 (m, 4 H), 7.24-7.09 (m, 2 H), 6.70-6.55 (m, 2 H), 5.75 (s, 1 H), 3.58-3.54 (m, 2 H), 3.16 (t, J=6.1 Hz, 2 H), 2.45-2.40 (m, 1 H), 1.44-1.17 (m, 4 H), 0.81 (t, J=7.6 Hz, 3 H). MS (ESI): m/z: 340 [M+H]$^+$.

EXAMPLE A-121

Benzyl N-[3-[1-[4-[trans-2-amino-2-ethyl-cyclopropyl]phenyl]triazol-4-yl]phenyl]carbamate hydrochloride

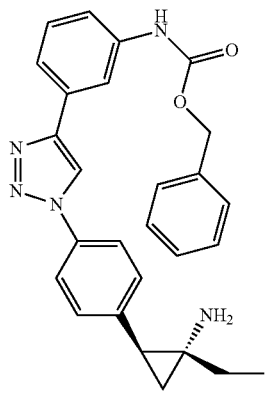 [SMILES: CC[C@@]1(N)C[C@H]1c1ccc(-n2cc(-c3cccc(NC(=O)OCc4ccccc4)c3)nn2)cc1]

Benzyl N-(3-ethynyl phenyl)carbamate 1.810 g Na$_2$CO$_3$ (17.07 mmol) and 1.6 g benzyl chloroformate (9.4 mmol, Sigma-Aldrich) was added to a solution 1.00 g of 3-ethynylaniline (8.54 mmol, Sigma-Aldrich) in THF/water (1:1, v:v). After 2 h at RT the solution was concentrated and the residue was partitioned between EtOAc and brine. The organic layer was washed with brine and concentrated to give 2.100 g benzyl N-(3-ethynylphenyl)carbamate (97.90%) as an oil. $^1$H NMR (CDCl$_3$) δ (ppm): 7.58-7.48 (m, 1 H), 7.45-7.12 (m, 8 H), 6.65 (s, 1 H), 5.22 (s, 2 H), 3.07 (s, 1 H). MS (ESI): m/z: 252 [M+H]$^+$.

tert-Butyl N-[trans-2-[4-[4-(3-benzyloxycarbonylaminophenyl)triazol-1-yl]phenyl]-1-ethyl-cyclopropyl]carbamate A 4 ml screw cup vial was charged with 25 mg benzyl N-(3-ethynylphenyl)carbamate (0.099 mmol), 2 mg sodium 2-[(1,2-dihydroxyethyl]-4-hydroxy-5-oxo-2H-furan-3-olate (0.01 mmol), 30 mg trans-tert-butyl N-[2-(4-azidophenyl)-1-ethyl-cyclopropyl]carbamate (0.099 mmol, prepared following the procedure for Example-49, first step), and 0.2 mg copper sulfate (0.001 mmol). 0.4 mL tert-BuOH:water (1:1, v:v) was added, nitrogen was bubbled into the mixture for about 5 min and the suspension was stirred at 65° C. for 3 h. The mixture was concentrated and purified by column chromatography (hexane/EtOAc 70:30) giving 0.046 g of tert-butyl N-[trans-2-[4-[4-(3-benzyloxycarbonylaminophenyl)triazol-1-yl]phenyl]-1-ethyl-cyclopropyl]carbamate (84%). $^1$H NMR (CDCl$_3$) δ (ppm): 8.19 (s, 1 H), 7.97 (s, 1 H), 7.76-6.63 (m, 13 H), 5.24 (s, 2 H), 5.06 (s, 1 H), 2.59-2.42 (m, 1 H), 1.90-1.39 (m, 10 H), 1.24-1.16 (m, 1 H), 1.11-0.98 (m, 1 H), 0.96-0.74 (m, 4 H). MS (ESI): m/z: 554 [M+H]$^+$.

Benzyl N-[3-[1-[4-[trans-2-amino-2-ethyl-cyclopropyl]phenyl]triazol-4-yl]phenyl]carbamate hydrochloride 0.035 mg of tert-butyl N-[trans-2-[4-[4-(3-benzyloxycarbonylaminophenyl)triazol-1-yl]phenyl]-1-ethyl-cyclopropyl]carbamate (0.063 mmol) was dissolved in 1.0 mL Et₂O. The solution was cooled in an ice bath and then 0.316 mL of a 2 M HCl in Et₂O (0.632 mmol l) was added. After stirring overnight at RT, the reaction mixture was concentrated. Et₂O was added and the suspension was filtered off. The residue was washed twice with Et₂O obtaining 22 mg benzyl N-[3-[1-[4-[trans-2-amino-2-ethyl-cyclopropyl]phenyl]triazol-4-yl]phenyl]carbamate hydrochloride (71%) as a solid. ¹H NMR (DMSO-d₆) δ (ppm): 9.93 (s, 1 H), 9.24 (s, 1 H), 8.51 (s, 3 H), 8.27-7.01 (m, 13 H), 5.18 (s, 2 H), 2.75-2.56 (m, 1 H), 1.54-1.36 (m, 3 H), 1.34-1.22 (m, 1 H), 0.83 (t, J=7.3 Hz, 3 H). MS (ESI): m/z: 454 [M+H]⁺.

The following compounds (table 7) were synthesized starting from the appropriate azide and the appropriate alkine intermediate according to the Click type reaction procedure described for example A-121

TABLE 7

| Ex. | Name | Structure | LC-MS | NMR |
|---|---|---|---|---|
| A-122 | trans-1-ethyl-2-[3-(4-phenyltriazol-1-yl)phenyl]cyclopropanamine hydrochloride | 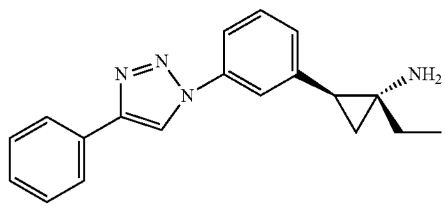 [SMILES: CC[C@@]1(N)C[C@H]1c1cccc(-n2cc(-c3ccccc3)nn2)c1] | 305 ([M + H]⁺) | |
| A-123 | benzyl N-[3-[1-[4-[2-amino-2-(2-naphthylmethyl)cyclopropyl]phenyl]triazol-4-yl]phenyl]carbamate hydrochloride | 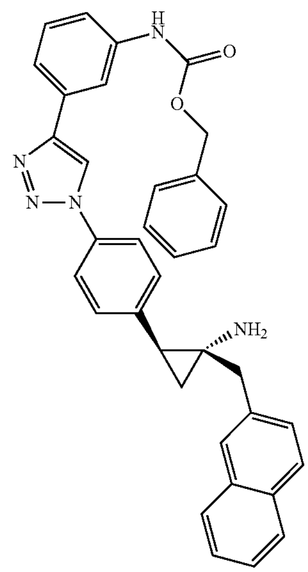 [SMILES: N[C@]1(Cc2ccc3ccccc3c2)C[C@H]1c1ccc(-n2cc(-c3cccc(NC(=O)OCc4ccccc4)c3)nn2)cc1] | 566 ([M + H]⁺) | ¹H NMR (DMSO-d₆) δ (ppm): 9.94 (s, 1 H), 9.39-9.15 (m, 1 H), 8.39 (s, 3 H), 8.24-7.19 (m, 20 H), 5.18 (s, 2 H) AB System: VA = 3.04, VB = 2.59, JAB = 17.7 Hz, 2.84-2.72 (m, 1 H), 2.03-1.89 (m, 1 H), 1.65-1.39 (m, 1 H). |
| A-124 | trans-1-(2-naphthylmethyl)-2-[4-(4-phenyltriazol-1-yl)phenyl]cyclopropanamine hydrochloride | 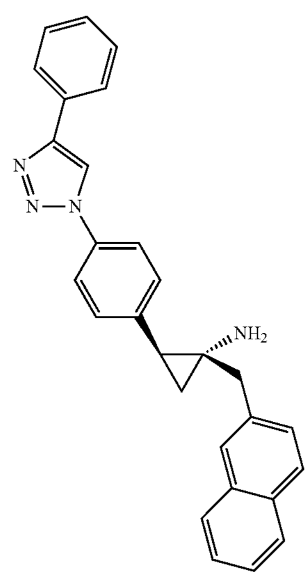 [SMILES: N[C@]1(Cc2ccc3ccccc3c2)C[C@H]1c1ccc(-n2cc(-c3ccccc3)nn2)cc1] | 417 ([M + H]⁺) | ¹H NMR (DMSO-d₆) δ (ppm): 9.35 (s, 1 H), 8.63-8.43 (m, 3 H), 8.08-7.17 (m, 16 H), AB System: VA = 3.07, VB = 2.58, JAB = 15.1 Hz, 2.87-2.75 (m, 1 H), 1.97-1.83 (m, 1 H), 1.61-1.49 (m, 1 H). |

TABLE 7-continued

| Ex. | Name | Structure | LC-MS | NMR |
|---|---|---|---|---|
| A-125 | trans 1-ethyl-2-[2-(4-phenyltriazol-1-yl)phenyl]cyclopropan amine hydrochloride | 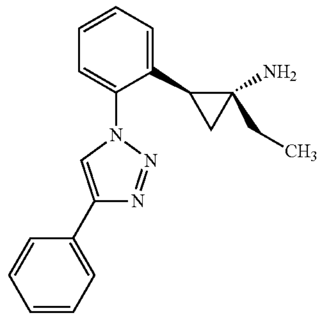 [SMILES: CC[C@@]1(N)C[C@H]1c1ccccc1-n1cc(-c2ccccc2)nn1] | 327 ([M + H]+) | 1H NMR (DMSO-d6) δ (ppm): 9.02 (s, 1 H), 8.44-7.16 (m, 12 H), 2.65-2.53 (m, 1 H), 1.67-0.93 (m, 4 H), 0.90-0.65 (m, 3 H). |
| A-126 | trans-1-benzyl-2-[4-(4-phenyltriazol-1-yl)phenyl]cyclopropan amine hydrochloride | 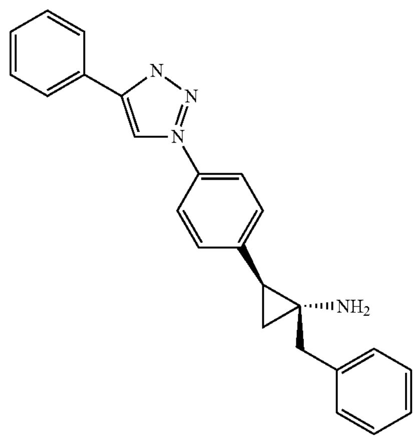 | 367 ([M + H]+) | 1H NMR (MeOH-d4) δ (ppm): 9.00-8.91 (m, 1 H), 8.05-7.87 (m, 4 H), 7.67-7.59 (m, 2 H), 7.53-7.45 (m, 2 H), 7.43-7.38 (m, 1 H), 7.37-7.26 (m, 3 H), 7.21-7.13 (m, 2 H), 2.99-2.88 (m, 1 H), 2.82-2.71 (m, 1 H), 2.60-2.51 (m, 1 H), 1.97-1.83 (m, 1 H), 1.64-1.53 (m, 1 H). |

EXAMPLE A-127

N-[4-[(1S,2R)-2-amino-2-ethyl-cyclopropyl]phenyl]-4-phenyl-benzamide hydrochloride

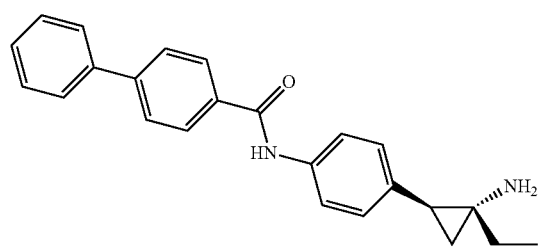 [SMILES: CC[C@@]1(N)C[C@H]1c1ccc(NC(=O)c2ccc(-c3ccccc3)cc2)cc1]

The compound was prepared according to the Ullmann type reaction procedure described for example A-30. 1H NMR (DMSO-d6) δ (ppm): 10.32 (s, 1 H), 8.36 (bs, 3 H), 8.09-8.00 (m, 2 H), 7.89-7.80 (m, 2 H), 7.79-7.71 (m, 4 H), 7.56-7.47 (m, 2 H), 7.47-7.39 (m, 1 H), 7.27-7.19 (m, 2 H), 2.56-2.51 (m, 1 H), 1.43-1.19 (m, 4 H), 0.82 (t, J=7.6 Hz, 3 H). MS (ESI): m/z: 357 [M-+H]+.

EXAMPLE A-128

N-[4-[(1R,2S)-2-amino-2-ethyl-cyclopropyl]phenyl]-4-phenyl-benzamide hydrochloride

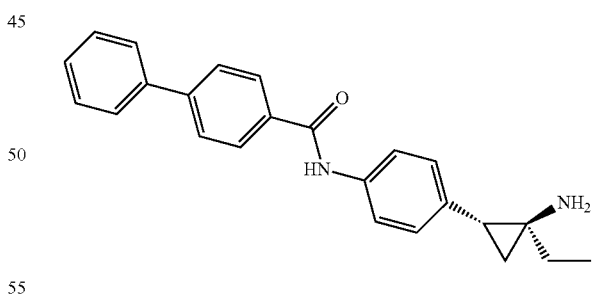

The compound was prepared according to the Ullmann type reaction procedure described for example A-30. 1H NMR (DMSO-d6) δ (ppm): 10.31 (s, 1 H), 8.34 (s, 3 H), 8.09-7.97 (m, 2 H), 7.88-7.80 (m, 2 H), 7.78-7.72 (m, 4 H), 7.56-7.47 (m, 2 H), 7.45-7.38 (m, 1 H), 7.28-7.18 (m, 2 H), 2.54-2.51 (m, 1 H), 1.45-1.18 (m, 4 H), 0.82 (t, J=7.6 Hz, 3 H). MS (ESI): m/z: 357 [M+H]+.

EXAMPLE A-129 trans 1-Benzyl-2-(3-methoxyphenyl)cyclopropanamine hydrochloride

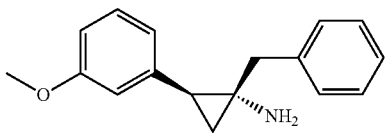 [SMILES: COc1cccc([C@@H]2C[C@]2(N)Cc2ccccc2)c1]

Compound A-129 was prepared according to the procedure described for example A-1 starting from the appropriate styrene oxide and phosphonoacetate. MS (ESI): m/z: 254 [M+H]$^+$.

EXAMPLE A-130

1-[3-[(trans-2-amino-2-ethyl-cyclopropyl]phenyl]-3-phenyl-imidazolidin-2-one hydrochloride

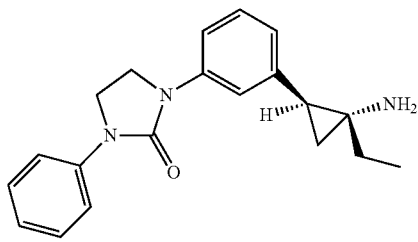 [SMILES: CC[C@@]1(N)C[C@H]1c1cccc(N2CCN(c3ccccc3)C2=O)c1]

Compound A-130 was prepared according to the procedure described for example A-30. $^1$H NMR (DMSO-d$_6$) δ (ppm): 8.32 (bs, 3 H), 7.53-7.77 (m, 3 H), 7.23-7.46 (m, 4 H), 7.07 (s, 1 H), 6.88-6.99 (m, 1 H), 3.85-4.06 (m, 4 H), 2.52-2.60 (m, 1 H), 1.16-1.50 (m, 4 H), 0.83 (t, J=7.34 Hz, 3 H). MS (ESI): m/z: 322 [M+H]$^+$.

EXAMPLE A-131 trans-1-Ethyl-2-[4-(4-phenyltriazol-1-yl)phenyl] cyclopropanamine hydrochloride

Compound A-131 was prepared according to the procedure described for example A-121. $^1$H NMR (DMSO-d$_6$) δ (ppm): 9.31 (s, 1 H), 8.36 (bs, 3 H), 7.93 (s, 4 H), 7.57-7.45 (m, 4 H), 7.43-7.35 (m, 1 H), 2.67-2.58 (m, 1 H), 1.47 (s, 1 H), 1.44-1.36 (m, 2 H), 1.35-1.25 (m, 1 H), 0.83 (t, J=7.6 Hz, 3 H). MS (ESI): m/z: 305 [M+H]$^+$.

EXAMPLE A-132 trans-1-ethyl-2-phenyl-cyclopropanamine hydrochloride

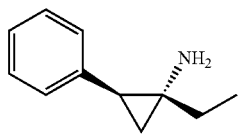

Compound A-132 was prepared according to the procedure described for example A-1. $^1$H NMR (DMSO-d$_6$) δ (ppm): 8.40 (s, 3 H), 7.37-7.29 (m, 2 H), 7.28-7.21 (m, 3 H), 2.58-2.51 (m, 1 H), 1.40-1.28 (m, 3 H), 1.26-1.17 (m, 1 H), 0.79 (t, J=7.6 Hz, 3 H). MS (ESI): m/z: 162 [M+H]$^+$.

EXAMPLE B-3 trans-1-(benzylamino)methyl-2-phenyl-cyclopropanamine dihydrochloride

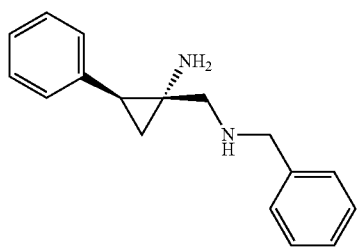 [SMILES: N[C@]1(CNCc2ccccc2)C[C@H]1c1ccccc1]

tert-butyl N-[1-formyl-trans-2-phenyl-cyclopropyl] carbamate 1 g of 3 Å activated molecular sieves and 910 mg (2.4 mmol) of PDC were added at RT to a solution of 488 mg (1.85 mmol) tert-butyl-N-[1-(hydroxymethyl)-trans-2-phenyl-cyclopropyl]carbamate (Example B-1, step 4) in dry CH$_2$Cl$_2$ (12 mL). After 7 h Et$_2$O was added and the mixture was filtered through a short pad of celite and eluted with CH$_2$Cl$_2$:Et$_2$O (1:1). Solvents were evaporated and the residue was purified by column chromatography (hexane/EtOAc from 95:5 to 6:4) to give 320 mg (66%) of tert-butyl N-[1-formyl-trans-2-phenyl-cyclopropyl]carbamate as a colourless solid. $^1$H NMR (CDCl$_3$) δ (ppm): 8.71 (bs, 1 H), 7.51-7.17 (m, 5 H), 5.21 (bs, 1 H), 3.11 (bs, 1 H), 2.21-2.12 (m, 1 H), 1.80 (bs, 1 H), 1.51 (s, 9 H). MS (ESI): m/z: 162 [M−100+H]$^+$.

tert-butyl N-1-[(benzylamino)methyl-trans-2-phenyl-cyclopropyl]carbamate 100 mg of activated 3 Å molecular sieves were added at RT to a solution of 30 mg (0.11 mmol) of tert-butyl N-[1-formyl-trans-2-phenyl-cyclopropyl]carbamate in 0.5 mL of DCE, followed by 0.013 mL (0.230 mmol) of acetic acid and 0.015 mL (0.14 mmol) of benzylamine. The mixture was stirred at RT for about 90 min, then 37 mg (0.17 mmol) of NaBH(OAc)$_3$ was added portion-wise at RT. After 90 min the reaction mixture was quenched with Na$_2$CO$_3$ and the aqueous phase was extracted with CH$_2$Cl$_2$. The combined organic layers were dried and evaporated and the crude mixture was purified by column chromatography (hexane/EtOAc 4:6) to give 30 mg (74%) of tert-butyl N-1-[(benzylamino)methyl-trans-2-phenyl-cyclopropyl]carbamate as a light yellow solid. $^1$H NMR (CDCl$_3$) δ (ppm): 7.35-7.01 (m, 10 H), 5.31 (bs, 1 H), 3.69-3.47 (m, 2 H), 2.67-2.31 (m, 3 H), 1.48 (s, 9 H), 1.32-1.20 (m, 2 H). MS (ESI): m/z: 353 [M+H]$^+$.

1-(benzylamino)methyl-trans-2-phenyl-cyclopropanamine dihydrochloride 0.21 mL (0.43 mmol) of 2 M HCl in Et$_2$O was added at −78° C. to a solution of 30 mg (0.085 mmol) of tert-butyl N-1-[(benzylamino)methyl-trans-2-phenyl -cyclopropyl] carbamate in 1.6 mL of dry MeOH/Et$_2$O (4:6). The resulting mixture was stirred at −78° C. for about 4 h. Then, 0.107 mL of 4 M HCl in 1,4-dioxane were added and the mixture was kept at 4° C. for about 40 h. Further 0.054 mL of 4 M HCl in 1,4-dioxane were added and the reaction mixture was first kept at 4° C. for 48 h and then at RT for additional 6 h. The solvents were then to give 20 mg (72%) of 1-(benzylamino) methyl-trans-2-phenyl-cyclopropanamine dihydrochloride as a beige powder. $^1$H NMR (DMSO-d$_6$) δ (ppm): 9.02 (bs, 5 H), 7.60-7.21 (m, 10 H), 4.17-3.98 (m, 2 H), 3.48-3.37 (m, 1 H), 2.77-2.66 (m, 1 H), 2.45-2.32 (m, 1 H), 1.98-1.54 (m, 2 H). MS (ESI): m/z: 253 [M+H]+.

The following compounds were prepared according to the procedure described for compound B-3 (table 8)

TABLE 8

| Ex. | Name | Structure | LC-MS | NMR |
|---|---|---|---|---|
| B-4 | trans 1-[(cyclopropylamino)methyl]-2-phenyl-cyclopropanamine dihydrochloride | 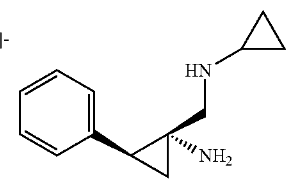 | 203 ([M + H]$^+$) | $^1$H NMR (DMSO-d$_6$) δ ppm: 8.99 (bs, 5 H), 7.44-7.23 (m, 5 H), 3.50-3.41 (m, 1 H), 2.79-2.61 (m, 2 H), 2.44-2.32 (m, 1 H), 1.95-1.84 (m, 1 H), 1.65-1.52 (m, 1 H), 0.89 (bs, 2 H), 0.74-0.53 (m, 2 H). |
| B-5 | trans-1-[(4-methylpiperazine-1-yl)methyl]-2-phenyl-cyclopropanamine trihydrochloride | 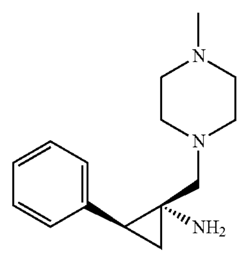 [SMILES: CN1CCN(C[C@@]2(N)C[C@H]2c2ccccc2)CC1] | 246 ([M + H]$^+$) | $^1$H NMR (DMSO-d$_6$) δ ppm: 10.97 (bs, 2 H), 8.92-8.67 (m, 3 H), 7.41-7.17 (m, 5 H), 3.39-3.24 (m, 2 H), 3.19-2.93 (m, 3 H), 2.91-2.73 (m, 2 H), 2.71-2.62 (m, 4 H), 2.58-2.25 (m, 2 H and DMSO), 2.12-1.93 (m, 1 H), 1.64-1.46 (m, 2 H). |

The following compounds (table 9) were synthesized starting from the appropriate amine and aldehyde according to the procedure described for example C-1. Compound C-19 was obtained by treating compound C-18 with HCl in Et$_2$O according to well known procedures. Compound C-20 was purified by preparative HPLC.

TABLE 9

| Ex. | Name | Structure | LC-MS | NMR |
|---|---|---|---|---|
| C-18 | 5-[[[trans-1-methyl-2-phenyl-cyclopropyl]amino]methyl] pyrimidin-2-amine | 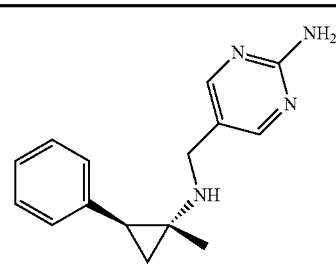 | 255 ([M + H]$^+$) | $^1$H NMR (DMSO-d$_6$) δ (ppm): 8.17 (s, 2 H), 7.30-7.04 (m, 5 H), 6.45 (s, 2 H), 3.58 (s, 2 H), 2.40 (bs, 1 H), 2.13-1.96 (m, 1 H), 1.01-0.95 (m, 1 H), 0.94-0.87 (m, 4 H). |

TABLE 9-continued

| Ex. | Name | Structure | LC-MS | NMR |
|---|---|---|---|---|
| C-19 | 5-{[(trans-1-methyl-2-phenyl-cyclopropyl)amino]methyl}pyrimidin-2-amine dihydrochloride | 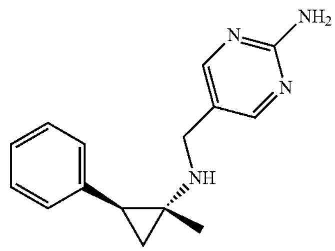 [SMILES: C[C@@]1(NCc2cnc(N)nc2)C[C@H]1c1ccccc1] | 255 ([M + H]⁺) | $^1$H NMR (DMSO-d$_6$ + D$_2$O) δ (ppm): 8.45 (s, 2 H), 7.40-7.16 (m, 5 H), AB System: VA = 4.2, VB = 4.18, JAB = 13.2 Hz, 2.75-2.63 (m, 1 H), 1.61-1.49 (m, 1 H), 1.41-1.27 (m, 1 H), 1.13 (s, 3 H). |
| C-20 | trans-N-[(2-methoxy-3-pyridyl)methyl]-1-methyl-2-phenyl-cyclopropanamine | 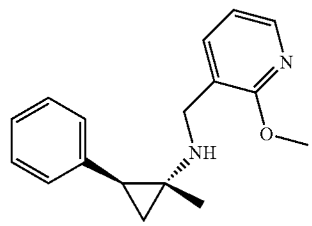 [SMILES: COc1ncccc1CN[C@]1(C)C[C@H]1c1ccccc1] | 269 ([M + H]⁺) | $^1$H NMR (DMSO-d$_6$) δ (ppm): 8.07-7.99 (m, 1 H), 7.76-7.22 (m, 2 H), 7.18-7.07 (m, 3 H), 6.98-6.92 (m, 1 H), 3.88 (s, 3 H), 3.75 (bs, 2 H), 2.43 (bs, 1 H), 2.12-2.03 (m, 1 H), 1.03-0.98 (m, 1 H), 0.97-0.91 (m, 4 H). |
| C-21 | trans-N-(2,3-dihydro-1,4-benzodioxin-6-ylmethyl)-1-methyl-2-phenyl-cyclopropanamine 2,2,2-trifluoroacetic acid | 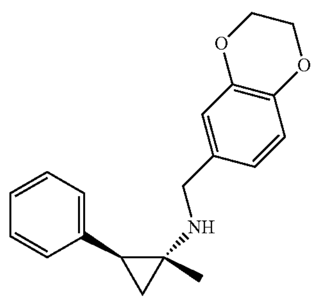 [SMILES: C[C@@]1(NCc2ccc3c(c2)OCCO3)C[C@H]1c1ccccc1] | 296 ([M + H]⁺) | $^1$H NMR (DMSO-d$_6$) δ (ppm): 9.13 (bs, 1 H), 8.90 (bs, 1 H), 7.36-7.30 (m, 2 H), 7.29-7.23 (m, 1 H), 7.23-7.18 (m, 2 H), 7.12-7.07 (m, 1 H), 7.03-6.98 (m, 1 H), 6.97-6.92 (m, 1 H), 4.34-4.16 (m, 6 H), 2.68-2.56 (m, 1 H), 1.39-1.28 (m, 1 H), 1.12 (s, 3 H). |

The following compounds (table 10) were synthesized starting from the appropriate BOC-protected amine and the appropriate chloro or bromo-alkyl derivative according to the procedure described for example C-3. Compounds C-21, C-22, C-25, and C-26 were purified by preparative HPLC. The cis compound C-26 was prepared according to the procedure described for example C-4. The cis compounds C-28 and C-22 were obtained using as starting material their corresponding cis-BOC-protected intermediates (tert-butyl N-[cis-1-methyl-2-phenyl-cyclopropyl]-N-[2-(4-methylpiperazin-1-yl)-2-oxo-ethyl]carbamate for C-28 and cis-N,1-dimethyl-2-phenyl-cyclopropanamine hydrochloride for C-22) which were formed by treatment of the trans-BOC intermediate with DMF and NaH according to the conditions described for the second step of the synthesis of example C-3 (about 10 to 20% relative to the trans analogues) and were separated from their corresponding trans analogues by column chromatography (eluent: CH$_2$Cl$_2$/MeOH/NH$_3$ 96:4:0.4 for C-28 and EtOAc/cyclohexane, 4:94 for C-22).

TABLE 10

| Ex. | Name | Structure | LC-MS | NMR |
|---|---|---|---|---|
| C-22 | cis-N, 1-dimethyl-2-phenyl-cyclopropanamine 2,2,2-trifluoroacetic acid | 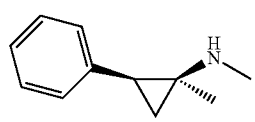 | 162 ([M + H]⁺) | $^1$H NMR (DMSO-d$_6$) δ (ppm): 8.46 (bs, 1 H), 7.94 (bs, 1 H), 7.45-7.24 (m, 5 H), 2.47-2.40 (m, 4 H), 1.52 (s, 3 H), 1.49-1.44 (m, 1 H), 1.26-1.19 (m, 1 H). |
| C-23 | 2-[[trans-1,2-diphenylcyclopropyl]amino]-1-(4-methylpiperazin-1-yl)ethanone dihydrochloride | 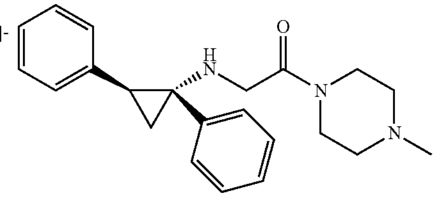 | 350 ([M + H]⁺) | $^1$H NMR (DMSO-d$_6$, D$_2$O) δ (ppm): 7.44-7.32 (m, 2 H), 7.26-7.17 (m, 3 H), 7.11-7.00 (m, 3 H), 6.98-6.88 (m, 2 H), 4.42-4.05 (m, 2 H), 3.88-3.65 (m, 2 H), 3.36-3.24 (m, 2 H), 3.10-2.69 (m, 8 H), 2.07-1.97 (m, 1 H), 1.94-1.80 (m, 1 H). |

| Ex. | Name | Structure | LC-MS | NMR |
|---|---|---|---|---|
| C-24 | 1-(4-methylpiperazin-1-yl)-2-[[trans-1-(2-naphthylmethyl)-2-phenyl-cyclopropyl]amino]ethanone dihydrochloride | 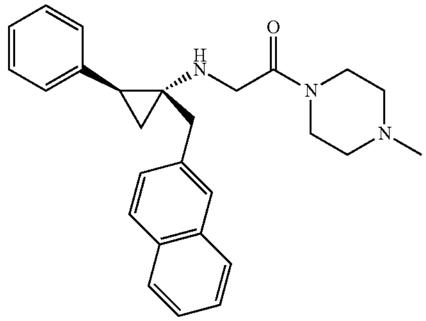 [SMILES: CN1CCN(C(=O)CN[C@]2(Cc3ccc4ccccc4c3)C[C@H]2c2ccccc2)CC1] | 414 ([M + H]$^+$) | $^1$H NMR (DMSO-d$_6$ + D$_2$O) δ (ppm): 7.88-7.82 (m, 1 H), 7.79-7.73 (m, 1 H), 7.69-7.62 (m, 1 H), 7.52-7.42 (m, 2 H), 7.40-7.25 (m, 6 H), 7.23-7.13 (m, 1 H), 4.44-4.02 (m, 2 H), 3.88 (bs, 1 H), 3.49-3.07 (m, 4 H), 3.06-2.68 (m, 8 H), 2.66-2.54 (m, 1 H), 1.71-1.42 (m, 2 H). |
| C-25 | 2-[[(1R,2S)-1-methyl-2-phenyl-cyclopropyl]amino]-1-(4-methylpiperazin-1-yl)ethanone 2,2,2-trifluoroacetic acid | 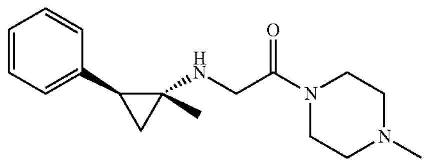 [SMILES: CN1CCN(C(=O)CN[C@]2(C)C[C@H]2c2ccccc2)CC1] | 288 ([M + H]$^+$) | $^1$H NMR (D2O) δ (ppm): 7.36-7.10 (m, 5 H), 4.48-4.39 (m, 1 H), 4.33-4.14 (m, 2 H), 3.97-3.87 (m, 1 H), 3.49 (bs, 3 H), 3.12-2.95 (m, 3 H), 2.82 (s, 3 H), 2.68-2.59 (m, 1 H), 1.50-1.41 (m, 1 H), 1.32-1.24 (m, 1 H), 1.01 (s, 3 H). |
| C-26 | 2-[[(1R,2R)-1-methyl-2-phenyl-cyclopropyl]amino]-1-(4-methylpiperazin-1-yl)ethanone 2,2,2-trifluoroacetic acid | 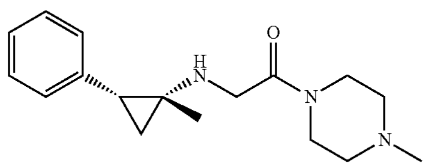 [SMILES: CN1CCN(C(=O)CN[C@]2(C)C[C@@H]2c2ccccc2)CC1] | 288 ([M + H]$^+$) | $^1$H NMR (D$_2$O) δ (ppm): 7.37-7.19 (m, 5 H), 4.23 (bs, 1 H), AB System: VA = 4.05, VB = 3.87, JAB = 16.9 Hz, 3.79-3.24 (m, 4 H), 3.14-2.67 (m, 6 H), 2.52-2.42 (m, 1 H), 1.61-1.55 (m, 1 H), 1.49 (s, 3 H), 1.25-1.15 (m, 1 H). |
| C-27 | 2-[[trans-1-methyl-2-phenyl-cyclopropyl]amino]-1-(4-methylpiperazin-1-yl)ethanone dihydrochloride | 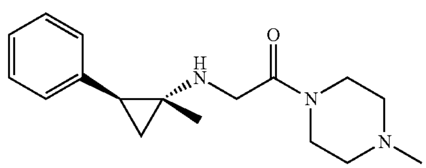 [SMILES: CN1CCN(C(=O)CN[C@]2(C)C[C@H]2c2ccccc2)CC1] | 288 ([M + H]$^+$) | $^1$H NMR (D2O) δ (ppm): 7.36-7.10 (m, 5 H), 4.49-4.39 (m, 1 H), 4.34-4.15 (m, 2 H), 3.99-3.87 (m, 1 H), 3.56-3.45 (m, 3 H), 3.14-2.95 (m, 3 H), 2.83 (s, 3 H), 2.66-2.58 (m, 1 H), 1.50-1.42 (m, 1 H), 1.32-1.25 (m, 1 H), 1.01 (s, 3 H). |
| C-28 | 2-[[cis-1-methyl-2-phenyl-cyclopropyl]amino]-1-(4-methylpiperazin-1-yl)ethanone dihydrochloride | 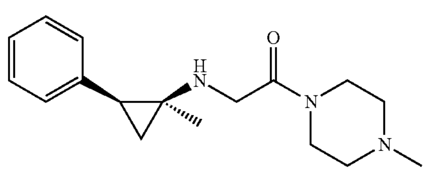 [SMILES: CN1CCN(C(=O)CN[C@@]2(C)C[C@H]2c2ccccc2)CC1] | 288 ([M + H]$^+$) | $^1$H NMR (D2O) δ (ppm): 7.37-7.19 (m, 5 H), 4.23 (bs, 1 H), AB System: VA = 4.05, VB = 3.86, JAB = 16.1 Hz, 3.77-3.24 (m, 4 H), 3.16-2.72 (m, 6 H), 2.53-2.43 (m, 1 H), 1.61-1.54 (m, 1 H), 1.50 (s, 3 H), 1.25-1.18 (m, 1 H). |
| C-29 | trans-N,1-dimethyl-2-phenyl-cyclopropanamine hydrochloride | 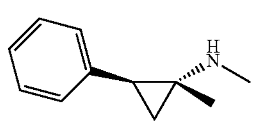 | 162 ([M + H]$^+$) | $^1$H NMR (DMSO-d$_6$) δ (ppm): 9.15 (bs, 2 H), 7.40-7.16 (m, 5 H), 2.66 (s, 3 H), 2.64-2.58 (m, 1 H), 1.53-1.46 (m, 1 H), 1.33-1.27 (m, 1 H), 1.02 (s, 3 H). |

EXAMPLE C-30

2-[(trans-1-Ethyl-2-phenyl-cyclopropyl)amino]-1-(1-piperidyl)ethanone hydrochloride

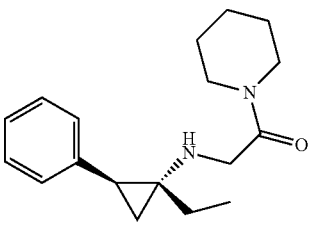 [SMILES: CC[C@@]1(NCC(=O)N2CCCCC2)C[C@H]1c1ccccc1]

Ethyl 2-[(trans-1-ethyl-2-phenyl-cyclopropyl)amino]acetate 0.34 mL DIPEA (2 mmol) was added to a solution of 0.2 g trans-1-ethyl-2-phenyl -cyclopropanamine hydrochloride (1 mmol, prepared as described for Example A-1) in 4 mL CH$_3$CN. After complete dissolution of the amine, 0.12 mL ethyl 2-bromoacetate (1.1 mmol, Sigma Aldrich) was added and the mixture was stirred at RT. After 40 h, 0.034 mL ethyl 2-bromoacetate wad added (0.3 mmol) and stirring was continued for additional 5 h. Solvent was removed under vacuum and the crude was purified by flash chromatography eluting with CH$_2$Cl$_2$ to get 0.211 g ethyl 2-[(trans-1-ethyl-2-phenyl -cyclopropyl)amino]acetate (84%) as colourless oil. $^1$H NMR (DMSO-d$_6$) δ (ppm): 9.42 (bs, 2 H), 7.42-7.12 (m, 5 H), 4.25 (q, J=7.3 Hz, 2 H), 4.15 (bs, 2 H), 2.71 (bs, 1 H), 1.57-1.39 (m, 2 H), 1.36-1.22 (m, 4 H), 1.18-1.07 (m, 1 H), 0.77 (t, J=7.3 Hz, 3 H). MS (ESI): m/z: 248 [M+H]$^+$.

2-[tert-butoxycarbonyl-(trans-1-ethyl-2-phenyl-cyclopropyl)amino]acetic acid A solution of 0.016 g LiOH (0.68 mmol) in 1.1 ml water was added to the solution of 0.140 g ethyl 2-[(trans-1-ethyl-2-phenyl-cyclopropyl)amino]acetate (0.56 mmol) in 4.5 mL THF and it was stirred vigorously for 2 h at RT. 0.170 mg di-tert-butyl carbonate (0.78 mmol) was added and the mixture was stirred overnight. After solvent removal the crude was taken up with EtOAc, washed with brine, and the organic layer was dried over Na$_2$SO$_4$. The solution was filtered, dried, and the crude mixture was purified by flash chromatography eluting with CH$_2$Cl$_2$/MeOH (100% CH$_2$Cl$_2$ to 90:10) to get 0.112 g 2-[tert-butoxycarbonyl-(trans-1-ethyl-2-phenyl-cyclopropyl)amino]acetic acid (62%) as a colourless oil. MS (ESI): m/z: 318 [M−H]$^-$.

tert-butyl N-[trans-1-ethyl-2-phenyl-cyclopropyl]-N-[2-oxo-2-(1-piperidyl)ethyl]carbamate 0.028 mg HOBt (0.21 mmol) and 0.048 mg EDC (0.25 mmol) were added to a solution of 0.068 mg 2-[tert-butoxycarbonyl-[trans-1-ethyl-2-phenyl-cyclopropyl]amino]acetic acid (0.21 mmol) in 1.5 mL dry DMF and cooled in an ice bath. The mixture was allowed to reach RT and stirred for 1.5 h. 0.025 mL piperidine (0.25 mmol) was added and stirring was continued for additional 30 min. The mixture was poured into water and extracted with EtOAc. The organic phase was washed with 1 M HCl, saturated NaHCO$_3$ and finally with brine. The solution was dried over Na$_2$SO$_4$, filtered and concentrated under vacuum to afford 0.070 g tert-butyl N-[trans-1-ethyl-2-phenyl-cyclopropyl]-N-[2-oxo-2-(1-piperidyl)ethyl]carbamate (85%) as a colourless oil. MS (ESI): m/z: 387 [M+H]$^+$.

2-[[trans-1-ethyl-2-phenyl-cyclopropyl]amino]-1-(1-piperidyl)ethanone hydrochloride 0.53 mL HCl 2 M in Et$_2$O (1.06 mmol) was slowly added to a solution of 0.041 g tert-butyl N-(trans-1-ethyl-2-phenyl-cyclopropyl)-N-[2-oxo-2-(1-piperidyl)ethyl]carbamate (0.106 mmol) in 0.8 mL dry Et$_2$O cooled in an ice bath. Then, the mixture was allowed to reach RT. After additional 2 h the mixture was cooled, 0.53 mL 4 M HCl in dioxane (2.12 mmol) was added and the solution was stirred overnight at RT. The crude mixture was dried, triturated with Et$_2$O, filtered and washed to afford 0.027 g 2-(trans-1-ethyl-2-phenyl-cyclopropyl]amino)-1-(1-piperidyl)ethanone hydrochloride (79%) as an off white solid. $^1$H NMR (DMSO-d$_6$) δ (ppm): 9.03 (bs, 2 H), 7.40-7.20 (m, 5 H), 4.17 (s, 2 H), 3.58-3.45 (m, 2 H), 3.40 (bs, 2 H), 2.76-2.68 (m, 1 H), 1.68-1.39 (m, 8 H), 1.35-1.28 (m, 1 H), 1.26-1.15 (m, 1 H), 0.75 (t, J=7.3 Hz, 3 H). MS (ESI): m/z: 287 [M+H]$^+$.

EXAMPLE C-31 trans-1-Ethyl-2-phenyl-N-[2-(1-piperidyl)ethyl]cyclopropanamine dihydrochloride

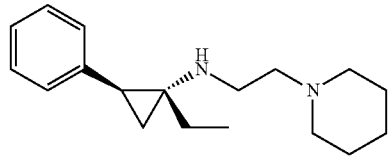 [SMILES: CC[C@@]1(NCCN2CCCCC2)C[C@H]1c1ccccc1]

tert-butyl N-[trans-1-ethyl-2-phenyl-cyclopropyl]-N-[2-(1-piperidyl)ethyl]carbamate A solution of 0.043 g tert-butyl N-[trans-1-ethyl-2-phenyl-cyclopropyl]-N-[2-oxo-2-(1-piperidyl)ethyl]carbamate (0.11 mmol, Example C-30, step 3) in 1 mL dry THF was added to a stirred and ice cooled solution of 1 M of LiAlH$_4$ in THF (0.132 mmol). Stirring was continued for 2 h at RT, then the mixture was poured into water and extracted with EtOAc. The organic phase was separated, dried over Na$_2$SO$_4$ and filtered. The crude mixture was purified by flash chromatography eluting with CH$_2$Cl$_2$/MeOH (97:3) to afford 0.08 mg tert-butyl N-[trans-1-ethyl-2-phenyl-cyclopropyl]-N-[2-(1-piperidyl)ethyl]carbamate (19%) as a colourless oil. MS (ESI): m/z: 373 [M+H]$^+$.

trans-1-ethyl-2-phenyl-N-[2-(1-piperidyl)ethyl]cyclopropanamine dihydrochloride 0.215 mL 2 M HCl in Et$_2$O (0.43 mmol) was slowly added to an ice cooled solution of 0.016 mg tert-butyl N-[trans-1-ethyl-2-phenyl-cyclopropyl]-N-[2-oxo-2-(1-piperidyl)ethyl]carbamate (0.043 mmol) in 0.4 mL dry Et$_2$O. The mixture was first allowed to reach RT, then after 1 h the mixture was cooled again to 0° C. 0.215 mL HCl (4 M in dioxane, 0.86 mmol) was added and the solution was stirred at RT for 72 h. The crude mixture was vacuum, triturated with Et$_2$O, filtered, washed and dried to afford 0.009 g trans-1-ethyl- 2-phenyl-N-[2-(1-piperidyl)ethyl]cyclopropanamine dihydrochloride (60%) as a beige solid. $^1$H NMR (DMSO-$d_6$) δ (ppm): 10.38 (bs, 1 H), 9.70 (bs, 2 H), 7.43-7.14 (m, 5 H), 3.73-3.42 (m, 6 H), 3.11-2.92 (m, 2 H), 2.88-2.77 (m, 1 H), 1.88-1.68 (m, 5 H), 1.65-1.33 (m, 4 H), 1.20-1.04 (m, 1 H), 0.85 (t, J=7.1 Hz, 3 H). MS (ESI): m/z: 273 [M+H]$^+$.

EXAMPLE C-32

5-[[[trans-1-methyl-2-phenyl-cyclopropyl]amino]methyl]-1,3,4-oxadiazol-2-amine

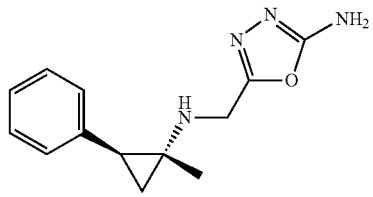 [SMILES: C[C@@]1(NCc2nnc(N)o2)C[C@H]1c1ccccc1]

N-[5-[[[trans-1-methyl-2-phenyl-cyclopropyl]amino]methyl]-1,3,4-oxadiazol-2-yl]carbamate 340 mg (2.46 mmol) K$_2$CO$_3$ and 215 mg (0.920 mmol) tert-butyl N-[5-(chloromethyl)-1,3,4-oxadiazol-2-yl]carbamate (prepared as described in WO 2012/013728) were added to a solution of 181 mg (1.23 mmol) trans-1-methyl-2-phenyl-cyclopropanamine in 3 mL DMF at RT. The reaction mixture was poured after 1 h into ice and extracted with EtOAc. The combined organic phases were washed with brine, dried over Na$_2$SO$_4$, filtered off and concentrated. The residue was purified by column chromatography first using CH$_2$Cl$_2$/MeOH 97:3 as eluent (column Biotage® KP-NH) and then repurified with CH$_2$Cl$_2$/EtOAc (from 8:2 to 9:1) to give 18 mg (4.2%) of a pale yellow oil. $^1$H NMR (CDCl$_3$) δ (ppm): 7.31-7.25 (m, 2 H), 7.22-7.17 (m, 1 H), 7.16-7.11 (m, 2 H), 4.12 (s, 2 H), 2.28-2.18 (m, 1 H), 1.55 (s, 9 H), 1.18-1.09 (m, 1 H), 1.01 (s, 3 H), 0.97-0.91 (m, 1 H) MS (ESI): m/z: 345 [M+H]$^+$.

5-[[[trans-1-methyl-2-phenyl-cyclopropyl]amino]methyl]-1,3,4-oxadiazol-2-amine

50 μL (0.65 mmol) of trifluoracetic acid was added to a stirred solution of 16 mg (0.046 mmol) of N-[5-[[[trans-1-methyl-2-phenyl-cyclopropyl]amino]methyl]-1,3,4-oxadiazol-2-yl]carbamate in 0.3 mL dry CH$_2$Cl$_2$ cooled at 0° C. The reaction mixture was allowed to reach RT and was stirred for 3 h. Then, the solvent was removed, the crude mixture was taken up in MeOH and eluted through a SCX cartridge (PoraPak Rxn CX, Waters) to give 8.8 mg (77%) of 5-[[[trans-1-methyl-2-phenyl-cyclopropyl]amino]methyl]-1,3,4-oxadiazol-2-amine as a pale yellow solid. $^1$H NMR (DMSO-$d_6$) δ (ppm): 7.29-7.20 (m, 2 H), 7.18-7.07 (m, 3 H), 6.92 (bs, 2 H), AB System: VA=3.8, VB=3.78, JAB=14.7 Hz, 2.79 (bs, 1 H), 2.04-1.95 (m, 1 H), 0.96-0.88 (m, 2 H), 0.87 (s, 3 H). MS (ESI): m/z: 245 [M+H]$^+$.

EXAMPLE D-3 trans-1-(4-nitrophenyl)-2-phenyl-cyclopropanamine hydrochloride

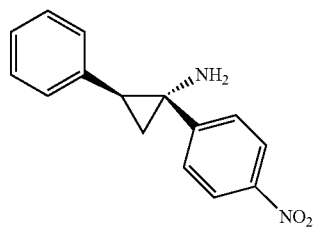 [SMILES: N[C@]1(c2ccc([N+](=O)[O-])cc2)C[C@H]1c1ccccc1]

Methyl (E)-2-(4-nitrophenyl)-3-phenyl-prop-2-enoate

HCl 37% (0.050 mL) and H$_2$SO$_4$ (0.050 mL) were added to a solution of 0.720 g (2-(4-nitrophenyl)-3-phenyl-prop-2-enoic acid (Sigma Aldrich, cat. No. S337463, 2.70 mmol) in dry MeOH (10 mL). After 7 h of heating under reflux, the reaction mixture was concentrated under vacuum. The crude mixture was dissolved in Et$_2$O and in an aqueous solution of Na$_2$CO$_3$ and extracted three times with 30 mL Et$_2$O. The resulting organic layers were dried over Na$_2$SO$_4$, filtered and concentrated to give the desired methyl (E)-2-(4-nitrophenyl)-3-phenyl-prop-2-enoate as a pale yellow solid (0.517 g, 1.83 mmol, 68%). $^1$H NMR (CDCl$_3$) δ=8.30-8.18 (m, 2 H), 7.98 (s, 1 H), 7.54-6.91 (m, 7 H), 3.82 (s, 3 H). MS (ESI): m/z: 284 [M+H]$^+$.

Methyl (E)-2-(4-nitrophenyl)-3-phenyl-prop-2-enoate

Sodium hydride (60% in mineral oil) was added in small portions to a stirred solution of trimethyl sulfoxonium iodide (0.486 g, 2.21 mmol) in dry DMSO (12 mL) under nitrogen atmosphere. Then, a solution of methyl (E)-2-(4-nitrophenyl)-3-phenyl-prop-2-enoate (0.500 g, 1.76 mmol) in dry DMSO (6 mL) was added dropwise and the mixture was first stirred for 2 h at RT, and then heated to 55° C. for 1.5 h. The solution was then diluted with water and extracted with Et$_2$O (three times 40 mL). The organic layers were dried over Na$_2$SO$_4$, filtered off, evaporated and purified by flash column chromatography (eluent: n-hexane/EtOAc 90:10) to give 0.182 g of trans-methyl-1-(4-nitrophenyl)-2-phenyl-cyclopropanecarboxylate (0.612 mmol, 35%) as a colorless oil. $^1$H NMR (CDCl$_3$) δ=8.04-7.94 (m, 2 H), 7.25-7.17 (m, 2 H), 7.13-7.05 (m, 3 H), 6.84-6.75 (m, 2 H), 3.69 (s, 3 H), 3.29-3.18 (m, 1 H), 2.28-2.19 (m, 1 H), 2.00-1.90 (m, 1 H).

trans-1-(4-Nitrophenyl)-2-phenyl-cyclopropanecarboxylic acid

EtOH (0.500 mL), water (0.500 mL) and lithium hydroxide (0.045 g, 1.9 mmol) were added to a solution of 0.140 g trans-Methyl-1-(4-nitrophenyl)-2-phenyl-cyclopropanecarboxylate (0.471 mmol) in THF (0.100 mL). The mixture was heated to 115° C. for 70 min under MW irradiation. The organic solvent was evaporated under vacuum and the resulting aqueous mixture was cooled down to 0° C., diluted with water and quenched with 2 M HCl. The precipitate was filtered off, the resulting solid was washed with water and dried to give 0.123 g of the trans-1-(4-nitrophenyl)-2-phenyl-cyclopropanecarboxylic acid (0.434 mmol, 92%). $^1$H NMR (DMSO-d$_6$) δ=12.78 (s, 1 H), 8.05-7.85 (m, 2 H), 7.40-7.26 (m, 2 H), 7.12-6.98 (m, 3 H), 6.95-6.85 (m, 2 H), 3.17-3.06 (m, 1 H), 2.22-2.12 (m, 1 H), 2.04-1.94 (m, 1 H). MS (ESI): m/z: 284 [M+H]$^+$.

tert-Butyl N-[trans-1-(4-nitrophenyl)-2-phenyl-cyclopropyl]carbamate

Diphenyl phosphoryl azide (0.092 mL, 0.430 mmol) and TEA (0.070 mL, 0.50 mmol) were added to a solution of 0.110 g (0.388 mmol) of trans-1-(4-nitrophenyl)-2-phenyl-cyclopropanecarboxylic acid in dry t-BuOH (3.00 mL). The resulting solution was stirred at 95° C. for 7 h. Then, the mixture was concentrated and partitioned between 10% aqueous Na$_2$CO$_3$ and CH$_2$Cl$_2$. The combined organic layers were dried over Na$_2$SO$_4$, filtered, concentrated under vacuum, and the crude mixture was purified by flash column chromatography (eluent: hexane/EtOAc 95:5) to give 0.096 g of the tert-butyl N-[trans-1-(4-nitrophenyl)-2-phenyl-cyclopropyl]carbamate (0.207 mmol, 70%). $^1$H NMR (DMSO-d$_6$) δ=8.19 (s, 1 H), 8.06-7.85 (m, 2 H), 7.43-7.25 (m, 2 H), 7.15-6.92 (m, 5 H), 2.88-2.74 (m, 1 H), 2.28-2.11 (m, 1 H), 1.63-1.47 (m, 1 H), 1.43-1.19 (m, 9 H). MS (ESI): m/z: 355 [M+H]$^+$.

trans-1-(4-nitrophenyl)-2-phenyl-cyclopropanamine hydrochloride 0.015 g of tert-butyl N-[trans-1-(4-nitrophenyl)-2-phenyl-cyclopropyl]carbamate (0.042 mmol) in 0.5 mL Et$_2$O was cooled down to 0° C. and 2.0 M HCl (0.212 mL, 0.423 mmol) in Et$_2$O was added. The reaction mixture was stirred at RT for 16 h. The formed precipitate was then filtered off and washed twice with Et$_2$O obtaining the desired trans-1-(4-nitrophenyl)-2-phenyl-cyclopropanamine hydrochloride (0.005 g, 0.02 mmol, 41%). $^1$H NMR (DMSO-d$_6$) δ=9.05 (s, 3 H), 8.15-8.05 (m, 2 H), 7.67-7.51 (m, 2 H), 7.18-6.92 (m, 5 H), 3.05-2.90 (m, 1 H), 2.35-2.23 (m, 1 H), 1.98-1.83 (m, 1 H). MS (ESI): m/z: 255 [M+H]$^+$.

According to the procedure described for example D-3 the following compounds (Table 11) were synthesized starting from the appropriate cinnamic acids. The starting phenyl cinnamic acids are commercially available or were prepared as reported in J. Med. Chem. 1971, 14, 921-925.

EXAMPLE D-6

N-[4-[trans-1-amino-2-phenyl-cyclopropyl]phenyl]acetamide hydrochloride

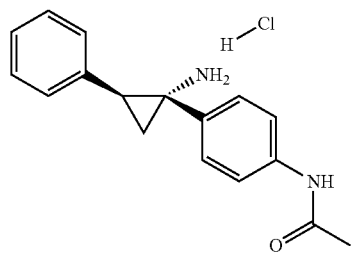

tert-Butyl N-[trans-1-(4-aminophenyl)-2-phenyl-cyclopropyl]carbamate

A 0.025 M solution of tert-butyl N-[trans-1-(4-nitrophenyl)-2-phenyl-cyclopropyl]carbamate (0.030 g, 0.085 mmol) in MeOH was hydrogenated in an H-Cube apparatus (PtO$_2$ cartridge, 1 bar, 20° C., flow 0.5 mL/min). The mixture was concentrated and purified by flash column chromatography (eluent: n-hexane/EtOAc 70:30) to give 0.020 g of tert-butyl N-[trans-1-(4-aminophenyl)-2-phenyl-cyclopropyl]carbamate (0.061 mmol, 73%) as a white solid. $^1$H NMR (CDCl$_3$) δ=7.19-6.34 (m, 9 H), 5.33 (s, 1 H), 3.66 (bs, 2 H), 2.84-2.68 (m, 1 H), 1.76-1.64 (m, 1 H), 1.62-1.56 (m, 1 H), 1.52-1.37 (m, 9 H). MS (ESI): m/z: 325 [M+H]$^+$.

tert-Butyl N-[trans-1-(4-acetamidophenyl)-2-phenyl-cyclopropyl]carbamate

A solution of tert-butyl N-[trans-1-(4-aminophenyl)-2-phenyl-cyclopropyl]carbamate (0.020 g, 0.061 mmol) in dry THF (0.5 mL) under nitrogen was cooled down to 0° C. Then TEA (0.017 mL, 0.12 mmol) and acetylchloride (0.0051 g, 0.065 mmol) were added in one portion. After 30 min at 0° C., the reaction mixture was concentrated and purified by flash chromatography (eluent: n-hexane/EtOAc 60:40) to give 0.022 g of the tert-butyl N-[trans-1-(4-acetamidophenyl)-2-phenyl-cyclopropyl]carbamate (0.060

TABLE 11

| Ex. | Name | Structure | LC-MS | NMR |
|---|---|---|---|---|
| D-4 | trans-2-(4-chlorophenyl)-1-phenyl-cyclopropanamine hydrochloride | 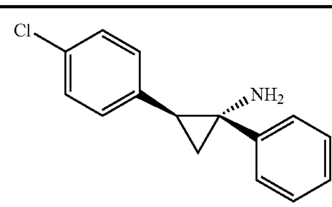 | 244 ([M + H]$^+$) | $^1$H NMR (DMSO-d$_6$) δ (ppm): 8.50 (s, 3 H), 7.17-7.27 (m, 9 H), 2.74-2.58 (m, 1 H), 2.00-1.86 (m, 1 H), 1.84-1.77 (m, 1 H). |
| D-5 | trans-2-(4-bromophenyl)-1-phenyl-cyclopropanamine hydrochloride | | 288 ([M + H]$^+$) | $^1$H NMR (DMSO-d$_6$) δ (ppm): 8.87 (s, 3 H), 7.49-6.70 (m, 9 H), 2.92-2.76 (m, 1 H), 2.20-2.04 (m, 1 H), 1.88-1.72 (m, 1 H). | mmol, 97%). $^1$H NMR (CDCl$_3$) δ=7.53-6.65 (m, 10 H), 5.43 (s, 1 H), 2.97-2.50 (m, 1 H), 2.11 (s, 3 H), 1.84-1.72 (m, 1 H), 1.66-1.60 (m, 1 H), 1.44 (s, 9 H). MS (ESI): m/z: 367 [M+H]$^+$.

N-[4-[trans-1-amino-2-phenyl-cyclopropyl]phenyl] acetamide hydrochloride

2 M HCl (0.25 mL, 0.49 mmol) in Et$_2$O was added to a solution of tert-butyl N-[trans-1-(4-acetamidophenyl)-2-phenyl-cyclopropyl]carbamate (0.018 g, 0.049 mmol) in 1.00 mL Et$_2$O at 0° C. and the mixture was then stirred at RT overnight. The formed precipitate was filtered off and the resulting solid was rinsed with Et$_2$O and dried giving 0.014 g of the desired N-[4-(trans-1-amino-2-phenyl-cyclopropyl) phenyl]acetamide as its hydrochloride salt (0.046 mmol, 94%). $^1$H NMR (DMSO-d$_6$) δ=9.97 (s, 1 H), 8.85 (s, 3 H), 7.45-7.20 (m, 4 H), 7.14-7.01 (m, 3 H), 6.93 (d, J=7.3 Hz, 2 H), 2.85-2.79 (m, 1 H), 2.05-2.00 (m, 1 H), 1.98 (s, 3 H), 1.80-1.74 (m, 1 H). MS (ESI): m/z: 267 [M+H]$^+$.

2. Biological Testing 2.1 Assay of Enzyme Inhibition of KDM1A (LSD1)

The complex of human recombinant KDM1A (LSD1)/CoRest protein was produced in *E. coli* as separate proteins and co-purified following previously reported procedures (Forneris F. et al. Trends Biochem. Sci. 2008, 33, 181-189; Forneris F. et al. J. Biol. Chem. 2007, 282, 20070-20074). The experiments were performed using a mono-methylated H3-K4 peptide containing 21 amino acids (custom synthesis done by Thermo Scientific) as substrate and in a 50 mM TRIS, pH 8, 0.05 mg/ml BSA buffer. The peptide purity was >90% as checked by analytical high-pressure liquid chromatography and mass spectrometry.

The demethylase activity was estimated under aerobic conditions and at RT by measuring the release of H$_2$O$_2$ produced during the catalytic process by the Amplex® UltraRed detection system coupled with peroxidase assay. Briefly, a fixed amount of KDM1A/CoRest complex was incubated at RT for 15 minutes in the absence and/or the presence of various concentrations of inhibitor (e.g. from 0 to 100 µM, depending on the inhibitor strength) and of Amplex® UltraRed detection system coupled with peroxidase assay. The inhibitors were tested twice in duplicates at each concentration. Tranylcypromine (Sigma) was used as control. After preincubation of the enzyme with the inhibitor, 4.5 µM of mono-methylated H3-K4 peptide was added and the experiment was left for additional 12 min. The conversion of the Amplex® Ultra Red reagent to resorufin was monitored in continuous by fluorescence (excitation at 540 nm, emission at 590 nm) using a microplate reader (Infinite 200, Tecan). Arbitrary units were used to measure the level of H$_2$O$_2$ produced in the absence and/or in the presence of inhibition. The maximum demethylase activity of KDM1A/CoRest was obtained in the absence of inhibitors and corrected for background fluorescence in the absence of KDM1A/CoRest. The IC$_{50}$ was calculated using GraphPad Software.

The results obtained are illustrated in the Table 12. IC$_{50}$ results were allocated to one of 3 ranges as follows: Range A: IC$_{50}$ from 1.0 to 5.0 µM; Range B: from 0.1 to 1.0 µM; Range C: ≤0.1 µM.

TABLE 12

Results of the KDM1A inhibition assay:

| Example | IC$_{50}$ [µM] | Example | IC$_{50}$ [µM] | Example | IC$_{50}$ [µM] |
|---|---|---|---|---|---|
| tranylcypromine | 11.63 | A-52 | B | A-102 | C |
| A-1 | B | A-53 | B | A-103 | C |
| A-2 | B | A-54 | B | A-104 | C |
| A-3 | A | A-55 | B | A-105 | C |
| A-4 | A | A-56 | B | A-106 | C |
| A-5 | A | A-57 | B | A-107 | C |
| A-6 | B | A-58 | C | A-108 | C |
| A-7 | A | A-59 | B | A109 | C |
| A-8 | B | A-60 | B | A-110 | C |
| A-9 | B | A-61 | B | A-111 | C |
| A-11 | B | A-62 | B | A-112 | C |
| A-12 | B | A-64 | A | A-113 | B |
| A-13 | B | A-65 | A | A-114 | C |
| A-15 | B | A-66 | C | A-115 | C |
| A-16 | A | A-67 | B | A-116 | C |
| A-17 | B | A-68 | C | A-117 | B |
| A-18 | B | A-69 | C | A-118 | C |
| A-19 | B | A-70 | b | A-120 | B |
| A20 | C | A-71 | C | A-121 | B |
| A21 | C | A-72 | B | A-122 | B |
| A22 | C | A-73 | B | A-123 | C |
| A23 | B | A-74 | C | A-124 | B |
| A24 | A | A-75 | C | A-125 | B |
| C-3 | C | A-76 | B | A-126 | B |
| A-25 | B | A-77 | B | A-128 | C |
| A-26 | B | A-78 | C | A-129 | B |
| A-27 | B | A-79 | C | A-130 | B |
| A-29 | B | A-80 | B | A-131 | C |
| A-33 | B | A-83 | C | B-3 | A |
| A-34 | C | A-84 | C | B-4 | A |
| A-35 | C | A-85 | C | B-5 | A |
| A-37 | C | A-86 | C | C-19 | B |
| A-39 | C | A-87 | C | C-20 | A |
| A-40 | C | A-88 | C | C-21 | B |
| A-41 | B | A-89 | C | C-23 | B |
| A-43 | B | A-90 | C | C-24 | B |
| A-44 | C | A-91 | B | C-25 | C |
| A-46 | C | A-92 | B | C-26 | A |
| A-47 | C | A-93 | B | C-27 | C |
| A-49 | C | A-94 | C | C28 | A |
| C-3 | A | A-95 | B | C-29 | A |
| C-5 | B | A-96 | B | C-31 | B |
| C-6 | C | A-97 | C | C-32 | B |
| C-13 | A | A-98 | C | D-3 | B |
| D-2 | B | A-99 | C | D-4 | B |
| A-50 | C | A-100 | C | D-5 | C |
| A-51 | C | A-101 | C | D-6 | B |

2.2 Cell Growth

CellTiter-Flor® (Promega) is as a nonlytic, single-reagent-addition fluorescence assay that measures the relative number of living cells in a culture population after experimental manipulation. The CellTiter-Fluor™ Cell Viability Assay measures the conserved and constitutive protease activity within live cells and therefore acts as a marker for cell viability.

Acute promyelocytic leukemia NB4 cells, (obtained from the Deutsche Sammlung von Mikroorganismen and Zellkulturen) in exponential growth, were incubated for 48 h with different concentrations of the inhibitors. After 48 h a volume of CellTiter-Fluor® Reagent equal to one fifth of volume of cell culture medium was added. The content was mixed and incubates for at least 90 min at 37° C. degree to obtain a stable signal. The fluorescence was recorded using an excitation wavelength of 360 nm and an emission at 535 nm. The IC$_{50}$ was calculated using GraphPad Software.

The obtained results are illustrated in Table 13. IC$_{50}$ results were allocated to one of 3 ranges as follows: Range A: IC$_{50}$ from 50 to 100 µM; Range B: from 10 to 50 µM; Range C: IC$_{50}$≤10 µM.

TABLE 13

Results of the cell growth inhibitory assay:

| Example | IC$_{50}$ [µM] | Example | IC$_{50}$ [µM] | Example | IC$_{50}$ [µM] |
|---|---|---|---|---|---|
| tranylcypromine | 10% inhibition at 100 µM | | | | |
| A-8 | A | A-67 | B | A-92 | B |
| A-11 | B | A-68 | B | A-95 | C |
| A-12 | B | A-70 | C | A-97 | B |
| A-13 | B | A-71 | C | A-98 | C |
| A-14 | B | A-72 | C | A-99 | C |
| A-15 | C | A-73 | B | A-101 | B |
| A24 | A | A-74 | B | A-113 | C |
| A-29 | B | A-75 | B | A-114 | C |
| A-30 | B | A-76 | C | A-115 | C |
| A-32 | B | A-77 | B | A-116 | C |
| A-33 | B | A-78 | C | A-117 | C |
| A-34 | B | A-78 | C | A-118 | C |
| A-36 | C | A-79 | B | A-119 | C |
| A-37 | B | A-80 | B | A-121 | A |
| A-38 | C | A-83 | C | A-122 | B |
| A-40 | C | A-84 | B | A-124 | B |
| A-41 | B | A-85 | C | B-3 | A |
| A-43 | B | A-86 | A | C-24 | B |
| A-44 | C | A-87 | B | D-3 | B |
| A-45 | C | A-88 | B | D-4 | A |
| A-46 | C | A-89 | C | D-5 | B |
| B-2 | A | A-90 | C | | |
| C-2 | A | A-91 | B | | |

2.3 Bioluminescent-Coupled Assay for Monoamine Oxidases (MAO-Glo Assay)

The MAO-Glo Assay from Promega (cat. V1402, Promega, Madison, Wis.) was used to measure the effect of inhibitors on MAO-A and MAO-B activity.

Human recombinant MAO A and MAO B were expressed in *Pichia pastoris* and purified as published (Binda C. et al. Proc. Natl. Acad. Sci. USA, 2003, 9750-9755). The assay was performed at RT in 50 µl (25 µl reaction solution+25 µl detection reagent) in 96 well half area white plates (cat. 3693, Corning, Corning, N.Y.). Luminescence was measured after 20 min incubation in the dark using a microplate reader (Infinite F200, Tecan Group, Switzerland) with an integration time of 0.25 s per well.

50 nM MAO-A or 125 nM MAO-B were incubated with five different inhibitor concentrations (from 0.004 µM to 100 µM) for 15 min at RT in Promega MAO Buffer or Promega MAO-B Buffer (MAO-Glo Assay kit, catalogue number V1402, Promega, Madison, Wis.). The Promega MAO substrate was at a concentration equal to the calculated $K_m$ (40 µM for MAO-A and 14 µM for MAO-B). After 30 minutes of incubation the reaction was stopped with the Promega detection reagent. The experiments were carried out in duplicate. IC$_{50}$ was calculated using GraphPad Prism version 4.0 (GraphPad Software, San Diego, Calif.). Table 14 reports the ratio of the IC$_{50}$ values against MAO-B over those obtained for LSD1 of compounds of this invention and tranylcypromine and two representative compounds of PCT application WO2012/013728.

In order to determine if any of the compounds inhibit the Luciferin Detection Reagent, the compounds was re-screened in the absence of MAOs using 0.5 µM D-luciferin methyl ester as substrate (Michael P. et al. Cell Notes, 2006, 14, 4-7, Promega Corporation and Promega Biosciences, Inc).

TABLE 14

Results of the MAO-B inhibitory assay

| Cpd | Name | Structure | IC$_{50}$ (MAO-B)/ IC$_{50}$ (LSD1) |
|---|---|---|---|
| | tranylcypromine | | 0.18 |
| * | 5-[[[(1R,2S)-2-(4-benzyloxyphenyl)cyclopropyl]amino]methyl]-1,3,4-oxadiazol-2-amine | | 0.57 |
| * | 5-[[[(1S,2R)-2-(4-benzyloxyphenyl)cyclopropyl]amino]methyl]-1,3,4-oxadiazol-2-amine | | 0.72 |
| A-4 | (1R,2S)-1-methyl-2-phenyl-cyclopropanamine 2,2,2-trifluoroacetic acid | 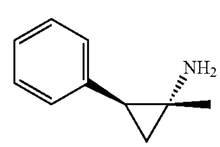 | 1.9 |

TABLE 14-continued

Results of the MAO-B inhibitory assay

| Cpd | Name | Structure | IC$_{50}$ (MAO-B)/IC$_{50}$ (LSD1) |
|---|---|---|---|
| A-11 | trans-1-phenethyl-2-phenyl-cyclopropanamine hydrochloride | 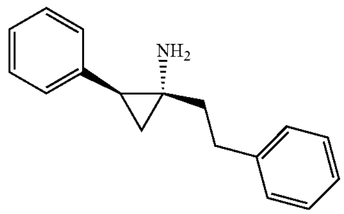 [SMILES: N[C@]1(CCc2ccccc2)C[C@H]1c1ccccc1] | 11 |
| A-15 | trans-1-(2-naphthylmethyl)-2-phenyl-cyclopropanamine hydrochloride | 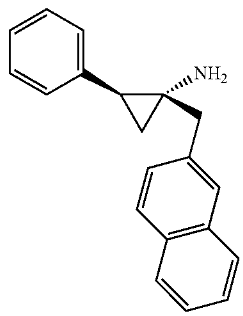 [SMILES: N[C@]1(Cc2ccc3ccccc3c2)C[C@H]1c1ccccc1] | >100 |
| A-36 | N-[4-(trans)-2-amino-2-ethyl-cyclopropyl]phenyl]-4-phenyl-benzamide hydrochloride | 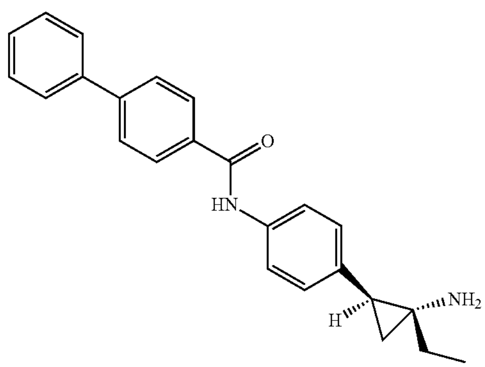 [SMILES: CC[C@@]1(N)C[C@H]1c1ccc(NC(=O)c2ccc(-c3ccccc3)cc2)cc1] | 16 |
| A-47 | N-[4-[trans-2-amino-2-ethyl-cyclopropyl]phenyl] benzamide hydrochloride | 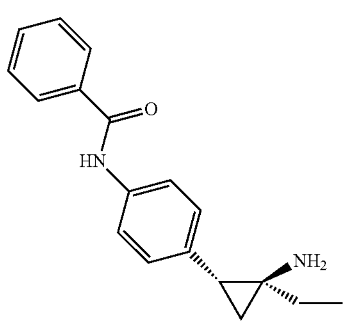 [SMILES: CC[C@]1(N)C[C@@H]1c1ccc(NC(=O)c2ccccc2)cc1] | >100 |

TABLE 14-continued

Results of the MAO-B inhibitory assay

| Cpd | Name | Structure | IC$_{50}$ (MAO-B)/ IC$_{50}$ (LSD1) |
|---|---|---|---|
| A-78 | N-[4-[trans-2-amino-2-ethyl-cyclopropyl]phenyl]-4-(3-furyl)benzamide hydrochloride | 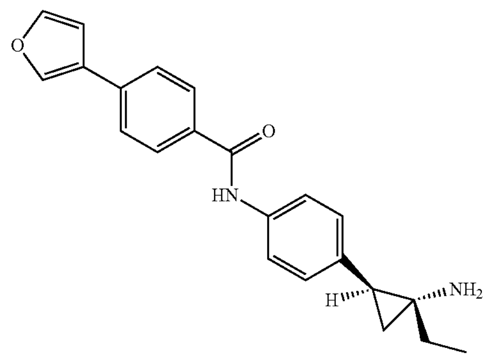 [SMILES: CC[C@@]1(N)C[C@H]1c1ccc(NC(=O)c2ccc(-c3ccoc3)cc2)cc1] | 60 |
| A-98 | N-[4-[trans-2-amino-2-ethyl-cyclopropyl]phenyl]-3-(2-oxooxazolidin-3-yl)benzamide 2,2,2-trifluoroacetic acid | 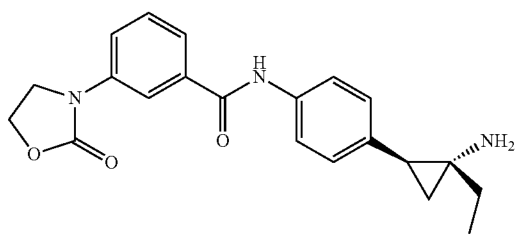 [SMILES: CC[C@@]1(N)C[C@H]1c1ccc(NC(=O)c2cccc(N3CCOC3=O)c2)cc1] | >100 |
| A-114 | N-[4-trans-2-amino-2-phenethyl-cyclopropyl)phenyl]benzamide hydrochloride | 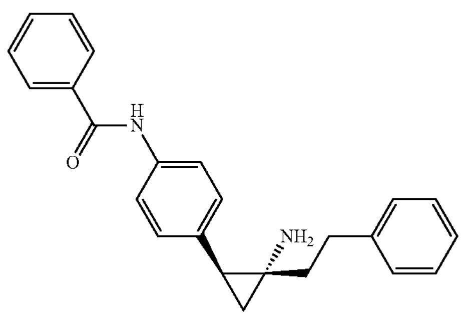 [SMILES: N[C@]1(CCc2ccccc2)C[C@H]1c1ccc(NC(=O)c2ccccc2)cc1] | >100 |
| A-116 | N-[4-(trans-2-amino-2-phenethyl-cyclopropyl)phenyl]-4-(4-methylpiperazin-1-yl)benzamide dihydrochloride | 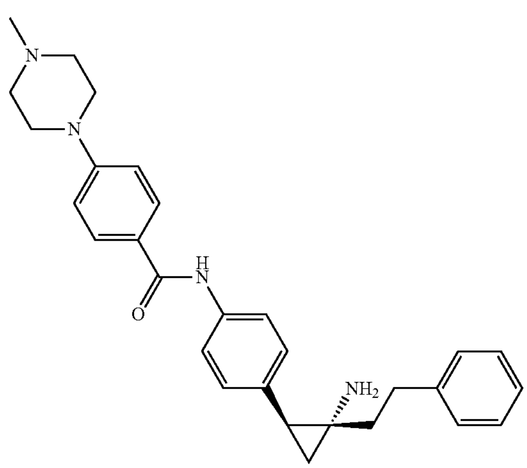 [SMILES: CN1CCN(c2ccc(C(=O)Nc3ccc([C@@H]4C[C@]4(N)CCc4ccccc4)cc3)cc2)CC1] | >100 |

TABLE 14-continued

Results of the MAO-B inhibitory assay

| Cpd | Name | Structure | $IC_{50}$ (MAO-B)/ $IC_{50}$ (LSD1) |
|---|---|---|---|
| D-2 | trans-1,2-diphenylcyclopropanamine hydrochloride | 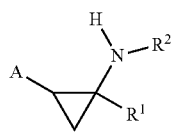 | >100 |

* WO2012/013728

2.4 In Vivo Activity

The in vivo activity was conducted on a mouse model as characterized by Minucci et al. (Minucci S. et al. Blood 2002, 100, 2989-2995) The model is characterized by the development of leukemia, resembling the human acute promyelocytic leukemia, which is associated to a blast infiltration of several organs as bone marrow, liver and particularly of the spleen. In the conducted experiment, splenomegaly was studied as read out of blast infiltration and development of leukemia.

For the in vivo analysis, one million of leukemic cells (obtained from 129SvEv mice, Minucci S. et al. Blood 2002, 100, 2989-2995, obtained from Taconic, One Hudson City Centre Hudson, N.Y. (USA)) were injected intravenously into non-irradiated syngenic recipients. Treatment started once blast cells are detected in the recipients' peripheral blood (9 days after injection). The compounds were intravenously or orally administered at doses of 10 and 30 mg/kg for 4 days. Five days after blast injection the mice were sacrificed and the spleens recovered. The weights of the spleen of the mice of the vehicle groups as well as of the treated groups were registered and used as evidence of effect on blast infiltration. The data are reported as mean±standard median error.

Compound A-36 administered orally at 30 mg/kg determined a reduction of the spleen weight of around 50% compared to mice treated with the vehicle (40% PEG-400, 60% aqueous solution containing 5% glucose) alone.

Should read:
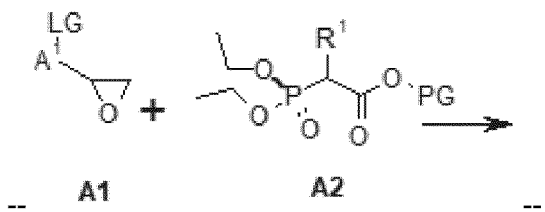
At Column 140, Claim number 17, Line numbers 48-58:
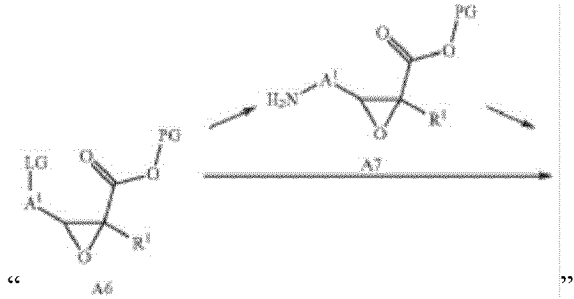
Should read:
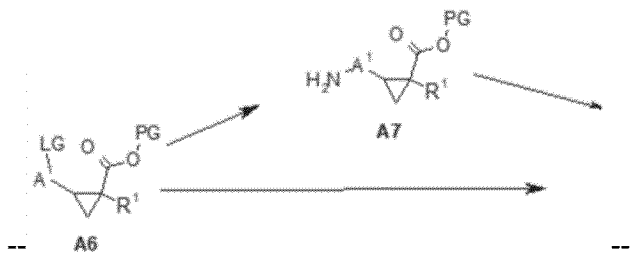
At Column 140, Claim number 17, Line numbers 59-67:
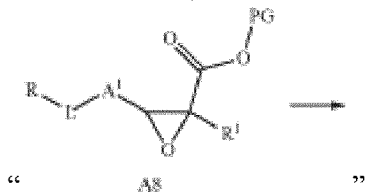
Should read:
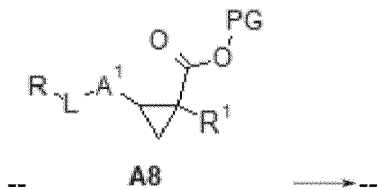

At Column 141, Claim number 17, Line numbers 1-14:
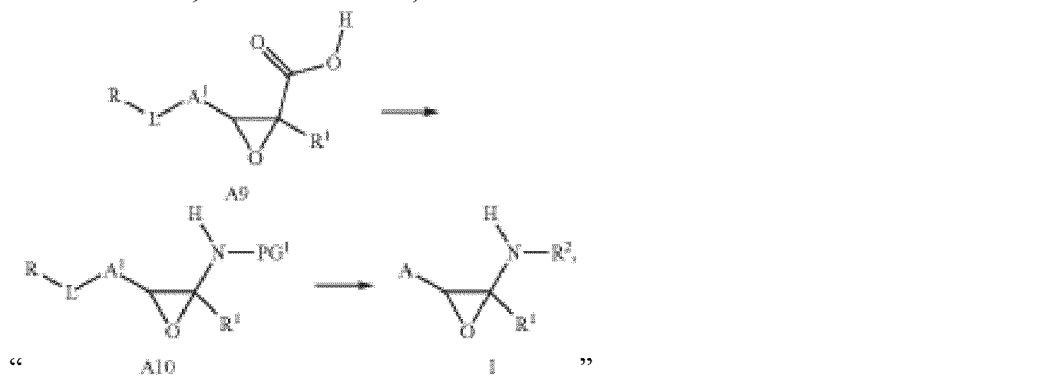
Should read:
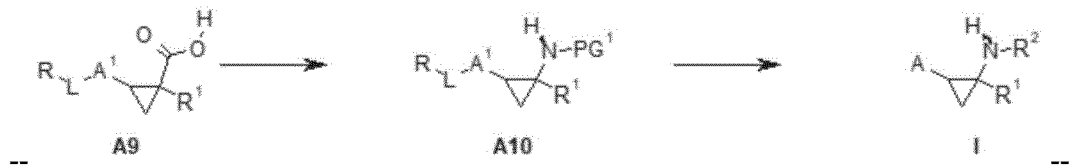
At Column 142, Claim number 19, Line number 9:
"with a compound of formula R$^1$-W, wherein R$^{10}$ is C$_1$-C$_6$ alkyl,"
Should read:
-- with a compound of formula R$^{10}$-W, wherein R$^{10}$ is C$_1$-C$_6$ alkyl, --
At Column 142, Claim number 19, Line numbers 30-44:
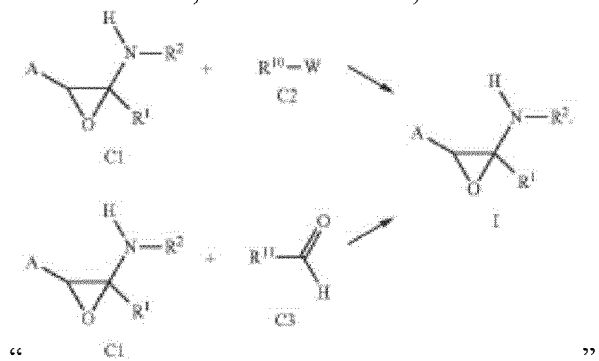
Should read:
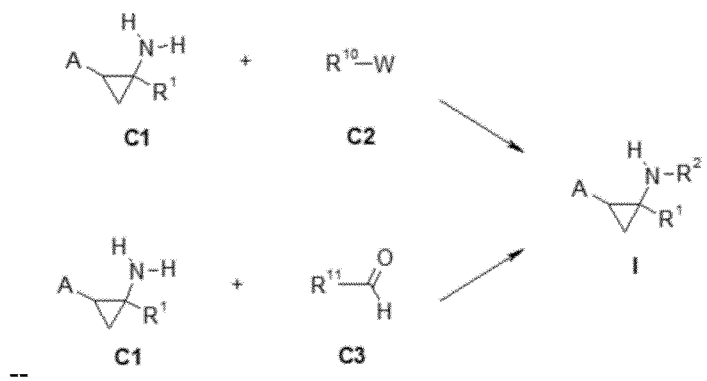

The invention claimed is:
1. A compound of formula (I)

(I)

wherein:
A is aryl or heteroaryl optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, OH, $C_1$-$C_6$ alkylamino, and R-L-;
R is aryl optionally substituted by one, two or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, $C_1$-$C_6$ alkylamino optionally substituted by OH, heterocyclylamino optionally substituted by $C_1$-$C_6$ alkyl, OH, phenyl, heterocyclyl optionally substituted by $C_1$-$C_6$ alkyl, heterocyclyl substituted by oxo, heteroaryl, and benzyloxycarbonylamino; or heteroaryl;
L is a single bond; $C_1$-$C_6$ alkylene; $C_2$-$C_6$ alkenylene; —$(CH_2)_m$X—$(CH_2)_n$—; —$(CH_2)_o(SO_2)NH$—; —$(CH_2)_p(CO)NR^3$—; —$(CH_2)_q NR^4(CO)$—; heterocyclyl substituted by oxo; or heteroaryl;
$R^1$ is $C_1$-$C_6$ alkyl, optionally substituted by aryl or heteroaryl; aryl; heteroaryl; or —$(CH_2)_r$—Y—$R^5$; and wherein the aryl or heteroaryl group may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, nitro, acetamido, and phenyl;
$R^2$ is hydrogen; $C_1$-$C_6$ alkyl, optionally substituted by aryl, heteroaryl, or heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2$(CO)$NR^6R^7$;
m, n, o, p, q are, independently, zero or an integer from 1 to 6;
r is an integer from 1 to 6;
X, Y are, independently, $NR^8$; O; or S;
$R^3$, $R^4$ are, independently, hydrogen; or $C_1$-$C_6$ alkyl;
$R^5$ is hydrogen, aryl or heteroaryl, wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and phenyl;
$R^6$, $R^7$ are, independently, hydrogen; $C_1$-$C_6$ alkyl; or $R^6$ and $R^7$ together with the nitrogen to which they are bound form a $C_4$-$C_{10}$-heterocyclic ring, optionally containing one or more further heteroatoms in the ring independently selected from $NR^9$, O or S and being optionally substituted by $NH_2$;
$R^8$ is hydrogen; $C_1$-$C_6$ alkyl, optionally substituted by aryl or heterocyclyl; or $C_{3-6}$ cycloalkyl;
$R^9$ is hydrogen or $C_1$-$C_6$ alkyl;
wherein each aryl is selected from phenyl, indenyl, indanyl, naphthyl, and tetrahydronaphthalenyl,
wherein each heteroaryl is selected from pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl;

or a stereoisomer or a pharmaceutically acceptable salt thereof, for use in the treatment of a disease or condition which is mediated by an excessive or inappropriate level of KDM1A (LSD1) activity.

2. The compound of claim 1 for use in the treatment of a disease or condition which is mediated by an excessive or inappropriate level of KDM1A (LSD1) activity selected from:
(1S,2R)-1-ethyl-2-phenyl-cyclopropanamine;
(1R,2S)-1-ethyl-2-phenyl-cyclopropanamine;
trans-1-methyl-2-phenyl-cyclopropanamine;
(1R,2S)-1-methyl-2-phenyl-cyclopropanamine;
(1S,2R)-1-methyl-2-phenyl-cyclopropanamine;
trans-1-propyl-2-phenyl-cyclopropanamine;
trans-1-i sopropyl-2-phenyl-cyclopropanamine;
trans-1-benzyl-2-phenyl-cyclopropanamine;
(1S,2S)-1-benzyl-2-phenyl-cyclopropanamine;
(1R,2R)-1-benzyl-2-phenyl-cyclopropanamine;
trans-1-phenethyl-2-phenyl-cyclopropanamine;
trans-2-(4-bromophenyl)-1-ethyl-cyclopropanamine;
trans-1-benzyl-2-(4-bromophenyl)cyclopropanamine;
trans-1-ethyl-2-(6-quinolyl)cyclopropanamine;
trans-1-(2-naphthylmethyl)-2-phenyl-cyclopropanamine;
trans-1-ethyl-2-(4-fluorophenyl)cyclopropanamine;
trans-1-ethyl-2-(4-chlorophenyl)cyclopropanamine;
trans-1-ethyl-2-[3-(trifluoromethyl)phenyl]cyclopropanamine;
trans-1-ethyl-2-[4-(trifluoromethyl)phenyl]cyclopropanamine;
trans-1-ethyl-2-(3-fluorophenyl)cyclopropanamine;
trans-1-ethyl-2-(3-chlorophenyl)-cyclopropanamine;
trans-1-ethyl-2-(3-bromophenyl)-cyclopropanamine;
trans-1-ethyl-2-[3-methoxyphenyl]cyclopropanamine;
1-ethyl-(trans)-2- [4-(trifluoromethoxy)phenyl]cyclopropanamine;
trans-1-ethyl-2-(2-fluorophenyl)cyclopropanamine;
trans-1-ethyl-2-(2-chlorophenyl)-cyclopropanamine;
trans-1-ethyl-2-(2-bromophenyl)-cyclopropanamine;
trans-1-(1-naphthylmethyl)-2-phenyl-cyclopropanamine;
trans-2-(4-bromophenyl)-1-(2-naphthylmethyl)cyclopropanamine;
trans-N-[4-[2-amino-2-ethyl-cyclopropyl]phenyl]naphthalene-2-carboxamide;
N-[2-[(trans)-2-amino-2-ethyl-cyclopropyl]phenyl]benzamide;
benzyl N-[3-[[2-[(trans)-2-amino-2-ethyl-cyclopropyl] phenyl]carbamoyl]phenyl]carba-mate;
benzyl N-[3-[[3-[(trans)-2-amino-2-ethyl-cyclopropyl] phenyl]carbamoyl]phenyl]carba-mate;
N-[4-[(trans)-2-amino-2-ethyl-cyclopropyl]phenyl]-3-chloro-benzamide;
N-[4-[(trans)-2-amino-2-ethyl-cyclopropyl]phenyl]-3-phenyl-benzamide;
N-[4-[(trans)-2-amino-2-ethyl-cyclopropyl]phenyl]-4-phenyl-benzamide;
benzyl N-[3-[[4-[(trans)-2-amino-2-ethyl-cyclopropyl] phenyl]carbamoyl]phenyl]carba-mate;
benzyl N-[4-[[4-[(trans)-2-amino-2-ethyl-cyclopropyl] phenyl]carbamoyl]phenyl]carba-mate;
N-[4-[(trans)-2-amino-2-ethyl-cyclopropyl]phenyl]-2-phenyl-acetamide;
N-[4-[(trans)-2-amino-2-ethyl-cyclopropyl]phenyl]-3-phenyl-propanamide;
2-(4-benzyloxyphenyl)-trans-1-ethyl-cyclopropanamine;
N-[4-[(2-amino-trans-2-ethyl-cyclopropyl]phenyl]benzenesulfonamide;
trans-1-benzyl-2-(4-benzyloxyphenyl)cyclopropanamine;
N-[4-[trans-2-amino-2-(2-naphthylmethyl)cyclopropyl] phenyl]benzamide;
Benzyl-N-[3-[[4-[(trans)-2-amino-2-(2-naphthylmethyl) cyclopropyl]phenyl]carbamoyl]phenyl]carbamate;
N-[4-[(trans)-2-amino-2-(2-naphthylmethyl)cyclopropyl] phenyl]-2-phenyl-acetamide;
N-[4-[trans-2-amino-2-ethyl-cyclopropyl]phenyl]benzamide;
trans-4-(2-amino-2-ethyl-cyclopropyl)aniline;
trans-2-(3-azidophenyl)-1-ethyl-cyclopropanamine;
1-amino-(trans)-2-phenyl-cyclopropyl]methanol;
1-amino-(cis)-2-phenyl-cyclopropyl]methanol;
(1R,2S)-1-ethyl-N-[(2-methoxyphenyl)methyl]-2-phenyl-cyclopropanamine;
(1R,2S)-1-ethyl-N-[(2-methoxy-1-naphthyl)methyl]-2-phenyl-cyclopropanamine;
2-[[(1S,2R)-1-methyl-2-phenyl-cyclopropyl]amino]-1-(4-methylpiperazin-1-yl)ethanone;
2-[[(1S,2S)-1-methyl-2-phenyl-cyclopropyl]amino]-1-(4-methylpiperazin-1-yl)ethanone;
1-[(3S)-3-aminopyrrolidin-1-yl]-2-[[(1S,2R)-1-methyl-2-phenyl-cyclopropyl]amino]ethanone;
trans-2-[[(1-ethyl-2-phenyl-cyclopropyl]amino]-1-(4-methylpiperazin-1-yl)ethanone;
cis-2-[[(1-ethyl-2-phenyl-cyclopropyl]amino]-1-(4-methylpiperazin-1-yl)ethanone;
trans-1-ethyl-N-methyl-2-phenyl-cyclopropanamine;
cis-1-ethyl-N-methyl-2-phenyl-cyclopropanamine;
trans-1-ethyl-N-ethyl-2-phenyl-cyclopropanamine;
cis-1-ethyl-N-ethyl-2-phenyl-cyclopropanamine;
trans-2-[[1-ethyl-2-phenyl-cyclopropyl]amino]acetamide;
trans-N-benzyl-1-ethyl-2-phenyl-cyclopropanamine;
trans-N-[(3,4-dimethoxyphenyl)methyl]-1-ethyl-2-phenyl-cyclopropanamine;
trans-N-[(4,7-dimethoxy-1-naphthyl)methyl]-1-ethyl-2-phenyl-cyclopropanamine;
trans-N-[(2-chloro-3-pyridyl)methyl]-1-ethyl-2-phenyl-cyclopropanamine;
trans-N-[(2,2-dimethylchroman-6-yl)methyl]-1-ethyl-2-phenyl-cyclopropanamine;
cis-1,2-diphenylcyclopropanamine;
trans-1,2-diphenylcyclopropanamine;
trans-1-ethyl-2-phenyl-cyclopropanamine;
trans-2-(4-bromo-3-fluoro-phenyl)-1-ethyl-cyclopropanamine;
trans 2-(3-bromophenyl)-1-phenethyl-cyclopropanamine;
(1R,2S)-1,2-diphenylcyclopropanamine;
(1S,2R)-1,2-diphenylcyclopropanamine;
trans-2-(4-fluorophenyl)-1-(2-naphthylmethyl)cyclopropanamine;
trans-2-(4-chlorophenyl)-1-(2-naphthylmethyl)cyclopropanamine;
trans-2-(3-chlorophenyl)-1-(2-naphthylmethyl)cyclopropanamine;
trans-2-(3-bromophenyl)-1-(2-naphthylmethyl)cyclopropanamine;
trans-2-(4-chlorophenyl)-1-phenethyl-cyclopropanamine;
trans-2-(4-fluorophenyl)-1-phenethyl-cyclopropanamine;
trans-1-benzyl-2-(4-fluorophenyl)cyclopropanamine;
trans-1-benzyl-2-(4-chlorophenyl)cyclopropanamine;
trans 2-(4-bromophenyl)-1-phenethyl-cyclopropanamine;
cis-1-ethyl-2-phenyl-cyclopropanamine;
N-[4-(trans-2-amino-2-ethyl-cyclopropyl)phenyl]-3-[(1-methyl-4-piperidyl)amino]-4-phenyl-benzamide;
2-(4-benzyloxyphenyl)-1-(2-naphthylmethyl)cyclopropanamine;

N-[4-trans-[2-amino-2-ethyl-cyclopropyl]phenyl]-2-(1-naphthyl)acetamide;
N-[4-trans-[2-amino-2-ethyl-cyclopropyl]phenyl]-2-(4-nitrophenyl)acetamide;
benzyl N-[4-[[4-[trans-2-amino-2-(2-naphthylmethyl)cyclopropyl]phenyl]carbamoyl]phenyl]carbamate;
N-[4-(trans-2-amino-2-ethyl-cyclopropyl)phenyl]naphthalene-1-carboxamide;
N-[4-[trans-2-amino-2-(2-naphthylmethyl)cyclopropyl]phenyl]naphthalene-2-carboxamide;
N-[4-[trans-2-amino-2-(2-naphthylmethyl)cyclopropyl]phenyl]-4-phenyl-benzamide;
N-[4-[trans-2-amino-2-ethyl-cyclopropyl]phenyl]-2-(2-naphthyl)acetamide;
N-[4-[trans-2-amino-2-phenyl-cyclopropyl]phenyl]benzamide;
N-[4-[trans-2-amino-2-(2-naphthylmethyl)cyclopropyl]phenyl]-2-(1-naphthyl)acetamide;
N-[3-[trans-2-amino-2-ethyl-cyclopropyl]phenyl]-2-(1-naphthyl)acetamide;
N-[4-[trans-2-amino-2-ethyl-cyclopropyl]phenyl]-4-(3-furyl)benzamide;
N-[4-[trans-2-amino-2-(2-naphthylmethyl)cyclopropyl]phenyl]-3-chloro-benzamide;
N-[3-[trans-2-amino-2-ethyl-cyclopropyl]phenyl]-3-chloro-benzamide;
N-[4-[trans-2-amino-2-(2-naphthylmethyl)cyclopropyl]phenyl]-3-phenyl-propanamide;
N-[4-[trans-2-amino-2-(2-naphthylmethyl)cyclopropyl]phenyl]-3-phenyl-benzamide;
N-[4-[trans-2-amino-2-ethyl-cyclopropyl]phenyl]-4-(2-oxooxazolidin-3-yl)benzamide;
benzyl N-[3-[(4- [trans-2-amino-2-phenyl-cyclopropyl]phenyl)carbamoyl]phenyl]carbamate;
N-[4-[trans-2-amino-2-phenyl-cyclopropyl]phenyl]naphthalene-2-carboxamide;
N-[4-[trans-2-amino-2-ethyl-cyclopropyl]-2-fluoro-phenyl]benzamide;
N-[4-[trans-2-amino-2-ethyl-cyclopropyl]-2-fluoro-phenyl]-4-phenyl-benzamide;
N-[4-[trans-2-amino-2-ethyl-cyclopropyl]phenyl]-4-morpholino-benzamide;
N-[4-[trans-2-amino-2-phenyl-cyclopropyl]phenyl]-4-phenyl-benzamide;
N-[4-[trans-2-amino-2-phenyl-cyclopropyl]phenyl]naphthalene-1-carboxamide;
N-[3-[trans-2-amino-2-ethyl-cyclopropyl]phenyl]-4-phenyl-benzamide;
N-[3-[trans-2-amino-2-ethyl-cyclopropyl]phenyl]naphthalene-2-carboxamide;
N-[3-[trans-2-amino-2-ethyl-cyclopropyl]phenyl-benzamide;
N-[4-[trans-2-amino-2-ethyl-cyclopropyl]-2-fluoro-phenyl]-2-(1-naphthyl)acetamide;
benzyl N-[4-[[4-[trans-2-amino-2-ethyl-cyclopropyl]-2-fluoro-phenyl]carbamoyl]phenyl]carbamate;
N-[4-[trans-2-amino-2-ethyl-cyclopropyl]-2-fluoro-phenyl]-4-(4-methylpiperazin-1-yl)benzamide;
N-[4-[trans-2-amino-2-ethyl-cyclopropyl]phenyl]-4-(4-methylpiperazin-1-yl)benzamide;
N-[4-[trans-2-amino-2-ethyl-cyclopropyl]phenyl]-3-(2-oxooxazolidin-3-yl)benzamide;
benzyl N-[5-[[4-[trans-2-amino-2-ethyl-cyclopropyl]phenyl]carbamoyl]-2-morpholino-phenyl]carbamate;
N-[4-[trans-2-amino-2-ethyl-cyclopropyl]phenyl]-4-(1-methyl-4-piperidyl)benzamide;
N-[4-(trans-2-amino-2-ethyl-cyclopropyl)phenyl]-4-(4-pyridyl)benzamide;
N-[4-(trans-2-amino-2-phenyl-cyclopropyl]phenyl]-3-chloro-benzamide;
N-[4-(trans-2-amino-2-phenyl-cyclopropyl]phenyl]-2-(1-naphthyl)acetamide;
N-[4-(trans-2-amino-2-phenyl-cyclopropyl)phenyl]-2-phenyl-acetamide;
N-[4-(trans-2-amino-2-phenyl-cyclopropyl)phenyl]-3-phenyl-benzamide;
N-[4-(trans-2-amino-2-phenyl-cyclopropyl)phenyl]-2-(2-naphthyl)acetamide;
N-[4-(trans-2-amino-2-phenyl-cyclopropyl)phenyl]-4-(1-methyl-4-piperidyl)benzamide;
N-[4-(trans-2-amino-2-phenyl-cyclopropyl)phenyl]-4-(4-methylpiperazin-1-yl)benzamide;
N-[4-(trans-2-amino-2-phenyl-cyclopropyl)phenyl]-3-(2-oxooxazolidin-3-yl)benzamide;
N-[4-(trans-2-amino-2-phenethyl-cyclopropyl)phenyl]-4-phenyl-benzamide;
N-[4-trans-2-amino-2-phenethyl-cyclopropyl)phenyl]benzamide;
N-[4-(trans-2-amino-2-phenethyl-cyclopropyl)phenyl]-4-(1-methyl-4-piperidyl)benzamide;
N-[4-(trans-2-amino-2-phenethyl-cyclopropyl)phenyl]-4-(4-methylpiperazin-1-yl)benzamide;
benzyl N-[5-[[4- [trans-2-amino-2-ethyl-cyclopropyl]phenyl]carbamoyl]-2-(4-methylpiperazin-1 -yl)phenyl]carbamate;
N-[4-(trans-2-amino-2-phenethyl-cyclopropyl)phenyl]-3-(2-oxooxazolidin-3-yl)benzamide;
4-[trans-2-amino-2-(2-naphthylmethyl)cyclopropyl]aniline;
N-[4-(trans-2-amino-2-ethyl-cyclopropyl]phenyl]-4-(2-hydroxyethylamino)benzamide;
benzyl N-[3-[1-[4-[2-amino-2-ethyl-cyclopropyl]phenyl]triazol-4-yl]phenyl]carbamate;
trans-1-ethyl-2- [3-(4-phenyltriazol-1-yl)phenyl]cyclopropanamine;
benzyl N-[3-[1-[4-[2-amino-2-(2-naphthylmethyl)cyclopropyl]phenyl]triazol-4-yl]phenyl]carbamate;
trans-1-(2-naphthylmethyl)-2-[4-(4-phenyltriazol-1-yl)phenyl]cyclopropanamine;
trans 1-ethyl-2-[2-(4-phenyltriazol-1-yl)phenyl]cyclopropanamine;
trans-1-benzyl-2-[4-(4-phenyltriazol-1-yl)phenyl]cyclopropanamine;
N-[4-[(1S,2R)-2-amino-2-ethyl-cyclopropyl]phenyl]-4-phenyl-benzamide;
N-[4-[(1R,2S)-2-amino-2-ethyl-cyclopropyl]phenyl]-4-phenyl-benzamide;
trans 1-benzyl-2-(3-methoxyphenyl)cyclopropanamine;
1-[3-[(trans-2-amino-2-ethyl-cyclopropyl]phenyl]-3-phenyl-imidazolidin-2-one;
trans-1-ethyl-2-[4-(4-phenyltriazol-1-yl)phenyl]cyclopropanamine;
trans 1-[(benzylamino)methyl]-2-phenyl-cyclopropanamine;
trans 1-[(cyclopropylamino)methyl]-2-phenyl-cyclopropanamine;
5-[[[trans-1-methyl-2-phenyl-cyclopropyl]amino]methyl]pyrimidin-2-amine;
trans-N-[(2-methoxy-3-pyridyl)methyl]-1-methyl-2-phenyl-cyclopropanamine;
trans-N-(2,3-dihydro-1,4-benzodioxin-6-ylmethyl)-1-methyl-2-phenyl-cyclopropanamine;
cis-N,1-dimethyl-2-phenyl-cyclopropanamine;

2-[[trans-1,2-diphenylcyclopropyl]amino]-1-(4-methyl-piperazin-1-yl)ethanone;
1-(4-methylpiperazin-1-yl)-2-[[trans-1-(2-naphthylmethyl)-2-phenyl-cyclopropyl]amino]ethanone;
2-[[(1R,2S)-1-methyl-2-phenyl-cyclopropyl]amino]-1-(4-methylpiperazin-1-yl)ethanone;
2-[[(1R,2R)-1-methyl-2-phenyl-cyclopropyl]amino]-1-(4-methylpiperazin-1-yl)ethanone;
2-[[trans-1-methyl-2-phenyl-cyclopropyl]amino]-1-(4-methylpiperazin-1-yl)ethanone;
2-[[cis-1-methyl-2-phenyl-cyclopropyl]amino]-1-(4-methylpiperazin-1-yl)ethanone;
trans-N,1-dimethyl-2-phenyl-cyclopropanamine;
2-[[trans-1-ethyl-2-phenyl-cyclopropyl]amino]-1-(1-piperidyl)ethanone;
trans-1-ethyl-2-phenyl-N-[2-(1-piperidyl)ethyl]cyclopropanamine;
5-[[[trans-1-methyl-2-phenyl-cyclopropyl]amino]methyl]-1,3,4-oxadiazol-2-amine;
trans-1-(4-nitrophenyl)-2-phenyl-cyclopropanamine;
trans-2-(4-chlorophenyl)-1-phenyl-cyclopropanamine;
trans-2-(4-bromophenyl)-1-phenyl-cyclopropanamine;
N-[4-(trans-1-amino-2-phenyl-cyclopropyl]phenyl]acetamide; and a stereoisomer or a pharmaceutically acceptable salt thereof.

3. The compound for use according to claim 1, wherein the disease or condition which is mediated by an excessive or inappropriate level of KDM1A (LSD1) activity is cancer or a tumor.

4. The compound for use according to claim 1, wherein the disease or condition which is mediated by an excessive or inappropriate level of KDM1A (LSD1) activity is HIV or herpes virus infection.

5. The compound for use of claim 1, provided that when A is an unsubstituted phenyl or imidazolyl and $R^1$ is methyl, then $R^2$ cannot be hydrogen or methyl.

6. The compound for use according to claim 5 selected from:
   (1S,2R)-1-ethyl-2-phenyl-cyclopropanamine;
   (1R,2S)-1-ethyl-2-phenyl-cyclopropanamine;
   trans-1-propyl-2-phenyl-cyclopropanamine;
   trans-1-isopropyl-2-phenyl-cyclopropanamine;
   trans-1-benzyl-2-phenyl-cyclopropanamine;
   (1S,2S)-1-benzyl-2-phenyl-cyclopropanamine;
   (1R,2R)-1-benzyl-2-phenyl-cyclopropanamine;
   trans-1-phenethyl-2-phenyl-cyclopropanamine;
   trans-2-(4-bromophenyl)-1-ethyl-cyclopropanamine;
   trans-1-benzyl-2-(4-bromophenyl)cyclopropanamine;
   trans-1-ethyl-2-(6-quinolyl)cyclopropanamine;
   trans-1-(2-naphthylmethyl)-2-phenyl-cyclopropanamine;
   trans-1-ethyl-2-(4-fluorophenyl)cyclopropanamine;
   trans-1-ethyl-2-(4-chlorophenyl)cyclopropanamine;
   trans-1-ethyl-2-[3-(trifluoromethyl)phenyl]cyclopropanamine;
   trans-1-ethyl-2-[4-(trifluoromethyl)phenyl]cyclopropanamine;
   trans-1-ethyl-2-(3-fluorophenyl)cyclopropanamine;
   trans-1-ethyl-2-(3-chlorophenyl)-cyclopropanamine;
   trans-1-ethyl-2-(3-bromophenyl)-cyclopropanamine;
   trans-1-ethyl-2- [3-methoxyphenyl]cyclopropanamine;
   1-ethyl-(trans)-2- [4-(trifluoromethoxy)phenyl]cyclopropanamine;
   trans-1-ethyl-2-(2-fluorophenyl)-cyclopropanamine;
   trans-1-ethyl-2-(2-chlorophenyl)-cyclopropanamine;
   trans-1-ethyl-2-(2-bromophenyl)-cyclopropanamine;
   trans-1-(1-naphthylmethyl)-2-phenyl-cyclopropanamine;
   trans-2-(4-bromophenyl)-1-(2-naphthylmethyl)cyclopropanamine;
   trans-N-[4-[2-amino-2-ethyl-cyclopropyl]phenyl]naphthalene-2-carboxamide;
   N-[2-[(trans)-2-amino-2-ethyl-cyclopropyl]phenyl]benzamide;
   benzyl N-[3-[[2-[(trans)-2-amino-2-ethyl-cyclopropyl]phenyl]carbamoyl]phenyl]carba-mate;
   benzyl N-[3-[[3-[(trans)-2-amino-2-ethyl-cyclopropyl]phenyl]carbamoyl]phenyl]carba-mate;
   N-[4-[(trans)-2-amino-2-ethyl-cyclopropyl]phenyl]-3-chloro-benzamide;
   N-[4-[(trans)-2-amino-2-ethyl-cyclopropyl]phenyl]-3-phenyl-benzamide;
   N-[4-[(trans)-2-amino-2-ethyl-cyclopropyl]phenyl]-4-phenyl-benzamide;
   benzyl N-[3-[[4-[(trans)-2-amino-2-ethyl-cyclopropyl]phenyl]carbamoyl]phenyl]carba-mate;
   benzyl N-[4-[[4-[(trans)-2-amino-2-ethyl-cyclopropyl]phenyl]carbamoyl]phenyl]carba-mate;
   N-[4-[(trans)-2-amino-2-ethyl-cyclopropyl]phenyl]-2-phenyl-acetamide;
   N-[4-[(trans)-2-amino-2-ethyl-cyclopropyl]phenyl]-3-phenyl-propanamide;
   2-(4-benzyloxyphenyl)-trans-1-ethyl-cyclopropanamine;
   N-[4-[(2-amino-trans-2-ethyl-cyclopropyl]phenyl]benzenesulfonamide;
   trans-1-benzyl-2-(4-benzyloxyphenyl)cyclopropanamine;
   N-[4-[trans-2-amino-2-(2-naphthylmethyl)cyclopropyl]phenyl]benzamide;
   Benzyl-N-[3-[[4-[(trans)-2-amino-2-(2-naphthylmethyl)cyclopropyl]phenyl]carbamoyl]phenyl]carbamate;
   N-[4-[(trans)-2-amino-2-(2-naphthylmethyl)cyclopropyl]phenyl]-2-phenyl-acetamide;
   N-[4-[trans-2-amino-2-ethyl-cyclopropyl]phenyl]benzamide;
   trans-4-(2-amino-2-ethyl-cyclopropyl)aniline;
   trans-2-(3-azidophenyl)-1-ethyl-cyclopropanamine;
   1-amino-(trans)-2-phenyl-cyclopropyl]methanol;
   1-amino-(cis)-2-phenyl-cyclopropyl]methanol;
   (1R,2S)-1-ethyl-N-[(2-methoxyphenyl)methyl]-2-phenyl-cyclopropanamine;
   (1R,2S)-1-ethyl-N-[(2-methoxy-1-naphthyl)methyl]-2-phenyl-cyclopropanamine;
   2-[[(1S,2R)-1-methyl-2-phenyl-cyclopropyl]amino]-1-(4-methylpiperazin-1-yl)ethanone;
   2-[[(1S,2S)-1-methyl-2-phenyl-cyclopropyl]amino]-1-(4-methylpiperazin-1-yl)ethanone;
   1-[(3S)-3-aminopyrrolidin-1-yl]-2-[[(1S,2R)-1-methyl-2-phenyl-cyclopropyl]amino]ethanone;
   trans-2-[[(1-ethyl-2-phenyl-cyclopropyl]amino]-1-(4-methylpiperazin-1-yl)ethanone;
   cis-2-[[(1-ethyl-2-phenyl-cyclopropyl]amino]-1-(4-methylpiperazin-1-yl)ethanone;
   trans-1-ethyl-N-methyl-2-phenyl-cyclopropanamine;
   cis-1-ethyl-N-methyl-2-phenyl-cyclopropanamine;
   trans-1-ethyl-N-ethyl-2-phenyl-cyclopropanamine;
   cis-1-ethyl-N-ethyl-2-phenyl-cyclopropanamine;
   trans-2-[[1-ethyl-2-phenyl-cyclopropyl]amino]acetamide;
   trans-N-benzyl-1-ethyl-2-phenyl-cyclopropanamine;
   trans-N-[(3,4-dimethoxyphenyl)methyl]-1-ethyl-2-phenyl-cyclopropanamine;
   trans-N-[(4,7-dimethoxy-1-naphthyl)methyl]-1-ethyl-2-phenyl-cyclopropanamine;
   trans-N-[(2-chloro-3-pyridyl)methyl]-1-ethyl-2-phenyl-cyclopropanamine;

trans-N-[(2,2-dimethylchroman-6-yl)methyl]-1-ethyl-2-phenyl-cyclopropanamine;
cis-1,2-diphenylcyclopropanamine;
trans-1,2-diphenylcyclopropanamine;
trans-1-ethyl-2-phenyl-cyclopropanamine;
trans-2-(4-bromo-3-fluoro-phenyl)-1-ethyl-cyclopropanamine;
trans 2-(3-bromophenyl)-1-phenethyl-cyclopropanamine;
(1R,2S)-1,2-diphenylcyclopropanamine;
(1S,2R)-1,2-diphenylcyclopropanamine;
trans-2-(4-fluorophenyl)-1-(2-naphthylmethyl)cyclopropanamine;
trans-2-(4-chlorophenyl)-1-(2-naphthylmethyl)cyclopropanamine;
trans-2-(3-chlorophenyl)-1-(2-naphthylmethyl)cyclopropanamine;
trans-2-(3-bromophenyl)-1-(2-naphthylmethyl)cyclopropanamine;
trans-2-(4-chlorophenyl)-1-phenethyl-cyclopropanamine;
trans-2-(4-fluorophenyl)-1-phenethyl-cyclopropanamine;
trans-1-benzyl-2-(4-fluorophenyl)cyclopropanamine;
trans-1-benzyl-2-(4-chlorophenyl)cyclopropanamine;
trans 2-(4-bromophenyl)-1-phenethyl-cyclopropanamine;
cis-1-ethyl-2-phenyl-cyclopropanamine;
N-[4-(trans-2-amino-2-ethyl-cyclopropyl)phenyl]-3-[(1-methyl-4-piperidyl)amino]-4-phenyl -benzamide;
2-(4-benzyloxyphenyl)-1-(2-naphthylmethyl)cyclopropanamine;
N-[4-trans-[2-amino-2-ethyl-cyclopropyl]phenyl]-2-(1-naphthyl)acetamide;
N-[4-trans-[2-amino-2-ethyl-cyclopropyl]phenyl]-2-(4-nitrophenyl)acetamide;
benzyl N-[4-[[4-[trans-2-amino-2-(2-naphthylmethyl)cyclopropyl]phenyl]carbamoyl]phenyl]carbamate;
N-[4-(trans-2-amino-2-ethyl-cyclopropyl)phenyl]naphthalene-1-carboxamide;
N-[4-[trans-2-amino-2-(2-naphthylmethyl)cyclopropyl]phenyl]naphthalene-2-carboxamide;
N-[4-[trans-2-amino-2-(2-naphthylmethyl)cyclopropyl]phenyl]-4-phenyl-benzamide;
N-[4-[trans-2-amino-2-ethyl-cyclopropyl]phenyl]-2-(2-naphthyl)acetamide;
N-[4-[trans-2-amino-2-phenyl-cyclopropyl]phenyl]benzamide;
N-[4-[trans-2-amino-2-(2-naphthylmethyl)cyclopropyl]phenyl]-2-(1-naphthyl)acetamide;
N-[3-[trans-2-amino-2-ethyl-cyclopropyl]phenyl]-2-(1-naphthyl)acetamide;
N-[4-[trans-2-amino-2-ethyl-cyclopropyl]phenyl]-4-(3-furyl)benzamide;
N-[4-[trans-2-amino-2-(2-naphthylmethyl)cyclopropyl]phenyl]-3-chloro-benzamide;
N-[3-[trans-2-amino-2-ethyl-cyclopropyl]phenyl]-3-chloro-benzamide;
N-[4-[trans-2-amino-2-(2-naphthylmethyl)cyclopropyl]phenyl]-3-phenyl-propanamide;
N-[4-[trans-2-amino-2-(2-naphthylmethyl)cyclopropyl]phenyl]-3-phenyl-benzamide;
N-[4-[trans-2-amino-2-ethyl-cyclopropyl]phenyl]-4-(2-oxooxazolidin-3-yl)benzamide;
benzyl N-[3-[(4-[trans-2-amino-2-phenyl-cyclopropyl]phenyl)carbamoyl]phenyl]carbamate;
N-[4-[trans-2-amino-2-phenyl-cyclopropyl]phenyl]naphthalene-2-carboxamide;
N-[4-[trans-2-amino-2-ethyl-cyclopropyl]-2-fluoro-phenyl]benzamide;
N-[4-[trans-2-amino-2-ethyl-cyclopropyl]-2-fluoro-phenyl]-4-phenyl-benzamide;
N-[4-[trans-2-amino-2-ethyl-cyclopropyl]phenyl]-4-morpholino-benzamide;
N-[4-[trans-2-amino-2-phenyl-cyclopropyl]phenyl]-4-phenyl-benzamide;
N-[4-[trans-2-amino-2-phenyl-cyclopropyl]phenyl]naphthalene-1-carboxamide;
N-[3-[trans-2-amino-2-ethyl-cyclopropyl]phenyl]-4-phenyl-benzamide;
N-[3-[trans-2-amino-2-ethyl-cyclopropyl]phenyl]naphthalene-2-carboxamide;
N-[3-[trans-2-amino-2-ethyl-cyclopropyl]phenyl]benzamide;
N-[4-[trans-2-amino-2-ethyl-cyclopropyl]-2-fluoro-phenyl]-2-(1-naphthyl)acetamide;
benzyl N-[4-[[4-[trans-2-amino-2-ethyl-cyclopropyl]-2-fluoro-phenyl]carbamoyl]phenyl]carbamate;
N-[4-[trans-2-amino-2-ethyl-cyclopropyl]-2-fluoro-phenyl]-4-(4-methylpiperazin-1-yl)benzamide;
N-[4-[trans-2-amino-2-ethyl-cyclopropyl]phenyl]-4-(4-methylpiperazin-1-yl)benzamide;
N-[4-[trans-2-amino-2-ethyl-cyclopropyl]phenyl]-3-(2-oxooxazolidin-3-yl)benzamide;
benzyl N-[5-[[4-[trans-2-amino-2-ethyl-cyclopropyl]phenyl]carbamoyl]-2-morpholino -phenyl]carbamate;
N-[4-[trans-2-amino-2-ethyl-cyclopropyl]phenyl]-4-(1-methyl-4-piperidyl)benzamide;
N-[4-(trans-2-amino-2-ethyl-cyclopropyl)phenyl]-4-(4-pyridyl)benzamide;
N-[4-(trans-2-amino-2-phenyl-cyclopropyl)phenyl]-3-chloro-benzamide;
N-[4-(trans-2-amino-2-phenyl-cyclopropyl)phenyl]-2-(1-naphthyl)acetamide;
N-[4-(trans-2-amino-2-phenyl-cyclopropyl)phenyl]-2-phenyl-acetamide;
N-[4-(trans-2-amino-2-phenyl-cyclopropyl)phenyl]-3-phenyl-benzamide;
N-[4-(trans-2-amino-2-phenyl-cyclopropyl)phenyl]-2-(2-naphthyl)acetamide;
N-[4-(trans-2-amino-2-phenyl-cyclopropyl)phenyl)-4-(1-methyl-4-piperidyl)benzamide;
N-[4-(trans-2-amino-2-phenyl-cyclopropyl)phenyl)-4-(4-methylpiperazin-1-yl)benzamide;
N-[4-(trans-2-amino-2-phenyl-cyclopropyl)phenyl]-3-(2-oxooxazolidin-3-yl)benzamide;
N-[4-(trans-2-amino-2-phenethyl-cyclopropyl)phenyl]-4-phenyl-benzamide;
N-[4-trans-2-amino-2-phenethyl-cyclopropyl)phenyl]benzamide;
N-[4-(trans-2-amino-2-phenethyl-cyclopropyl)phenyl]-4-(1-methyl-4-piperidyl)benzamide;
N-[4-(trans-2-amino-2-phenethyl-cyclopropyl)phenyl]-4-(4-methylpiperazin-1-yl)benzamide;
benzyl N-[5-[[4-[trans-2-amino-2-ethyl-cyclopropyl]phenyl]carbamoyl]-2-(4-methylpiperazin-1-yl)phenyl]carbamate;
N-[4-(trans-2-amino-2-phenethyl-cyclopropyl)phenyl]-3-(2-oxooxazolidin-3-yl)benzamide;
4-[trans-2-amino-2-(2-naphthylmethyl)cyclopropyl]aniline;
N-[4-(trans-2-amino-2-ethyl-cyclopropyl]phenyl)-4-(2-hydroxyethylamino)benzamide;
benzyl N-[3-[1-[4-[2-amino-2-ethyl-cyclopropyl]phenyl]triazol-4-yl]phenyl]carbamate;
trans-1-ethyl-2-[3-(4-phenyltriazol-1-yl)phenyl]cyclopropanamine;

benzyl N-[3-[1-[4-[2-amino-2-(2-naphthylmethyl)cyclopropyl]phenyl]triazol-4-yl]phenyl]carbamate;
trans-1-(2-naphthylmethyl)-2-[4-(4-phenyltriazol-1-yl)phenyl]cyclopropanamine;
trans 1-ethyl-2-[2-(4-phenyltriazol-1-yl)phenyl]cyclopropanamine;
trans-1-benzyl-2-[4-(4-phenyltriazol-1-yl)phenyl]cyclopropanamine;
N-[4-[(1S,2R)-2-amino-2-ethyl-cyclopropyl]phenyl]-4-phenyl-benzamide;
N-[4-[(1R,2S)-2-amino-2-ethyl-cyclopropyl]phenyl]-4-phenyl-benzamide;
trans 1-benzyl-2-(3-methoxyphenyl)cyclopropanamine;
1-[3-[(trans-2-amino-2-ethyl-cyclopropyl)phenyl]-3-phenyl-imidazolidin-2-one;
trans-1-ethyl-2-[4-(4-phenyltriazol-1-yl)phenyl]cyclopropanamine;
trans 1-[(benzylamino)methyl]-2-phenyl-cyclopropanamine;
trans 1-[(cyclopropylamino)methyl]-2-phenyl-cyclopropanamine;
5-[[[trans-1-methyl-2-phenyl-cyclopropyl]amino]methyl]pyrimidin-2-amine;
trans-N-[(2-methoxy-3-pyridyl)methyl]-1-methyl-2-phenyl-cyclopropanamine;
trans-N-(2,3-dihydro-1,4-benzodioxin-6-ylmethyl)-1-methyl-2-phenyl-cyclopropanamine;
2-[[trans-1,2-diphenylcyclopropyl]amino]-1-(4-methylpiperazin-1-yl)ethanone;
1-(4-methylpiperazin-1-yl)-2-[[trans-1-(2-naphthylmethyl)-2-phenyl-cyclopropyl]amino]ethanone;
2-[[(1R,2S)-1-methyl-2-phenyl-cyclopropyl]amino]-1-(4-methylpiperazin-1-yl)ethanone;
2-[[(1R,2R)-1-methyl-2-phenyl-cyclopropyl]amino]-1-(4-methylpiperazin-1-yl)ethanone;
2-[[trans-1-methyl-2-phenyl-cyclopropyl]amino]-1-(4-methylpiperazin-1-yl)ethanone;
2-[[cis-1-methyl-2-phenyl-cyclopropyl]amino]-1-(4-methylpiperazin-1-yl)ethanone;
2-[[trans-1-ethyl-2-phenyl-cyclopropyl]amino]-1-(1-piperidyl)ethanone;
trans-1-ethyl-2-phenyl-N-[2-(1-piperidyl)ethyl]cyclopropanamine;
5-[[[trans-1-methyl-2-phenyl-cyclopropyl]amino]methyl]-1,3,4-oxadiazol-2-amine;
trans-1-(4-nitrophenyl)-2-phenyl-cyclopropanamine;
trans-2-(4-chlorophenyl)-1-phenyl-cyclopropanamine;
trans-2-(4-bromophenyl)-1-phenyl-cyclopropanamine;
N-[4-(trans-1-amino-2-phenyl-cyclopropyl)phenyl]acetamide; and a stereoisomer or a pharmaceutically acceptable salt thereof.

7. A compound of formula (I)

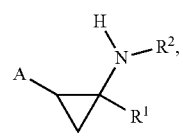

(I)

wherein:
A is aryl or heteroaryl optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, OH, $C_1$-$C_6$ alkylamino, and R-L-;

R is aryl optionally substituted by one, two or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, $C_1$-$C_6$ alkylamino optionally substituted by OH, heterocyclylamino optionally substituted by $C_1$-$C_6$ alkyl, OH, phenyl, heterocyclyl optionally substituted by $C_1$-$C_6$ alkyl, heterocyclyl substituted by oxo, heteroaryl, and benzyloxycarbonylamino; or heteroaryl;

L is a single bond; $C_1$-$C_6$ alkylene; $C_2$-$C_6$ alkenylene; —$(CH_2)_mX$—$(CH_2)_n$—; —$(CH_2)_o(SO_2)NH$—; —$(CH_2)_p(CO)NR^3$—; —$(CH_2)_qNR^4(CO)$—; heterocyclyl substituted by oxo; or heteroaryl;

$R^1$ is $C_1$-$C_6$ alkyl, optionally substituted by aryl or heteroaryl; aryl; heteroaryl; or —$(CH_2)_r$—Y—$R^5$; and wherein the aryl or heteroaryl group may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, nitro, acetamido, and phenyl;

$R^2$ is hydrogen; $C_1$-$C_6$ alkyl, optionally substituted by aryl, heteroaryl, or heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$;

m, n, o, p, q are, independently, zero or an integer from 1 to 6;

r is an integer from 1 to 6;

X, Y are, independently, $NR^8$; O; or S;

$R^3$, $R^4$ are, independently, hydrogen; or $C_1$-$C_6$ alkyl;

$R^5$ is hydrogen, aryl or heteroaryl, wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and phenyl;

$R^6$, $R^7$ are, independently, hydrogen; $C_1$-$C_6$ alkyl; or $R^6$ and $R^7$ together with the nitrogen to which they are bound form a $C_4$-$C_{10}$-heterocyclic ring, optionally containing one or more further heteroatoms in the ring independently selected from $NR^9$, O or S and being optionally substituted by $NH_2$;

$R^8$ is hydrogen; $C_1$-$C_6$ alkyl, optionally substituted by aryl or heterocyclyl; or $C_{3-6}$ cycloalkyl;

$R^9$ is hydrogen or $C_1$-$C_6$ alkyl;

or a stereoisomer or pharmaceutically acceptable salt thereof;

wherein each aryl is selected from phenyl, indenyl, indanyl, naphthyl, and tetrahydronaphthalenyl, wherein each heteroaryl is selected from pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl, provided that when A is an unsubstituted phenyl or imidazolyl and $R^1$ is methyl, then $R^2$ cannot be hydrogen or methyl; and that when A is an unsubstituted phenyl and $R^1$ is n-propyl, phenyl, 2-fluorophenyl, fluorophenyl, 3-chlorophenyl, 4-chlorophenyl, 2,4-dichlorophenyl, 2-methoxyphenyl, 4-methoxyphenyl 3,4-dimethoxyphenyl, 1-naphthyl, benzyl, or 4-chlorobenzyl, then $R^2$ cannot be hydrogen; and that when A is 4-chlorophenyl, 2,4dichlorophenyl, 4-fluorophenyl, 2,4-difluorophenyl, 2-chloro-4-fluorophenyl, 2-fluoro-4-chlorophenyl, 4-trifluoromethylphenyl, 4-trifluoromethoxyphenyl, or 4-(4-chlorophenyl)phenyl and $R^1$ is methyl or ethyl, then $R^2$ cannot be hydrogen; and with the exclusion of the following compounds:
2-[2-chloro-4-(4-chlorophenyl)phenyl]-1-methyl-cyclopropanamine;
2-(4-chlorophenyl)-1-phenyl-cyclopropanamine;
2-(4-methoxyphenyl)-1-phenyl-cyclopropanamine;
[1-(benzylamino)-2-phenyl-cyclopropyl]methanol;
or a stereoisomer or pharmaceutically acceptable salt thereof.

8. The compound according to claim 7 provided that when A is phenyl substituted by 4-methoxy, 4-trifluoromethyl, 4-trifluoromethoxy, 4-(4-chlorophenyl), or one or two halogens selected from fluoro and chloro and $R^1$ is methyl; ethyl; n-propyl; phenyl, optionally substituted by one or two fluoro, chloro or methoxy; 1-naphthyl; or benzyl, then $R^2$ cannot be hydrogen, and with the exclusion of the following compounds:
2-[2-chloro-4-(4-chlorophenyl)phenyl]-1-methyl-cyclopropanamine;
[1-(benzylamino)-2-phenyl-cyclopropyl]methanol;
or a stereoisomer or a pharmaceutically acceptable salt thereof.

9. The compound of claim 7, wherein A is phenyl substituted by R-L-, L is —$(CH_2)_p(CO)NR^3$—, and $R^2$ is hydrogen.

10. The compound of claim 7, wherein $R^1$ is ethyl substituted by phenyl.

11. The compound of claim 7, wherein $R^2$ is $C_1$-$C_6$ alkyl, optionally substituted by aryl, heteroaryl, or heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$.

12. The compound of claim 7, selected from:
(1S,2R)-1-ethyl-2-phenyl-cyclopropanamine;
(1R,2S)-1-ethyl-2-phenyl-cyclopropanamine;
trans-1-isopropyl-2-phenyl-cyclopropanamine;
trans-1-phenethyl-2-phenyl-cyclopropanamine;
trans-2-(4-bromophenyl)-1-ethyl-cyclopropanamine;
trans-1-benzyl-2-(4-bromophenyl)cyclopropanamine;
trans-1-ethyl-2-(6-quinolyl)cyclopropanamine;
1-(2-naphthylmethyl)-2-phenyl-cyclopropanamine;
trans-1-ethyl-2-[3-(trifluoromethyl)phenyl]cyclopropanamine;
trans-1-ethyl-2-(3-fluorophenyl)cyclopropanamine;
trans-1-ethyl-2-(3-chlorophenyl)-cyclopropanamine;
trans-1-ethyl-2-(3-bromophenyl)-cyclopropanamine;
trans-1-ethyl-2-[3-methoxyphenyl]cyclopropanamine;
trans-1-ethyl-2-(2-fluorophenyl)-cyclopropanamine;
trans-1-ethyl-2-(2-chlorophenyl)-cyclopropanamine;
trans-1-ethyl-2-(2-bromophenyl)-cyclopropanamine;
trans-1-(1-naphthylmethyl)-2-phenyl-cyclopropanamine;
trans-2-(4-bromophenyl)-1-(2-naphthylmethyl)cyclopropanamine;
trans-N-[4-[2-amino-2-ethyl-cyclopropyl]phenyl]naphthalene-2-carboxamide;
N-[2-[(trans)-2-amino-2-ethyl-cyclopropyl]phenyl]benzamide;
benzyl N-[3-[[2-[(trans)-2-amino-2-ethyl-cyclopropyl]phenyl]carbamoyl]phenyl]carba-mate;
benzyl N-[3-[[3-[(trans)-2-amino-2-ethyl-cyclopropyl]phenyl]carbamoyl]phenyl]carba-mate;
N-[4-[(trans)-2-amino-2-ethyl-cyclopropyl]phenyl]-3-chloro-benzamide
N-[4-[(trans)-2-amino-2-ethyl-cyclopropyl]phenyl]-3-phenyl-benzamide;
N-[4-[(trans)-2-amino-2-ethyl-cyclopropyl]phenyl]-4-phenyl-benzamide;
benzyl N-[3-[[4-[(trans)-2-amino-2-ethyl-cyclopropyl]phenyl]carbamoyl]phenyl]carba-mate;
benzyl N-[4-[[4-[(trans)-2-amino-2-ethyl-cyclopropyl]phenyl]carbamoyl]phenyl]carba-mate;
N-[4-[(trans)-2-amino-2-ethyl-cyclopropyl]phenyl]-2-phenyl-acetamide;
N-[4-[(trans)-2-amino-2-ethyl-cyclopropyl]phenyl]-3-phenyl-propanamide;
2-(4-benzyloxyphenyl)-trans-1-ethyl-cyclopropanamine;
N-[4-[(2-amino-trans-2-ethyl-cyclopropyl]phenyl]benzenesulfonamide;
trans-1-benzyl-2-(4-benzyloxyphenyl)cyclopropanamine;
N-[4-[trans-2-amino-2-(2-naphthylmethyl)cyclopropyl]phenyl]benzamide;
Benzyl-N-[3-[[4-[(trans)-2-amino-2-(2-naphthylmethyl)cyclopropyl]phenyl]carbamoyl]phenyl]carbamate;
N-[4-[(trans)-2-amino-2-(2-naphthylmethyl)cyclopropyl]phenyl]-2-phenyl-acetamide;
N-[4-[trans-2-amino-2-ethyl-cyclopropyl]phenyl]benzamide;
trans-4-(2-amino-2-ethyl-cyclopropyl)aniline;
trans-2-(3-azidophenyl)-1-ethyl-cyclopropanamine;
1-amino-(trans)-2-phenyl-cyclopropyl]methanol;
1-amino-(cis)-2-phenyl-cyclopropyl]methanol;
(1R,2S)-1-ethyl-N-[(2-methoxyphenyl)methyl]-2-phenyl-cyclopropanamine;
(1R,2S)-1-ethyl-N-[(2-methoxy-1-naphthyl)methyl]-2-phenyl-cyclopropanamine;
2-[[(1S,2R)-1-methyl-2-phenyl-cyclopropyl]amino]-1-(4-methylpiperazin-1-yl)ethanone;
2-[[(1S,2S)-1-methyl-2-phenyl-cyclopropyl]amino]-1-(4-methylpiperazin-1-yl)ethanone;
1-[(3S)-3-aminopyrrolidin-1-yl]-2-[[(1S,2R)-1-methyl-2-phenyl-cyclopropyl]amino]ethanone;
trans-2-[[(1-ethyl-2-phenyl-cyclopropyl]amino]-1-(4-methylpiperazin-1-yl)ethanone;
cis-2-[[(1-ethyl-2-phenyl-cyclopropyl]amino]-1-(4-methylpiperazin-1-yl)ethanone;
trans-1-ethyl-N-methyl-2-phenyl-cyclopropanamine;
cis-1-ethyl-N-methyl-2-phenyl-cyclopropanamine;
trans-1-ethyl-N-ethyl-2-phenyl-cyclopropanamine;
cis-1-ethyl-N-ethyl-2-phenyl-cyclopropanamine;
trans-2-[[1-ethyl-2-phenyl-cyclopropyl]amino]acetamide;
trans-N-benzyl-1-ethyl-2-phenyl-cyclopropanamine;
trans-N-[(3,4-dimethoxyphenyl)methyl]-1-ethyl-2-phenyl-cyclopropanamine;
trans-N-[(4,7-dimethoxy-1-naphthyl)methyl]-1-ethyl-2-phenyl-cyclopropanamine;
trans-N-[(2-chloro-3-pyridyl)methyl]-1-ethyl-2-phenyl-cyclopropanamine;
trans-N-[(2,2-dimethylchroman-6-yl)methyl]-1-ethyl-2-phenyl-cyclopropanamine;
trans-1-ethyl-2-phenyl-cyclopropanamine;
trans-2-(4-bromo-3-fluoro-phenyl)-1-ethyl-cyclopropanamine;
trans 2-(3-bromophenyl)-1-phenethyl-cyclopropanamine;
trans-2-(4-fluorophenyl)-1-(2-naphthylmethyl)cyclopropanamine;

trans-2-(4-chlorophenyl)-1-(2-naphthylmethyl)cyclopropanamine;
trans-2-(3-chlorophenyl)-1-(2-naphthylmethyl)cyclopropanamine;
trans-2-(3-bromophenyl)-1-(2-naphthylmethyl)cyclopropanamine;
trans-2-(4-chlorophenyl)-1-phenethyl-cyclopropanamine;
trans-2-(4-fluorophenyl)-1-phenethyl-cyclopropanamine;
trans-1-benzyl-2-(4-fluorophenyl)cyclopropanamine;
trans-1-benzyl-2-(4-chlorophenyl)cyclopropanamine;
trans 2-(4-bromophenyl)-1-phenethyl-cyclopropanamine;
cis-1-ethyl-2-phenyl-cyclopropanamine;
N-[4-(trans-2-amino-2-ethyl-cyclopropyl)phenyl]-3-[(1-methyl-4-piperidyl)amino]-4-phenyl-benzamide;
2-(4-benzyloxyphenyl)-1-(2-naphthylmethyl)cyclopropanamine;
N-[4-trans-[2-amino-2-ethyl-cyclopropyl]phenyl]-2-(1-naphthyl)acetamide;
N-[4-trans-[2-amino-2-ethyl-cyclopropyl]phenyl]-2-(4-nitrophenyl)acetamide;
benzyl N-[4-[[4-[trans-2-amino-2-(2-naphthylmethyl)cyclopropyl]phenyl]carbamoyl]phenyl]carbamate;
N-[4-(trans-2-amino-2-ethyl-cyclopropyl)phenyl]naphthalene-1-carboxamide;
N-[4-[trans-2-amino-2-(2-naphthylmethyl)cyclopropyl]phenyl]naphthalene-2-carboxamide;
N-[4-[trans-2-amino-2-(2-naphthylmethyl)cyclopropyl]phenyl]-4-phenyl-benzamide;
N-[4-trans-2-amino-2-ethyl-cyclopropyl]phenyl]-2-(2-naphthyl)acetamide;
N-[4-[trans-2-amino-2-phenyl-cyclopropyl]phenyl]benzamide;
N-[4-[trans-2-amino-2-(2-naphthylmethyl)cyclopropyl]phenyl]-2-(1-naphthyl)acetamide;
N-[3-[trans-2-amino-2-ethyl-cyclopropyl]phenyl]-2-(1-naphthyl)acetamide;
N-[4-[trans-2-amino-2-ethyl-cyclopropyl]phenyl]-4-(3-furyl)benzamide;
N-[4- [trans-2-amino-2-(2-naphthylmethyl)cyclopropyl]phenyl]-3-chloro-benzamide;
N-[3-[trans-2-amino-2-ethyl-cyclopropyl]phenyl]-3-chloro-benzamide;
N-[4-[trans-2-amino-2-(2-naphthylmethyl)cyclopropyl]phenyl]-3-phenyl-propanamide;
N-[4-[trans-2-amino-2-(2-naphthylmethyl)cyclopropyl]phenyl]-3-phenyl-benzamide;
N-[4-[trans-2-amino-2-ethyl-cyclopropyl]phenyl]-4-(2-oxooxazolidin-3-yl)benzamide;
benzyl N-[3-[(4-[trans-2-amino-2-phenyl-cyclopropyl]phenyl)carbamoyl]phenyl]carbamate;
N-[4-[trans-2-amino-2-phenyl-cyclopropyl]phenyl]naphthalene-2-carboxamide;
N-[4-[trans-2-amino-2-ethyl-cyclopropyl]-2-fluoro-phenyl]benzamide;
N-[4-[trans-2-amino-2-ethyl-cyclopropyl]-2-fluoro-phenyl]-4-phenyl-benzamide;
N-[4-[trans-2-amino-2-ethyl-cyclopropyl]phenyl]-4-morpholino-benzamide;
N-[4-[trans-2-amino-2-phenyl-cyclopropyl]phenyl]-4-phenyl-benzamide;
N-[4-[trans-2-amino-2-phenyl-cyclopropyl]phenyl]naphthalene-1-carboxamide;
N-[3-[trans-2-amino-2-ethyl-cyclopropyl]phenyl]-4-phenyl-benzamide;
N-[3-[trans-2-amino-2-ethyl-cyclopropyl]phenyl]naphthalene-2-carboxamide;
N-[3-[trans-2-amino-2-ethyl-cyclopropyl]phenyl-benzamide;
N-[4-[trans-2-amino-2-ethyl-cyclopropyl]-2-fluoro-phenyl]-2-(1-naphthyl)acetamide;
benzyl N-[4-[[4-[trans-2-amino-2-ethyl-cyclopropyl]-2-fluoro-phenyl]carbamoyl]phenyl]carbamate;
N-[4-[trans-2-amino-2-ethyl-cyclopropyl]-2-fluoro-phenyl]-4-(4-methylpiperazin-1-yl)benzamide;
N-[4-[trans-2-amino-2-ethyl-cyclopropyl]phenyl]-4-(4-methylpiperazin-1-yl)benzamide;
N-[4-[trans-2-amino-2-ethyl-cyclopropyl]phenyl]-3-(2-oxooxazolidin-3-yl)benzamide;
benzyl N-[5-[[4-[trans-2-amino-2-ethyl-cyclopropyl]phenyl]carbamoyl]-2-morpholino -phenyl]carbamate;
N-[4-[trans-2-amino-2-ethyl-cyclopropyl]phenyl]-4-(1-methyl-4-piperidyl)benzamide;
N-[4-(trans-2-amino-2-ethyl-cyclopropyl]phenyl]-4-(4-pyridyl)benzamide;
N-[4-(trans-2-amino-2-phenyl-cyclopropyl)phenyl]-3-chloro-benzamide;
N-[4-(trans-2-amino-2-phenyl-cyclopropyl)phenyl]-2-(1-naphthyl)acetamide;
N-[4-(trans-2-amino-2-phenyl-cyclopropyl)phenyl]-2-phenyl-acetamide;
N-[4-(trans-2-amino-2-phenyl-cyclopropyl)phenyl]-3-phenyl-benzamide;
N-[4-(trans-2-amino-2-phenyl-cyclopropyl)phenyl]-2-(2-naphthyl)acetamide;
N-[4-(trans-2-amino-2-phenyl-cyclopropyl)phenyl]-4-(1-methyl-4-piperidyl)benzamide;
N-[4-(trans-2-amino-2-phenyl-cyclopropyl)phenyl]-4-(4-methylpiperazin-1-yl)benzamide;
N-[4-(trans-2-amino-2-phenyl-cyclopropyl)phenyl]-3-(2-oxooxazolidin-3-yl)benzamide;
N-[4-(trans-2-amino-2-phenethyl-cyclopropyl)phenyl]-4-phenyl-benzamide;
N-[4-trans-2-amino-2-phenethyl-cyclopropyl)phenyl]benzamide;
N-[4-(trans-2-amino-2-phenethyl-cyclopropyl)phenyl]-4-(1-methyl-4-piperidyl)benzamide;
N-[4-(trans-2-amino-2-phenethyl-cyclopropyl)phenyl]-4-(4-methylpiperazin-1-yl)benzamide;
benzyl N-[5-[[4- [trans-2-amino-2-ethyl-cyclopropyl]phenyl]carbamoyl]-2-(4-methylpiperazin-1 -yl)phenyl]carbamate;
N-[4-(trans-2-amino-2-phenethyl-cyclopropyl)phenyl]-3-(2-oxooxazolidin-3-yl)benzamide;
4-[trans-2-amino-2-(2-naphthylmethyl)cyclopropyl]aniline;
N-[4-(trans-2-amino-2-ethyl-cyclopropyl)phenyl)-4-(2-hydroxyethylamino)benzamide;
benzyl N-[3-[1-[4-[2-amino-2-ethyl-cyclopropyl]phenyl]triazol-4-yl]phenyl]carbamate;
trans-1-ethyl-2-[3-(4-phenyltriazol-1-yl)phenyl]cyclopropanamine;
benzyl N-[3-[1-[4-[2-amino-2-(2-naphthylmethyl)cyclopropyl]phenyl]triazol-4-yl]phenyl]carbamate;
trans-1-(2-naphthylmethyl)-2-[4-(4-phenyltriazol-1-yl)phenyl]cyclopropanamine;
trans 1-ethyl-2-[2-(4-phenyltriazol-1-yl)phenyl]cyclopropanamine;
trans-1-benzyl-2-[4-(4-phenyltriazol-1-yl)phenyl]cyclopropanamine;
N-[4-[(1S,2R)-2-amino-2-ethyl-cyclopropyl]phenyl]-4-phenyl-benzamide;
N-[4-[(1R,2S)-2-amino-2-ethyl-cyclopropyl]phenyl]-4-phenyl-benzamide;

trans 1-benzyl-2-(3-methoxyphenyl)cyclopropanamine;
1-[3-[(trans-2-amino-2-ethyl-cyclopropyl]phenyl]-3-phenyl-imidazolidin-2-one;
trans-1-ethyl-2-[4-(4-phenyltriazol-1-yl)phenyl]cyclopropanamine;
trans 1-[(benzylamino)methyl]-2-phenyl-cyclopropanamine;
trans 1-[(cyclopropylamino)methyl]-2-phenyl-cyclopropanamine;
5-[[[trans-1-methyl-2-phenyl-cyclopropyl]amino]methyl] pyrimidin-2-amine;
trans-N-[(2-methoxy-3-pyridyl)methyl]-1-methyl-2-phenyl-cyclopropanamine;
trans-N-(2,3-dihydro-1,4-benzodioxin-6-ylmethyl)-1-methyl-2-phenyl-cyclopropanamine;
2-[[trans-1,2-diphenylcyclopropyl]amino]-1-(4-methyl-piperazin-1-yl)ethanone;
1-(4-methylpiperazin-1-yl)-2-[[trans-1-(2-naphthylmethyl)-2-phenyl-cyclopropyl]amino]ethanone;
2-[[(1R,2S)-1-methyl-2-phenyl-cyclopropyl]amino]-1-(4-methylpiperazin-1-yl)ethanone;
2-[[(1R,2R)-1-methyl-2-phenyl-cyclopropyl]amino]-1-(4-methylpiperazin-1-yl)ethanone;
2-[[trans-1-methyl-2-phenyl-cyclopropyl]amino]-1-(4-methylpiperazin-1-yl)ethanone;
2-[[cis-1-methyl-2-phenyl-cyclopropyl]amino]-1-(4-methylpiperazin-1-yl)ethanone;
2-[[trans-1-ethyl-2-phenyl-cyclopropyl]amino]-1-(1-piperidyl)ethanone;
trans-1-ethyl-2-phenyl-N-[2-(1-piperidyl)ethyl]cyclopropanamine;
5-[[[trans-1-methyl-2-phenyl-cyclopropyl]amino] methyl]-1,3,4-oxadiazol-2-amine;
trans-1-(4-nitrophenyl)-2-phenyl-cyclopropanamine;
trans-2-(4-bromophenyl)-1-phenyl-cyclopropanamine;
N-[4-(trans-1-amino-2-phenyl-cyclopropyl)phenyl]acetamide;
and a stereoisomer or a pharmaceutically acceptable salt thereof.

13. A pharmaceutical composition comprising a compound of claim 7, together with a pharmaceutically acceptable excipient, diluent or combination thereof.

14. The pharmaceutical composition according to claim 13, in the form of tablets, capsules, oral preparations, powders, granules, pills, injectable or infusible liquid, solutions, suspensions, emulsions, suppositories, ointments, creams, lotions, gels, pastes, transdermal delivery devices.

15. A compound selected from:
N-[4-(trans-2-amino-2-ethyl-cyclopropyl)phenyl]pyridine-4-carboxamide;
N-[4-(trans-2-amino-2-phenyl-cyclopropyl)phenyl]pyridine-4-carboxamide;
N-[4-(trans-2-amino-2-phenethyl-cyclopropyl)phenyl] pyridine-4-carboxamide;
trans 1-[(4-methylpiperazin-1-yl)methyl]-2-phenyl-cyclopropanamine;
and a stereoisomer or a pharmaceutically acceptable salt thereof.

16. A process for preparing a compound of claim 7, wherein $R^2$ is hydrogen, the process comprising the preparation of compounds of formula A3 by reaction of a compound of formula A1 with the phosphonate of formula A2, the deprotection of a compound of formula A3 to obtain a compound of formula A4 the transformation of a compound of formula A4 to obtain a compound of formula A5 and the deprotection of a compound of formula A5 to obtain a compound of formula (I), as represented below:

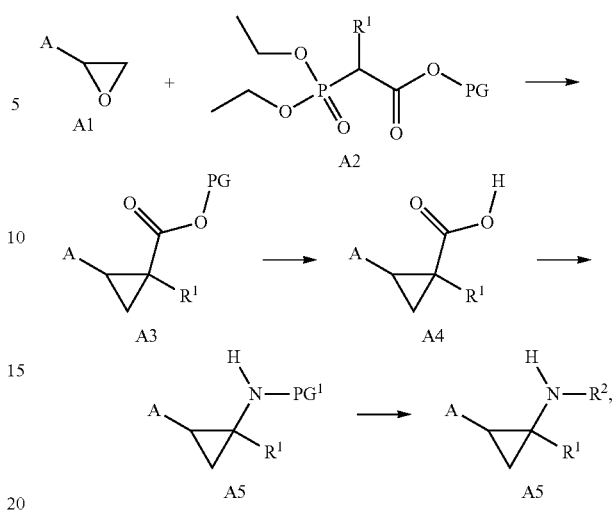

wherein PG and $PG^1$ are protecting groups.

17. A process for preparing a compound of claim 7, wherein $R^2$ is hydrogen, A is aryl or heteroaryl substituted by R-L and L is —$(CH_2)_p(CO)NH$—; —$(CH_2)_mX$—; —$(CH_2)_o(SO_2)NH$— or —$(CH_2)_p(CO)NR^3$—; the process comprising the preparation of compounds of formula A6 by reaction of a compound of formula A1 with the phosphonate of formula A2, the transformation of a compound of formula A6 to obtain a compound of formula A7 or A8, the transformation of a compound of formula A7 to obtain a compound of formula A8, the deprotection of a compound of formula A8 to obtain a compound of formula A9, the transformation of a compound of formula A9 to obtain a compound of formula A10 and the deprotection of a compound of formula A10 to obtain a compound of formula (I), as represented below:

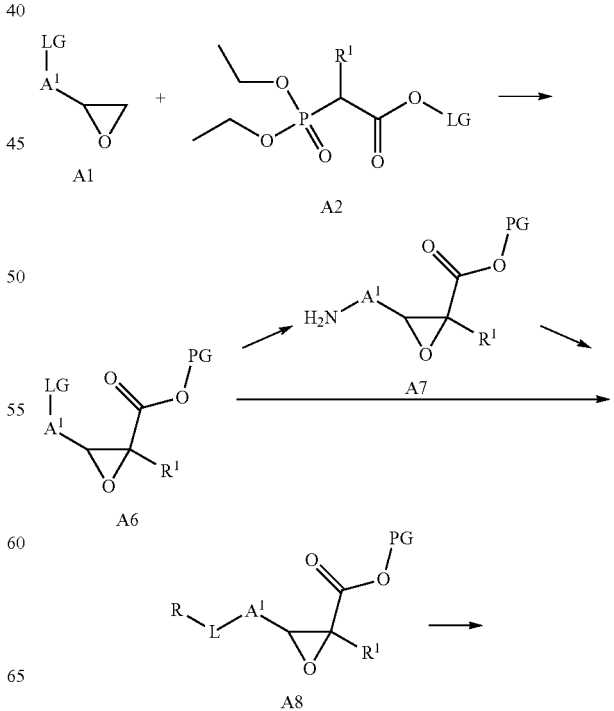

-continued

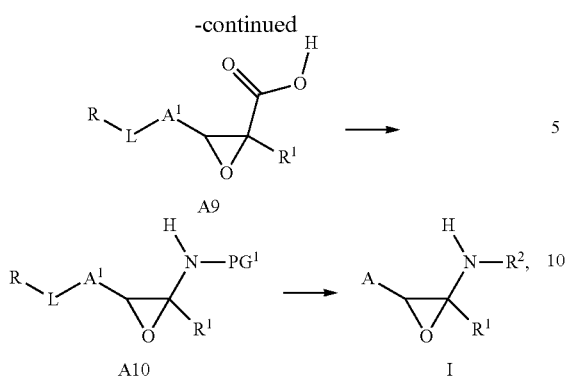

wherein PG and PG¹ are protecting groups and LG is a leaving group selected from Br, I, and Cl.

18. A process for preparing a compound of claim 7, wherein $R^1$ is $CH_2OH$ and $R^2$ is hydrogen, the process comprising the preparation of a compound of formula B3 via reaction of a compound of formula B1 with a compound of formula B2, the reduction of a compound of formula B3 to give an amine of formula B4, the protection of a compound of formula B4 to obtain a compound of formula B5, the transformation of a compound of formula B5 to obtain a compound of formula B6, the deprotection of a compound of formula B6 to obtain a compound of formula (I), as represented below:

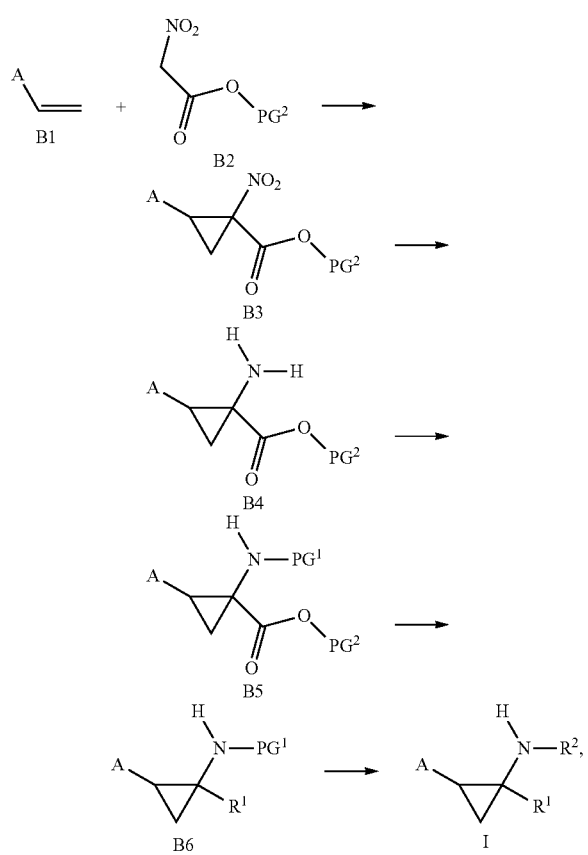

wherein PG¹ is carboxybenzyl, tert-butyloxycarbonyl (BOC), or 9-fluorenylmethyloxycarbonyl and PG² is ethyl.

19. A process for preparing a compound of claim 7, wherein $R^2$ is $C_1$-$C_6$ alkyl, optionally substituted by aryl, heteroaryl, or heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$, the process comprising the reaction of a compound of formula C1, with a compound of formula $R^1$—W, wherein $R^{10}$ is $C_1$-$C_6$ alkyl, optionally substituted by aryl, heteroaryl, or heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2(CO)NR^6R^7$ and W is a halogen atom, in a solvent in the presence of a base at a temperature between 0° C. to the boiling point of the solvent, or the process comprising the reaction of a compound of formula C1, with a compound of formula $R^{11}$—CHO, wherein $R^{11}$ is hydrogen; $C_1$-$C_5$ alkyl, optionally substituted by aryl, heteroaryl, or heterocyclyl; and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$, in a suitable organic solvent in the presence of a reducing agent, as represented below:

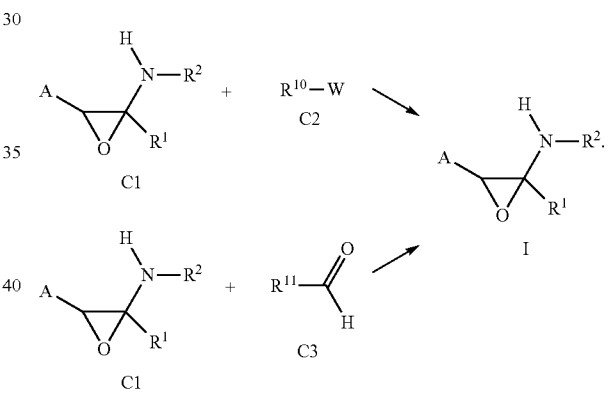

20. A method for treating a disease or condition mediated by an excessive or inappropriate level of KDM1A (LSD1) activity, comprising administering to a patient a pharmacologically useful quantity of one or more compounds of claim 7, or a stereoisomer or pharmaceutically acceptable salt thereof.

21. The method of claim 20, wherein the disease or condition mediated by an excessive or inappropriate level of KDM1A (LSD1) activity is cancer, a tumor, HIV, or herpes virus infection.

22. A method for treating a disease or condition mediated by an excessive or inappropriate level of KDM1A (LSD1) activity, comprising administering to a patient a pharmacologically useful quantity of one or more compounds of claim 15, or a stereoisomer or pharmaceutically acceptable salt thereof.

23. The method of claim 22, wherein the disease or condition mediated by an excessive or inappropriate level of KDM1A (LSD1) activity is cancer, a tumor, HIV, or herpes virus infection.

24. A method for treating a disease or condition mediated by an excessive or inappropriate level of KDM1A (LSD1)

activity, comprising administering to a patient a pharmacologically useful quantity of one or more compounds of formula (I)

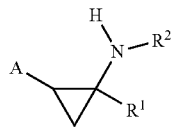
(I)

wherein:
A is aryl or heteroaryl optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, OH, $C_1$-$C_6$ alkylamino, and R-L-;

R is aryl optionally substituted by one, two or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, CN, nitro, $NH_2$, azide, $C_1$-$C_6$ alkylamino optionally substituted by OH, heterocyclylamino optionally substituted by $C_1$-$C_6$ alkyl, OH, phenyl, heterocyclyl optionally substituted by $C_1$-$C_6$ alkyl, heterocyclyl substituted by oxo, heteroaryl, and benzyloxycarbonylamino; or heteroaryl;

L is a single bond; $C_1$-$C_6$ alkylene; $C_2$-$C_6$ alkenylene; —$(CH_2)_m$X—$(CH_2)_n$—; —$(CH_2)_o$($SO_2$)NH—; —$(CH_2)_p$(CO)$NR^3$—; —$(CH_2)_q NR^4$(CO)—; heterocyclyl substituted by oxo; or heteroaryl;

$R^1$ is $C_1$-$C_6$ alkyl, optionally substituted by aryl or heteroaryl; aryl; heteroaryl; or —$(CH_2)_r$—Y—$R^5$; and wherein the aryl or heteroaryl group may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, nitro, acetamido, and phenyl;

$R^2$ is hydrogen; $C_1$-$C_6$ alkyl, optionally substituted by aryl, heteroaryl, or heterocyclyl and wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and $NH_2$; or —$CH_2$(CO)$NR^6R^7$;

m, n, o, p, q are, independently, zero or an integer from 1 to 6;

r is an integer from 1 to 6;

X, Y are, independently, $NR^8$; O; or S;

$R^3$, $R^4$ are, independently, hydrogen; or $C_1$-$C_6$ alkyl;

$R^5$ is hydrogen, aryl or heteroaryl, wherein the aryl or heteroaryl may be optionally substituted by one or more substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, and phenyl;

$R^6$, $R^7$ are, independently, hydrogen; $C_1$-$C_6$ alkyl; or $R^6$ and $R^7$ together with the nitrogen to which they are bound form a $C_4$-$C_{10}$-heterocyclic ring, optionally containing one or more further heteroatoms in the ring independently selected from $NR^9$, O or S and being optionally substituted by $NH_2$;

$R^8$ is hydrogen; $C_1$-$C_6$ alkyl, optionally substituted by aryl or heterocyclyl; or $C_{3-6}$ cycloalkyl;

$R^9$ is hydrogen or $C_1$-$C_6$ alkyl;

wherein each aryl is selected from phenyl, indenyl, indanyl, naphthyl, and tetrahydronaphthalenyl;

wherein each heteroaryl is selected from pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl;

or a stereoisomer or a pharmaceutically acceptable salt thereof.

25. The method of claim 24, wherein the disease or condition mediated by an excessive or inappropriate level of KDM1A (LSD1) activity is cancer, a tumor, HIV, or herpes virus infection.

* * * * *

UNITED STATES PATENT AND TRADEMARK OFFICE
CERTIFICATE OF CORRECTION

PATENT NO. : 9,944,589 B2
APPLICATION NO. : 14/650292
DATED : April 17, 2018
INVENTOR(S) : Mario Varasi et al.

It is certified that error appears in the above-identified patent and that said Letters Patent is hereby corrected as shown below:

In the Claims

At Column 135, Claim number 7, Line number 1:
"that when A is 4-chlorophenyl, 2,4dichlorophenyl,"
Should read:
-- that when A is 4-chlorophenyl, 2,4-dichlorophenyl, --

At Column 140, Claim number 16, Line numbers 14-20:

"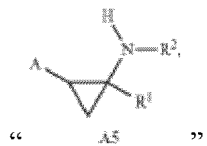"

Should read:

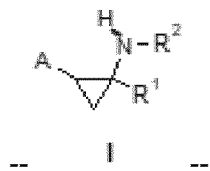

At Column 140, Claim number 17, Line numbers 41-47:

"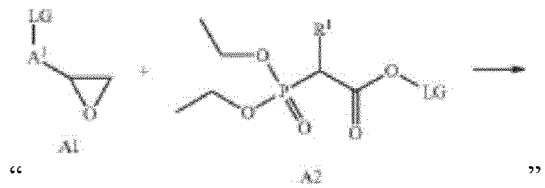"

Signed and Sealed this
Second Day of October, 2018

Andrei Iancu
*Director of the United States Patent and Trademark Office*